United States Patent
Ni et al.

(10) Patent No.: US 7,824,675 B2
(45) Date of Patent: Nov. 2, 2010

(54) USE OF AN ANTIBODY THAT BINDS HUMAN TUMOR NECROSIS FACTOR RECEPTOR-LIKE 2

(75) Inventors: Jian Ni, Germantown, MD (US); Craig A. Rosen, Laytonsville, MD (US); Reiner L. Gentz, Belo Horizonte (BR)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 12/241,203

(22) Filed: Sep. 30, 2008

(65) Prior Publication Data

US 2009/0092608 A1    Apr. 9, 2009

Related U.S. Application Data

(60) Division of application No. 09/533,262, filed on Mar. 22, 2000, now Pat. No. 7,429,646, and a continuation-in-part of application No. 08/741,095, filed on Oct. 30, 1996, now Pat. No. 7,427,492, which is a continuation-in-part of application No. 08/464,595, filed on Jun. 5, 1995, now abandoned, and a continuation-in-part of application No. 08/462,962, filed on Jun. 5, 1995, now abandoned, and a continuation-in-part of application No. 08/462,315, filed on Jun. 5, 1995, now abandoned, each which is a continuation-in-part of application No. PCT/US95/05058, filed on Apr. 27, 1995.

(60) Provisional application No. 60/147,383, filed on Aug. 6, 1999, provisional application No. 60/135,169, filed on May 19, 1999, provisional application No. 60/126,522, filed on Mar. 26, 1999, provisional application No. 60/125,683, filed on Mar. 22, 1999.

(51) Int. Cl.
*A61K 39/00* (2006.01)
*A61K 39/395* (2006.01)

(52) U.S. Cl. ............... 424/130.1; 424/133.1; 424/135.1; 424/139.1; 424/141.1; 424/142.1; 424/143.1

(58) Field of Classification Search ........................ None
See application file for complete search history.

(56) References Cited

U.S. PATENT DOCUMENTS

| | | | |
|---|---|---|---|
| 4,002,531 A | 1/1977 | Royer | |
| 4,444,887 A | 4/1984 | Hoffmann | |
| 4,474,893 A | 10/1984 | Reading | |
| 4,714,681 A | 12/1987 | Reading | |
| 4,716,111 A | 12/1987 | Osband et al. | |
| 4,925,648 A | 5/1990 | Hansen et al. | |
| 4,946,778 A | 8/1990 | Ladner et al. | |
| 4,946,788 A | 8/1990 | DeLespesse | |
| 5,112,946 A | 5/1992 | Maione | |
| 5,194,596 A | 3/1993 | Tischer et al. | |
| 5,223,409 A | 6/1993 | Ladner et al. | |
| 5,225,539 A | 7/1993 | Winter | |
| 5,258,498 A | 11/1993 | Huston et al. | |
| 5,310,662 A | 5/1994 | Evans et al. | |
| 5,314,995 A | 5/1994 | Fell, Jr. et al. | |
| 5,336,603 A | 8/1994 | Capon et al. | |
| 5,349,052 A | 9/1994 | Delgado et al. | |
| 5,349,053 A | 9/1994 | Landolfi | |
| 5,350,836 A | 9/1994 | Kopchick et al. | |
| 5,359,039 A | 10/1994 | Smith et al. | |
| 5,359,046 A | 10/1994 | Capon et al. | |
| 5,395,760 A | 3/1995 | Smith et al. | |
| 5,403,484 A | 4/1995 | Ladner et al. | |
| 5,413,923 A | 5/1995 | Kucherlapati et al. | |
| 5,427,908 A | 6/1995 | Dower et al. | |
| 5,447,851 A | 9/1995 | Buetler et al. | |
| 5,464,938 A | 11/1995 | Smith et al. | |
| 5,474,981 A | 12/1995 | Leder et al. | |
| 5,478,925 A | 12/1995 | Wallach et al. | |
| 5,516,637 A | 5/1996 | Huang et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,571,698 A | 11/1996 | Ladner et al. | |
| 5,573,920 A | 11/1996 | Randle | |

(Continued)

FOREIGN PATENT DOCUMENTS

CA    2045869    12/1991

(Continued)

OTHER PUBLICATIONS

Zhang (2004, Curr. Opin. Struct. Biol. 14:154-160).*

(Continued)

*Primary Examiner*—Elizabeth C. Kemmerer

(57) ABSTRACT

The present invention relates to novel members of the Tumor Necrosis Factor family of receptors. The invention provides isolated nucleic acid molecules encoding a human TR2 receptor and two splice variants thereof. TR2 polypeptides are also provided as are vectors, host cells and recombinant methods for producing the same. The invention further relates to screening methods for identifying agonists and antagonists of TR2 receptor activity. Also provided are diagnostic methods for detecting disease states related to the aberrant expression of TR2 receptors. Further provided are therapeutic methods for treating disease states related to aberrant proliferation and differentiation of cells which express the TR2 receptors.

19 Claims, 28 Drawing Sheets

U.S. PATENT DOCUMENTS

| | | | |
|---|---|---|---|
| 5,580,717 | A | 12/1996 | Dower et al. |
| 5,585,089 | A | 12/1996 | Queen et al. |
| 5,601,819 | A | 2/1997 | Wong et al. |
| 5,605,690 | A | 2/1997 | Jacobs et al. |
| 5,612,460 | A | 3/1997 | Zalipsky |
| 5,622,929 | A | 4/1997 | Willner et al. |
| 5,625,126 | A | 4/1997 | Lonberg et al. |
| 5,633,425 | A | 5/1997 | Lonberg et al. |
| 5,643,575 | A | 7/1997 | Martinez et al. |
| 5,658,727 | A | 8/1997 | Barbas et al. |
| 5,661,016 | A | 8/1997 | Lonberg et al. |
| 5,698,426 | A | 12/1997 | Huse |
| 5,733,743 | A | 3/1998 | Johnson et al. |
| 5,750,753 | A | 5/1998 | Kimae et al. |
| 5,780,225 | A | 7/1998 | Wigler et al. |
| 5,807,715 | A | 9/1998 | Morrison et al. |
| 5,811,097 | A | 9/1998 | Allison et al. |
| 5,814,318 | A | 9/1998 | Lonberg et al. |
| 5,821,047 | A | 10/1998 | Garrard et al. |
| 5,939,598 | A | 8/1999 | Kucherlapati et al. |
| 6,303,336 | B1 | 10/2001 | Spear et al. |

FOREIGN PATENT DOCUMENTS

| | | |
|---|---|---|
| CA | 2260754 | 1/1998 |
| EP | 0 239 400 B1 | 9/1987 |
| EP | 0 282 317 A2 | 9/1988 |
| EP | 0 307 434 B2 | 3/1989 |
| EP | 0 367 166 A1 | 5/1990 |
| EP | 0 393 438 A2 | 10/1990 |
| EP | 0 396 387 | 11/1990 |
| EP | 0 399 816 B1 | 11/1990 |
| EP | 0 401 384 B1 | 12/1990 |
| EP | 0 506 477 B1 | 9/1992 |
| EP | 0 519 596 A1 | 12/1992 |
| EP | 0 555 880 | 8/1993 |
| EP | 0 585 939 A2 | 3/1994 |
| EP | 0 592 106 A1 | 4/1994 |
| EP | 0 682 110 A1 | 11/1995 |
| EP | 0 822 984 | 2/1998 |
| WO | WO-89/01036 | 2/1989 |
| WO | WO-89/12624 | 12/1989 |
| WO | WO-90/13649 | 11/1990 |
| WO | WO-91/00360 | 1/1991 |
| WO | WO-91/02078 | 2/1991 |
| WO | WO-91/06570 | 5/1991 |
| WO | WO-91/09045 | 6/1991 |
| WO | WO-91/09967 | 7/1991 |
| WO | WO-91/10741 | 7/1991 |
| WO | WO-91/14438 | 10/1991 |
| WO | WO-92/05793 | 4/1992 |
| WO | WO-92/06194 | 4/1992 |
| WO | WO-92/08495 | 5/1992 |
| WO | WO-92/08802 | 5/1992 |
| WO | WO-92/22324 | 12/1992 |
| WO | WO-93/11236 | 6/1993 |
| WO | WO-93/17715 | 9/1993 |
| WO | WO-93/20219 | 10/1993 |
| WO | WO-93/21232 | 10/1993 |
| WO | WO-94/09137 | 4/1994 |
| WO | WO-94/13808 | 6/1994 |
| WO | WO-95/06058 | 3/1995 |
| WO | WO-95/15982 | 6/1995 |
| WO | WO-95/20401 | 8/1995 |
| WO | WO-96/04388 | 2/1996 |
| WO | WO-96/14328 | 5/1996 |
| WO | WO-96/26736 | 9/1996 |
| WO | WO-96/33735 | 10/1996 |
| WO | WO-96/34095 | 10/1996 |
| WO | WO-96/34096 | 10/1996 |
| WO | WO-96/39515 | 12/1996 |
| WO | WO-96/40281 | 12/1996 |
| WO | WO-97/04658 | 2/1997 |
| WO | WO-97/06251 | 2/1997 |
| WO | WO-97/33904 | 9/1997 |
| WO | WO-97/34911 | 9/1997 |
| WO | WO-98/02543 | 1/1998 |
| WO | WO-98/06842 | 2/1998 |
| WO | WO-98/07832 | 2/1998 |
| WO | WO-98/07880 | 2/1998 |
| WO | WO-98/16654 | 4/1998 |
| WO | WO-98/18921 | 5/1998 |
| WO | WO-98/24893 | 6/1998 |
| WO | WO-98/25967 | 6/1998 |
| WO | WO-98/30693 | 7/1998 |
| WO | WO-98/30694 | 7/1998 |
| WO | WO-98/31799 | 7/1998 |
| WO | WO-98/32466 | 7/1998 |
| WO | WO-98/32856 | 7/1998 |
| WO | WO-98/41629 | 9/1998 |
| WO | WO-98/46645 | 10/1998 |
| WO | WO-98/50433 | 11/1998 |
| WO | WO-98/51346 | 11/1998 |
| WO | WO-98/54202 | 12/1998 |
| WO | WO-98/56892 | 12/1998 |

OTHER PUBLICATIONS

Toussirot et al. (2004, Expert Opin. Pharmacother. 5:581-594).*
Jacobsohn (2002, Expert Opin. Investig. Drugs 11:1271-1280).*
Hoentjen et al. (2009, World J. Gastroenterol. 152067-2073).*
Ramos-Casals et al. (2008, Best Practice & Research Clinical Rheumatology 22:847-861).*
Pirard et al. (2006, Dermatology 213:182-186).*
Winkelmann et al. (2008, J. Neurol. 255 [Suppl. 6]:109-114).*
Sicotte et al. (2001, Neurology 57:1885-1888).*
U.S. Appl. No. 08/509,024, Not Published, Spear, et al.
Adams, et al., "Complementary DNA sequencing: expressed sequence tags and human genome project," *Science*, 252:1651-1656 (1991).
Adams, et al., "Sequence identification of 2,375 human brain genes," *Nature*, 355:632-634 (1992).
Aggarwal, et al., "Tumor necrosis factors: developments during the last decade," *Eur. Cytokine Netw.*, 7(2):93-124 (May 1996).
Altschul, et al., "Basic local alignment search tool," *J. Mol. Biol.*, 215:403-410 (Oct. 1990).
Ames, et al., "Conversion of murine Fabs isolated from a combinatorial phage display library to full length immunoglobulins," *J. Immunol. Meth.*, 184:177-186 (Aug. 1995).
Armitage, R.J., "Tumor necrosis factor receptor superfamily members and their ligands," *Curr. Opin. Immunol.*, 6:407-413 (Jun. 1994).
Ashkenazi, et al., "Protection against endotoxic shock by a tumor necrosis factor receptor immunoadhesin," *Proc. Natl. Acad. Sci. USA*, 88:10535-10539 (1991).
Badley, et al., "Upregulation of Fas ligand expression by human immunodeficiency virus in human macrophages mediates apoptosis of uninfected T lymphocytes," *J. Virol.*, 70:199-206 (Jan. 1996).
Baens, et al., "Construction and evaluation of a hncDNA library of human 12p transcribed sequences derived from a somatic cell hybrid," *Genomics*, 16:214-218 (1993).
Baker, et al., "Chromosomal location of the human tumor necrosis factor receptor genes," *Cytogenet. Cell Genet.*, 57:117-118 (1991).
Banchereau, et al., "Long-term human B cell lines dependent on interleukin-4 and antibody to CD40," *Science*, 251:70-72 (1991).
Banner, et al., "Crystal structure of the soluble human 55 kd receptor-human TNFβ complex: implications for TNF receptor activation," *Cell*, 73:431-445 (1993).
Bartůněek, et al., "Avian stem cell factor (SCF): production and characterization of the recombinant HIS-tagged SCF of chicken and its neutralizing antibody," *Cytokine*, 8:14-20 (Jan. 1996).
Baum, et al., "Molecular characterization of murine and human OX40/OX40 ligand systems: identification of a human OX40 ligand as the HTLV-1-regulated protein gp34," *EMBO J.*, 13(17):3992-4001 (Sep. 1994).

Benjamin, et al., "A plasticity window for blood vessel remodeling is defined by pericyte coverage of the preformed endothelial network and is regulated by PDGF-B and VEGF," *Development*, 125(9):1591-1598 (May 1998).
Better, et al., "*Escherichia coli* secretion of an active chimeric antibody fragment," *Science*, 240:1041-1043 (1988).
Beutler, et al., "Tumor necrosis, cachexia, shock, and inflammation: a common mediator," *Ann. Rev. Biochem.*, 57:505-518 (1988).
Beutler, et al., "The biology of cachectin/TNF—a primary mediator of the host response," *Ann. Rev. Immunol.*, 7:625-655 (1989).
Beutler, et al., "Unraveling function of the TNF ligand and receptor families," *Science*, 264:667-668 (Apr. 1994).
Bird, et al., "Single-chain antigen-binding proteins," *Science*, 242:423-426 (1988).
Birkeland, et al., "Gene structure and chromosomal localization of the mouse homologue of rat OX40 protein," *Eur. J. Immunol.*, 25:926-930 (Apr. 1995).
Bork, P., "Powers and pitfalls in sequence analysis: the 70% hurdle," *Genome Res.*, 10(4):398-400 (Apr. 2000).
Bork, P., "Go hunting in sequence databases but watch out for the traps," *Trends Genet.*, 12:425-427 (Oct. 1996).
Brenner, S.E., "Errors in genome annotation," *Trends Genet.*, 15(4):132-133 (Apr. 1999).
Brinkmann, et al., "Phage display of disulfide-stabilized Fv fragments," *J. Immunol. Meth.*, 182:41-50 (May 1995).
Caliceti, et al., "Biopharmaceutical properties of uricase conjugated to neutral and amphiphilic polymers," *Bioconjugate Chem.*, 10:638-646 (Aug. 1999).
Camerini, et al., "The T cell activation antigen CD27 is a member of the nerve growth factor/tumor necrosis factor receptor gene family," *J. Immunol.*, 147(9):3165-3169 (1991).
Carlson, et al., "Identification of amino acids in the glutamate receptor GluR3, important for antibody-binding and receptor-specific activation," *J. Biol. Chem.*, 272:11295-11301 (Apr. 1997).
Chang, et al., "Identification of a new member of the steroid receptor superfamily by cloning and sequence analysis," *Biochem. Biophys. Res. Comm.*, 155(2):971-977 (Sep. 15, 1988).
Chen, et al., "Effects of interleukin-1α, Interleukin-1 receptor antagonist, and neutralizing antibody on proinflammatory cytokine expression by human squamous cell carcinoma lines," *Cancer Res.*, 58:3668-3676 (Aug. 1998).
Chinnaiyan, et al., "Signal transduction by DR3, a death domain-containing receptor related to TNFR-1 and CD95," *Science*, 274:990-992 (1996).
Delgado, et al., "The uses and properties of PEG-linked proteins," *Clin. Rev. Ther. Drug Carrier Systems*, 9:249-304 (1992).
Deng, et al., "An agonist murine monoclonal antibody to the human c-Mpl receptor stimulates megakaryocytopoiesis," *Blood*, 92:1981-1988 (Sep. 1998).
Doerks, et al., "Protein annotation: detective work for function prediction," *Trends Genet.*, 14(6):248-250 (Jun. 1998).
Dürkop, et al., "Molecular cloning and expression of a new member of the nerve growth factor receptor family that is characteristic for Hodgkin's Disease," *Cell*, 68:421-427 (1992).
Engelmann, et al., "Two tumor necrosis factor-binding proteins purified from human urine," *J. Biol. Chem.*, 265(3):1531-1536 (1990).
Feinstein, et al., "The death domain: a module shared by proteins with diverse cellular functions," *TIBS*, 20:342-344 (Sep. 1995).
Fell, et al., "Genetic construction and characterization of a fusion protein consisting of a chimeric F(ab') with specificity for carcinomas and human IL-2," *J. Immunol.*, 146:2446-2452 (1991).
Fiers, W., "Tumor necrosis factor," *FEBS Lett.*, 285:199-212 (1991).
Folkman, J., "Clinical applications of research on angiogenesis," *New England J. Med.*, 333:1757-1763 (Dec. 1995).
Førre, et al., "New treatment possibilities in rheumatoid arthritis," *Scan. J. Rheumatol.*, 29:73-84 (2000).
Francis, et al., "PEGylation of cytokines and other therapeutic proteins and peptides: the importance of biological optimisation of coupling techniques," *Intl. J. Hematol.*, 68:1-18 (Jul. 1998).
Gillette-Ferguson, et al., "A specific intercellular pathway of apoptotic cell death is defective in the mature peripheral T cells of autoimmune *lpr* and *gld* mice," *Eur. J. Immunol.*, 24:1181-1185 (May 1994).

Gillies, et al., "High-level expression of chimeric antibodies using adapted cDNA variable region cassettes," *J. Immunol. Meth.*, 125:191-202 (1989).
Gilles, et al., "Antibody-targeted interleukin 2 stimulates T-cell killing of autologous tumor cells," *Proc. Natl. Acad. Sci. USA.*, 89:1428-1432 (1992).
Goodwin, et al., "Molecular cloning of a ligand for the inducible T cell gene 4-1BB: a member of an emerging family of cytokines with homology to tumor necrosis factor," *Eur. J. Immunol.*, 23:2631-2641 (1993).
Gruss, et al., "Pleiotropic Effects of the CD30 Ligand on CD30-Expressing Cells and Lymphoma Cell Lines," *Blood*, 83:2045-2056 (Apr. 1994).
Hahne, et al., "APRIL, a new ligand of the tumor necrosis factor family, stimulates tumor cell growth," *J. Exp. Med.*, 188:1185-1190 (Sep. 1998).
Hansson, et al., "Evolution of differential substrate specificities in Mu class glutathione transferases probed by DNA shuffling," *J. Mol. Biol.*, 287:265-276 (Mar. 1999).
Harrop, et al., "Herpesvirus entry mediator ligand (HVEM-L), a novel ligand for HVEM/TR2, stimulates proliferation of T cells and inhibits HT29 cell growth," *J. Biol. Chem.*, 273:27548-27556 (Oct. 1998).
Harrop, et al., "Antibodies to TR2 (herpesvirus entry mediator), a new member of the TNF receptor superfamily, block T cell proliferation, expression of activation markers, and production of cytokines," *J. Immunol.*, 161:1786-1794 (Aug. 1998).
Hauser, et al., "A heparin-binding form of placenta growth factor (P1GF-2) is expressed in human umbilical vein endothelial cells and in placenta," *Growth Factors*, 9:259-268 (1993).
Himmler, et al., "Molecular cloning and expression of human and rat tumor necrosis factor receptor chain (p60) and its soluble derivative, tumor necrosis factor-binding protein," *DNA and Cell Biol.*, 9(10):705-715 (1990).
Hohmann, et al., "Two different cell types have different major receptors for human tumor necrosis ractor (TNFα)," *J. Biol. Chem.*, 264:14927-14934 (1989).
Hoppe, et al., "A parallel three stranded α-helical bundle at the nucleation site of collagen triple-helix formation," *FEBS Lett.*, 344:191-195 (May 1994).
Howard, et al., "Vaccinia virus homologues of the Shope Fibroma virus inverted terminal repeat proteins and a discontinuous ORF related to the tumor necrosis factor receptor family," *Virol.*, 180:633-647 (1991).
Hsu, et al., "Differential expression and ligand binding properties of tumor necrosis factor receptor chimeric mutants," *J. Biol. Chem.*, 268(22):16430-16436 (1993).
Hu, et al., "Cowpox virus contains two copies of an early gene encoding a soluble secreted form of the Type II TNF receptor," *Virol.*, 204:343-356 (Oct. 1994).
Huston, et al., "Protein engineering of single-chain Fv analogs and fusion proteins," *Methods Enzymol.*, 203:46-88 (1991).
Huston, et al., "Protein engineering of antibody binding sites: recovery of specific activity in an anti-dioxin single-chain Fv analogue produced in *Eschericia coli*," *Proc. Natl., Acad. Sci. USA.*, 85:5879-5883 (1988).
Inui, et al., "Identification of the intracytoplasmic region essential for signal transduction through a B cell activation molecule, CD40," *Eur. J. Immunol.*, 20:1747-1753 (1990).
Itoh, et al., "The Polypeptide Encoded by the cDNA for Human Cell Surface Antigen Fas Can Mediate Apoptosis," *Cell*, 66:233-243 (1991).
Ji, et al., "G protein coupled receptors," *J. Biol. Chem.*, 273:17299-17302 (1998).
Johnson, et al., "Expression and Structure of the Human NGF Receptor," *Cell*, 47:545-554 (1986).
Katsikis, et al., "Fas antigen stimulation induces marked apoptosis of T lymphocytes in human immunodeficiency virus-infected individuals," *J. Exp. Med.*, 181:2029-2036 (Jun. 1995).
Keystone, E.G., "The role of tumor necrosis factor antagonism in clinical practice," *J. Rheumatol.*, 26(Suppl. 57):22-28 (May 1999).
Kostelny, et al., "Formation of a bispecific antibody by the use of leucine zippers," *J. Immunol.*, 148:1547-1553 (1992).

Krammer, et al., "Regulation of apoptosis in the immune system," *Curr. Opin. Immunol.*, 6:279-289 (Apr. 1994).

Kütemeir, et al., "Assembly of humanized antibody genes from synthetic oligonucleotides using a single-round PCR," *BioTechniques*, 17:242-246 (Aug. 1994).

Kwon, et al., "A newly identified member of the tumor necrosis factor receptor superfamily with a wide tissue distribution and involvement in lymphocyte activation," *J. Biol. Chem.*, 272:14272-14276 (May 1997).

Kwon, et al., "Genomic organization and chromosomal localization of the T-cell agntigen 4-1BB," *J. Immunol.*, 152:2256-2262 (Mar. 1994).

Kwon, et al., "cDNA sequences of two inducible T-cell genes," *Proc. Natl. Acad. Sci. USA*, 86:1963-1967 (1989).

Lewis, et al., "Cloning and expression of cDNAs for two distinct murine tumor necrosis factor receptors demonstrate one receptor is species specific," *Proc. Natl. Acad. Sci. USA*, 88:2830-2834 (1991).

Liautard, et al., "Specific inhibition of IL-6 signalling with monoclonal antibodies against the gp130 receptor," *Cytokine*, 9:233-241 (Apr. 1997).

Loetscher, et al., "Molecular cloning and expression of the human 55 kd tumor necrosis factor receptor," *Cell*, 61:351-359 (1990).

Lonberg, et al., "Human antibodies from transgenic mice," *Intern. Rev. Immunol.*, 13:65-93 (1995).

Malik, et al., "Polyethylene glycol (PEG)-modified granulocyte-macrophage colony-stimulating factor (GM-CSF) with conserved biological activity," *Exp. Hematol.*, 20:1028-1035 (1992).

Mallett, et al., "Characterization of the MRC OX40 antigen of activated CD4 positive T lymphocytes—a molecule related to nerve growth factor receptor," *EMBO J.*, 9:1063-1068 (1990).

Mallett, et al., "A new superfamily of cell surface proteins related to the nerve growth factor receptor," *Immunol. Today*, 12(7):220-223 (1991).

Massagué, J., "The TGF-beta family of growth and differentiation factors," *Cell*, 49:437-438 (May 22, 1987).

Matsubara, et al., "cDNA analysis in the human genome project," *Gene*, 135(2):265-274 (Dec. 15, 1993).

Matsubara, et al., "Identification of new genes by systematic analysis of cDNAs and database construction," Current Opinion in Biotechnology, 4(6):672-677 (Dec. 1, 1993).

Montgomery, et al., "A New Member of the TNG/NGF Receptor Family Can Mediate Herpes Simplex Virus 1 Entry Into Cells," *Eur. Cytokine Netw.*, 7(2):159, Abstract No. L7 (Apr.-Jun. 1996).

Montgomery, et al., "Herpes simplex virus-1 entry into cells mediated by a novel member of the TNF/NGF receptor family," *Cell*, 87(3):427-436 (Nov. 1996).

Morpurgo, et al., "Covalent modification of mushroom tyrosinase with different amphiphic polymers for pharmaceutical and biocatalysis applications," *App. Biochem. Biotech.*, 56:59-72 (Jan. 1996).

Morrison, et al., "Chimeric human antibody molecules: mouse antigen-binding domains with human constant region domains," *Proc. Natl. Acad. Sci. USA*, 81:6851-6855 (1984).

Morrison, S.L., "Transfectomas provide novel chimeric antibodies," *Science*, 229:1202-1207 (1985).

Moses, et al., "Inhibitors of angiogenesis," *Biotechnol.*, 9:630-634 (1991).

Muller, et al., "VEGF and the Fab fragment of a humanized neutralizing antibody: crystal structure of the complex at 2.4 Å resolution and mutational analysis of the interface," *Structure*, 6:1153-1167 (Sep. 1998).

Mullinax, et al., "Expression of a heterodimeric Fab antibody protein in one cloning step," *BioTechniques*, 12:864-869 (1992).

Murdoch, et al., "Chemokine receptors and their role in inflammation and infectious diseases," *Blood*, 95(10):3032-3043 (May 15, 2000).

Muzio, et al., "FLICE, a novel FADD-homologous ICD/CED-3-like protease, is recruited to the CD95 (Fas/APO-1) death-inducing signaling complex," *Cell*, 85:817-827 (Jun. 1996).

Neuberger, et al., "Recombinant antibodies possessing novel effector functions," *Nature*, 312:604-608 (Dec. 1984).

Nophar, et al., "Soluble forms of tumor necrosis factor receptors (TNF-Rs). The cDNA for the type 1 TNF-R, cloned using amino acid sequence data of its soluble form, encodes both the cell surface and a soluble form of the receptor," *EMBO J.*, 9(10):3269-3278 (1990).

Oi, et al., "Chimeric antibodies," *BioTechniques*, 4:214-221 (1986).

Okubo, et al., "Large scale cDNA sequencing for analysis of quantitative and qualitative aspects of gene expression," Nature Genetics, 2(3):173-179 (Nov. 1, 1992).

Old, L.J., "Tumor necrosis factor," *Scientific American*, 258:59-75 (1988).

Padlan, E.A., "A possible procedure for reducing the immunogenicity of antibody variable domains while preserving their ligand-binding properties," *Mol. Immunol.*, 28:489-498 (1991).

Patten, et al., "Applications of DNA shuffling to pharmaceuticals and vaccines," *Curr. Opin. Biotechnol.*, 8:724-733 (Dec. 1997).

Persic, et al., "An integrated vector system for the eukaryotic expression of antibodies or their fragments after selection from phage display libraries," *Gene*, 187:9-18 (Mar. 1997).

Pfeffer, et al., "Mice deficient for the 55 kd tumor necrosis factor receptor are resistant to endotoxic shock, yet succumb to L. monocytogenes infection," *Cell*, 73:457-467 (1993).

Pilbeam, et al., "Comparison of the effects of various lengths of synthetic human parathyroid hormone-related peptide (hPTHrP) of malignancy on bone resorption and formation in organ culture," *Bone*, 14(5):717-720 (Sep.-Oct. 1993).

Piguet, et al., "Evolution of collagen arthritis in mice is arrested by treatment with anti-tumor necrosis factor (TNF) antibody or a recombinant soluble TNF receptor," *Immunol.*, 77:510-514 (1992).

Pitard, et al., "Production and characterization of monoclonal antibodies against the leukemia inhibitory factor low affinity receptor, gp190," *J. Immunol. Meth.*, 205:177-190 (Jul. 1997).

Pollock, et al., "Inducible T Cell Antigen 4-1BB," *J. Immunol.*, 150(3):771-781 (1993).

Porter, A.G., "The prospects for therapy with tumour necrosis factors and their antagonists," *TIBTECH*, 9:158-162 (May 1991).

Prat, et al., "Agonistic monoclonal antibodies against the Met receptor dissect the biological responses to HGF," *J. Cell Sci.*, 111:237-247 (Jan. 1998).

Radeke, et al., "Gene transfer and molecular cloning of the rat nerve growth factor receptor," *Nature*, 325:593-597 (1987).

Riechmann, et al., "Reshaping human antibodies for therapy," *Nature*, 332:323-327 (1988).

Roguska, et al., "Humanization of murine monoclonal antibodies through variable domain resurfacing," *Proc. Natl. Acad. Sci. USA*, 91:969-973 (Feb. 1994).

Rossol-Voth, et al., "In vivo protective effect of tumor necrosis factor α against experimental infection with herpes simplex virus type 1," *J. Gen. Virol.*, 72:143-147 (1991).

Rothe, et al., "A Novel Family of Putative Signal Transducers Associated with the Cytoplasmic Domain of the 75 kDa Tumor Necrosis Factor Receptor," *Cell*, 78:681-692 (Aug. 1994).

Sandhu, J.S., "Protein engineering of antibodies," *Critical Rev. Biotechnol.*, 12:437-462 (1992).

Sawai, et al., "Direct production of the Fab fragment derived from the sperm immobilizing antibody using polymerase chain reaction and cDNA expression vectors," *Am. J. Reproductive Immunol.*, 34:26-34 (Jul. 1995).

Schall, et al., "Molecular Cloning and Expression of a Receptor for Human Tumor Necrosis Factor," *Cell*, 61:361-370 (1990).

Shu, et al., "Secretion of a single-gene-encoded immunoglobulin from myeloma cells," *Proc. Natl. Acad. Sci. USA*, 90:7995-7999 (1993).

Skerra, et al., "Assembly of a functional immunoglobulin $F_v$ fragment in *Escherichia coli*," *Science*, 240:1038-1041 (1988).

Skolnick, et al., "From genes to protein structure and function: novel applications of computational approaches in the genomic era," *Trends Biotechnol.*, 18(1):34-39 (Jan. 2000).

Smith, et al., "The TNF receptor superfamily of cellular and viral proteins: activation, costimulation, and death," *Cell*, 76:959-962 (Mar. 1994).

Smith, et al., "A Receptor for Tumor Necrosis Factor Defines an Unusual Family of Cellular and Viral Proteins," *Science*, 248:1019-1023 (1990).

Smith, et al., "T2 open reading frame from the Shope Fibroma Virus encodes a soluble form of the TNF receptor," *Biochem. Biophys. Res. Comm.*, 176(1):335-342 (1991).

Smith, et al., "CD30 antigen, a marker for Hodgkin's Lymphoma, is a receptor whose ligand defines an emerging family of cytokines with homology to TNF," *Cell*, 73:1349-1360 (1993).

Smith, et al., "Vaccinia virus glycoproteins and immune evasion," *J. Gen. Virol.*, 74:1725-1740 (1993).

Smith, et al., "The challenges of genome sequence annotation or 'the devil is in the details'," *Nat Biotechnol.*, 15(12):1222-1223 (Nov. 1997).

Stamenkovic, et al., "A B-lymphocyte activation molecule related to the nerve growth factor receptor and induced by cytokines in carcinomas," *EMBO J.*, 8(5):1403-1410 (1989).

Studnicka, et al., "Human-engineered monoclonal antibodies retain full specific binding activity by preserving non-CDR complementarity-modulating residues," *Protein Engineering*, 7:805-814 (Jun. 1994).

Takeda, et al., "Construction of chimaeric processed immunoglobulin genes containing mouse variable and human constant region sequences," *Nature*, 314:452-454 (1985).

Tartaglia, et al., "The two different receptors for tumor necrosis factor mediate distinct cellular responses," *Proc. Natl. Acad. Sci. USA*, 88:9292-9296 (1991).

Tartaglia, et al., "Tumor necrosis factor receptor signaling," *J. Biol. Chem.*, 267(7):4304-4307 (1992).

Tartaglia, et al., "A Novel Domain within the 55 kd TNF Receptor Signals Cell Death," *Cell*, 74:845-853 (1993).

Tartaglia, et al., "Tumor necrosis factor's cytotoxic activity is signaled by the p55 TNF receptor," *Cell*, 73:213-216 (Apr. 1993).

Torcia, et al., "Nerve growth factor Is an autocrine survival factor for memory B lymphocytes," *Cell*, 85:345-356 (1996).

Tutt, et al., "Trispecific F(ab')$_3$ derivatives that use cooperative signaling via the TCR/CD3 complex and CD2 to activate and redirect resting cytotoxic T cells," *J. Immunol.*, 147:60-69 (1991).

Twyman, et al., "Glutamate receptor antibodies activate a subset of receptors and reveal an agonist binding site," *Neuron*, 14:755-762 (Apr. 1995).

Van Lier, et al., "Tissue distribution and biochemical and functional properties of Tp55 (CD27), a novel T cell differentiation antigen," *J. Immunol.*, 139(5):1589-1596 (1987).

Van Ostade, et al., "Human tumor necrosis factor mutants with preferential binding to and activity on either the R55 or R75 receptor," *Eur. J. Biochem.*, 220:771-779 (Mar. 1994).

Vandenabeele, et al., "Two tumor necrosis factor receptors: structure and function," *Trends Cell. Biol.*, 5:392-399 (Oct. 1995).

Vié, et al., "Human fusion proteins between interleukin 2 and IgM heavy chain are cytotoxic for cells expressing the interleukin 2 receptor," *Proc. Natl. Acad. Sci. USA*, 89:11337-11341 (1992).

Vorobjev, et al., "Oligonucleotide conjugated to linear and branched high molecular weight polyethylene glycol as substrates for RNase H.," *Nucleosides & Nucleotides*, 18:2745-2750 (Nov.-Dec. 1999).

Vukicevic, et al., "Induction of nephrogenic mesenchyme by osteogenic protein 1 (bone morphogenic protein 7)," *PNAS USA*, 93:9021-9026 (Aug. 20, 1996).

Wallace, et al., "Predicting remission in juvenile rheumatoid arthritis with methotrexate treatment," *J. Rheumatol.*, 20:118-122 (Jan. 1993).

Ward, et al., "Binding activities of a repertoire of single immunoglobul in variable domains secreted from *Escherichia coli*," *Nature*, 341:544-546 (1989).

Weinstock, et al., "cDNA sequencing: a means of understanding cellular physiology," *Current Opinion in Biotechnology*, 5(6):599-603 (Jan. 1, 1994).

Yoon, et al., "Antibodies to domains II and III of the IL-1 receptor accessory protein inhibit IL-1β activity but not binding: regulation of IL-1 responses is via type I receptor, not the accessory protein," *J. Immunol.*, 160:3170-3179 (Apr. 1998).

Zheng, et al., "Administration of noncytolytic IL-10/Fc in murine models of lipopolysaccharides-induced septic shock and allogeniec islet transplantation," *J. Immunol.*, 154:5590-5600 (May 1995).

Zhu, et al., "Inhibition of vascular endothelial growth factor-induced receptor activation with anti-kinase insert domain-containing receptor single-chain antibodies from a phage display library," *Cancer Res.*, 58:3209-3214 (Aug. 1998).

Database Embl-new3 on MASPAR, Acc. No. L23876, Glascow, E., and Schechter, N., "Nucleotide sequence of a GFAP-like Intermediate Filament cDNA from Goldfish retina," (Sep. 1993).

Database EST-STS on MASPAR, Acc. No. H14106, Hillier, L., et al., "WashU-Merck EST Project," (Jul. 1995).

Database EMBL/GenBank/DDJB on MASPAR, Genetique Moleculaire (sic) et Biologie du developpement (Villejuif Cedex, France), Acc. No. Z38433, Genexpress, Direct Submission (Oct. 1994).

Database EST-STS on MASPAR, Whitehead Institute/MIT Center for Genome Research, Acc. No. G11923, Hudson, T., "Whitehead Institute/MIT Center for Genome Research; Physically Mapped STSs" (Oct. 1995).

Database EMBL-new3 on MASPAR, Acc. No. X60370, X60371, X60550, Zauner, W., et al., "Identification of Two Distinct microtubule Binding Domains on Recombinant Rat MAP 1B," (Oct. 1992).

Database EMBL-new3 on MASPAR, Acc. No. X75491, Aslanidis, C., et al., "Genomic Organization of the Human Lysosomal Acid Lipase Gene (LIPA)" (Mar. 1994).

Database A-Geneseq24 on MASPAR, Acc. No. R38859, Aruffo, A.A., et al.,"CD4OCR Receptor and its' (sic) Ligands used to Inhibit B-Cell Activation in Allergy and Auto-immune Disease," Submitted Feb. 7, 1994, EP, A, 555880 (Aug. 1993).

International Search Report from PCT/US96/15003.

International Search Report from PCT/US96/18540.

International Search Report from PCT/US96/16849.

Supplementary Partial European Search Report issued in European Patent Application No. EP 959117662 on Mar. 16, 2000.

Supplementary Partial European Search Report issued in European Patent Application No. EP 96942776, dated Jun. 2, 2003.

NCBI Entrez, GenBank Report, Accession No. Z38440, from Auffray, C., et al. (Oct. 1994).

NCBI Entrez, GenBank Report, Accession No. Z42185, from Auffray, C., et al. (Nov. 1994).

NCBI Entrez, GenBank Report, Accession No. H51006, from Hillier, L., et al. (Sep. 1995).

NCBI Entrez, GenBank Report, Accession No. W32997, from Hillier, L., et al. (Oct. 1996).

NCBI Entrez, GenBank Report, Accession No. W35383, from Hillier, L., et al. (Oct. 1996).

NCBI Entrez, GenBank Report, Accession No. AA088190, Hillier, L., et al. (Oct. 1996).

NCBI Entrez, GenBank Report, Accession No. AA088363, Hillier, L., et al. (Oct. 1996).

NCBI Entrez, GenBank Report, Accession No. AA015734, Hillier, L., et al. (Nov. 1996).

NCBI Entrez, GenBank Report, Accession No. AA015831, Hillier, L., et al. (Nov. 1996).

NCBI Entrez, GenBank Report, Accession No. AA018179, Hillier, L., et al. (Nov. 1996).

NCBI Entrez, GenBank Report, Accession No. AA020824, Hillier, L., et al. (Jan. 1997).

NCBI Entrez, GenBank Report, Accession No. AA020847, Hillier, L., et al. (Jan. 1997).

NCBI Entrez, GenBank Report, Accession No. AA021564, Hillier, L., et al. (Jan. 1997).

NCBI Entrez, GenBank Report, Accession No. AA021617, Hillier, L., et al. (Jan. 1997).

NCBI Entrez, GenBank Report, Accession No. AA297974, Adams, M.D., et al. (Apr. 1997).

NCBI Entrez, GenBank Report, Accession No. AA433981, Hillier, L., et al. (May 1997).

NCBI Entrez, GenBank Report, Accession No. AA293583, Hillier, L., et al. (Aug. 1997).

NCBI Entrez, GenBank Report, Accession No. AA481843, Hillier, L., et al. (Aug. 1997).

NCBI Entrez, GenBank Report, Accession No. AA481990, Hillier, L., et al. (Aug. 1997).

NCBI Entrez, GenBank Report, Accession No. AA261917, NCI-CGAP (Aug. 1997).

NCBI Entrez, GenBank Report, Accession No. AA262421, NCI-CGAP (Aug. 1997).

NCBI Entrez, GenBank Report, Accession No. AA573503, NCI-CGAP (Aug. 1997).

NCBI Entrez, GenBank Report, Accession No. AA573487, NCI-CGAP (Sep. 1997).

NCBI Entrez, GenBank Report, Accession No. AA577277, NCI-CGAP (Sep. 1997).

NCBI Entrez, GenBank Report, Accession No. AA418865, Hillier, L., et al. (Oct. 1997).

NCBI Entrez, GenBank Report, Accession No. AA418866, Hillier, L., et al. (Oct. 1997).

NCBI Entrez, GenBank Report, Accession No. AA426526, Hillier, L., et al. (Oct. 1997).

NCBI Entrez, GenBank Report, Accession No. AA430530, Hillier, L., et al. (Oct. 1997).

NCBI Entrez, GenBank Report, Accession No. AA613360, NCI-CGAP (Oct. 1997).

NCBI Entrez, GenBank Report, Accession No. AA683532, Hillier, L., et al. (Dec. 1997).

NCBI Entrez, GenBank Report, Accession No. AA722732, Hillier, L., et al. (Jan. 1998).

NCBI Entrez, GenBank Report, Accession No. AA761384, NCI-CGAP (Feb. 1998).

NCBI Entrez, GenBank Report, Accession No. AA768114, NCI-CGAP (Feb. 1998).

NCBI Entrez, GenBank Report, Accession No. AA831386, NCI-CGAP (Apr. 1998).

NCBI Entrez, GenBank Report, Accession No. AA902924, NCI-CGAP (Apr. 1998).

NCBI Entrez, GenBank Report, Accession No. AA864866, NCI-CGAP (May 1998).

NCBI Entrez, GenBank Report, Accession No. AA844171, NCI-CGAP (Dec. 1998).

NCBI Entrez, GenBank Report, Accession No. AA890591, NCI-CGAP (Jan. 1999).

Sequence cited and provided to Applicants by Examiner in U.S. Appl. No. 08/741,095 in correspondence dated Mar. 23, 1998: Derwent Genseq. Database, Accession No. R42248, from Leonard, W.J., et al. (May 1995).

Sequence cited and provided to Applicants by Examiner in U.S. Appl. No. 08/741,095 in correspondence dated Mar. 23, 1998: Derwent Genseq. Databse, Accession I54182, from Baens, M., et al. (May 1996).

US 5,843,791, 12/1998, Hauptmann et al. (withdrawn)

* cited by examiner

```
                     10                      30                      50
        GCACGAGCTGCCTCCCGCAGGCGCCACCTGTGTCCCCCAGCGCCGCTCCACCCAGCAGGC
                     70                      90                     110
        CTGAGCCCCTCTCTGCTGCCAGACACCCCTGCTGCCCACTCTCCTGCTGCTCGGGTTCT
                    130                     150                     170
        GAGGCACAGCTTGTCACACCGAGGCGGATTCTCTTTCTCTTTCTCTTTCTCTTCTGGCCC
                    190                     210                     230
        ACAGCCGCAGCAATGGCGCTGAGTTCCTCTGCTGGAGTTCATCCTGCTAGCTGGGTTCCC
                    250                     270                     290
        GAGCTGCCGGTCTGAGCCTGAGGCATGGAGCCTCCTGGAGACTGGGGGCCTCCTCCCTGG
                                  M   E   P   P   G   D   W   G   P   P   P   W
                    310                     330                     350
        AGATCCACCCCCAAAACCGACGTCTTGAGGCTGGTGCTGTATCTCACCTTCCTGGGAGCC
         R   S   T   P   K   T   D   V   L   R   L   V   L   Y   L   T   F   L   G   A
                    370                     390                     410.
        CCCTGCTACGCCCCAGCTCTGCCGTCCTGCAAGGAGGACGAGTACCCAGTGGGCTCCGAG
         P   C   Y   A   P   A   L   P   S   C   K   E   D   E   Y   P   V   G   S   E
                    430                     450                     470
        TGCTGCCCCAAGTGCAGTCCAGGTTATCGTGTGAAGGAGGCCTGCGGGGAGCTGACGGGC
         C   C   P   K   C   S   P   G   Y   R   V   K   E   A   C   G   E   L   T   G
                    490                     510                     530
        ACAGTGTGTGAACCCTGCCCTCCAGGCACCTACATTGCCCACCTCAATGGCCTAAGCAAG
         T   V   C   E   P   C   P   P   G   T   Y   I   A   H   L   N   G   L   S   K
                    550                     570                     590
        TGTCTGCAGTGCCAAATGTGTGACCCAGCCATGGGCCTGCGCGCGAGCCGGAACTGCTCC
         C   L   Q   C   Q   M   C   D   P   A   M   G   L   R   A   S   R   N   C   S
                    610                     630                     650 .
        AGGACAGAGAACGCCGTGTGTGGCTGCAGCCCAGGCCACTTCTGCATCGTCCAGGACGGG
         R   T   E   N   A   V   C   G   C   S   P   G   H   F   C   I   V   Q   D   G
                    670                     690                     710
        GACCACTGCGCCGCGTGCCGCGCTTACGCCACCTCCAGCCCGGGCCAGAGGGTGCAGAAG
         D   H   C   A   A   C   R   A   Y   A   T   S   S   P   G   Q   R   V   Q   K
                    730                     750                     770
        GGAGGCACCGAGAGTCAGGACACCCTGTGTCAGAACTGCCCCCCGGGGACCTTCTCTCCC
         G   G   T   E   S   Q   D   T   L   C   Q   N   C   P   P   G   T   F   S   P
                    790                     810                     830
        AATGGGACCCTGGAGGAATGTCAGCACCAGACCAAGTGCAGCTGGCTGGTGACGAAGGCC
         N   G   T   L   E   E   C   Q   H   Q   T   K   C   S   W   L   V   T   K   A
                    850                     870                     890
        GGAGCTGGGACCAGCAGCTCCCACTGGGTATGGTGGTTTCTCTCAGGGAGCCTCGTCATC
         G   A   G   T   S   S   H   W   V   W   W   F   L   S   G   S   L   V   I
                    910                     930                     950
        GTCATTGTTTGCTCCACAGTTGGCCTAATCATATGTGTGAAAAGAAGAAAGCCAAGGGGT
         V   I   V   C   S   T   V   G   L   I   I   C   V   K   R   R   K   P   R   G
                    970                     990                    1010
```

FIG. 1A

```
GATGTAGTCAAGGTGATCGTCTCCGTCCAGCGGAAAAGACAGGAGGCAGAAGGTGAGGCC
 D   V   V   K   V   I   V   S   V   Q   R   K   R   Q   E   A   E   G   E   A
             1030                    1050                    1070
ACAGTCATTGAGGCCCTGCAGGCCCCTCCGGACGTCACCACGGTGGCCGTGGAGGAGACA
 T   V   I   E   A   L   Q   A   P   P   D   V   T   T   V   A   V   E   E   T
         1090                    1110                    1130
ATACCCTCATTCACGGGGAGGAGCCCAAACCACTGACCCACAGACTCTGCACCCCGACGC
 I   P   S   F   T   G   R   S   P   N   H   *
         1150                    1170                    1190
CAGAGATACCTGGAGCGACGGCTGAATGAAAGAGGCTGTCCACCTGGCGGAACCACCGGA
         1210                    1230                    1250
GCCCGGAGGCTTGGGGGCTCCACCCTGGACTGGCTTCCGTCTCCTCCAGTGGAGGGAGAG
         1270                    1290                    1310
GTGGCGCCCCTGCTGGGGTAGAGCTGGGACGCCACGTGCCATTCCCATGGGCCAGTGAG
         1330                    1350                    1370
GGCCTGGGGCCTCTGTTCTGCTGTGGCCTGAGCTCCCCAGAGTCCTGAGGAGGAGCGCCA
         1390                    1410                    1430
GTTGCCCCTCGCTCACAGACCACACACCCAGCCCTCCTGGGCCAACCCAGAGGGCCTTCA
         1450                    1470                    1490
GACCCCAGCTGTGTGCGCGTCTGACTCTTGTGGCCTCAGCAGGACAGGCCCCGGGCACTG
         1510                    1530                    1550
CCTCACAGCCAAGGCTGGACTGGGTTGGCTGCAGTGTGGTGTTTAGTGGATACCACATCG
         1570                    1590                    1610
GAAGTGATTTTCTAAATTGGATTTGAATTCGGCTCCTGTTTTCTATTTGTCATGAAACAG
         1630                    1650                    1670
TGTATTTGGGGAGATGCTGTGGGAGGATGTAAATATCTTGTTTCTCCTCAAAAAAAAAAA
         1690
AAAAAAAAAAAAAAAAAAAAAAA
```

FIG. 1B

Percent Similarity: 46.591    Percent Identity: 28.788

```
  1 MEPPGDWGPPPWRSTPKTDVLRLVLYLTFLGAPCYAPALPSCKEDEYPVG  50
                   ...: ||. .:.  |  .:..  ..  ..|.:.:|   :
  1 ...............MVSLPRLCALWGCLLTAVHLGQCVTCSDKQYLHD  34

51 SECCPKCSPGYRVKEACGELTGTVCEPCPPGTYIAHLNGLSKCLQCQMCD 100
    ::||.  |  || |:..  |..|.  |  |.||..|.:  |::|   :|  |.  |:
 35 GQCCDLCQPGSRLTSHCTALEKTQCHPCDSGEFSAQWNREIRCHQHRHCE  84

101 PAMGLRASRNCSRTENAVCGCSPGHFCIVQDGDHCAACRAYATSSPGQRV 150
    |. |||..::..   ..:-||.|..|:  |. -|   |.||  ....:  ||  |
 85 PNQGLRVKKEGTAESDTVCTCKEGQHCTSKD...CEACAQHTPCIPGFGV 131

151 QKGGTESQDTLCQNCPPGTFSPNGTL.EECQHQTKC.SWLVTKAGAGTSS 198
     -:||-  ||:|:  ||-|   ||   .:-|  |-|   - |-|  ..  :.   - |||
132 MEMATETTDTVCHPCPVGFFSNQSSLFEKCYPWTSCEDKNLEVLQKGTSQ 181

199 SH......WVWWFLSGSLVIVIVCSTVGLIICVKR..RKPRGDVVKVIV 239
    -:           :::  :|   .:|:.|:....|:::::|:    :||::: : ..
182 TNVICGLKSRMRALLVIPVVMGILITIFGVFLYIKKVVKKPKDNEMLPPA 231

240 SVQRKRQEAEG......EATVIEALQAPPDVTTVAVEETIPSFTGRSPNH 283
     .....|| |:    .|.| |.|::...||   ...|.   |- .:|  ...
232 ARRQDPQEMEDYPGHNTAAPVQETLHGCQPVTQEDGKESRISVQERQVTD 281
```

FIG. 2

```
           10                    30                     50
CCCCCTTCTACAGGAAACCCGGAGTGGACTGGAACGGTGCAGGGGGAGAACTCGCCCCTC
           70                    90                    110
CCATCGGGCGCCTCCTTCATACCGGCCCTTCCCCTCGGCTTTGCCTGGACAGCTCCTGCC
          130                   150                    170
TCAGGCAGCGCCACCTGTGTCGCCCAGCGCCGCTCCACCCAGCAGGCCTGAGCCCCTCTC
          190                   210                    230
TGCTGCCAGACACCCCTGCTGCCCACTACTCCTGCTGCTCGGGTTCTGAGGCACAGCTT
          250                   270                    290
GTCACACCGAGGCGGATTCTCTTTCTCTTTCTCTTTCTCTTCTGGCCCACAGCCGCAGCA
          310                   330                    350
ATGGCGCTGAGTTCCTCTGCTGGAGTTCATCCTGCTAGCTGGGTTCCCGAGCTGCCGGTC
          370                   390                    410
TGAGCCTGAGTCATGGAGCCTCCTGGAGACTGGGGCCTCCTCCCTGGAGATCCACCCCC
                 M  E  P  P  G  D  W  G  P  P  P  W  R  S  T  P
          430                   450                    470
AGAACCGACGTCTTGAGGCTGGTGCTGTATCTCACCTTCCTGGGAGCCCCCTGCTACGCC
 R  T  D  V  L  R  L  V  L  Y  L  T  F  L  G  A  P  C  Y  A
          490                   510                    530
CCAGCTCTGCCGTCCTGCAAGGAGGACGAGTACCCAGTGGGCTCCGAGTGCTGCCCCAAG
 P  A  L  P  S  C  K  E  D  E  Y  P  V  G  S  E  C  C  P  K
          550                   570                    590
TGCAGTCCAGGTTATCGTGTGAAGGAGGCCTGCGGGAGCTGACGGGCACAGTGTGTGAA
 C  S  P  G  Y  R  V  K  E  A  C  G  E  L  T  G  T  V  C  E
          610                   630                    650
CCCTGCCCTCCAGGCACCTACATTGCCCACCTCAATGGCCTAAGCAAGTGTCTGCAGTGC
 P  C  P  P  G  T  Y  I  A  H  L  N  G  L  S  K  C  L  Q  C
          670                   690                    710
CAAATGTGTGACCCAGATATTGGTTCCCCCTGTGACCTCAGGGGAAGAGGTCACCTGGAG
 Q  M  C  D  P  D  I  G  S  P  C  D  L  R  G  R  G  H  L  E
          730                   750                    770
GCTGGTGCCCACCTGAGTCCAGGCAGACAGAAAGGGGAACCAGACCCAGAGGTGGCCTTT
 A  G  A  H  L  S  P  G  R  Q  K  G  E  P  D  P  E  V  A  F
          790                   810                    830
GAGTCACTGAGCGCAGAGCCTGTCCATGCGGCCAACGGCTCTGTCCCCTTGGAGCCTCAT
 E  S  L  S  A  E  P  V  H  A  A  N  G  S  V  P  L  E  P  H
          850                   870                    890
GCCAGGCTCAGCATGGCCAGTGCTCCCTGCGGCCAGGCAGGACTGCACCTGCGGGACAGG
 A  R  L  S  M  A  S  A  P  C  G  Q  A  G  L  H  L  R  D  R
          910                   930                    950
GCTGACGGCACACCTGGGGGCAGGGCCTGAGCCTACAGGGAGGCACAGGGCAGGTGGGCT
 A  D  G  T  P  G  G  R  A  *
          970                   990                   1010
AGCCATGAACAGAAGAGGAAGCTGGAGTGCTTTGGGGGTTCATGCATGTAGGCTGGGATT
```

FIG. 4A

```
      1030                  1050                  1070
TGGGGCTCACACCTCAACCTGCATGCCCAGTTCCATGCCCCTCCCCTCTTGTGAAAGCAC
      1090                  1110                  1130
CTGTCTACTTGGGCTGAGGATGTGGGGCACAGGTGGCAGGTGAGGCTGCCCTCAGGAGG
      1150                  1170                  1190
GGCCCAGGCCCAGCTTGTACCCCACCTCCACCAGTACCTGAAGAAGTGGGGCTCTCACCC
      1210                  1230                  1250
TACCTGCCTCTGCCATTGGAATGGCCTGGTTTGCACAGATGGGAAACCCGTTTGAGGGT
      1270                  1290                  1310
GGGTGTCTGGGTGGGCACGTGGGGCGAGGACCTGCCTGAGGGACCCTGCCCTGGAACTGA
      1330                  1350                  1370
CAGTGCAAGCTCGGCGTCCTGCCCATCTGGGCAGAAGGCTGGTTTCTCCCATCAACGAAG
      1390                  1410                  1430
CCCTCCCAGGACCTTCCTGCAAGCCCTCGTCCCACACGCAGCTCTGCCGTCCCTTGGTGT
      1450                  1470                  1490
CCCTCCCGGCCTCAGGTCCTCCATGCTGGGTACCTCTGGGCACCTCGTTTGGCTGAGCCA
      1510                  1530                  1550
GGGGTTCAGCCTGGCAGGGCGCCCTGGCAGCAGTCCTTGGCCTGTGGATGCTGTCCTGGC
      1570                  1590                  1610
CTGTGGATGGTGTCCCGCCCTCCACGTACCCCTCTCACCCCCTCCTCTTGGACTCCAGCC
      1630                  1650                  1670
ATGGGCCTGCGCGCGAGCCGGAACTGCTCCAGGACAGAGAACGCCGTGTGTGGCTGCAGC
      1690                  1710                  1730
CCAGGCCACTTCTGCATCGTCCAGGACGGGGACCACTGCGCCGCGTGCCGCGCTTACGCC
      1750                  1770                  1790
ACCTCCAGCCCGGGCCAGAGGGTGCAGAAGGGAGGCACCGAGAGTCAGGACACCCTGTGT
      1810                  1830                  1850
CAGAACTGCCCCCCGGGGACCTTCTCTCCCAATGGGACCCTGGAGGAATGTCAGCACCAG
      1870                  1890                  1910
ACCAATTGGCCTAATCATATGTGTGAAAAGAAGAAAGCCAAGGGGTGAGCACACGGTGGC
      1930                  1950                  1970
CCCATCAGGGTTCATGTCCCCAGCCGTCACCTCTTGGAGCTCTGTCACCCCAAGCCTGGG
      1990                  2010                  2030
AGGTGGCCCCAGAGCTTTTCCAGGATCCGCGGCTCCTCCCAGGGCAGCCACTGCAGGCTG
      2050                  2070                  2090
GGGCAGGTGTATGTAGTCAAGGTGATCGTCTCCGTCCAGCGGTAAAAGACAGGAGGCAGA
      2110                  2130                  2150
AGGTGAGGCCACAGTCATTGAGCCCTGCAGGCCCCTCCGGACGTCACCACGGTGGCCGTG
      2170                  2190                  2210
GAGGAGACAATACCCTCATTCACGGGGAGGAGCCCAAACCACTGACCCACAGACTCTGCA
      2230                  2250                  2270
CCCCGACGCCAGAGATACCTGGAGAGACGGCTGCTGATAGAGGCTGTCCACCTGGCGAAA
      2290                  2310                  2330
CCACCGGAGCCCGGAGGCTTGGGGGCTCCGCCCTGGGCTGGTTTCCGTCTCCTCCAGTGG
      2350                  2370                  2390
AGGGAGAGGTGGTGCCCCTGCTGGTGGTAGAGCTGGGGACGCCACGTGCCATTCCCATGG
      2410                  2430                  2450
TTCAGTGAGGGGCTGGTGGCCTCTGTTCTGCTGTGGCCTGAGCTCCCCAGAGTCCTGAGG
      2470                  2490                  2510
AGGAGCCCCAGTTGCCCCTCGCTCACAGACCACACACCCAGCCCTCCTGGGCCAACCCAG
      2530                  2550                  2570
AGGCCCCTTCAGACCCCAGCTGTCTGCGCGTCTGACTCTTGTGGCCTCAGCAGGACAGGC
      2590                  2610                  2630
CCCGGGCACTGCCTCACAGCCAAGGCTGGAATGGGTTGGCTGCAGTGTGGTGTTTAGTGG
      2650                  2670                  2690
ATACCACATCGGAAGTGATTTTCTAAAAATTGGATTTGAATTCGGAAAAAAA
```

FIG. 4B

Percent Similarity: 47.541   Percent Identity: 24.590

```
  1 MEPPGDWGPPPWRSTPRTDVLRLVLYLTFLGAPCYAPALPSCKEDEY..P  48
    |.|.: |:: :    :...  |. :.| .|: :.: ..|:  ||  .
  1 MAPVAVWAALAVGLELWAAAHALPAQVAF..TPYAPEPGSTCRLREYYDQ  48

49 VGSECCPKCSPGYRVKEACGELTGTVCEPCPPGTYIAHLNGLSKCLQCQM  98
    .:  || |||||  :.|  |..  .:|||:.|..:||..  :|  :..|| |.
 49 TAQMCCSKCSPGQHAKVFCTKTSDTVCDSCEDSTYTQLWNWVPECLSCGS  98

99 ..CDPDIGSPCDLRGRGHL.............EAGAHLSPGRQKGEPDPE 133
    :...::.__   |:..::        :.|.:|::. .|. |: :
 99 RCSSDQVETQACTREQNRICTCRPGWYCALSKQEGCRLCAPLRKCRPGFG 148

134 VA............................FESLSAEPVHAANGS 150
    ||                            : .: | |.:|. :.
149 VARPGTETSDVVCKPCAPGTFSNTTSSTDICRPHQICNVVAIPGNASMDA 198

151 VPLEPHARLSMASAPC..GQAGLHLRDRADGTPGGRA............ 185
    |. .. :  |||.::.  .|:.   .::.:.||:...
199 VCTSTSPTRSMAPGAVHLPQPVSTRSQHTQPTPEPSTAPSTSFLLPMGPS 248
```

FIG. 5

```
                10                      30                      50
AAAGCTCGGGCTCCACCGGGGACGACCGCTCCTAGAAACTGAGTGGTATCCCCCGGGCCT
                70                      90                      110
GCAGGAATTCCAACCTGCCTGAAGGGACCCTGCCCTGGAACTGACAGTGCAAGCTCGGCG
                130                     150                     170
TCCTGCCCATCTGGGAAGAAGGCTGGTTTCTCCCATCAACGAAGCCCTCCCAGGACCTTC
                190                     210                     230
CTGCAAGCCCTCGTCCCACACGCAGCTCTGCCGTCCCTTGGTGTCCCTCCCGGCCTCAGG
                250                     270                     290
TCCTCCATGCTGGGTACCTCTGGGCACCTCGTTTGGCTGAGCCAGGGGTTCAGCCTGGCA
              M  L  G  T  S  G  H  L  V  W  L  S  Q  G  F  S  L  A
                310                     330                     350
GGGCGCCCTGGCAGCAGTCCTTGGCCTGTGGATGCTGTCCTGGCCTGTGGATGGTGTCCC
           G  R  P  G  S  S  P  W  P  V  D  A  V  L  A  C  W  C  P
                370                     390                     410
GGCCTCCACGTACCCCCTCTCAGCCCCTCCTCTTGGACTCCAGCCATGGGCCTGCGCGCG

G  L  H  V  P  P  L  S  P  S  S  W  T  P  A  M  G  L  R  A
                430                     450                     470
AGCCGGAACTGCTCCAGGACAGAGAACGCCGTGTGTGGCTGCAGCCCAGGCGACTTCTGC
           S  R  N  C  S  R  T  E  N  A  V  C  G  C  S  P  G  H  F  C
                490                     510                     530
ATCGTCCAGGACGGGGACCACTGCGCCGCGTGCCGCGCTTACGCCACCTCCAGCCCGGGC
           I  V  Q  D  G  D  H  C  A  A  C  R  A  Y  A  T  S  S  P  G
                550                     570                     590
CAGAGGGTGCAGAAGGGAGGCACCGAGAGTCAGGACACCCTGTGTCAGAACTGCCCCCGG
           Q  R  V  Q  K  G  G  T  E  S  Q  D  T  L  C  Q  N  C  P  R
                610                     630                     650
GGACCTTCTCTCCCAATGGGACCCTGGAGGAATGTCAGCACCAGACCAAGTAAGTGAACC
           G  P  S  L  P  M  G  P  W  R  N  V  S  T  R  P  S  K  *
                670                     690                     710
CGGGGGAGGCCAGCTCTGTGCCCTGGGGAGGGGGCTCCACGTTGCTTCCCTGGGAGATGA
                730                     750                     770
CCGTCTTCTCCAGCAGAAAGGTTGAAGGTCCCACCCTGAGCGGCACCCTGGTCACATGCC
                790                     810                     830
TGCGTCCAGGAGAGCTGCAGGGTGAAGCCTGTGTGCCCCAGATAACCCCTTCCATGGGCC
                850                     870                     890
CAGACAAAGCCTCATCAGATCTGAGCTTCCTGGAGGCTCAGGATGGGCCTTCCCAGAAGC
                910                     930                     950
AGGCCCAGAGGGAGGCTGCCTCCAGATCCCCTGTCCCCTGGGGCTGTGGGTGTCCCTGAA
                970                     990                     1010
TGTCAGGGCCATGGGAGGGCCCCTGGGCTTCAGGGGTTGGGGAAAGTGAACACTCTGCTC
                1030                    1050                    1070
TTTGTCCACCTTCGGGAGGACAACCTTCAAATGCTGACCCTGGGCCCCTAACTGACCTGA
                1090                    1110                    1130
GACTTCAGAGCTTCTTGGGAGGAGCTGGGGTCCCCAGCGGAGCCTGGGATGGAGCAGGG
                1150                    1170                    1190
ATGGCTGCCCCAGGGAGGGGCGGTGGGGCCTTCCATCCTGCTCTGCCCTCCTCGTCCTC
                1210                    1230                    1250
TGGCCCCAGCTCAGTCCTGTCCATCTCCAGCTCTAACCATTTGTGGCCCGACACTGGCTC
                1270                    1290                    1310
TCCCTCTACCTTCTGTCCTTGTCTGACACTGGTCTCCCGTGCTCTGGGGTCTCTGCACTG
                1330                    1350                    1370
ATGGCTGCCTCCCGCTTCTCTCCCCTCTCCCTCTGCCGTCCTGTCTCCTGTGGCCAGTCT
```

FIG. 7A

```
      1390                1410                1430
CTCCTTGTTTCTCTTCTCCTCCTTCCTTCTCTCCACCTCCCCATAGCCGAGCTTGGAAAA
      1450                1470                1490
GTCAGACAGACCTCTGAGGTCTCATCCTGGAGCTGCCACCAGCCCAGCCTCCCTGGGACC
      1510                1530                1550
TGTCTTCACTGCCTGGGGCCCTGGGAGCCAGGGAGGCTCCCTGAGGCTGAGTGAACACTG
      1570                1590                1610
GGCGCTGCACCTGCCTCTCCCACGTCCTCGGCCCCACTCCCGCAGGTGCAGCTGGCTGGT
      1630                1650                1670
GACGAAGCCCGGAGCTGGGACCAGCAGCTCCCACTGGGTATGGTGGTTTCTCTCAGGGAG
      1690                1710                1730
CCTCGTCATCGTCATTGTTTGCTCCACAGTTGGCCTAATCATATGTGTGAAAAGAAGAAA
      1750                1770                1790
GCCAAGGGGTGATGTAGTCAAGGTGATCGTCTCCGTCCAGGTATTGATCCTCCTCCCCCT
      1810                1830                1850
CTCCCTCCCCCCTCCACCTTCCCACCTCCCCTCTCCCCGCTGGGGCTGGTGTTTCTGGTG
      1870                1890                1910
TACATGGTGGGGGCTCCCAGTTCTCTGAGGGTCCTGAGTCTTTCAAGTACAGCCACGGTA
      1930                1950                1970
GCTCAGGAAAGAACCCACCCCCTCAAACTGAAAGCAGTAAAATGAACCCGAGAACCTGGA
      1990                2010                2030
GTCCCAGGGGGGCCTGAGCAGGCAGGGTCTCCACGATTCGTGTGCTCACAGCGGGAAAAG
      2050                2070                2090
ACAGGAGGCAGAAGGTGAGGCCACAGTCATTGAGGCCCTGCAGGCCCCTCCGGACGTCAC
      2110                2130                2150
CACGGTGGCCGTGGAGGAGACAATACCCTCATTCACGGGGGAGGAGCCCAAACCACTGAC
      2170                2190                2210
CCACAGACTCTGCACCCCGACGCCAGAGATACCTGGAGCGACGGCTGCTGAAAGAGGCTG
      2230                2250                2270
TCCACCTGGCGAAACCACCGGAGCCCGGAGGTTTGGGGGCTCCGCCCTGGGCTGGTTTCC
      2290                2310                2330
GTCTCCTCCAGTGGAGGGAGAGGTGGGGCCCCTGCTGGGGTAGAGCTGGGGACGCCACGT
      2350                2370                2390
GCCATTCCCATGGGCCAGTGAGGGCCTGGGGCCTCTGTTCTGCTGTGGCCTGAGCTCCCC
      2410                2430                2450
AGAGTCCTGAGGAGGAGCGCCAGTTGCCCCTCGCTCACAGACCACACACCCAGCCCTCCT
      2470                2490                2510
GGGTCCAGCCCAGAGGGCCCTTCAGACCCCAGCTGTCTGCGCGTCTGACTCTTGTGGCCT
      2530                2550                2570
CAGCAGGACAGGCCCCGGGCACTGCCTTCAAGCCAAGGCTGGACTGGGTTGGCTGCAGTG
      2590                2610                2630
TGGTGTTTAGTGGATACCACATCGGAAGTGATTTTCTAAATTGGATTTGAAAAAAAA
```

FIG. 7B

Percent Similarity: 45.522   Percent Identity: 26.866

```
  1 MLGTSGHLVWLSQGFSL...............AGRPGSSPWPVD..... 29
    ::. : :. |. |:-|               |- |||..: :
  1 .MAPVAVWAALAVGLELWAAAHALPAQVAFTPYAPEPGSTCRLREYYDQT 49

30 AVLACGWC.PGLHV.........................PPLSPSSW 50
    | :-|:-| || |-                          --||.:|:
 50 AQMCCSKCSPGQHAKVFCTKTSDTVCDSCEDSTYTQLWNWVPECLSCGSR 99

51 TPAMGLRASRNCSRTENAVCGCSPGHFCIVQDGDHCAACRAYATSSPGQR 100
    ... .: ....|-|-:| :|.|.|| :| = ..: | | :. -:-||
100 CSSDQV.ETQACTREQNRICTCRPGWYCALSKQEGCRLCAPLRKCRPGFG 148

101 VQKGGTESQDTLCQNCPRGPSLPMGPWRNVSTRPSK.............. 136
    |-:-|||- |-:|- |:-|-    ... ::: --
149 VARPGTETSDVVCKPCAPGTFSNTTSSTDICRPHQICNVVAIPGNASMDA 198
```

FIG. 8

Percent Similarity: 73.370    Percent Identity: 59.783

```
  1 MEPPGDWGPPPWRSTPKTDVLRLVLYLTFLGAPCYAPALPSCKEDEYPVG 50
    |||||||||||||||:|||||||||||||||||||||||||||||||||
  1 MEPPGDWGPPPWRSTPRTDVLRLVLYLTFLGAPCYAPALPSCKEDEYPVG 50

51 SECCPKCSPGYRVKEACGELTGTVCEPCPPGTYIAHLNGLSKCLQCQMCD 100

101 PAMGLRAS.RNCSRTENAVCGCSPGHFCIVQDGDHCAACRAYATSSPGQR 149
    |.:|  ...|. ::|.:     :|::  ..: :...:  |:.. |::.
101 PDIGSPCDLRGRGHLEAG......AHLSPGRQKGEPDPEVAFESLSAEPV 144

150 VQKGGTESQDTLCQNCPPGTFSPNGTLEECQHQTKCSWLVTKAGAGTSSS 199
     .|.  . :.  .. : ::. :..:.|.          |  .:|::...::.
145 HAANGSVPLEPHARLSMASAPCGQAGLH..........LRDRADGTPGGR 184

200 HWVWWFLSGSLVIVIVCSTVGLIICVKRRKPRGDVVKVIVSVQRKRQEAE 249
```

FIG. 10

Percent Similarity: 70.588    Percent Identity: 60.294

```
  1 MEPPGDWGPPPWRSTPKTDVLRLVLYLTFLGAPCYAPALPSCKEDEYPVG  50
         .    .....:::|    :.: | |. .|         :||:
  1 ............MLGTSGHLVWLSQGFSLAGRPGSSP........WPVD  29

51 SECCPKCSPGYRVKEACGELTGTVCEPCPPGTYIAHLNGLSKCLQCQMCD 100
      . .. :||.:|       ·        .| .|:.:         .
 30 AVLACGWCPGLHV............PPLSPSSW...............T  51

101 PAMGLRASRNCSRTENAVCGCSPGHFCIVQDGDHCAACRAYATSSPGQRV 150
    |||||||||||||||||||||||||||||||||||||||||||||||||
 52 PAMGLRASRNCSRTENAVCGCSPGHFCIVQDGDHCAACRAYATSSPGQRV 101

151 QKGGTESQDTLCQNCPPGTFSPNGTLEECQHQTKCSWLVTKAGAGTSSSH 200
    |||||||||||||||.|.   | |.: :-    |:.|.
102 QKGGTESQDTLCQNCPRGPSLPMGPWRNV...STRPSK............ 136
```

FIG. 11

Percent Similarity: 37.984    Percent Identity: 20.155

1 MEPPGDWGPPPWRSTPRTDVLRLVLYLTFLGAPCYAP.......ALPSCK 43
         . ......:::|    :.: | |. .|      | ..|.
  1 ............MLGTSGHLVWLSQGFSLAGRPGSSPWPVDAVLACGWCP 38

44 EDEYPVGSECCPKCSPGYRVKEACGELTGTVCEPCPPGTYIAHLNGLSKC 93
    : . |. |.:: ... |.|.. .|: ...||:.:|. :| :.: ..|
 39 GLHVPPLSPSSWTPAMGLRASRNCSRTENAVCGCSPGHFCI..VQDGDHC 86

94 LQCQMCDPDIGSPCDLRGRGHLEAGAHLSPGRQKGEPDPEVAFESLSAEP 143
    .|. :.. :||.:  .:|  |... |:.. .:|.. | ..:. .:|. |
 87 AACRAYAT..SSPGQRVQKGGTESQDTLCQNCPRGPSLPMGPWRNVSTRP 134

144 VHAANGSVPLEPHARLSMASAPCGQAGLHLRDRADGTPGGRA. 185
    .                                         |
135 SK......................................... 136

FIG. 12

Percent Similarity: 92.168    Percent Identity: 92.168

```
   1 ........GCACGAGCTGCCTCCCGCAGGCGCCACCTGTGTCCCCAGCG  42
             ||  |||||||  |||  ||||||||||||||  ||||||
 101 TTGCCTGGACAGCTCCTGCCTCAGGCA.GCGCCACCTGTGTCGCCCAGCG 149

43 CCGCTCCACCCAGCAGGCCTGAGCCCCTCTCTGCTGCCAGACACCCCCTG  92
     ||||||||||||||||||||||||||||||||||||||||||||||||||
 150 CCGCTCCACCCAGCAGGCCTGAGCCCCTCTCTGCTGCCAGACACCCCCTG 199

93 CTGCCCACT.CTCCTGCTGCTCGGGTTCTGAGGCACAGCTTGTCACACCG 141
     |||||||||  |||||||||||||| ||||||||||||||||||||||||
 200 CTGCCCACTACTCCTGCTGCTCGGGTTCTGAGGCACAGCTTGTCACACCG 249

142 AGGCGGATTCTCTTTCTCTTTCTCTTTCTCTTCTGGCCCACAGCCGCAGC 191
     ||||||||||||||||||||||||||||||||||||||||||||||||||
 250 AGGCGGATTCTCTTTCTCTTTCTCTTTCTCTTCTGGCCCACAGCCGCAGC 299

192 AATGGCGCTGAGTTCCTCTGCTGGAGTTCATCCTGCTAGCTGGGTTCCCG 241
     ||||||||||||||||||||||||||||||||||||||||||||||||||
 300 AATGGCGCTGAGTTCCTCTGCTGGAGTTCATCCTGCTAGCTGGGTTCCCG 349

242 AGCTGCCGGTCTGAGCCTGAGGCATGGAGCCTCCTGGAGACTGGGGGCCT 291
     ||||||||||||||||||||| ||||||||||||||||||||||||||||
 350 AGCTGCCGGTCTGAGCCTGAGTCATGGAGCCTCCTGGAGACTGGGGGCCT 399

292 CCTCCCTGGAGATCCACCCCCAAAACCGACGTCTTGAGGCTGGTGCTGTA 341
     ||||||||||||||||||||| ||||||||||||||||||||||||||||
 400 CCTCCCTGGAGATCCACCCCCAGAACCGACGTCTTGAGGCTGGTGCTGTA 449

342 TCTCACCTTCCTGGGAGCCCCCTGCTACGCCCCAGCTCTGCCGTCCTGCA 391
     ||||||||||||||||||||||||||||||||||||||||||||||||||
 450 TCTCACCTTCCTGGGAGCCCCCTGCTACGCCCCAGCTCTGCCGTCCTGCA 499

392 AGGAGGACGAGTACCCAGTGGGCTCCGAGTGCTGCCCCAAGTGCAGTCCA 441
     ||||||||||||||||||||||||||||||||||||||||||||||||||
 500 AGGAGGACGAGTACCCAGTGGGCTCCGAGTGCTGCCCCAAGTGCAGTCCA 549

442 GGTTATCGTGTGAAGGAGGCCTGCGGGGAGCTGACGGGCACAGTGTGTGA 491
     ||||||||||||||||||||||||||||||||||||||||||||||||||
 550 GGTTATCGTGTGAAGGAGGCCTGCGGGGAGCTGACGGGCACAGTGTGTGA 599

492 ACCCTGCCCTCCAGGCACCTACATTGCCCACCTCAATGGCCTAAGCAAGT 541
     ||||||||||||||||||||||||||||||||||||||||||||||||||
 600 ACCCTGCCCTCCAGGCACCTACATTGCCCACCTCAATGGCCTAAGCAAGT 649

542 GTCTGCAGTGCCAAATGTGTGAC........................... 564
     |||||||||||||||||||||||
 650 GTCTGCAGTGCCAAATGTGTGACCCAGATATTGGTTCCCCCTGTGACCTC 699

565 ................CCAGCCATGGGCCTGCGCGCGAGCCGGAACTGCTC 599
                     ||||||||||||||||||||||||||||||||||||
1600 CCCTCCTCTTGGACTCCAGCCATGGGCCTGCGCGCGAGCCGGAACTGCTC 1649

600 CAGGACAGAGAACGCCGTGTGTGGTTGCAGCCCAGGCCACTTCTGCATCG 649
     |||||||||||||||||||||||||| |||||||||||||||||||||||
```

FIG. 13A

```
1650 CAGGACAGAGAACGCCGTGTGTGGCTGCAGCCCAGGCCACTTCTGCATCG 1699

650 TCCAGGACGGGGACCACTGCGCCGCGTGCCGCGCTTACGCCACCTCCAGC  699
     ||||||||||||||||||||||||||||||||||||||||||||||||||
1700 TCCAGGACGGGGACCACTGCGCCGCGTGCCGCGCTTACGCCACCTCCAGC 1749

700 CCGGGCCAGAGGGTGCAGAAGGGAGGCACCGAGAGTCAGGACACCCTGTG  749
     ||||||||||||||||||||||||||||||||||||||||||||||||||
1750 CCGGGCCAGAGGGTGCAGAAGGGAGGCACCGAGAGTCAGGACACCCTGTG 1799

750 TCAGAACTGCCCCCCGGGGACCTTCTCTCCCAATGGGACCCTGGAGGAAT  799
     ||||||||||||||||||||||||||||||||||||||||||||||||||
1800 TCAGAACTGCCCCCCGGGGACCTTCTCTCCCAATGGGACCCTGGAGGAAT 1849

800 GTCAGCACCAGACCAAGTG...............................  818
     ||||||||||||||| ||
1850 GTCAGCACCAGACCAATTGGCCTAATCATATGTGTGAAAAGAAGAAAGCC 1899

819 CAGCTGGCTGGTGACGAAGGCCGGAGCTGGG........ACCAGCAGCTC  860
     ||  |   |   |||    ||||  |  |||        ||||| |
1900 AAGGGGTGAGCACACGGTGGCCCCATCAGGGTTCATGTCCCCAGCCGTCA 1949

861 CCACTGGGTATGGTGGTTTCTCTCAGGGAGCCTCGTCATCGTCATTGTTT  910
     || || ||    ||   ||         |           |  |   |||
1950 CCTCTTGGAGCTCTGTCACCCCAAGCCTGGGAGGTGGCCCCAGAGCTTTT 1999

911 GCTCCACAGTTGGCCTAATCATATGTGTGAAAAGAAGAAAGCCAAGGGGT  960
      |   |   |||   |    |    |  |||  |        |    ||
2000 CCAGGATCCGCGGCTCCTCCCAGGGCAGCCACTGCAGGCTGGGGCAGGTG 2049

961 GATGTAGTCAAGGTGATCGTCTCCGTCCAGCGG.AAAAGACAGGAGGCAG 1009
     |||||||||||||||||||||||||||||||||  |||||||||||||||
2050 TATGTAGTCAAGGTGATCGTCTCCGTCCAGCGGTAAAAGACAGGAGGCAG 2099

1010 AAGGTGAGGCCACAGTCATTGAGGCCCTGCAGGCCCCTCCGGACGTCACC 1059
     ||||||||||||||||||||||| ||||||||||||||||||||||||||
2100 AAGGTGAGGCCACAGTCATTGA.GCCCTGCAGGCCCCTCCGGACGTCACC 2148

1060 ACGGTGGCCGTGGAGGAGACAATACCCTCATTCACGGGGAGGAGCCCAAA 1109
     ||||||||||||||||||||||||||||||||||||||||||||||||||
2149 ACGGTGGCCGTGGAGGAGACAATACCCTCATTCACGGGGAGGAGCCCAAA 2198

1110 CCACTGACCCACAGACTCTGCACCCCGACGCCAGAGATACCTGGAGCGAC 1159
     |||||||||||||||||||||||||||||||||||||||||||||||  |
2199 CCACTGACCCACAGACTCTGCACCCCGACGCCAGAGATACCTGGAGAGAC 2248

1160 GGCTGAATGAAAGAGGCTGTCCACCTGGCGGAACCACCGGAGCCCGGAGG 1209
     |||||   |||  ||||||||||||||||  |||||||||||||||||||
2249 GGCTG.CTGATAGAGGCTGTCCACCTGGCGAAACCACCGGAGCCCGGAGG 2297

1210 CTTGGGGGCTCCACCCTGGACTGGCTTCCGTCTCCTCCAGTGGAGGGAGA 1259
     ||||||||||||| ||||||  ||||  ||||||||||||||||||||||
2298 CTTGGGGGCTCCGCCCTGGGCTGGTTTCCGTCTCCTCCAGTGGAGGGAGA 2347

1260 GGTGGCGCCCCTGCTGG.GGTAGAGCTGGGGACGCCACGTGCCATTCCCA 1308
     ||||| |||||||||||  |||||||||||||||||||||||||||||||
2348 GGTGGTGCCCCTGCTGGTGGTAGAGCTGGGGACGCCACGTGCCATTCCCA 2397
```

FIG. 13B

```
1309 TGGGCCAGTGAGGGCCTGG.GGCCTCTGTTCTGCTGTGGCCTGAGCTCCC 1357
     |||  ||||||||| ||||  ||||||||||||||||||||||||||||||
2398 TGGTTCAGTGAGGGGCTGGTGGCCTCTGTTCTGCTGTGGCCTGAGCTCCC 2447

1358 CAGAGTCCTGAGGAGGAGCGCCAGTTGCCCCTCGCTCACAGACCACACAC 1407
     |||||||||||||||||||| |||||||||||||||||||||||||||||
2448 CAGAGTCCTGAGGAGGAGCCCCAGTTGCCCCTCGCTCACAGACCACACAC 2497

1408 CCAGCCCTCCTGGGCCAACCCAGAGG.GCCTTCAGACCCCAGCTGTGTGC 1456
     |||||||||||||||||||||||||| |||||||||||||||||||| |||
2498 CCAGCCCTCCTGGGCCAACCCAGAGGCCCCTTCAGACCCCAGCTGTCTGC 2547

1457 GCGTCTGACTCTTGTGGCCTCAGCAGGACAGGCCCCGGGCACTGCCTCAC 1506
     ||||||||||||||||||||||||||||||||||||||||||||||||||
2548 GCGTCTGACTCTTGTGGCCTCAGCAGGACAGGCCCCGGGCACTGCCTCAC 2597

1507 AGCCAAGGCTGGACTGGGTTGGCTGCAGTGTGGTGTTTAGTGGATACCAC 1556
     |||||||||||| |||||||||||||||||||||||||||||||||||||
2598 AGCCAAGGCTGGAATGGGTTGGCTGCAGTGTGGTGTTTAGTGGATACCAC 2647

1557 ATCGGAAGTGATTTTCT..AAATTGGATTTGAATTCGGCTCCTGTTTTCT 1604
     |||||||||||||||||  ||||||||||||||||||||
2648 ATCGGAAGTGATTTTCTAAAAATTGGATTTGAATTCGGAAAAAAA..... 2692
```

FIG. 13C

```
  1 ......................GCACGAGCTGCCTCCCGCAGGCGC  24
                          | | ||| |       | | |
701 GTTGCTTCCCTGGGAGATGACCGTCTTCTCCAGCAGAAAGGTTGAAGGTC 750

25 CACCTGTGTCCCCCAGCGCCGCTCCACCCAGCAGGCCTGAGCCCCTCTCT  74
    | |  ||  |  ||| |  ||  |   ||| |    ||
751 CCACCCTGAGCGGCACCCTGGTCACATGCCTGCGTCCAGGAGAGCTGCAG 800

75 GCTGCCAGACACCCCCTGCTGCCCACTCTCCTGCTGCTCGGGTTCTGAGG 124
    | ||        | | |   ||| |     || |     | ||
801 GGTGAAGCCTGTGTGCCCAGATAACCCCTTCCATGGGCCCAGACAAAGC  850

125 CACAGCTTGTCACACCGAGGCGGATTCTCTTTCTCTTTCTCTTTCTCTTC 174
    | || |   || | |    ||| |||     ||          |
851 CTCATCAGATCTGAGCTTCCTGGAGGCTCAGGATGGGCCTTCCCAGAAGC  900

175 TGGCCCACA.....GCCGCAGCAATGGCGCTGAGTTCCTCTGCTGGAGTT 219
    ||||||  |    || || || ||      |||    | |
901 AGGCCCAGAGGGAGGCTGCCTCCAGATCCCCTGTCCCCTGGGGCTGTGGG  950

220 CATCCTGCTAGCTGGGTTCCCGAGCTGCCGGTCTGAGCCTGAGGCATGGA 269
    |||     |  |  || | |         ||| || | ||| | |
951 TGTCCCTGAATGTCAGGGCCATGGGAGGGCCCCTGGGCTTCAGGGGTTGG 1000

270 GCCTCCTGGAGACTGGGGGCCTCCTCC.....CTGGAGATCCACCCCCAA 314
    |    || | ||| |  ||  |||      | |||| | ||| |||
1001 GGAAAGTGAACACTCTGCTCTTTGTCCACCTTCGGGAGGACAACCTTCAA 1050

315 A.......ACCGACGTCTTGAGGCTGGTGCTGTATCTCACCTTCCTGGGA 357
    |      | |   |||    ||   ||  | ||||  ||||
1051 ATGCTGACCCTGGGCCCCTAACTGACCTGAGACTTCAGAGCTTCTTGGGA 1100
```

FIG. 14A

```
 358 GCCCCCTGCTACGCCCCAGCTCTGCCGTCCTGCAAGGAGGACGAGTACCC  407
     |  |  |   |||         | |   ||  |    ||| |   | |||
1101 GGAGCTGGGGTCCCCCAGCGGAGCCTGGGATGGAGCAGGGATGGCTGCCC 1150

408 AGTGGGCTCCGAGTGCTGCCCCAAGTGCAGTCCAGGTTATCGTGTGAAGG  457
     ||      |  |    | ||    |    |    |   |   || |
1151 CAGGGAGGGGCGGTGGGGCCTTCCATCCTGCTCTGCCCTCCTCGTCCTC  1200

458 AGG..CCTGCGGGGAGCTGACGGGCACAGTGTGTGAACCCTGCCCTCCAG  505
      ||  || ||    |  |||   ||   | ||||     |    || |
1201 TGGCCCCAGCTCAGTCCTGTCCATCTCCAGCTCTAACCATTTGTGGCCCG 1250

506 GCACCTACATTGCCCACCTCAATGGCCTAAGCAAGTGTCTGCAGTGCC..  553
     |||  |  | ||     |  |    | |    |   |   ||| |  ||
1251 ACACTGGCTCTCCCTCTACCTTCTGTCCTTGTCTGACACTGGTCTCCCGT 1300

554 .AAATGTGTGACCCAGCCATGGGCCTGCGCGCGAGCCGGAACTGCTCCAG  602
      |||      |    |    | ||||    |        |   |  |||
1301 GCTCTGGGGTCTCTGCACTGATGGCTGCCTCCCGCTTCTCTCCCCTCTCC 1350

603 GACAGAGAACGCCGTGTGTGGTTGCAGCCCAGGCCACTTCTGCATCGTCC  652
     | |             ||   ||  |||       |  || |  |
1351 CTCTGCCGTCCTGTCTCCTGTGGCCAGTCTCTCCTTGTTTCTCTTCTCCT 1400

653 AGGACGGGGACCACTGCGCCGCGTGCCGCGCTTACGCCACCTCCAGCCCG  702
       |    |   |  |   ||||| |     |  |  |   |   ||  |
1401 CCTTCCTTCTCTCCACCTCCCCATAGCCGAGCTTGGAAAAGTCAGACAGA 1450

703 GGCCAGAGGGTGCAGAAGGGAGGCACCGAGAGTCAGGACACCCTGTGTCA  752
     | ||||   ||   ||||   ||    ||  |  | |||||| | |
1451 CCTCTGAGGTCTCATCCTGGAGCTGCCACCAGCCCAGCCTCCCTGGGACC 1500

753 GAACTGCCC..CCCGGGGACCTTCTCTCCCAATGGGACCCTGGAGG....  796
     ||| |  |   ||  |||| ||| ||   || |  || || ||||
1501 TGTCTTCACTGCCTGGGGCCCTGGGAGCCAGGGAGGCTCCCTGAGGCTGA 1550

797 .............................AATGTCAGCACCAG         810
                                   | |  |||
1551 GTGAACACTGGGCGCTGCACCTGCCTCTCCCACGTCCTCGGCCCCACTCC 1600

811 ACCAAGTGCAGCTGGCTGGTGACGAAGGCCGGAGCTGGGACCAGCAGCTC  860
     || ||||||||||||||||||||||| |||||||||| ||||||||||||
1601 CGCAGGTGCAGCTGGCTGGTGACGAAGCCCGGAGCTGGGACCAGCAGCTC 1650

861 CCACTGGGTATGGTGGTTTCTCTCAGGGAGCCTCGTCATCGTCATTGTTT  910
     ||||||||||||||||||||||||||||||||||||||||||||||||||
1651 CCACTGGGTATGGTGGTTTCTCTCAGGGAGCCTCGTCATCGTCATTGTTT 1700

911 GCTCCACAGTTGGCCTAATCATATGTGTGAAAAGAAGAAAGCCAAGGGGT  960
     ||||||||||||||||||||||||||||||||||||||||||||||||||
1701 GCTCCACAGTTGGCCTAATCATATGTGTGAAAAGAAGAAAGCCAAGGGGT 1750

961 GATGTAGTCAAGGTGATCGTCTCCGTCCAG....................  990
     ||||||||||||||||||||||||||||||
1751 GATGTAGTCAAGGTGATCGTCTCCGTCCAGGTATTGATCCTCCTCCCCCT 1800

991 ..............................CGGAAAAGACAGGAGGCA   1008
```

FIG. 14B

```
                                     |||||||||||||||||||
2001 GGCAGGGTCTCCACGATTCGTGTGCTCACAGCGGGAAAAGACAGGAGGCA 2050

1009 GAAGGTGAGGCCACAGTCATTGAGGCCCTGCAGGCCCCTCCGGACGTCAC 1058
     ||||||||||||||||||||||||||||||||||||||||||||||||||
2051 GAAGGTGAGGCCACAGTCATTGAGGCCCTGCAGGCCCCTCCGGACGTCAC 2100

1059 CACGGTGGCCGTGGAGGAGACAATACCCTCATTCAC.GGGGAGGAGCCCA 1107
     ||||||||||||||||||||||||||||||||||| ||||||||||||||
2101 CACGGTGGCCGTGGAGGAGACAATACCCTCATTCACGGGGAGGAGCCCA 2150

1108 AACCACTGACCCACAGACTCTGCACCCCGACGCCAGAGATACCTGGAGCG 1157
     ||||||||||||||||||||||||||||||||||||||||||||||||||
2151 AACCACTGACCCACAGACTCTGCACCCCGACGCCAGAGATACCTGGAGCG 2200

1158 ACGGCTGAATGAAAGAGGCTGTCCACCTGGCGGAACCACCGGAGCCCGGA 1207
     |||||||  |||||||||||||||||||||| ||||||||||||||||||
2201 ACGGCTG.CTGAAAGAGGCTGTCCACCTGGCGAAACCACCGGAGCCCGGA 2249

1208 GGCTTGGGGGCTCCACCCTGGACTGGCTTCCGTCTCCTCCAGTGGAGGGA 1257
     || |||||||||| ||||| |||| |||||||||||||||||||||||||
2250 GGTTTGGGGGCTCCGCCCTGGGCTGGTTTCCGTCTCCTCCAGTGGAGGGA 2299

1258 GAGGTGGCGCCCCTGCTGGGGTAGAGCTGGGGACGCCACGTGCCATTCCC 1307
     ||||||| ||||||||||||||||||||||||||||||||||||||||||
2300 GAGGTGGGGCCCCTGCTGGGGTAGAGCTGGGGACGCCACGTGCCATTCCC 2349

1308 ATGGGCCAGTGAGGGCCTGGGGCCTCTGTTCTGCTGTGGCCTGAGCTCCC 1357
     ||||||||||||||||||||||||||||||||||||||||||||||||||
2350 ATGGGCCAGTGAGGGCCTGGGGCCTCTGTTCTGCTGTGGCCTGAGCTCCC 2399

1358 CAGAGTCCTGAGGAGGAGCGCCAGTTGCCCCTCGCTCACAGACCACACAC 1407
     ||||||||||||||||||||||||||||||||||||||||||||||||||
2400 CAGAGTCCTGAGGAGGAGCGCCAGTTGCCCCTCGCTCACAGACCACACAC 2449

1408 CCAGCCCTCCTGGG.CCAACCCAGAGGG.CCTTCAGACCCCAGCTGTGTG 1455
     |||||||||||||| ||| |||||||||| |||||||||||||||||| ||
2450 CCAGCCCTCCTGGGTCCAGCCCAGAGGGCCCTTCAGACCCCAGCTGTCTG 2499

1456 CGCGTCTGACTCTTGTGGCCTCAGCAGGACAGGCCCCGGGCACTGCCTCA 1505
     ||||||||||||||||||||||||||||||||||||||||||||||||
2500 CGCGTCTGACTCTTGTGGCCTCAGCAGGACAGGCCCCGGGCACTGCCTTC 2549

1506 CAGCCAAGGCTGGACTGGGTTGGCTGCAGTGTGGTGTTTAGTGGATACCA 1555
     |||||||||||||||||||||||||||||||||||||||||||||||||
2550 AAGCCAAGGCTGGACTGGGTTGGCTGCAGTGTGGTGTTTAGTGGATACCA 2599

1556 CATCGGAAGTGATTTTCTAAATTGGATTTGAATTCGGCTCCTGTTTTCTA 1605
     |||||||||||||||||||||||||||||||||
2600 CATCGGAAGTGATTTTCTAAATTGGATTTGAAAAAAA............ 2637
```

FIG. 14C

Percent Similarity: 53.479    Percent Identity: 53.479

1 CCCCCTTCTACAGGAAACCCGGAGTGGACTGGAACGGTGCAGGGGGAGAA 50
   ||   |    ||||| |||| |   |    | | | i

FIG. 15A

```
  1 ...AAAGCTCGGGCTCCACCGGGGACGACCGCTCCTAGAAACTGAGTGGT  47

51 CTCGCCCCTCCCATCGGGCGCCTCCTTCATACCGGCCCTTCCCCTCGGCT 100
    || |||   || | ||    |||  | |||      ||||     ||
 48 ATCCCCCGGGCCTGCAGG.AATTCCAACCTGCCTGAAGGGACCCTGCCCT  96

101 TTGCCTGGACAGCTCCTGCCTCAGGCAGCGCCACCTGTGTCGCCCAGCGC 150
    |||      || ||  |||  |    | | || ||         ||
 97 GGAACTG..ACAGTGCAAGCTCGGCGTCCTGCCCATCTGGGAAGAAGGCT 144

151 CGCTCCACCCAGCAGGCCTGAGCCCCTCTCTGCTGCCAGACACCCCCTGC 200
    | |  ||||  ||    |  ||   || ||  | |  || |
145 GGTTTCTCCCATCAACGAAGCCCTCCCAGGACCTTCCTGCAAGCCCTCGT 194

201 TGCCCACTACTCCTGCTGCTCGGGTTCTGAGGCACAGCTTGTCACACCGA 250
    | |||   |    ||    |  |  ||    |    ||   |||    |
195 CCCACACGCAGCTCTGCCGTCCCTTGGTGTCCCTCCCGGCCTCA...GGT 241

251 GGCGGATTCTCTTTCTCTTTCTCTTTCTTCTGGCCCA.CAGCCGCAGC   299
    ||  ||    |  |||   |     ||| |||    |    |
242 CCTCCATGCTGGGTACCTCTGGGCACCTCGTTGGCTGAGCCAGGGGTTC  291

300 AATGGCGCTGAGTTCCTCTGCTGGAGTTCATCCTGCTAGCTGGGTTCCCG 349
    |       |||| || || || | ||||     |    |    | ||
292 AGCCTGGCAGGGCGCCCTGGCAGCAGTCCTTGGCCTGTGGATGCTGTCCT 341

350 AGCTGCCGGTCTGAGCCTGAGTCATGGAGCCTCCTGGAGACTGGGGGCCT 399
    ||    ||   |  |   |   | ||| ||      ||     |||
342 GGCCTGTGGATGGTGTC.....CCGGCCTCCACGTACCCCCTCTCAGCCC 386

400 CCTCCCTGGAGATCCACCCCCAGAACCGACGTCTTGAGGCTGGTGCTGTA 449
    |  ||  |   |||| ||   |  |    |   |     ||||    |
387 CTCCTCTTGGACTCCAGCCATGGGCCTGCGCGCGAGCCGGAACTGCTCCA 436

450 TCTCACCTTCCTGGGAGCCCCCTGCTACGCCCCAGCTCTGCCG.TCCTGC 498
    ||       |  |   |  | |  ||||   | ||   ||   ||   |
437 GGACAGAGAACGCCGTGTGTGGCTGCAGCCCAGGCCACTTCTGCATCGTC 486

499 AAGGAGGACGAGTACCCAGTGGGCTCCGAGTGCTGCCCCAAGTGCAGTCC 548
    ||||  |  ||  |   | |  | |  ||    |  |  |||  |||| |
487 CAGGACGGGGACCACTGCGCCGCGTGCCGCGCTTACGCCACCTCCAGCCC 536

549 AGGTTATCGTGTGAAGGAGGCCTGCGGGGAGCTGACGGGCACAGTGTGTG 598
    ||   | |   ||| ||| ||| || |||   ||  ||| |||||
537 GGGCCAGAGGGTGCAGAAGGGAGGCACCGAGAGTCAGGACACCCTGTGTC 586

599 AACCCTGCCCTCCAGGCACCTACATTGCCCACCTCAATGGCCTAAGCAAG 648
    |  ||||||| |  ||  |   |   |  |      |  ||   |  ||
587 AGAACTGCCCCCGGGGACCTT..CTCTCCCAATGGGACCCTGGAGGAATG 634

649 TGTCTGCAGTGCCAAATGTGTGACCCAGATATTGGTTCCCCCTGTGACCT 698
    |    |   ||||   |||| |||  ||    |  | |||||   |||
635 TCAGCACCAGACCAAGTAAGTGAACCCGGGGAGGCCAGCTCTGTGCCCT  684

699 CAGGGGAAGAGGTCACCTGGAGGCTGGTGCCCACCTGAGTCCAGGCAGAC 748
    ||| |    |||||  |    |   |    |      |||   |    |
685 GGGGAGGGGGCTCCACGTTGCTTCCCTGGGAGATGACCGTCTTCTCCAGC 734
```

FIG. 15B

```
 749 AGAAAGG.....GGAACCAGACCCAGAGGTGGCCTTTGAGTCACTGAGCG  793
     |||||||    ||  |||  |  ||  ||   |||          |||
 735 AGAAAGGTTGAAGGTCCCACCCTGAGCGGCACCCTGGTCACATGCCTGCG  784

794 CAGAGCCTGTCCATGCGGCCAACGGCTCTGTCCCCTTGGAGCCTCATGCC  843
     ||    |    ||  ||  ||            ||||     |  | ||
 785 TCCAGGAGAGCTGCAGGGTGAAGCCTGTGTGCCCCAGATAACCCCTTCCA  834

844 AGGCTCAGCATGGCCAGTGCTCCCTGCGGCCAGGCAGGACTGCACCTGCG  893
     ||  |   |        | ||    | |        |   |  |||  |
 835 TGGGCCCAGACAAAGCCTCATCAGATCTGAGCTTCCTGGAGGCTCAGGAT  884

894 GGACAGGGCTGACGGCACACCTGGGGGCAGGGCCTGAGCCTACAGGGAGG  943
     ||| |     |   |||  ||  |  ||  |||             |
 885 GGGCCTTCCCAGAAGCAGGCCCAGAGGGAGGCTGCCTCCAGATCCCCTGT  934

944 CACAGGGCAGGTGGGCTAGCCATGAACAGAAGAGGAAGCTGGAGTGCTTT  993
     |  |  ||   || || | |  | ||||   ||  |  |   |  | |
 935 CCCCTGGGGCTGTGGGTGTCCCTGAATGTCAGGGCCATGGGAGGCCCCT  984

994 GGGGGTTCATGCATGTAGGCTGGGATTTGGGGCTCACACCTCAACCTGCA  1043
     ||| |     |  |  |   | |     |  |               ||  ||||| |
 985 GGGCTTCAGGGGTTGGGGAAAAGTGAACACTCTGCTCTTTGTCCACCTTCG  1034

1044 TGCCCAGTTCCATGCCCCTCCCCTCTTGTGAAAGCACCTGTCTACTTGGG  1093
     |    |  |||    |    | | |    | ||         |
1035 GGAGGACAACCTTCAAATGCTGACCCTGGGCCCCTAACT........GA  1075

1094 CTGAGGATGTGGGGGCACAGGTGGCAGGTGAGGCTGCCCTCAGGAGGGGC  1143
     |    ||  |   |    ||         ||  |  ||  |||  ||| |||   |||
1076 CCTGAGACTTCAGAGCTTCTTGGGAGGAGCTGGGGTCCCCAGCGGAGCC  1125

1144 CCAGGCCCAGCTTGTACCCCACCTCCACCAGTACCTGAAGAAGTGGGGCT  1193
     |    |||  || |    | |||       ||   ||   ||
1126 TGGGATGGAGCAGGGATGGCTGCCCCA........GGGAGGGGCGGTGG  1167

1194 CTCACCCTACCTGCCTCTGCCATTGGAATGGCCTGGTTTGCACAGATGGG  1243
     |   |  |    |||||||    |     ||||        |  |
1168 GGCCTTCCATCCTGCTCTGCCCTCCTCGTCCTCTGGCCCCAGCTCAGTCC  1217

1244 AAACCCGTTTGAGGGGTGGGTGTCTGGGTGGGCACGTGGGGCGAGGACCT  1293
      ||   |   ||   |  |||   ||    ||   ||    ||
1218 TGTCCATCTCCAGCTCTAACCATTTGTGGCCCGACACTGGCTCTCCCTCT  1267

1294 GCCTGAGGGACCCTGCCCTGGAACTGACAGTGCAAGCTCGGCGTCCTGCC  1343
     |||   |  |                   |        |  ||  ||  ||||
1268 ACCTTCTGTCCTTGTCTGACACTGGTCTCCCGTGCTCTGGGGTCTCTGCA  1317

1344 CATCTGGGCAGAAGGCTGGTTTCTCCCATCAACGAAGCCCTCCCAGGACC  1393
     |   |||      |   | ||||||  || |      ||  || ||     |
1318 CTGATGGCTGCCTCCCGCTTCTCTCCCTCTCCCTCTGCCGTCCTGTCTC  1367

1394 TTCCTGCAAGCCCTCGTCCCACACGCAGCTCTGCCGTCCCTTGGTGTCCC  1443
     |    ||  || ||             |    |||   ||  ||| |    |   ||
1368 CTGTGGCCAGTCTCTCCTTGTTTCTCTTCTCCTCCTTCCTTCTCTCCACC  1417

1444 TCCCGGCCTCAGGTCCTCCA....TGCTGGGTACCTCTGGGCACCTCGTT  1489
     ||||     ||  |  |  |         ||||||||   |   |
```

FIG. 15C

```
1418 TCCCCATAGCCGAGCTTGGAAAAGTCAGACAGACCTCTGAGGTCTCATCC 1467

1490 TGGCTGAGCCAGGGGTTCAGCCTGGCAGGGCGCCCTGGCAGCAGTCCTTG 1539
     |||    ||||  | ||||||  ||||  | |      | ||     |
1468 TGGAGCTGCCACCAGCCCAGCCTCCCTGGGACCTGTCTTCACTGCCTGGG 1517

1540 GCCTGTGGATGCTGTCCTGGCCTGTG.GATGGTGTCCGCCCTCCACGTA 1588
     |||  ||| || |  | |  ||| ||      |       |
1518 GCCCTGGGAGCCAGGGAGGCTCCCTGAGGCTGAGTGAACACTGGGCGCTG 1567

1589 CCCCTCTCACCCCCTCCTCTTGGACTCCAGCCATGGGCCTGCGCGCGAGC 1638
     | |||  | | ||| | ||| | |||             || ||
1568 CACCTGCCTCTCCCACGTCCTCGGCCCCA...............CTCCGC 1603

1639 CGGAACTGCTCCAGGACAGAGAACGCCGTGTGTGGCTGCAGCCCAGGCCA 1688
     ||  | |||    |   |||  |||    |||  ||||       |||
1604 AGGTGCAGCTGGCTGGTGACGAAGCCCGGAGCTGGACCAGCAGCTCCCA 1653

1689 CTTCTGCATCGTCCAGGACGGGGACCACTGCGCCGCGTGCCGCGCTTACG 1738
     ||            |   |  |  |||   |   |   | ||  |||
1654 CTGGGTATGGTGGTTTCTCTCAGGGAGCCTCGTCATCGTCATTGTTTGCT 1703

1739 CCACCTCCAGCCCGGGCCAGAGGGTGCAGAAGGGAGGCACCGAGAGTCAG 1788
     ||||    |||    |    |  ||| | |  ||      |     |||
1704 CCACAGTTGGCCTAATCATATGTGTGAAAAGAAGAAAGCCAAGGGGTGAT 1753

1789 GACACCCTGTGTCAGAACTGCCCCCCGG...GGACCTTCTCTCCCAATGG 1835
     |   |   |||  || || ||    ||||   || |   |||
1754 GTAGTCAAGGTGATCGTCTCCGTCCAGGTATTGATCCTCCTCCCCCTCTC 1803

1836 GACCCTGGAGGAATGTCAGCACCAGACCAATTGGCCTAATCATATGTGTG 1885
     ||          |  |    |||| ||  |                ||||
1804 CCTCCCCCTCCACCTTCCCACCTCCCCTCTCCCCGCTGGGGCTGGTGTT 1853

1886 AAAAGAAGAAAGCCAAGGGG...TGAGCACACGGTGGCCCCATCAGGGTT 1932
     |  ||   ||||   ||  |||||  ||
1854 TCTGGTGTACATGGTGGGGGCTCCCAGTTCTCTGAGGGTCCTGAGTCTTT 1903

1933 CATGTCCCCAGCCGTCACCTCTTGGAGCTCTGTCACCCCAAGCCTGGGAG 1982
     || || |    || | |||  ||      | |||| ||     |
1904 CAAGTACAGCCACGGTAGCTCAGGAA......AGAACCCACCCCCTCAAA 1947

1983 GTGGCCCCAGAGCTTTTCCAGGATCCGCGGCTCCTCCCAGGGCAGCCACT 2032
     ||   |||   |      |    |     ||||||||| |||
1948 CTGAAAGCAGTAAAATGAACCCGAGAACCTGGAGTCCCAGGGGGCCTGA 1997

2033 GCAGGCTGGGGCAGGTGTATGTAGTCAAGGTGATCGTCTCCGTCCAGCGG 2082
     |||||| ||| |     ||             |||| ||  |||||
1998 GCAGGCAGGGTCTCCACGAT............TCGTGTGCTCACAGCGG 2034

2083 TAAAAGACAGGAGGCAGAAGGTGAGGCCACAGTCATTGA.GCCCTGCAGG 2131
     |||||||||||||||||||||||||||||||||||||||  ||||||||
2035 GAAAAGACAGGAGGCAGAAGGTGAGGCCACAGTCATTGAGGCCCTGCAGG 2084

2132 CCCCTCCGGACGTCACCACGGTGGCCGTGGAGGAGACAATACCCTCATTC 2181
     |||||||||||||||||||||||||||||||||||||||||||||||||
2085 CCCCTCCGGACGTCACCACGGTGGCCGTGGAGGAGACAATACCCTCATTC 2134
```

FIG. 15D

```
2182 AC.GGGGAGGAGCCCAAACCACTGACCCACAGACTCTGCACCCCGACGCC 2230
     || |||||||||||||||||||||||||||||||||||||||||||||||
2135 ACGGGGGAGGAGCCCAAACCACTGACCCACAGACTCTGCACCCCGACGCC 2184

2231 AGAGATACCTGGAGAGACGGCTGCTGATAGAGGCTGTCCACCTGGCGAAA 2280
     |||||||||||||| ||||||||||| |||||||||||||||||||||||
2185 AGAGATACCTGGAGCGACGGCTGCTGAAAGAGGCTGTCCACCTGGCGAAA 2234

2281 CCACCGGAGCCCGGAGGCTTGGGGGCTCCGCCCTGGGCTGGTTTCCGTCT 2330
     ||||||||||||||||||| ||||||||||||||||||||||||||||||
2235 CCACCGGAGCCCGGAGGTTTGGGGGCTCCGCCCTGGGCTGGTTTCCGTCT 2284

2331 CCTCCAGTGGAGGGAGAGGTGGTGCCCCTGCTGGTGGTAGAGCTGGGGAC 2380
     |||||||||||||||||||||| ||||||||||| |||||||||||||||
2285 CCTCCAGTGGAGGGAGAGGTGGGGCCCCTGCTGG.GGTAGAGCTGGGGAC 2333

2381 GCCACGTGCCATTCCCATGGTTCAGTGAGGGGCTGGTGGCCTCTGTTCTG 2430
     ||||||||||||||||||| |||||||| |||| ||||||||||||||||
2334 GCCACGTGCCATTCCCATGGGCCAGTGAGGGCTGG.GGCCTCTGTTCTG 2382

2431 CTGTGGCCTGAGCTCCCCAGAGTCCTGAGGAGGAGCCCCAGTTGCCCCTC 2480
     |||||||||||||||||||||||||||||||||||| |||||||||||||
2383 CTGTGGCCTGAGCTCCCCAGAGTCCTGAGGAGGAGCGCCAGTTGCCCCTC 2432

2481 GCTCACAGACCACACACCCAGCCCTCCTGGG.CCAACCCAGAGGCCCCTT 2529
     ||||||||||||||||||||||||||||||| ||| |||||||| |||||
2433 GCTCACAGACCACACACCCAGCCCTCCTGGGTCCAGCCCAGAGGGCCCTT 2482

2530 CAGACCCCAGCTGTCTGCGCGTCTGACTCTTGTGGCCTCAGCAGGACAGG 2579
     ||||||||||||||||||||||||||||||||||||||||||||||||||
2483 CAGACCCCAGCTGTCTGCGCGTCTGACTCTTGTGGCCTCAGCAGGACAGG 2532

2580 CCCCGGGCACTGCCTCACAGCCAAGGCTGGAATGGGTTGGCTGCAGTGTG 2629
     |||||||||||||| ||||||||||||||| |||||||||||||||||||
2533 CCCCGGGCACTGCCTTCAAGCCAAGGCTGGACTGGGTTGGCTGCAGTGTG 2582

2630 GTGTTTAGTGGATACCACATCGGAAGTGATTTTCTAAAAATTGGATTTGA 2679
     |||||||||||||||||||||||||||||||||||||        |||
2583 GTGTTTAGTGGATACCACATCGGAAGTGATTTTCTAAA........TTGG 2624

2680 ATTCGGAAAAAAA 2692
     ||| | ||||||||
2625 ATTTGAAAAAAAA 2637
```

USE OF AN ANTIBODY THAT BINDS HUMAN TUMOR NECROSIS FACTOR RECEPTOR-LIKE 2

CROSS-REFERENCE TO RELATED APPLICATIONS

The present application is a divisional of U.S. patent application Ser. No. 09/533,262, filed Mar. 22, 2000 (now U.S. Pat. No. 7,429,646), which claims benefit to the filing dates of U.S. Provisional Application No. 60/147,383, filed Aug. 6, 1999; U.S. Provisional Application No. 60/135,169, filed May 20, 1999; U.S. Provisional Application No. 60/126,522, filed Mar. 26, 1999; and U.S. Provisional Application No. 60/125,683, filed Mar. 22, 1999, and is a continuation-in-part of U.S. application Ser. No. 08/741,095, filed Oct. 30, 1996 (now U.S. Pat. No. 7,427,492); said Ser. No. 08/741,095 is a continuation-in-part of U.S. application Ser. No. 08/464,595 now abandoned, U.S. application Ser. No. 08/462,962 now abandoned, and U.S. application Ser. No. 08/462,315 now abandoned, each of which was filed Jun. 5, 1995; said U.S. application Ser. Nos. 08/464,595, 08/462,962 and 08/462,315 are each continuations-in-part of PCT/US95/05058, filed Apr. 27, 1995. Each of the above-identified patent applications is incorporated by reference herein in its entirety.

STATEMENT UNDER 37 C.F.R. §1.77(b)(5)

This application refers to a "Sequence Listing" listed below, which is provided as a text document. The document is entitled "PF173P5D1_SeqList.txt" (41,159 bytes, created Jul. 24, 2008), and is hereby incorporated by reference in its entirety herein.

BACKGROUND OF THE INVENTION

1. Field of the Invention

The present invention relates to novel members of the Tumor Necrosis Factor (TNF) receptor family. More specifically, isolated nucleic acid molecules are provided encoding a human TNF receptor-related protein, referred to herein as the TR2 receptor of FIG. 1A-1B, having considerable homology to murine CD40. Two different TR2 splice variants, referred to as TR2-SV1 and TR2-SV2, are also provided. TR2 polypeptides are also provided with homology to human type 2 TNF receptor (TNF-RII). Further provided are vectors, host cells and recombinant methods for producing the same. The invention also relates to both the inhibition and enhancement of functional activities of TR2 receptor polypeptides and diagnostic methods for detecting TR2 receptor gene expression.

2. Related Art

Human tumor necrosis factors α (TNF-α) and β (TNF-β or lymphotoxin) are related members of a broad class of polypeptide mediators, which includes the interferons, interleukins and growth factors, collectively called cytokines (Beutler, B. and Cerami, A., *Annu. Rev. Immunol.* 7:625-655 (1989)).

Tumor necrosis factor (TNF-α and TNF-β) was originally discovered as a result of its anti-tumor activity, however, now it is recognized as a pleiotropic cytokine playing important roles in a host of biological processes and pathologies. To date, there are ten known members of the TNF-related cytokine family, TNF-α, TNF-β (lymphotoxin-α), LT-β, TRAIL and ligands for the Fas receptor, CD30, CD27, CD40, OX40 and 4-1BB receptors. These proteins have conserved C-terminal sequences and variable N-terminal sequences which are often used as membrane anchors, with the exception of TNF-β. Both TNF-α and TNF-β function as homotrimers when they bind to TNF receptors.

TNF is produced by a number of cell types, including monocytes, fibroblasts, T-cells, natural killer (NK) cells and predominately by activated macrophages. TNF-α has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al., *J. Immunol.* 136(7):2483 (1987)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death.

TNF-β has many activities, including induction of an anti-viral state and tumor necrosis, activation of polymorphonuclear leukocytes, induction of class I major histocompatibility complex antigens on endothelial cells, induction of adhesion molecules on endothelium and growth hormone stimulation (Ruddle, N. and Homer, R., *Prog. Allergy* 40:162-182 (1988)).

Both TNF-α and TNF-β are involved in growth regulation and interact with hemopoietic cells at several stages of differentiation, inhibiting proliferation of various types of precursor cells, and inducing proliferation of immature myelomonocytic cells. Porter, A., *Tibtech* 9:158-162 (1991).

Recent studies with "knockout" mice have shown that mice deficient in TNF-β production show abnormal development of the peripheral lymphoid organs and morphological changes in spleen architecture (reviewed in Aggarwal et al., *Eur Cytokine Netw.* 7(2):93-124 (1996)). With respect to the lymphoid organs, the popliteal, inguinal, para-aortic, mesenteric, axillary and cervical lymph nodes failed to develop in TNF-β-/- mice. In addition, peripheral blood from TNF-β-/- mice contained a three fold reduction in white blood cells as compared to normal mice. Peripheral blood from TNF-β-/- mice, however, contained four fold more B cells as compared to their normal counterparts. Further, TNF-β, in contrast to TNF-α has been shown to induce proliferation of EBV-infected B cells. These results indicate that TNF-β is involved in lymphocyte development.

The first step in the induction of the various cellular responses mediated by TNF-α or TNF-β is their binding to specific cell surface or soluble receptors. Two distinct TNF receptors of approximately 55-KDa (TNF-RI) and 75-KDa (TNF-RII) have been identified (Hohman et al., *J. Biol. Chem.*, 264:14927-14934 (1989)), and human and mouse cDNAs corresponding to both receptor types have been isolated and characterized (Loetscher et al., *Cell,* 61:351 (1990)). Both TNF-Rs share the typical structure of cell surface receptors including extracellular, transmembrane and intracellular regions.

These molecules exist not only in cell bound forms, but also in soluble forms, consisting of the cleaved extra-cellular domains of the intact receptors (Nophar et al., *EMBO Journal,* 9(10):3269-76 (1990)) and otherwise intact receptors wherein the transmembrane domain is lacking. The extracellular domains of TNF-RI and TNF-RII share 28% identity and are characterized by four repeated cysteine-rich motifs with significant intersubunit sequence homology. The majority of cell types and tissues appear to express both TNF receptors and both receptors are active in signal transduction, however, they are able to mediate distinct cellular responses. Further, TNF-RII was shown to exclusively mediate human T-cell proliferation by TNF as shown in PCT WO 94/09137.

TNF-RI dependent responses include accumulation of C-FOS, IL-6, and manganese superoxide dismutase mRNA, prostaglandin E2 synthesis, IL-2 receptor and MHC class I and II cell surface antigen expression, growth inhibition, and cytotoxicity. TNF-RI also triggers second messenger systems such as phospholipase $A_2$, protein kinase C, phosphatidylcholine-specific phospholipase C and sphingomyelinase (Pfefferk et al., *Cell*, 73:457-467 (1993)).

Several interferons and other agents have been shown to regulate the expression of TNF receptors. Retinoic acid, for example, has been shown to induce the production of TNF receptors in some cells type while down regulating production in other cells. In addition, TNF-α has been shown to affect the localization of both types of receptor. TNF-α induces internalization of TNF-RI and secretion of TNF-RII (reviewed in Aggarwal et al., supra). Thus, the production and localization of both TNF-Rs are regulated by a variety of agents.

Both the yeast two hybrid system and co-precipitation and purification have been used to identify ligands which associate with both types of the TNF-Rs (reviewed in Aggarwal et al., supra and Vandenabeele et al., *Trends in Cell Biol.* 5:392-399 (1995)). Several proteins have been identified which interact with the cytoplasmic domain of a murine TNF-R. Two of these proteins appear to be related to the baculovirus inhibitor of apoptosis, suggesting a direct role for TNF-R in the regulation of programmed cell death.

SUMMARY OF THE INVENTION

The present invention provides isolated nucleic acid molecules comprising, or alternatively consisting of, polynucleotides encoding TR2 receptors and splice variants thereof having the amino acid sequences shown in SEQ ID NO:26, FIG. 1A-1B (SEQ ID NO:2), FIG. 4A-4B (SEQ ID NO:5) and FIG. 7A-7B (SEQ ID NO:8) or the amino acid sequence encoded by the cDNA encoding the TR2 receptors deposited as ATCC™ Deposit Numbers 97059, 97058 and 97057 on Feb. 13, 1995. The present invention also relates to recombinant vectors, which include the isolated nucleic acid molecules of the present invention, and to host cells containing the recombinant vectors, as well as to methods of making such vectors and host cells and for using them for production of TR2 polypeptides or peptides by recombinant techniques.

The invention further provides isolated TR2 polypeptides having amino acid sequences encoded by the polynucleotides described herein.

The present invention also provides a screening method for identifying compounds capable of enhancing or inhibiting a cellular response induced by TR2 receptors, which involves contacting cells which express TR2 receptors with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for agonists and antagonists is provided which involves determining the effect a candidate compound has on the binding of cellular ligands to TR2 receptors. In particular, the method involves contacting TR2 receptors with a ligand polypeptide and a candidate compound and determining whether ligand binding to the TR2 receptors is increased or decreased due to the presence of the candidate compound.

The invention further provides a diagnostic method useful during diagnosis or prognosis of a disease states resulting from aberrant cell proliferation due to alterations in TR2 receptor expression.

An additional aspect of the invention is related to a method for treating an individual in need of an increased level of a TR2 receptor activity in the body comprising administering to such an individual a composition comprising a therapeutically effective amount of isolated TR2 polypeptides of the invention or an agonist thereof.

A still further aspect of the invention is related to a method for treating an individual in need of a decreased level of a TR2 receptor activity in the body comprising administering to such an individual a composition comprising a therapeutically effective amount of a TR2 receptor antagonist.

The invention additionally provides soluble forms of the polypeptides of the present invention. Soluble peptides are defined by amino acid sequences wherein the sequence comprises, or alternatively consists of, the polypeptide sequences lacking a transmembrane domain. Such soluble forms of the TR2 receptors are useful as antagonists of the membrane bound forms of the receptors.

BRIEF DESCRIPTION OF THE FIGURES

FIG. 1A-1B shows the nucleotide (SEQ ID NO:1) and deduced amino acid (SEQ ID NO:2) sequences of a TR2 receptor. The protein has a predicted leader sequence of about 36 amino acid residues (underlined) (amino acid residues –36 to –1 in SEQ ID NO:2) and a deduced molecular weight of about 30,417 kDa. It is further predicted that amino acid residues from about 37 to about 200 (amino acid residues 1 to 164 in SEQ ID NO:2) constitute the extracellular domain; from about 201 to about 225 (amino acid residues 165 to 189 in SEQ ID NO:2) the transmembrane domain (underlined); and from about 226 to about 283 (amino acid residues 190 to 247 in SEQ ID NO:2) the intracellular domain. Two potential asparagine-linked glycosylation sites are located at amino acid positions 110 and 173 (amino acid residues 74 to 137 in SEQ ID NO:2).

FIG. 2 shows the regions of similarity between the amino acid sequences of the TR2 receptor protein of FIG. 1A-1B and a murine CD40 protein (SEQ ID NO:3).

FIG. 4A-4B shows the nucleotide (SEQ ID NO:4) and deduced amino acid (SEQ ID NO:5) sequences of the TR2-SV1 receptor. The protein has a predicted leader sequence of about 36 amino acid residues (underlined) (amino acid residues –36 to –1 in SEQ ID NO:5) and a deduced molecular weight of about 19.5 kDa.

FIG. 5 shows the regions of similarity between the amino acid sequences of the full-length TR2-SV1 receptor protein and a human type 2 TNF receptor (SEQ ID NO:6).

FIG. 7A-7B shows the nucleotide (SEQ ID NO:7) and deduced amino acid (SEQ ID NO:8) sequences of the TR2-SV2 receptor. This protein lacks a putative leader sequence and has a deduced molecular weight of about 14 kDa.

FIG. 8 shows the regions of similarity between the amino acid sequences of the TR2-SV2 receptor protein and a human type 2 TNF receptor (SEQ ID NO:9).

FIG. 10 shows the regions of similarity between the amino acid sequences of the TR2 receptor protein of FIG. 1A-1B and the TR2-SV1 receptor protein of FIG. 4A-4B.

FIG. 11 shows the regions of similarity between the amino acid sequences of the TR2 receptor protein of FIG. 1A-1B and the TR2-SV2 receptor protein of FIG. 7A-7B.

FIG. 12 shows the regions of similarity between the amino acid sequences of the TR2-SV1 and the TR2-SV2 receptor proteins.

FIG. 13A-13C shows the regions of similarity between the nucleotide sequences encoding the TR2 receptor protein of FIG. 1A-1B and the TR2-SV1 receptor protein of FIG. 4A-4B.

FIG. 14A-14C shows the regions of similarity between the nucleotide sequences encoding the TR2 receptor protein of FIG. 1A-1B and the TR2-SV2 receptor protein of FIG. 7A-7B.

FIG. 15A-15E shows the regions of similarity between the nucleotide sequences encoding the TR2-SV1 and the TR2-SV2 receptor proteins.

FIG. 16 shows an alignment of the amino acid sequence of the TR2 receptor of FIG. 1A-1B (SEQ ID NO:2) with other TNFR family members. The amino acid sequence of TR2 was aligned with those of TNFR-I (SEQ ID NO:10), TNFR-II (SEQ ID NO:11), CD40 (SEQ ID NO:12) and 4-1BB (SEQ ID NO:13) on the basis of sequence homology and conserved cysteine residues. Cysteine repeat regions are defined by amino acid residues 5 to 40, 41 to 84, 85 to 127, and 128 to 166 in SEQ ID NO:2, respectively referred to as cysteine repeat regions A-D.

DETAILED DESCRIPTION OF THE PREFERRED EMBODIMENTS

Figure 3:
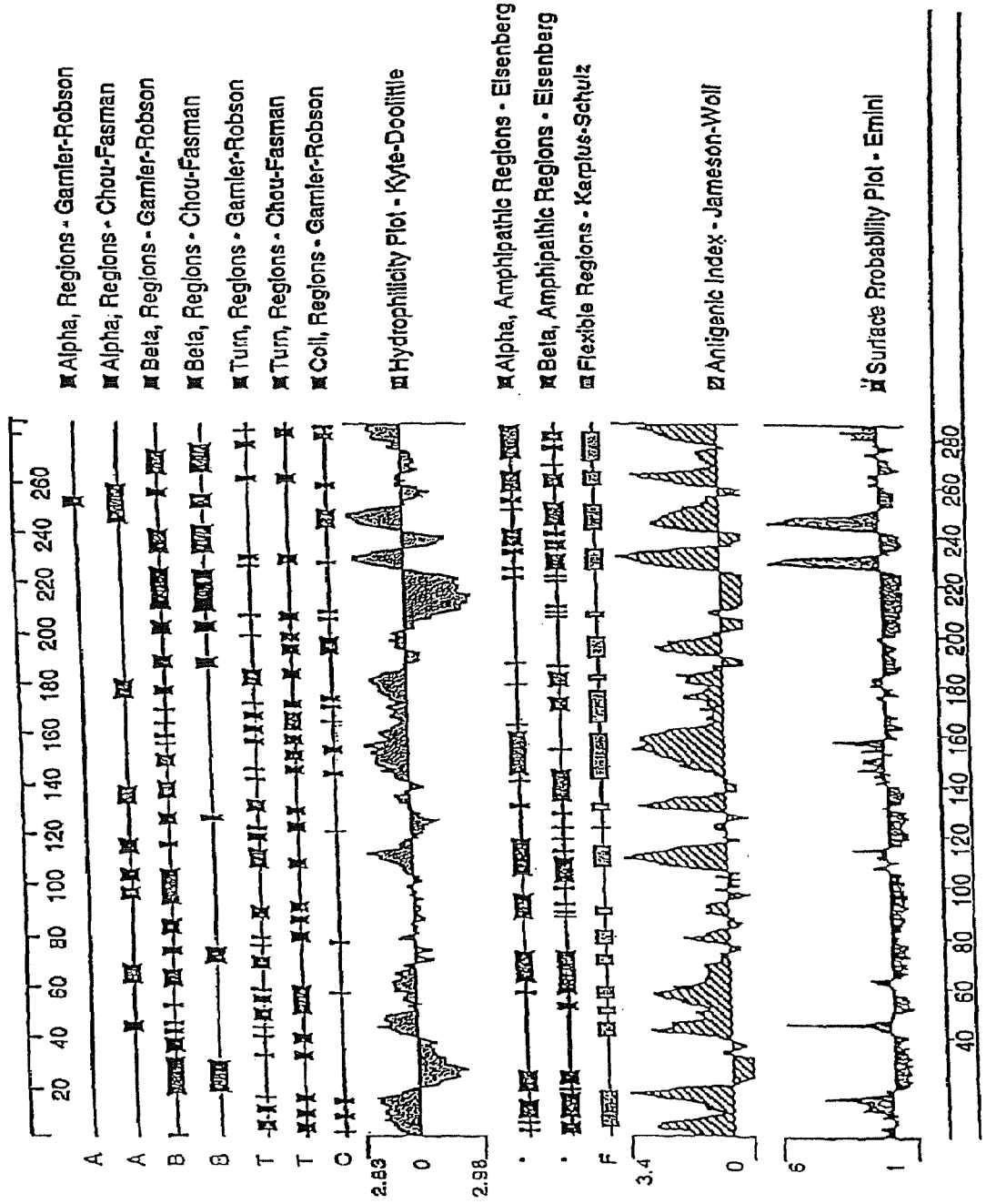
FIG. 3 shows an analysis of the TR2 receptor amino acid sequence of FIG. 1A-1B. Alpha, beta, turn and coil regions; hydrophilicity and hydrophobicity; amphipathic regions; flexible regions; antigenic index and surface probability are shown. In the "Antigenic Index-Jameson-Wolf" graph, amino acid residues 39 to 70, 106 to 120, 142 to 189 and 276 to 283 in FIG. 1A-1B (amino acid residues 3 to 34, 70 to 84, 106 to 153 and 240 to 247 in SEQ ID NO:2) correspond to the shown highly antigenic regions of the TR2 receptor protein.

The present invention provides isolated nucleic acid molecules comprising, or alternatively consisting of, polynucleotides encoding a TR2 polypeptide (FIG. 1A-1B (SEQ ID NO:2)) and splice variants thereof, TR2-SV1 (FIG. 4A-4B (SEQ ID NO:5)) and TR2-SV2 (FIG. 7A-7B (SEQ ID NO:8)), the amino acid sequences of which were determined by sequencing cDNAs. The TR2 protein shown in FIG. 1A-1B shares sequence homology with the murine CD40 receptor (FIG. 2 (SEQ ID NO:3)). On Feb. 13, 1995 a deposit was made at the American Type Culture Collection, 10801 University Blvd., Manassas, Va. 20110-2209, USA, and given ATCC™ Accession No. 97059. The nucleotide sequence shown in FIG. 1A-1B (SEQ ID NO:1) was obtained by sequencing a cDNA which is believed to contain the same amino acid coding sequences as the cDNA contained in the deposited plasmid assigned ATCC™ Accession No. 97059 (Clone ID HLHAB49).

The TR2 receptors of the present invention include several allelic variants containing alterations in at least four nucleotides and two amino acids. Nucleotide sequence variants which have been identified include either guanine or adenine at nucleotide 314 and either thymine or cytosine at nucleotides 386, 624 and 627 shown in FIG. 1A-1B (SEQ ID NO:1). While the identified alteration at nucleotides 624 and 627 are silent, the alteration at nucleotide 386 results in the codon at nucleotides 385 to 387 encoding either serine or phenylalanine and the alteration at nucleotide 314 results in the codon at nucleotides 313 to 315 encoding either lysine or arginine.

The nucleotide sequences shown in FIG. 4A-4B (SEQ ID NO:4) and FIG. 7A-7B (SEQ ID NO:7) were also obtained by sequencing cDNAs deposited on Feb. 13, 1995 at the American Type Culture Collection and given accession numbers 97058 (TR2-SV1) and 97057 (TR2-SV2), respectively. The deposited cDNAs are contained in the pBluescript SK(–) plasmid (Stratagene, LaJolla, Calif.).

As used herein the phrase "splice variant" refers to cDNA molecules produced from a RNA molecules initially transcribed from the same genomic DNA sequence which have undergone alternative RNA splicing. Alternative RNA splicing occurs when a primary RNA transcript undergoes splicing, generally for the removal of introns, which results in the production of more than one mRNA molecule each of which may encode different amino acid sequences. The term "splice variant" also refers to the proteins encoded by the above cDNA molecules.

As used herein, "TR2 proteins", "TR2 receptors", "TR2 receptor proteins" and "TR2 polypeptides" refer to all proteins resulting from the alternate splicing of the genomic DNA sequences encoding proteins having regions of amino acid sequence identity and receptor activity which correspond to the proteins shown in SEQ ID NO:26, FIG. 1A-1B (SEQ ID NO:2), FIG. 4A-4B (SEQ ID NO:5) or FIG. 7A-7B (SEQ ID NO:8), as well as TR2 allelic variants. The TR2 proteins shown in SEQ ID NO:26 and FIG. 1A-1B, the TR2-SV1 protein shown FIG. 4A-4B, and the TR2-SV2 protein shown in FIG. 7A-7B are examples of such receptor proteins.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in SEQ ID NO:26, FIG. 1A-1B, FIG. 4A-4B or FIG. 7A-7B, nucleic acid molecules of the present invention encoding TR2 polypeptides may be obtained using standard cloning and screening procedures, such as those used for cloning cDNAs using mRNA as starting material. Illustrative of the invention, the nucleic acid molecule described in FIG. 1A-1B (SEQ ID NO:1) was discovered in a cDNA library derived from activated human T-lymphocytes. The nucleic acid molecules described in FIG. 4A-4B (SEQ ID NO:4) and FIG. 7A-7B (SEQ ID NO:7) were discovered in cDNAs library derived from human fetal heart and human stimulated monocytes, respectively.

As described in Example 6, TR2 mRNA was detected in numerous tissues including lung, spleen and thymus and may be ubiquitously expressed in human cells. TR2 RNA was also found to be expressed in B lymphocytes (CD19$^+$), both CD4$^+$ (T$_{H1}$ and T$_{H2}$ clones) and CD8$^+$ T lymphocytes, monocytes and endothelial cells.

As also noted in Example 6, the production of TR2 mRNA was inducible in MG 63 cells by TNFα. Further, the accumulation of TR2 mRNA was observed in HL60, U937 and THP1 cells upon PMA or DMSO treatment. PMA and DMSO are agents known to induce differentiation of these three cell types.

The determined nucleotide sequence of the TR2 cDNA of FIG. 1A-1B (SEQ ID NO:1) contains an open reading frame encoding a protein of about 283 amino acid residues, with a predicted leader sequence of about 36 amino acid residues, and a deduced molecular weight of about 30,417 kDa. The amino acid sequence of the predicted mature TR2 receptor is shown in FIG. 1A-1B from amino acid residue about 37 to residue about 283 (amino acid residues 1 to 247 in SEQ ID NO:2). In this context "about" includes the particularly recited value and values larger or smaller by several (5, 4, 3, 2, or 1) amino acids. As noted in Example 6, the location of the leader sequence cleavage site was confirmed for a TR2-Fc fusion protein and found to be between amino acids 36 and 37 shown in FIG. 1A-1B (amino acid residues –1 to 1 in SEQ ID NO:2). The TR2 protein shown in FIG. 1A-1B (SEQ ID NO:2) is about 29% identical and about 47% similar to the murine CD40 protein shown in SEQ ID NO:3 (see FIG. 2).

Similarly, the determined cDNA nucleotide sequences of the TR2-SV1 splice variant of TR2 (FIG. 4A-4B (SEQ ID NO:4)) contains an open reading frame encoding a protein of about 185 amino acid residues, with a predicted leader sequence of about 36 amino acid residues, and a deduced molecular weight of about 19.5 kDa. The amino acid sequence of the predicted mature TR2-SV1 receptor is shown in FIG. 4A-4B (SEQ ID NO:5) from amino acid residue about 37 to residue about 185 (amino acid residues 1 to 149 in SEQ ID NO:5). In this context "about" includes the particularly recited value and values larger or smaller by several (5, 4, 3, 2, or 1) amino acids. The TR2-SV1 protein shown in FIG. 4A-4B (SEQ ID NO:5) is about 25% identical and about 48% similar to the human type 2 TNF receptor protein shown in SEQ ID NO:6 (see FIG. 5).

The determined cDNA nucleotide sequences of the TR2-SV2 splice variant of TR2 (FIG. 7A-7B (SEQ ID NO:7)) contains an open reading frame encoding a protein of about 136 amino acid residues, without a predicted leader sequence, and a deduced molecular weight of about 14 kDa. The amino acid sequence of the predicted TR2-SV2 receptor is shown in FIG. 7A-7B (SEQ ID NO:8) from amino acid residue about 1 to residue about 136. In this context "about" includes the particularly recited value and values larger or smaller by several (5, 4, 3, 2, or 1) amino acids. The TR2-SV2 protein shown in FIG. 7A-7B (SEQ ID NO:8) is about 27% identical and about 45% similar to the human type 2 TNF receptor protein shown in SEQ ID NO:9 (see FIG. 8).

A comparison of both the nucleotide and amino acid sequences of the TR2, TR2-SV1 and TR2-SV2 receptor proteins shown in FIG. 1A-1B, FIG. 4A-4B and FIG. 7A-7B shows several regions of near identity. While the amino acid sequence of the TR2 receptor protein, shown in FIG. 1A-1B (SEQ ID NO:2), is about 60% identical and about 73% similar to the amino acid sequence of the TR2-SV1 receptor protein, shown in FIG. 4A-4B (SEQ ID NO:5), in approximately the first one hundred amino acids of their respective sequences the two proteins differ in one location (FIG. 10).

Similarly, the amino acid sequence of the TR2 receptor protein of FIG. 1A-1B (SEQ ID NO:2) is about 60% identical and about 71% similar to the amino acid sequence of the TR2-SV2 receptor protein, shown in FIG. 7A-7B (SEQ ID NO:8); however, the two proteins are almost identical over a 60 amino acid stretch in the central portion of the TR2-SV2 protein (FIG. 11).

In contrast, the TR2-SV1 and TR2-SV2 proteins are only about 20% identical and about 38% similar at the amino acid level to each other. Unlike the comparisons of either of these proteins to the TR2 protein shown in FIG. 1A-1B (SEQ ID NO:2), these proteins share their homology over the entire 136 amino acid sequence of the TR2-SV2 protein (FIG. 12).

With respect to their nucleotide sequences of the cDNAs encoding the disclosed TR2 proteins, a comparison of these sequences indicates that the TR2 cDNAs share large regions of near identity at the nucleic acid level (FIG. 13A-13C, FIG. 14A-14C and FIG. 15A-15E). The cDNA sequences encoding the TR2 and TR2-SV1 proteins, for example, share large regions of near identity in their nucleotide sequences which encode both the N termini of the respective proteins and their 5' and 3' noncoding regions (FIG. 13A-13C). Further, the nucleotide sequences of the cDNAs encoding the TR2-SV1 and TR2-SV2 proteins share considerable homology but this identity is limited to their 3' regions well beyond their respective coding sequences (FIG. 15A-15E).

Such regions of near identity between two different cDNA sequences, when maintained over an extended stretch of sequence, indicates to one skilled in the art that the respective molecules were originally transcribed from the same genomic DNA sequence. One skilled in the art would further recognize that, since more than one codon can encode the same amino acid, identity between two proteins at the amino acid level does not necessarily mean that the DNA sequences encoding those proteins will share similar regions of identity. The above data indicates that the TR2 receptors of the present invention are transcribed from a single genomic DNA sequence and represent multiple splice variants of one initial RNA transcript.

Related proteins which are produced from alternately spliced RNA, referred to as splice variants, are known in the art. The transcript of the src gene, for example, undergoes alternate RNA splicing to produce cell type specific products. In most cells the Src protein consists of 533 amino acids while in nerve cells an additional short exon is included in the mRNA resulting in a protein of 539 amino acids. See Alberts, B. et al., MOLECULAR BIOLOGY OF THE CELL (3rd Edition, Garland Publishing, Inc., 1994), 455. Similarly, sex specific mRNA transcripts have been identified in *Drosophila* where alternate mRNA splicing results in a protein named Dsx which is approximately 550 amino acids in length in males and 430 amino acids in length in females. These two splice variant proteins share a common core sequence of about 400 amino acids. See id. at 457.

In the present instance, the TR2 receptor protein shown in FIG. 1A-1B (SEQ ID NO:2) is believed to be the full-length polypeptide encoded by the RNA from which the TR2 receptor proteins are translated. The RNA encoding the TR2-SV1 splice variant shown in FIG. 4A-4B (SEQ ID NO:5) is believed to contain an insertion in the region encoding amino acid residue 102 of the amino acid sequence shown in FIG. 1A-1B and a deletion in the region encoding amino acid residue 184 of the amino acid sequence shown in FIG. 1A-1B. The RNA encoding the TR2-SV2 splice variant shown in FIG. 7A-7B is believed to begin with the nucleotide sequence encoding amino acid residue 102 of the amino acid sequence shown in FIG. 1A-1B and contain insertions in the regions encoding amino acid residues 184 and 243 of the amino acid sequence shown in FIG. 1A-1B.

As indicated, the present invention also provides the mature forms of the TR2 receptors of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides nucleotide sequences encoding mature TR2 polypeptides having the amino acid sequences encoded by the cDNAs contained in the deposits identified as ATCC™ Deposit Numbers 97059 and 97058 and as shown in SEQ ID NO:26, FIG. 1A-1B (SEQ ID NO:2) and FIG. 4A-4B (SEQ ID NO:5). By the mature TR2 polypeptides having the amino acid sequences encoded by the cDNAs contained in the deposits identified as ATCC™ Deposit Numbers 97059 and 97058 is meant the mature form (s) of the TR2 receptors produced by expression in a mammalian cell (e.g., COS cells, as described below) of the complete open reading frame encoded by the human DNA sequence of the cDNA contained in the deposited plasmids.

The invention also provides nucleic acid sequences encoding the TR2-SV2 receptor protein of FIG. 7A-7B (SEQ ID NO:8), having the amino acid sequence encoded by the cDNA contained in ATCC™ Deposit Number 97057, which does not contain a secretory leader sequence.

Methods for predicting whether a protein has a secretory leader as well as the cleavage point for that leader sequence are available. For instance, the methods of McGeoch (*Virus Res.* 3:271-286 (1985)) and von Heinje (*Nucleic Acids Res.* 14:4683-4690 (1986)) can be used. The accuracy of predicting the cleavage points of known mammalian secretory proteins for each of these methods is in the range of 75-80%. von Heinje, supra. However, the two methods do not always produce the same predicted cleavage point(s) for a given protein.

In the present case, the predicted amino acid sequences of the complete TR2 polypeptides shown in FIG. 1A-1B (SEQ ID NO:2), FIG. 4A-4B (SEQ ID NO:5) and FIG. 7A-7B (SEQ ID NO:8) were analyzed by a computer program ("PSORT") (K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids −1 and 1 in SEQ ID NO:2 and SEQ ID NO:5. Thereafter, the complete amino acid sequences were further analyzed by visual inspection, applying a simple form of the (−1,−3) rule of von Heine. von Heinje, supra. Thus, the leader sequences for the TR2 protein shown in SEQ ID NO:2 and the TR2-SV1 protein are predicted to consist of amino acid residues −36 to −1 in both SEQ ID NO:2 and SEQ ID NO:5, while the predicted mature TR2 proteins consist of amino acid residues 1 to 247 for the TR2 protein shown in SEQ ID NO:2 and residues 1 to 149 for the TR2-SV1 protein shown in SEQ ID NO:5.

As noted in Example 6, the cleavage site of the leader sequence of a TR2-Fc fusion protein was confirmed using amino acid analysis of the expressed fusion protein. This fusion protein was found to begin at amino acid 37, which corresponds to amino acid 1 in SEQ ID NO:2 and SEQ ID NO:5, indicating that the cleavage site of the leader sequence is between amino acids 36 and 37 in this protein (corresponding to amino acid residues −1 to 1 in SEQ ID NO:2 and SEQ ID NO:5).

As one of ordinary skill would appreciate, however, due to the possibilities of sequencing errors, as well as the variability of cleavage sites for leaders in different known proteins, the TR2 receptor polypeptide encoded by the cDNA of ATCC™ Deposit Number 97059 comprises about 283 amino acids, but may be anywhere in the range of 250 to 316 amino acids; and the leader sequence of this protein is about 36 amino acids, but may be anywhere in the range of about 30 to about 42 amino acids. Similarly, the TR2-SV1 receptor polypeptide encoded by the cDNA of ATCC™ Deposit Number 97058 comprises about 185 amino acids, but may be anywhere in the range of 163-207 amino acids; and the leader sequence of this protein is about 36 amino acids, but may be anywhere in the range of about 30 to about 42 amino acids. Further, the TR2-SV2 receptor polypeptide encoded by the cDNA of ATCC™ Deposit Number 97057 comprises about 136 amino acids, but may be anywhere in the range of 120-152 amino acids. In this context "about" includes the particularly recited value and values larger or smaller by several (5, 4, 3, 2, or 1) amino acids.

The leader sequences for the TR2 protein shown in SEQ ID NO:26 is predicted to consist of amino acid residues −38 to −1 in SEQ ID NO:26, while the predicted mature TR2 protein consists of amino acid residues 1 to 245 in SEQ ID NO:26.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

However, a nucleic acid contained in a clone that is a member of a library (e.g., a genomic or cDNA library) that has not been isolated from other members of the library (e.g., in the form of a homogeneous solution containing the clone and other members of the library) or a chromosome isolated or removed from a cell or a cell lysate (e.g., a "chromosome spread," as in a karyotype), is not "isolated" for the purposes of the invention. As discussed further herein, isolated nucleic acid molecules according to the present invention may be produced naturally, recombinantly, or synthetically.

Isolated nucleic acid molecules of the present invention include DNA molecules comprising, or alternatively consisting of, an open reading frame (ORF) shown in SEQ ID NO:26 or FIG. 1A-1B (SEQ ID NO:1); DNA molecules comprising, or alternatively consisting of, the coding sequence for the mature TR2 receptor shown in SEQ ID NO:26 (last 245 amino acids) or FIG. 1A-1B (SEQ ID NO:2) (last 247 amino acids); and DNA molecules which comprise, or alternatively consist of, a sequence substantially different from those described above but which, due to the degeneracy of the genetic code, still encode the TR2 receptor protein shown in SEQ ID NO:26 or FIG. 1A-1B (SEQ ID NO:2). Of course, the genetic code is well known in the art. Thus, it would be routine for one skilled in the art to generate such degenerate variants.

Similarly, isolated nucleic acid molecules of the present invention include DNA molecules comprising, or alternatively consisting of, an open reading frame (ORF) shown in FIG. 4A-4B (SEQ ID NO:4); DNA molecules comprising, or alternatively consisting of, the coding sequence for the mature TR2-SV1 receptor shown in FIG. 4A-4B (SEQ ID NO:5) (last 149 amino acids); and DNA molecules which comprise, or alternatively consist of, a sequence substantially different from those described above but which, due to the degeneracy of the genetic code, still encode the TR2-SV1 receptor.

Further, isolated nucleic acid molecules of the present invention include DNA molecules comprising, or alternatively consisting of, an open reading frame (ORF) shown in FIG. 7A-7B (SEQ ID NO:7) and DNA molecules which comprise, or alternatively consist of, a sequence substantially different from those described above but which, due to the degeneracy of the genetic code, still encode the TR2-SV2 receptor.

In another aspect, the invention provides isolated nucleic acid molecules encoding the TR2, TR2-SV1 and TR2-SV2 polypeptides having the amino acid sequences encoded by the cDNAs contained in the plasmid deposited as ATCC™ Deposit No. 97059, 97058 and 97057, respectively, on Feb. 13, 1995. In a further embodiment, these nucleic acid molecules will encode a mature polypeptide or the full-length polypeptide lacking the N-terminal methionine. The invention further provides isolated nucleic acid molecules having the nucleotide sequences shown in SEQ ID NO:25, FIG. 1A-1B (SEQ ID NO:1), FIG. 4A-4B (SEQ ID NO:4), and FIG. 7A-7B (SEQ ID NO:7); the nucleotide sequences of the cDNAs contained in the above-described deposited cDNAs; or nucleic acid molecules having a sequence complementary to one of the above sequences. Such isolated molecules, particularly DNA molecules, are useful, for example, as probes for gene mapping, by in situ hybridization with chromosomes, and for detecting expression of the TR2 receptor genes of the present invention in human tissue, for instance, by Northern blot analysis.

Further embodiments of the invention include isolated nucleic acid molecules comprising, or alternatively consisting of, a polynucleotide having a nucleotide sequence at least 80% identical, and more preferably at least 85%, 90%, 92%, 95%, 96%, 97%, 98% or 99% identical to (a) a nucleotide sequence encoding the TR2 polypeptide having the complete amino acid sequence shown in SEQ ID NO:26, FIG. 1A-1B (amino acid residues −36 to 247 in SEQ ID NO:2), FIG. 4A-4B (amino acid residues −36 to 149 in SEQ ID NO:5), or FIG. 7A-7B (amino acid residues 1 to 136 in SEQ ID NO:8); (b) a nucleotide encoding the complete amino sequence shown in SEQ ID NO:26, FIG. 1A-1B (amino acid residues −35 to 247 in SEQ ID NO:2), FIG. 4A-4B (amino acid residues −35 to 149 in SEQ ID NO:5), or FIG. 7A-7B (amino acid residues 2 to 136 in SEQ ID NO:8) but lacking the N-terminal methionine; (c) a nucleotide sequence encoding the mature TR2 receptors (full-length polypeptide with any attending leader sequence removed) having the amino acid sequence at positions from about 1 to about 245 in SEQ ID NO:26, from about 37 to about 283 in FIG. 1A-1B (amino acid residues 1 to 247 in SEQ ID NO:2) or the amino acid sequence at positions from about 37 to about 185 in FIG. 4A-4B (amino acid residues 1 to 149 in SEQ ID NO:5), or the amino acid sequence at positions from about 1 to about 136 in FIG. 7A-7B (SEQ ID NO:8); (d) a nucleotide sequence encoding the TR2, TR2-SV1 or TR2-SV2 polypeptides having the complete amino acid sequence including the leader encoded by the cDNAs contained in ATCC™ Deposit Numbers 97059, 97058, and 97057, respectively; (e) a nucleotide sequence encoding the mature TR2 or TR2-SV1 receptors having the amino acid sequences encoded by the cDNAs contained in ATCC™ Deposit Numbers 97059 and 97058, respectively; (f) a nucleotide sequence encoding the TR2 or TR2-SV1 receptor extracellular domain; (g) a nucleotide sequence encoding the TR2 receptor transmembrane domain; (h) a nucleotide sequence encoding the TR2 receptor intracellular domain; (i) a nucleotide sequence encoding the TR2 receptor extracellular and intracellular domains with all or part of the transmembrane domain deleted; and (j) a nucleotide sequence complementary to any of the nucleotide sequences in (a), (b), (c), (d), (e), (f), (g), (h), or (i). In this context "about" includes the particularly recited value and values larger or smaller by several (5, 4, 3, 2, or 1) amino acids.

By a polynucleotide having a nucleotide sequence at least, for example, 95% "identical" to a reference nucleotide sequence encoding a TR2 receptor polypeptide is intended that the nucleotide sequence of the polynucleotide is identical to the reference sequence except that the polynucleotide sequence may include up to five mismatches per each 100 nucleotides of the reference nucleotide sequence encoding a TR2 receptor. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire TR2 receptor encoding nucleotide sequence shown in SEQ ID NO:25, FIG. 1A-1B (SEQ ID NO:1), FIG. 4A-4B (SEQ ID NO:4), or FIG. 7A-7B (SEQ ID NO:7) or any TR2 receptor polynucleotide fragment (e.g., a polynucleotide encoding the amino acid sequence of any of the TR2 receptor N- and/or C-terminal deletions described herein), variant, derivative or analog, as described herein.

As a practical matter, whether any particular nucleic acid molecule is at least 80%, 85%, 90%, 92%, 95%, 96%, 97%, 98% or 99% identical to, for instance, the encoding nucleotide sequence shown in SEQ ID NO:25, FIG. 1A-1B (SEQ ID NO:1), FIG. 4A-4B (SEQ ID NO:4), or FIG. 7A-7B (SEQ ID NO:7), or to the nucleotide sequence of the deposited cDNAs, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 80%, 85%, 90%, 92%, 95%, 96%, 97%, 98% or 99% identical to the nucleic acid sequences disclosed herein, (e.g., encoding a polypeptide having the amino acid sequence of an N and/or C terminal deletion disclosed herein, such as, for example, a nucleic acid molecule encoding amino acids 50 to 283 of SEQ ID NO:2), irrespective of whether they encode a polypeptide having a TR2 receptor functional activity. This is because even where a particular nucleic acid molecule does not encode a polypeptide having TR2 receptor activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR2 receptor activity include, inter alia, (1) isolating a TR2 receptor gene or allelic or splice variants thereof in a cDNA library; (2) in situ hybridization (e.g., "FISH") to metaphase chromosomal spreads to provide precise chromosomal location of a TR2 receptor gene, as described in Verma et al., *Human Chromosomes: A Manual of Basic Techniques*, Pergamon Press, New York (1988); and (3) Northern Blot analysis for detecting TR2 receptor mRNA expression in specific tissues.

Preferred, however, are nucleic acid molecules having sequences at least 80%, 85%, 90%, 92%, 95%, 96%, 97%, 98% or 99% identical to the nucleic acid sequence shown in SEQ ID NO:25, FIG. 1A-1B (SEQ ID NO:1), FIG. 4A-4B (SEQ ID NO:4), or FIG. 7A-7B (SEQ ID NO:7) or to the nucleic acid sequence of the deposited cDNAs which do, in fact, encode a polypeptide having TR2 receptor activity.

Preferably, the polynucleotide fragments of the invention encode a polypeptide which demonstrates a TR2 functional activity. By "a polypeptide having TR2 receptor activity" is intended polypeptides exhibiting activity similar, but not necessarily identical, to an activity of the TR2 receptors of the present invention (e.g., complete (full-length) TR2 receptor polypeptides, mature TR2 receptor polypeptides, secreted TR2 receptor polypeptides, and soluble TR2 receptor polypeptides (e.g., having sequences contained in the extracellular domain of a TR2 receptor) as measured, for example, in a particular immunoassay or biological assay. For example, a TR2 receptor activity can routinely be measured by determining the ability of a TR2 receptor polypeptide to bind a TR2 receptor ligand (e.g., AIM II (International Publication No. WO 97/34911), Lymphotoxin-$\alpha$, and the Herpes virus protein HSV1 gD). TR2 receptor activity can be measured by determining the ability of a polypeptide-Fc fusion protein to inhibit lymphocyte proliferation as described below in Example 6. TR2 receptor activity may also be measured by determining the ability of a polypeptide, such as cognate ligand which is free or expressed on a cell surface, to confer proliferatory activity in intact cells expressing the receptor.

Other methods will be known to the skilled artisan and are within the scope of the invention.

Of course, due to the degeneracy of the genetic code, one of ordinary skill in the art will immediately recognize that a large number of the nucleic acid molecules having a sequence at least 80%, 85%, 90%, 92%, 95%, 96%, 97%, 98% or 99% identical to the nucleic acid sequence of the deposited cDNAs or the nucleic acid sequences shown in SEQ ID NO:25, FIG. 1A-1B (SEQ ID NO:1), FIG. 4A-4B (SEQ ID NO:4), or FIG. 7A-7B (SEQ ID NO:7) will encode polypeptides "having TR2 receptor activity." In fact, since degenerate variants of any of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TR2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that proteins are surprisingly tolerant of amino acid substitutions.

The present invention is further directed to polynucleotides comprising, or alternatively consisting of, fragments of the isolated nucleic acid molecules described herein. By a fragment of an isolated nucleic acid molecule having the nucleotide sequence of the deposited cDNAs or the nucleotide sequence shown in SEQ ID NO:25, FIG. 1A-1B (SEQ ID NO:1), FIG. 4A-4B (SEQ ID NO:4), or FIG. 7A-7B (SEQ ID NO:7) is intended fragments at least about 15 nt, and more preferably at least about 20 nt, still more preferably at least about 30 nt, and even more preferably, at least about 40 nt in length which are useful as diagnostic probes and primers as discussed herein. In this context "about" includes the particularly recited value and values larger or smaller by several (5, 4, 3, 2, or 1) nucleotides.

Of course, larger fragments 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825 or 848 nt in length are also useful according to the present invention as are fragments corresponding to most, if not all, of the nucleotide sequences of the deposited cDNAs or as shown in SEQ ID NO:25, FIG. 1A-1B (SEQ ID NO:1), FIG. 4A-4B (SEQ ID NO:4), or FIG. 7A-7B (SEQ ID NO:7). By a fragment at least 20 nt in length, for example, is intended fragments which include 20 or more contiguous bases from the nucleotide sequences of the deposited cDNAs or the nucleotide sequences as shown in SEQ ID NO:25, FIG. 1A-1B (SEQ ID NO:1), FIG. 4A-4B (SEQ ID NO:4), or FIG. 7A-7B (SEQ ID NO:7).

Preferred nucleic acid fragments of the present invention include nucleic acid molecules encoding polypeptides comprising, or alternatively consisting of, the mature TR2-SV1 receptor (predicted to constitute amino acid residues from about 37 to about 185 in FIG. 4A-4B (amino acid residues 1 to 149 in SEQ ID NO:5)) and the complete TR2-SV2 receptor (predicted to constitute amino acid residues from about 1 to about 136 in FIG. 7A-7B (SEQ ID NO:8)). In this context "about" includes the particularly recited value and values larger or smaller by several (5, 4, 3, 2, or 1) amino acids.

As above with the leader sequence, the amino acid residues constituting the extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain. In this context "about" includes the particularly recited value and values larger or smaller by several (5, 4, 3, 2, or 1) amino acids.

Preferred nucleic acid fragments of the present invention also include nucleic acid molecules encoding: a polypeptide comprising, or alternatively consisting of, the TR2 receptor protein of FIG. 1A-1B (SEQ ID NO:2) extracellular domain (predicted to constitute amino acid residues from about 37 to about 200 in FIG. 1A-1B (amino acid residues 1 to 164 in SEQ ID NO:2)); a polypeptide comprising, or alternatively consisting of, the TR2 receptor transmembrane domain (amino acid residues 201 to 225 in FIG. 1A-1B (amino acid residues 165 to 189 in SEQ ID NO:2)); a polypeptide comprising, or alternatively consisting of, the TR2 receptor intracellular domain (predicted to constitute amino acid residues from about 226 to about 283 in FIG. 1A-1B (amino acid residues 190 to 247 in SEQ ID NO:2)); and a polypeptide comprising, or alternatively consisting of, the TR2 receptor protein of FIG. 1A-1B (SEQ ID NO:2) extracellular and intracellular domains with all or part of the transmembrane domain deleted. In this context "about" includes the particularly recited value and values larger or smaller by several (5, 4, 3, 2, or 1) amino acids.

Preferred nucleic acid fragments of the present invention also include nucleic acid molecules encoding amino acid residues the extracellular domain of the TR2 protein having the amino acid sequence set out in SEQ ID NO:26, both with and without the associated leader sequence (amino acid residues –38 to 162 of SEQ ID NO:26 and amino acid residues 1 to 162 of SEQ ID NO:26, respectively).

Preferred nucleic acid fragments of the present invention also include nucleic acid molecules encoding epitope-bearing portions of the TR2 receptor proteins. In particular, such nucleic acid fragments of the present invention include nucleic acid molecules encoding: a polypeptide comprising, or alternatively consisting of, one, two, three, four, five or more amino acid sequences selected from amino acid residues from about 39 to about 70 in FIG. 1A-1B (amino acid residues 3 to 34 in SEQ ID NO:2); a polypeptide comprising, or alternatively consisting of, amino acid residues from about 106 to about 120 in FIG. 1 (amino acid residues 70 to 84 in SEQ ID NO:2); a polypeptide comprising, or alternatively consisting of, amino acid residues from about 142 to about 189 in FIG. 1A-1B (amino acid residues 106 to 153 in SEQ ID NO:2); a polypeptide comprising, or alternatively consisting of, amino acid residues from about 276 to about 283 in FIG. 1A-1B (amino acid residues 240 to 247 in SEQ ID NO:2); a polypeptide comprising, or alternatively consisting of, amino acid residues from about 39 to about 70 in FIG. 4A-4B (amino acid residues 3 to 34 in SEQ ID NO:5); amino acid residues from about 99 to about 136 in FIG. 4A-4B (amino acid residues 63 to 100 in SEQ ID NO:5); amino acid residues from about 171 to about 185 in FIG. 4A-4B (amino acid residues 135 to 149 in SEQ ID NO:5); amino acid residues from about 56 to about 68 in FIG. 7A-7B (SEQ ID NO:8); amino acid residues from about 93 to about 136 in FIG. 7A-7B (SEQ ID NO:8). In this context "about" includes the particularly recited value and values larger or smaller by several (5, 4, 3, 2, or 1) amino acids. The inventors have determined that the above polypeptide fragments are antigenic regions of the TR2 receptors. Methods for determining other such epitope-bearing portions of the TR2 proteins are described in detail below. Polypeptides encoded by these polynucleotides are also encompassed by the invention.

Representative examples of TR2 receptor polynucleotide fragments of the invention include, for example, fragments that comprise, or alternatively, consist of, a sequence from about nucleotide 1 to 64, 65 to 100, 101 to 150, 151 to 200, 201 to 250, 225-265, 251 to 300, 301 to 350, 351 to 372, 373 to 450, 451 to 500, 501 to 550, 551 to 600, 601 to 650, 651 to 700, 701 to 750, 751 to 800, 801 to 850, 851 to 900, 901 to 950, 951 to 1000, 1001 to 1050, 1051 to 1100, 1070-1113, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, or 1601 to 1670, of SEQ ID NO:1, the cDNA contained in the deposited identified as ATCC™ Deposit No. 97059, or the complementary strand of any of these fragments. In this context "about" includes the particularly recited ranges, larger or smaller by several (5, 4, 3, 2, or 1) nucleotides, at either terminus or at both termini. Polypeptides encoded by these polynucleotides are also encompassed by the invention.

Further representative examples of TR2 receptor polynucleotide fragments of the invention include, for example, fragments that comprise, or alternatively, consist of, a sequence from about nucleotide 373 to 433, 373 to 450, 451 to 500, 501 to 550, 551 to 600, 601 to 650, 651 to 700, 701 to 750, 751 to 800, 801 to 850, 851 to 900, or 901 to 927 of SEQ ID NO:4, from about nucleotide 247 to 300, 301 to 350, 351 to 372, 373 to 450, 451 to 500, 501 to 550, 551 to 600, or 601 to 654 of SEQ ID NO:7, or the cDNA contained in the deposited identified as ATCC™ Deposit No. 97058 or 97057, or the complementary strand of any of these polynucleotides. In this context "about" includes the particularly recited ranges, larger or smaller by several (5, 4, 3, 2, or 1) nucleotides, at either terminus or at both termini. Polypeptides encoded by these polynucleotides are also encompassed by the invention.

It is believed one or more of the cysteine repeat regions of the TR2 receptor disclosed in FIG. 1A-1B are important for interactions between the TR2 receptor and its ligands (e.g., AIM II (International Publication No. WO 97/34911), Lymphotoxin-α, and the Herpes virus protein HSV1 glycoprotein D (gD)). Accordingly, specific embodiments of the invention are directed to polynucleotides encoding polypeptides which comprise, or alternatively consist of, the amino acid sequence of cysteine repeat region A, B, C, or D disclosed in FIG. 16 and described in Example 6. Additional embodiments of the invention are directed to polynucleotides encoding TR2 receptor polypeptides which comprise, or alternatively consist of, any combination of 1, 2, 3, or all 4 of cysteine repeat regions A-D disclosed in FIG. 16 and described in Example 6. Additional preferred embodiments of the invention are directed to polypeptides which comprise, or alternatively consist of, the TR2 receptor amino acid sequence of cysteine repeat region A, B, C, or D disclosed in FIG. 16 and described in Example 6. Additional embodiments of the invention are directed to TR2 receptor polypeptides which comprise, or alternatively consist of, any combination of 1, 2, 3, or all 4 of cysteine repeat regions A-D disclosed in FIG. 16 and described in Example 6.

In certain embodiments, polynucleotides of the invention comprise, or alternatively consist of, a polynucleotide sequence at least 80%, 85%, 90%, 92%, 95%, 96%, 97%, 98% or 99% identical to the polynucleotide sequence encoding one, two, or all three of the cysteine-rich motifs described above. The present invention also encompasses the above polynucleotide sequences fused to a heterologous polynucleotide sequence. Polypeptides encoded by these nucleic acids and/or polynucleotide sequences are also encompassed by the invention.

In another embodiment, the invention provides an isolated nucleic acid molecule comprising, or alternatively consisting of, a polynucleotide which hybridizes under stringent hybridization conditions to one, two, or all three of the cysteine-rich motifs described above polynucleotides of the invention described above, or the complementary strand thereof. The meaning of the phrase "stringent conditions" as used herein is described infra.

Preferably, the polynucleotide fragments of the invention encode a polypeptide which demonstrates one or more TR2 receptor functional activities. By a polypeptide demonstrating a TR2 receptor "functional activity" is meant, a polypeptide capable of displaying one or more known functional activities associated with a full-length (complete) TR2 receptor protein. Such functional activities include, but are not limited to, biological activity (e.g., inhibition of B cell proliferation), antigenicity, immunogenicity (ability to generate antibody which binds to a TR2 receptor polypeptide), the ability to bind (or compete with a TR2 receptor polypeptide for binding) to an anti-TR2 receptor antibody, the ability to form multimers with TR2 receptor polypeptides of the invention, and ability to bind to a receptor or ligand for a TR2 receptor polypeptide (e.g., AIM II (International Publication No. WO 97/34911), Lymphotoxin-α, and the Herpes virus protein HSV1 glycoprotein D (gD)).

The functional activity of TR2 receptor polypeptides, and fragments, variants derivatives, and analogs thereof, can be assayed by various methods.

For example, in one embodiment where one is assaying for the ability to bind or compete with full-length TR2 receptor polypeptides for binding to anti-TR2 receptor antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a TR2 receptor ligand is identified (e.g., AIM II (International Publication No. WO 97/34911), Lymphotoxin-α, and the Herpes virus protein HSV1 gD), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., *Microbiol. Rev.* 59:94-123 (1995). In another embodiment, physiological correlates of TR2 receptor binding to its substrates (signal transduction) can be assayed.

In addition, assays described herein (see, e.g., Examples 6 and 8 and otherwise known in the art may routinely be applied to measure the ability of TR2 receptor polypeptides and fragments, variants derivatives and analogs thereof to elicit TR2 receptor related biological activity (e.g., inhibition of B cell proliferation in vitro or in vivo). Other methods will be known to the skilled artisan and are within the scope of the invention.

In another aspect, the invention provides isolated nucleic acid molecules comprising, or alternatively consisting of, polynucleotides which hybridizes under stringent hybridization conditions to a portion of the polynucleotide of one of the nucleic acid molecules of the invention described above, for instance, the complement of a polynucleotide fragment described herein, or the cDNAs contained in ATCC™ Deposits 97059, 97058 and 97057. By "stringent hybridization conditions" is intended overnight incubation at 42° C. in a solution comprising, or alternatively consisting of: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1× SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. In this context "about" includes the particularly recited value and values larger or smaller by several (5, 4, 3, 2, or 1) nucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNAs or the nucleotide sequences as shown in SEQ ID NO:25, FIG. 1A-1B (SEQ ID NO:1), FIG. 4A-4B (SEQ ID NO:4), or FIG. 7A-7B (SEQ ID NO:7)).

Of course, a polynucleotide which hybridizes only to a poly A sequence (such as the 3' terminal poly(A) tract of the TR2 receptor cDNA sequences shown in SEQ ID NO:25, FIG. 1A-1B (SEQ ID NO:1), FIG. 4A-4B (SEQ ID NO:4), or FIG. 7A-7B (SEQ ID NO:7)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated from an oligo-dT primed cDNA library).

As indicated, nucleic acid molecules of the present invention which encode TR2 polypeptides may include, but are not limited to those encoding the amino acid sequences of the mature polypeptides, by itself; the coding sequence for the mature polypeptides and additional sequences, such as those encoding the about 36 amino acid leader or secretory sequences, such as pre-, or pro- or prepro-protein sequences; the coding sequence of the mature polypeptides, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptides may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the TR2 receptors fused to IgG-Fc at the N- or C-terminus.

The present invention further relates to variants of the nucleic acid molecules of the present invention, which encode portions, analogs or derivatives of the TR2 receptors. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985).

Non-naturally occurring variants may be produced using art-known mutagenesis techniques, which include, but are not limited to: oligonucleotide mediated mutagenesis, alanine scanning, PCR mutagenesis, site directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London Ser. A* 317:415 (1986)).

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TR2 receptors or portions thereof. Also especially preferred in this regard are conservative substitutions.

Vectors and Host Cells

The present invention also relates to vectors which include the isolated DNA molecules of the present invention, host cells which are genetically engineered with the recombinant vectors, and the production of TR2 polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate heterologous hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, human hIL-5 receptor has been fused with Fc portions for the purpose of high-throughput screening assays to identify antagonists of hIL-5. See, D. Bennett et al., *Journal of Molecular Recognition*, Vol. 8:52-58 (1995) and K. Johanson et al., *The Journal of Biological Chemistry*, Vol. 270, No. 16:9459-9471 (1995).

TR2 receptors can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., the TR2 receptor coding sequence), and/or to include genetic material (e.g., heterologous polynucleotide sequences) that is operably associated with TR2 receptor polynucleotides of the invention, and which activates, alters, and/or amplifies endogenous TR2 receptor polynucleotides. For example, techniques known in the art may be used to operably associate heterologous control regions (e.g., promoter and/or enhancer) and endogenous TR2 receptor polynucleotide sequences via homologous recombination (see, e.g., U.S. Pat. No. 5,641,670, issued Jun. 24, 1997; International Publication Number WO 96/29411, published Sep. 26, 1996; International Publication Number WO 94/12650, published Aug. 4, 1994; Koller et al., *Proc. Natl. Acad. Sci. U.S.A.* 86:8932-8935 (1989); and Zijlstra et al., *Nature* 342:435-438 (1989), the disclosures of each of which are incorporated by reference in their entireties).

TR2 Polypeptides and Fragments

The invention further provides isolated TR2 polypeptides having the amino acid sequence encoded by the deposited cDNAs, or the amino acid sequence shown in SEQ ID NO:26, FIG. 1A-1B (SEQ ID NO:2), FIG. 4A-4B (SEQ ID NO:5), or FIG. 7A-7B (SEQ ID NO:8), or a peptide or polypeptide comprising, or alternatively consisting of, a portion of the above polypeptides.

The polypeptides of this invention may be membrane bound or may be in a soluble circulating form. Soluble peptides are defined by amino acid sequence wherein the sequence comprises, or alternatively consists of, the polypeptide sequence lacking the transmembrane domain. One example of such a soluble form of the TR2 receptor is the TR2-SV1 splice variant which has a secretory leader sequence but lacks both the intracellular and transmembrane domains. Thus, the TR2-SV1 receptor protein appears to be secreted in a soluble form from cells which express this protein.

The polypeptides of the present invention may exist as a membrane bound receptor having a transmembrane region and an intra- and extracellular region or they may exist in soluble form wherein the transmembrane domain is lacking. One example of such a form of the TR2 receptor is the TR2 receptor shown in FIG. 1A-1B (SEQ ID NO:2) which contains, in addition to a leader sequence, transmembrane, intracellular and extracellular domains. Thus, this form of the TR2 receptor appears to be localized in the cytoplasmic membrane of cells which express this protein.

The polypeptides of the present invention also include the polypeptide encoded by the deposited cDNAs including the leader; the polypeptide encoded by the deposited the cDNAs minus the leader (i.e., the mature protein); the polypeptides of SEQ ID NO:26, FIG. 1A-1B (SEQ ID NO:2) or FIG. 4A-4B (SEQ ID NO:5) including the leader; the polypeptides of SEQ ID NO:26, FIG. 1A-1B (SEQ ID NO:2) or FIG. 4A-4B (SEQ ID NO:5) including the leader but minus the N-terminal methionine; the polypeptides of SEQ ID NO:26, FIG. 1A-1B (SEQ ID NO:2) or FIG. 4A-4B (SEQ ID NO:5) minus the leader; the polypeptide of FIG. 7A-7B (SEQ ID NO:8); the extracellular domain, the transmembrane domain, and the intracellular domain of the TR2 receptor shown in SEQ ID NO:26 or FIG. 1A-1B (SEQ ID NO:2); and polypeptides which are at least 80% identical, more preferably at least 85%, 90%, 92% or 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a TR2 polypeptide is intended that the amino acid sequence of the polypeptide is identical to the reference sequence except that the polypeptide sequence may include up to five amino acid alterations per each 100 amino acids of the reference amino acid of a TR2 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequence shown in SEQ ID NO:26, FIG. 1A-1B (SEQ ID NO:2), FIG. 4A-4B (SEQ ID NO:5), or FIG. 7A-7B (SEQ ID NO:8) or to the amino acid sequence encoded by one of the deposited cDNAs can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

It will be recognized in the art that some amino acid sequences of the TR2 receptors can be varied without significant effect to the structure or function of the protein. If such differences in sequence are contemplated, it should be remembered that there will be critical areas on the protein which determine activity. Thus, the invention further includes variations of the TR2 receptors which show substantial TR2 receptor activity or which include regions of TR2 proteins such as the protein portions discussed below. Such mutants include deletions, insertions, inversions, repeats, and type substitutions. Guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, the fragment, derivative or analog of the polypeptides of SEQ ID NO:26, FIG. 1A-1B (SEQ ID NO:2), FIG. 4A-4B (SEQ ID NO:5), and FIG. 7A-7B (SEQ ID NO:8), or that encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein. Polynucleotides encoding these fragments, derivatives or analogs are also encompassed by the invention.

Of particular interest are substitutions of charged amino acids with another charged amino acid and with neutral or negatively charged amino acids. The latter results in proteins with reduced positive charge to improve the characteristics of the TR2 proteins. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-α to only one of the two known types of TNF receptors. Thus, the TR2 receptors of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table I).

TABLE I

CONSERVATIVE AMINO ACID SUBSTITUTIONS.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the TR2 proteins of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides of the present invention are preferably provided in an isolated form. By "isolated polypeptide", is intended a polypeptide removed from its native environment. Thus, a polypeptide produced and contained within a recombinant host cell would be considered "isolated" for purposes of the present invention. Also intended as an "isolated polypeptide" are polypeptides that have been purified, partially or substantially, from a recombinant host. For example, recombinantly produced versions of the TR2 receptors can be substantially purified by the one-step method described in Smith and Johnson, *Gene* 67:31-40 (1988).

The polypeptides of the present invention have uses which include, but are not limited to, as sources for generating antibodies that bind the polypeptides of the invention, and as molecular weight markers on SDS-PAGE gels or on molecular sieve gel filtration columns using methods well known to those of skill in the art.

TR2 polypeptides of the invention can also inhibit mixed lymphocyte reactions (MLRs). As discussed below in Example 6, TR2 polypeptides inhibit three-way MLRs. An additional method for performing three-way MLRs is discussed in Harrop et al., *Jour. Immunol.* 161: 1786-1794 (1998), which incorporated herein by reference.

The present application is also directed to proteins containing polypeptides at least 80%, 85%, 90%, 92%, 95%, 96%, 97%, 98% or 99% identical to the TR2 receptor polypeptide sequence set forth herein as $n^1-m^1$, $n^2-m^2$, $n^3-m^3$, $n^4-m^4$, and/or $n^5-m^5$. In preferred embodiments, the application is directed to proteins containing polypeptides at least 80%, 85%, 90%, 92%, 95%, 96%, 97%, 98% or 99% identical to polypeptides having the amino acid sequence of the specific TR2 receptor N- and C-terminal deletions recited herein. Polynucleotides encoding these polypeptides are also encompassed by the invention.

In certain preferred embodiments, TR2 receptor proteins of the invention comprise, or alternatively consist of, fusion proteins as described above wherein the TR2 receptor polypeptides are those described as $n^1-m^1$, $n^2-m^2$, $n^3-m^3$, $n^4-m^4$, and/or $n^5-m^5$ herein. In preferred embodiments, the application is directed to nucleic acid molecules at least 80%, 85%, 90%, 92%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

As mentioned above, even if deletion of one or more amino acids from the N-terminus of a protein results in modification of loss of one or more biological functions of the protein, other biological activities may still be retained. Thus, the ability of shortened TR2 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a TR2 mutein with a large number of deleted N-terminal amino acid residues may retain some biological or immunogenic activities. In fact, peptides composed of as few as six TR2 amino acid residues may often evoke an immune response.

Accordingly, the present invention further provides polypeptides having one or more residues deleted from the amino terminus of the TR2 amino acid sequence shown in FIG. 1A-1B (i.e., SEQ ID NO:2), up to the glycine residue at position number 278 and polynucleotides encoding such polypeptides. In particular, the present invention provides polypeptides comprising, or alternatively consisting of, the amino acid sequence of residues $n^1$-283 of FIG. 1A-1B (SEQ ID NO:2), where $n^1$ is an integer in the range of 2 to 278. Polynucleotides encoded by these polypeptides are also encompassed by the invention.

More in particular, the invention provides polynucleotides encoding polypeptides comprising, or alternatively consisting of, the amino acid sequence of residues of E-2 to H-283; P-3 to H-283; P-4 to H-283; G-5 to H-283; D-6 to H-283; W-7 to H-283; G-8 to H-283; P-9 to H-283; P-10 to H-283; P-11 to H-283; W-12 to H-283; R-13 to H-283; S-14 to H-283; T-15 to H-283; P-16 to H-283; K-17 to H-283; T-18 to H-283; D-19 to H-283; V-20 to H-283; L-21 to H-283; R-22 to H-283; L-23 to H-283; V-24 to H-283; L-25 to H-283; Y-26 to H-283; L-27 to H-283; T-28 to H-283; F-29 to H-283; L-30 to H-283; G-31 to H-283; A-32 to H-283; P-33 to H-283; C-34 to H-283; Y-35 to H-283; A-36 to H-283; P-37 to H-283; A-38 to H-283; L-39 to H-283; P-40 to H-283; S-41 to H-283; C-42 to H-283; K-43 to H-283; E-44 to H-283; D-45 to H-283; E-46 to H-283; Y-47 to H-283; P-48 to H-283; V-49 to H-283; G-50 to H-283; S-51 to H-283; E-52 to H-283; C-53 to H-283; C-54 to H-283; P-55 to H-283; K-56 to H-283; C-57 to H-283; S-58 to H-283; P-59 to H-283; G-60 to H-283; Y-61 to H-283; R-62 to H-283; V-63 to H-283; K-64 to H-283; E-65 to H-283; A-66 to H-283; C-67 to H-283; G-68 to H-283; E-69 to H-283; L-70 to H-283; T-71 to H-283; G-72 to H-283; T-73 to H-283; V-74 to H-283; C-75 to H-283; E-76 to H-283; P-77 to H-283; C-78 to H-283; P-79 to H-283; P-80 to H-283; G-81 to H-283; T-82 to H-283; Y-83 to H-283; I-84 to H-283; A-85 to H-283; K-86 to H-283; L-87 to H-283; N-88 to H-283; G-89 to H-283; L-90 to H-283; S-91 to H-283; K-92 to H-283; C-93 to H-283; L-94 to H-283; Q-95 to H-283; C-96 to H-283; Q-97 to H-283; M-98 to H-283; C-99 to H-283; D-100 to H-283; P-101 to H-283; A-102 to H-283; M-103 to H-283; G-104 to H-283; L-105 to H-283; R-106 to H-283; A-107 to H-283; S-108 to H-283; R-109 to H-283; N-110 to H-283; C-111 to H-283; S-112 to H-283; R-113 to H-283; T-114 to H-283; E-115 to H-283; N-116 to H-283; A-117 to H-283; V-118 to H-283; C-119 to H-283; G-120 to H-283; C-121 to H-283; S-122 to H-283; P-123 to H-283; G-124 to H-283; H-125 to H-283; F-126 to H-283; C-127 to H-283; I-128 to H-283; V-129 to H-283; Q-130 to H-283; D-131 to H-283; G-132 to H-283; D-133 to H-283; H-134 to H-283; C-135 to H-283; A-136 to H-283; A-137 to H-283; C-138 to H-283; R-139 to H-283; A-140 to H-283; Y-141 to H-283; A-142 to H-283; T-143 to H-283; S-144 to H-283; S-145 to H-283; P-146 to H-283; G-147 to H-283; Q-148 to H-283; R-149 to H-283; V-150 to H-283; Q-151 to H-283; K-152 to H-283; G-153 to H-283; G-154 to H-283; T-155 to H-283; E-156 to H-283; S-157 to H-283; Q-158 to H-283; D-159 to H-283; T-160 to H-283; L-161 to H-283; C-162 to H-283; Q-163 to H-283; N-164 to H-283; C-165 to H-283; P-166 to H-283; P-167 to H-283; G-168 to H-283; T-169 to H-283; F-170 to H-283; S-171 to H-283; P-172 to H-283; N-173 to H-283; G-174 to H-283; T-175 to H-283; L-176 to H-283; E-177 to H-283; E-178 to H-283; C-179 to H-283; Q-180 to H-283; H-181 to H-283; Q-182 to H-283; T-183 to H-283; K-184 to H-283; C-185 to H-283; S-186 to H-283; W-187 to H-283; L-188 to H-283; V-189 to H-283; T-190 to H-283; K-191 to H-283; A-192 to H-283; G-193 to H-283; A-194 to H-283; G-195 to H-283; T-196 to H-283; S-197 to H-283; S-198 to H-283; S-199 to H-283; H-200 to H-283; W-201 to H-283; V-202 to H-283; W-203 to H-283; W-204 to H-283; F-205 to H-283; L-206 to H-283; S-207 to H-283; G-208 to H-283; S-209 to H-283; L-210 to H-283; V-211 to H-283; I-212 to H-283; V-213 to H-283; I-214 to H-283; V-215 to H-283; C-216 to H-283; S-217 to H-283; T-218 to H-283; V-219 to H-283; G-220 to H-283; L-221 to H-283; I-222 to H-283; I-223 to H-283; C-224 to H-283; V-225 to H-283; K-226 to H-283; R-227 to H-283; R-228 to H-283; K-229 to H-283; P-230 to H-283; R-231 to H-283; G-232 to H-283; D-233 to H-283; V-234 to H-283; V-235 to H-283; K-236 to H-283; V-237 to H-283; I-238 to H-283; V-239 to H-283; S-240 to H-283; V-241 to H-283; Q-242 to H-283; R-243 to H-283; K-244 to H-283; R-245 to H-283; Q-246 to H-283; E-247 to H-283; A-248 to H-283; E-249 to H-283; G-250 to H-283; E-251 to H-283; A-252 to H-283; T-253 to H-283; V-254 to H-283; I-255 to H-283; E-256 to H-283; A-257 to H-283; L-258 to H-283; Q-259 to H-283; A-260 to H-283; P-261 to H-283; P-262 to H-283; D-263 to H-283; V-264 to H-283; T-265 to H-283; T-266 to H-283; V-267 to H-283; A-268 to H-283; V-269 to H-283; E-270 to H-283; E-271 to H-283; T-272 to H-283; I-273 to H-283; P-274 to H-283; S-275 to H-283; F-276 to H-283; T-277 to H-283; and G-278 to H-283 of the TR2 sequence shown in FIG. 1A-1B. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

Also as mentioned above, even if deletion of one or more amino acids from the C-terminus of a protein results in modification of loss of one or more biological functions of the protein, other biological activities may still be retained. Thus, the ability of the shortened TR2 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TR2 mutein with a large number of deleted C-terminal amino acid residues may retain some biological or immunogenic activities. In fact, peptides composed of as few as six TR2 amino acid residues may often evoke an immune response.

Accordingly, the present invention further provides polypeptides having one or more residues deleted from the carboxy terminus of the amino acid sequence of the TR2 polypeptide shown in FIG. 1A-1B (SEQ ID NO:2), up to the aspartic acid residue at position number 6, and polynucleotides encoding such polypeptides. In particular, the present invention provides polypeptides comprising, or alternatively consisting of, the amino acid sequence of residues 1-$m^1$ of FIG. 1A-1B (i.e., SEQ ID NO:2), where $m^1$ is an integer in the range of 6 to 282. Polynucleotides encoded by these polypeptides are also encompassed by the invention.

More in particular, the invention provides polynucleotides encoding polypeptides comprising, or alternatively consisting of, the amino acid sequence of residues M-1 to N-282; M-1 to P-281; M-1 to S-280; M-1 to R-279; M-1 to G-278; M-1 to T-277; M-1 to F-276; M-1 to S-275; M-1 to P-274; M-1 to I-273; M-1 to T-272; M-1 to E-271; M-1 to E-270; M-1 to V-269; M-1 to A-268; M-1 to V-267; M-1 to T-266; M-1 to T-265; M-1 to V-264; M-1 to D-263; M-1 to P-262; M-1 to P-261; M-1 to A-260; M-1 to Q-259; M-1 to L-258; M-1 to A-257; M-1 to E-256; M-1 to I-255; M-1 to V-254; M-1 to T-253; M-1 to A-252; M-1 to E-251; M-1 to G-250; M-1 to E-249; M-1 to A-248; M-1 to E-247; M-1 to Q-246; M-1 to R-245; M-1 to K-244; M-1 to R-243; M-1 to Q-242; M-1 to V-241; M-1 to S-240; M-1 to V-239; M-1 to I-238; M-1 to V-237; M-1 to K-236; M-1 to V-235; M-1 to V-234; M-1 to D-233; M-1 to G-232; M-1 to R-231; M-1 to P-230; M-1 to K-229; M-1 to R-228; M-1 to R-227; M-1 to K-226; M-1 to V-225; M-1 to C-224; M-1 to I-223; M-1 to I-222; M-1 to L-221; M-1 to G-220; M-1 to V-219; M-1 to T-218; M-1 to S-217; M-1 to C-216; M-1 to V-215; M-1 to I-214; M-1 to V-213; M-1 to I-212; M-1 to V-211; M-1 to L-210; M-1 to S-209; M-1 to G-208; M-1 to S-207; M-1 to L-206; M-1 to F-205; M-1 to W-204; M-1 to W-203; M-1 to V-202; M-1 to W-201; M-1 to H-200; M-1 to S-199; M-1 to S-198; M-1 to S-197; M-1 to T-196; M-1 to G-195; M-1 to A-194; M-1 to G-193; M-1 to A-192; M-1 to K-191; M-1 to T-190; M-1 to V-189; M-1 to L-188; M-1 to W-187; M-1 to S-186; M-1 to C-185; M-1 to K-184; M-1 to T-183; M-1 to Q-182; M-1 to H-181; M-1 to Q-180; M-1 to C-179; M-1 to E-178; M-1 to E-177; M-1 to L-176; M-1 to T-175; M-1 to G-174; M-1 to N-173; M-1 to P-172; M-1 to S-171; M-1 to F-170; M-1 to T-169; M-1 to G-168; M-1 to P-167; M-1 to P-166; M-1 to C-165; M-1 to N-164; M-1 to Q-163; M-1 to C-162; M-1 to L-161; M-1 to T-160; M-1 to D-159; M-1 to Q-158; M-1 to S-157; M-1 to E-156; M-1 to T-155; M-1 to G-154; M-1 to G-153; M-1 to K-152; M-1 to Q-151; M-1 to V-150; M-1 to R-149; M-1 to Q-148; M-1 to G-147; M-1 to P-146; M-1 to S-145; M-1 to S-144; M-1 to T-143; M-1 to A-142; M-1 to Y-141; M-1 to A-140; M-1 to R-139; M-1 to C-138; M-1 to A-137; M-1 to A-136; M-1 to C-135; M-1 to H-134; M-1 to D-133; M-1 to G-132; M-1 to D-131; M-1 to Q-130; M-1 to V-129; M-1 to I-128; M-1 to C-127; M-1 to F-126; M-1 to H-125; M-1 to G-124; M-1 to P-123; M-1 to S-122; M-1 to C-121; M-1 to G-120; M-1 to C-119; M-1 to V-118; M-1 to A-117; M-1 to N-116; M-1 to E-S5; M-1 to T-114; M-1 to R-113; M-1 to S-112; M-1 to C-111; M-1 to N-110; M-1 to R-109; M-1 to S-108; M-1 to A-107; M-1 to R-106; M-1 to L-105; M-1 to G-104; M-1 to M-103; M-1 to A-102; M-1 to P-101; M-1 to D-100; M-1 to C-99; M-1 to M-98; M-1 to Q-97; M-1 to C-96; M-1 to Q-95; M-1 to L-94; M-1 to C-93; M-1 to K-92; M-1 to S-91; M-1 to L-90; M-1 to G-89; M-1 to N-88; M-1 to L-87; M-1 to H-86; M-1 to A-85; M-1 to I-84; M-1 to Y-83; M-1 to T-82; M-1 to G-81; M-1 to P-80; M-1 to P-79; M-1 to C-78; M-1 to P-77; M-1 to E-76; M-1 to C-75; M-1 to V-74; M-1 to T-73; M-1 to G-72; M-1 to T-71; M-1 to L-70; M-1 to E-69; M-1 to G-68; M-1 to C-67; M-1 to A-66; M-1 to E-65; M-1 to K-64; M-1 to V-63; M-1 to R-62; M-1 to Y-61; M-1 to G-60; M-1 to P-59; M-1 to S-58; M-1 to C-57; M-1 to K-56; M-1 to P-55; M-1 to C-54; M-1 to C-53; M-1 to E-52; M-1 to S-51; M-1 to G-50; M-1 to V-49; M-1 to P-48; M-1 to Y-47; M-1 to E-46; M- to D-45; M-1 to E-44; M-1 to K-43; M-1 to C-42; M-1 to S-41; M-1 to P-40; M-1 to L-39; M-1 to A-38; M-1 to P-37; M-1 to A-36; M-1 to Y-35; M-1 to C-34; M-1 to P-33; M-1 to A-32; M-1 to G-31; M-1 to L-30; M-1 to F-29; M-1 to T-28; M-1 to L-27; M-1 to Y-26; M-1 to L-25; M-1 to V-24; M-1 to L-23; M-1 to R-22; M-1 to L-21; M-1 to V-20; M-1 to D-19; M-1 to T-18; M-1 to K-17; M-1 to P-16; M-1 to T-15; M-1 to S-14; M-1 to R-13; M-1 to W-12; M-1 to P-11; M-1 to P-10; M-1 to P-9; M-1 to G-8; M-1 to W-7; and M-1 to D-6 of the sequence of the TR2 sequence shown in FIG. 1A-1B. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

The invention also provides polypeptides having one or more amino acids deleted from both the amino and the carboxyl termini of a TR2 polypeptide, which may be described generally as having residues $n^1$-$m^1$ of FIG. 1A-1B (i.e., SEQ ID NO:2), where $n^1$ and $m^1$ are integers as described above. Polynucleotides encoded by these polypeptides are also encompassed by the invention.

Also mentioned above, even if deletion of one or more amino acids from the N-terminus of a protein results in modification of loss of one or more biological functions of the protein, other biological activities may still be retained. Thus, the ability of shortened TR2-SV1 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a TR2-SV1 mutein with a large number of deleted N-terminal amino acid residues may retain some biological or immunogenic activities. In fact, peptides composed of as few as six TR2-SV1 amino acid residues may often evoke an immune response.

Accordingly, the present invention further provides polypeptides having one or more residues deleted from the amino terminus of the TR2-SV1 amino acid sequence shown in FIG. 4A-4B (i.e., SEQ ID NO:5), up to the threonine residue at position number 180 and polynucleotides encoding such polypeptides. In particular, the present invention provides polypeptides comprising, or alternatively consisting of, the amino acid sequence of residues $n^2$-185 of FIG. 4A-4B (SEQ ID NO:5), where $n^2$ is an integer in the range of 2 to 180, and 180 is the position of the first residue from the N-terminus of the complete TR2-SV1 polypeptide believed to be required for at least immunogenic activity of the TR2-SV1 polypeptide. Polynucleotides encoded by these polypeptides are also encompassed by the invention.

More in particular, the invention provides polynucleotides encoding polypeptides comprising, or alternatively consisting of, the amino acid sequence of residues of E-2 to A-185; P-3 to A-185; P-4 to A-185; G-5 to A-185; D-6 to A-185; W-7 to A-185; G-8 to A-185; P-9 to A-185; P-10 to A-185; P-11 to A-185; W-12 to A-185; R-13 to A-185; S-14 to A-185; T-15 to A-185; P-16 to A-185; R-17 to A-185; T-18 to A-185; D-19 to A-185; V-20 to A-185; L-21 to A-185; R-22 to A-185; L-23 to A-185; V-24 to A-185; L-25 to A-185; Y-26 to A-185; L-27 to A-185; T-28 to A-185; F-29 to A-185; L-30 to A-185; G-31 to A-185; A-32 to A-185; P-33 to A-185; C-34 to A-185; Y-35 to A-185; A-36 to A-185; P-37 to A-185; A-38 to A-185; L-39 to A-185; P-40 to A-185; S-41 to A-185; C-42 to A-185; K-43 to A-185; E-44 to A-185; D-45 to A-185; E-46 to A-185; Y-47 to A-185; P-48 to A-185; V-49 to A-185; G-50 to A-185; S-51 to A-185; E-52 to A-185; C-53 to A-185; C-54 to A-185; P-55 to A-185; K-56 to A-185; C-57 to A-185; S-58 to A-185; P-59 to A-185; G-60 to A-185; Y-61 to A-185; R-62 to A-185; V-63 to A-185; K-64 to A-185; E-65 to A-185; A-66 to A-185; C-67 to A-185; G-68 to A-185; E-69 to A-185; L-70 to A-185; T-71 to A-185; G-72 to A-185; T-73 to A-185; V-74 to A-185; C-75 to A-185; E-76 to A-185; P-77 to A-185; C-78 to A-185; P-79 to A-185; P-80 to A-185; G-81 to A-185; T-82 to A-185; Y-83 to A-185; I-84 to A-185; A-85 to A-185; H-86 to A-185; L-87 to A-185; N-88 to A-185; G-89 to A-185; L-90 to A-185; S-91 to A-185; K-92 to A-185; C-93 to A-185; L-94 to A-185; Q-95 to A-185; C-96 to A-185; Q-97 to A-185; M-98 to A-185; C-99 to A-185; D-100 to A-185; P-101 to A-185; D-102 to A-185; I-103 to A-185; G-104 to A-185; S-105 to A-185; P-106 to A-185; C-107 to A-185; D-108 to A-185; L-109 to A-185; R-110 to A-185; G-111 to A-185; R-112 to A-185; G-113 to A-185; H-114 to A-185; L-115 to A-185; E-116 to A-185; A-117 to A-185; G-118 to A-185; A-119 to A-185; H-120 to A-185; L-121 to A-185; S-122 to A-185; P-123 to A-185; G-124 to A-185; R-125 to A-185; Q-126 to A-185; K-127 to A-185; G-128 to A-185; E-129 to A-185; P-130 to A-185; D-131 to A-185; P-132 to A-185; E-133 to A-185; V-134 to A-185; A-135 to A-185; F-136 to A-185; E-137 to A-185; S-138 to A-185; L-139 to A-185; S-140 to A-185; A-141 to A-185; E-142 to A-185; P-143 to A-185; V-144 to A-185; H-145 to A-185; A-146 to A-185; A-147 to A-185; N-148 to A-185; G-149 to A-185; S-150 to A-185; V-151 to A-185; P-152 to A-185; L-153 to A-185; E-154 to A-185; P-155 to A-185; H-156 to A-185; A-157 to A-185; R-158 to A-185; L-159 to A-185; S-160 to A-185; M-161 to A-185; A-162 to A-185; S-163 to A-185; A-164 to A-185; P-165 to A-185; C-166 to A-185; G-167 to A-185; Q-168 to A-185; A-169 to A-185; G-170 to A-185; L-171 to A-185; H-172 to A-185; L-173 to A-185; R-174 to A-185; D-175 to A-185; R-176 to A-185; A-177 to A-185; D-178 to A-185; G-179 to A-185; and T-180 to A-185 of the TR2-SV1 sequence shown in FIG. 4A-4B. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

Also as mentioned above, even if deletion of one or more amino acids from the C-terminus of a protein results in modification of loss of one or more biological functions of the protein, other biological activities may still be retained. Thus, the ability of the shortened TR2-SV1 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TR2-SV1 mutein with a large number of deleted C-terminal amino acid residues may retain some biological or immunogenic activities. In fact, peptides composed of as few as six TR2-SV1 amino acid residues may often evoke an immune response.

Accordingly, the present invention further provides polypeptides having one or more residues deleted from the carboxy terminus of the amino acid sequence of the TR2-SV1 polypeptide shown in FIG. 4A-4B (SEQ ID NO:5), up to the aspartic acid residue at position number 6, and polynucleotides encoding such polypeptides. In particular, the present invention provides polypeptides comprising, or alternatively consisting of, the amino acid sequence of residues 1-$m^2$ of FIG. 4A-4B (i.e., SEQ ID NO:5), where $m^2$ is an integer in the range of 6 to 184. Polynucleotides encoded by these polypeptides are also encompassed by the invention.

More in particular, the invention provides polynucleotides encoding polypeptides comprising, or alternatively consisting of, the amino acid sequence of residues M-1 to R-184; M-1 to G-183; M-1 to G-182; M-1 to P-181; M-1 to T-180; M-1 to G-179; M-1 to D-178; M-1 to A-177; M-1 to R-176; M-1 to D-175; M-1 to R-174; M-1 to L-173; M-1 to H-172; M-1 to L-171; M-1 to G-170; M-1 to A-169; M-1 to Q-168; M-1 to G-167; M-1 to C-166; M-1 to P-165; M-1 to A-164; M-1 to S-163; M-1 to A-162; M-1 to M-161; M-1 to S-160; M-1 to L-159; M-1 to R-158; M-1 to A-157; M-1 to H-156; M-1 to P-155; M-1 to E-154; M-1 to L-153; M-1 to P-152; M-1 to V-151; M-1 to S-150; M-1 to G-149; M-1 to N-148; M-1 to A-147; M-1 to A-146; M-1 to H-145; M-1 to V-144; M-1 to P-143; M-1 to E-142; M-1 to A-141; M-1 to S-140; M-1 to L-139; M-1 to S-138; M-1 to E-137; M-1 to F-136; M-1 to A-135; M-1 to V-134; M-1 to E-133; M-1 to P-132; M-1 to D-131; M-1 to P-130; M-1 to E-129; M-1 to G-128; M-1 to K-127; M-1 to Q-126; M-1 to R-125; M-1 to G-124; M-1 to P-123; M-1 to S-122; M-1 to L-121; M-1 to H-120; M-1 to A-119; M-1 to G-118; M-1 to A-117; M-1 to E-116; M-1 to L-115; M-1 to H-114; M-1 to G-113; M-1 to R-112; M-1 to G-111; M-1 to R-110; M-1 to L-109; M-1 to D-108; M-1 to C-107; M-1 to P-106; M-1 to S-105; M-1 to G-104; M-1 to I-103; M-1 to D-102; M-1 to P-101; M-1 to D-100; M-1 to C-99; M-1 to M-98; M-1 to Q-97; M-1 to C-96; M-1 to Q-95; M-1 to L-94; M-1 to C-93; M-1 to K-92; M-1 to S-91; M-1 to L-90; M-1 to G-89; M-1 to N-88; M-1 to L-87; M-1 to H-86; M-1 to A-85; M-1 to I-84; M-1 to Y-83; M-1 to T-82; M-1 to G-81; M-1 to P-80; M-1 to P-79; M-1 to C-78; M-1 to P-77; M-1 to E-76; M-1 to C-75; M-1 to V-74; M-1 to T-73; M-1 to G-72; M-1 to T-71; M-1 to L-70; M-1 to E-69; M-1 to G-68; M-1 to C-67; M-1 to A-66; M-1 to E-65; M-1 to K-64; M-1 to V-63; M-1 to R-62; M-1 to Y-61; M-1 to G-60; M-1 to P-59; M-1 to S-58; M-1 to C-57; M-1 to K-56; M-1 to P-55; M-1 to C-54; M-1 to C-53; M-1 to E-52; M-1 to S-51; M-1 to G-50; M-1 to V-49; M-1 to P-48; M-1 to Y-47; M-1 to E-46; M-1 to D-45; M-1 to E-44; M-1 to K-43; M-1 to C-42; M-1 to S-41; M-1 to P-40; M-1 to L-39; M-1 to A-38; M-1 to P-37; M-1 to A-36; M-1 to Y-35; M-1 to C-34; M-1 to P-33; M-1 to A-32; M-1 to G-31; M-1 to L-30; M-1 to F-29; M-1 to T-28; M-1 to L-27; M-1 to Y-26; M-1 to L-25; M-1 to V-24; M-1 to L-23; M-1 to R-22; M-1 to L-21; M-1 to V-20; M-1 to D-19; M-1 to T-18; M-1 to R-17; M-1 to P-16; M-1 to T-15; M-1 to S-14; M-1 to R-13; M-1 to W-12; M-1 to P-11; M-1 to P-10; M-1 to P-9; M-1 to G-8; M-1 to W-7; and M-1 to D-6 of the sequence of the TR2-SV1 sequence shown in FIG. 4A-4B. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

The invention also provides polypeptides having one or more amino acids deleted from both the amino and the carboxyl termini of a TR2-SV1 polypeptide, which may be described generally as having residues $n^2$-$m^2$ of FIG. 4A-4B

(i.e., SEQ ID NO:5), where n² and m² are integers as described above. Polynucleotides encoded by these polypeptides are also encompassed by the invention.

Also mentioned above, even if deletion of one or more amino acids from the N-terminus of a protein results in modification of loss of one or more biological functions of the protein, other biological activities may still be retained. Thus, the ability of shortened TR2-SV2 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a TR2-SV2 mutein with a large number of deleted N-terminal amino acid residues may retain some biological or immunogenic activities. In fact, peptides composed of as few as six TR2-SV2 amino acid residues may often evoke an immune response.

Accordingly, the present invention further provides polypeptides having one or more residues deleted from the amino terminus of the TR2-SV2 amino acid sequence shown in FIG. 7A-7B (i.e., SEQ ID NO:8), up to the serine residue at position number 131 and polynucleotides encoding such polypeptides. In particular, the present invention provides polypeptides comprising, or alternatively consisting of, the amino acid sequence of residues n³-136 of FIG. 7A-7B (i.e., SEQ ID NO:8), where n³ is an integer in the range of 2 to 131. Polynucleotides encoded by these polypeptides are also encompassed by the invention.

More in particular, the invention provides polynucleotides encoding polypeptides comprising, or alternatively consisting of, the amino acid sequence of residues of L-2 to K-136; G-3 to K-136; T-4 to K-136; S-5 to K-136; G-6 to K-136; H-7 to K-136; L-8 to K-136; V-9 to K-136; W-10 to K-136; L-11 to K-136; S-12 to K-136; Q-13 to K-136; G-14 to K-136; F-15 to K-136; S-16 to K-136; L-17 to K-136; A-18 to K-136; G-19 to K-136; R-20 to K-136; P-21 to K-136; G-22 to K-136; S-23 to K-136; S-24 to K-136; P-25 to K-136; W-26 to K-136; P-27 to K-136; V-28 to K-136; D-29 to K-136; A-30 to K-136; V-31 to K-136; L-32 to K-136; A-33 to K-136; C-34 to K-136; G-35 to K-136; W-36 to K-136; C-37 to K-136; P-38 to K-136; G-39 to K-136; L-40 to K-136; H-41 to K-136; V-42 to K-136; P-43 to K-136; P-44 to K-136; L-45 to K-136; S-46 to K-136; P-47 to K-136; S-48 to K-136; S-49 to K-136; W-50 to K-136; T-51 to K-136; P-52 to K-136; A-53 to K-136; M-54 to K-136; G-55 to K-136; L-56 to K-136; R-57 to K-136; A-58 to K-136; S-59 to K-136; R-60 to K-136; N-61 to K-136; C-62 to K-136; S-63 to K-136; R-64 to K-136; T-65 to K-136; E-66 to K-136; N-67 to K-136; A-68 to K-136; V-69 to K-136; C-70 to K-136; G-71 to K-136; C-72 to K-136; S-73 to K-136; P-74 to K-136; G-75 to K-136; H-76 to K-136; F-77 to K-136; C-78 to K-136; I-79 to K-136; V-80 to K-136; Q-81 to K-136; D-82 to K-136; G-83 to K-136; D-84 to K-136; H-85 to K-136; C-86 to K-136; A-87 to K-136; A-88 to K-136; C-89 to K-136; R-90 to K-136; A-91 to K-136; Y-92 to K-136; A-93 to K-136; T-94 to K-136; S-95 to K-136; S-96 to K-136; P-97 to K-136; G-98 to K-136; Q-99 to K-136; R-100 to K-136; V-101 to K-136; Q-102 to K-136; K-103 to K-136; G-104 to K-136; G-105 to K-136; T-106 to K-136; E-107 to K-136; S-108 to K-136; Q-109 to K-136; D-110 to K-136; T-111 to K-136; L-112 to K-136; C-113 to K-136; Q-114 to K-136; N-115 to K-136; C-116 to K-136; P-117 to K-136; R-118 to K-136; G-119 to K-136; P-120 to K-136; S-121 to K-136; L-122 to K-136; P-123 to K-136; M-124 to K-136; G-125 to K-136; P-126 to K-136; W-127 to K-136; R-128 to K-136; N-129 to K-136; V-130 to K-136; and S-131 to K-136 of the TR2-SV2 sequence shown in FIG. 7A-7B.

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

Also as mentioned above, even if deletion of one or more amino acids from the C-terminus of a protein results in modification of loss of one or more biological functions of the protein, other biological activities may still be retained. Thus, the ability of the shortened TR2-SV2 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TR2-SV2 mutein with a large number of deleted C-terminal amino acid residues may retain some biological or immunogenic activities. In fact, peptides composed of as few as six TR2-SV2 amino acid residues may often evoke an immune response.

Accordingly, the present invention further provides polypeptides having one or more residues deleted from the carboxy terminus of the amino acid sequence of the TR2-SV2 polypeptide shown in FIG. 7A-7B (i.e., SEQ ID NO:8), up to the glycine residue at position number 6, and polynucleotides encoding such polypeptides. In particular, the present invention provides polypeptides comprising, or alternatively consisting of, the amino acid sequence of residues 1-m³ of FIG. 7A-7B (i.e., SEQ ID NO:8), where m³ is an integer in the range of 6 to 135. Polynucleotides encoded by these polypeptides are also encompassed by the invention.

More in particular, the invention provides polynucleotides encoding polypeptides comprising, or alternatively consisting of, the amino acid sequence of residues M-1 to S-135; M-1 to P-134; M-1 to R-133; M-1 to T-132; M-1 to S-131; M-1 to V-130; M-1 to N-129; M-1 to R-128; M-1 to W-127; M-1 to P-126; M-1 to G-125; M-1 to M-124; M-1 to P-123; M-1 to L-122; M-1 to S-121; M-1 to P-120; M-1 to G-119; M-1 to R-118; M-1 to P-117; M-1 to C-116; M-1 to N-115; M-1 to Q-114; M-1 to C-113; M-1 to L-112; M-1 to T-111; M-1 to D-110; M-1 to Q-109; M-1 to S-108; M-1 to E-107; M-1 to T-106; M-1 to G-105; M-1 to G-104; M-1 to K-103; M-1 to Q-102; M-1 to V-101; M-1 to R-100; M-1 to Q-99; M-1 to G-98; M-1 to P-97; M-1 to S-96; M-1 to S-95; M-1 to T-94; M-1 to A-93; M-1 to Y-92; M-1 to A-91; M-1 to R-90; M-1 to C-89; M-1 to A-88; M-1 to A-87; M-1 to C-86; M-1 to H-85; M-1 to D-84; M-1 to G-83; M-1 to D-82; M-1 to Q-81; M-1 to V-80; M-1 to I-79; M-1 to C-78; M-1 to F-77; M-1 to H-76; M-1 to G-75; M-1 to P-74; M-1 to S-73; M-1 to C-72; M-1 to G-71; M-1 to C-70; M-1 to V-69; M-1 to A-68; M-1 to N-67; M-1 to E-66; M-1 to T-65; M-1 to R-64; M-1 to S-63; M-1 to C-62; M-1 to N-61; M-1 to R-60; M-1 to S-59; M-1 to A-58; M-1 to R-57; M-1 to L-56; M-1 to G-55; M-1 to M-54; M-1 to A-53; M-1 to P-52; M-1 to T-51; M-1 to W-50; M-1 to S-49; M-1 to S-48; M-1 to P-47; M-1 to S-46; M-1 to L-45; M-1 to P-44; M-1 to P-43; M-1 to V-42; M-1 to H-41; M-1 to L-40; M-1 to G-39; M-1 to P-38; M-1 to C-37; M-1 to W-36;

M-1 to G-35; M-1 to C-34; M-1 to A-33; M-1 to L-32; M-1 to V-31; M-1 to A-30; M-1 to D-29; M-1 to V-28; M-1 to P-27; M-1 to W-26; M-1 to P-25; M-1 to S-24; M-1 to S-23; M-1 to G-22; M-1 to P-21; M-1 to R-20; M-1 to G-19; M-1 to A-18; M-1 to L-17; M-1 to S-16; M-1 to F-15; M-1 to G-14; M-1 to Q-13; M-1 to S-12; M-1 to L-11; M-1 to W-10; M-1 to V-9; M-1 to L-8; M-1 to H-7; and M-1 to G-6 of the sequence of the TR2-SV2 sequence shown in FIG. 7A-7B. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

The invention also provides polypeptides having one or more amino acids deleted from both the amino and the carboxyl termini of a TR2-SV2 polypeptide, which may be described generally as having residues $n^3$-$m^3$ of FIG. 7A-7B (i.e., SEQ ID NO:8), where $n^3$ and $m^3$ are integers as described above. Polynucleotides encoded by these polypeptides are also encompassed by the invention.

In addition, the present invention further provides polypeptides having one or more residues deleted from the amino terminus of the predicted extracellular domain of the TR2 amino acid sequence shown in SEQ ID NO:2 (FIG. 1A-1B), up to the glycine residue at position number 159 and polynucleotides encoding such polypeptides. In particular, the present invention provides polypeptides comprising, or alternatively consisting of, the amino acid sequence of residues $n^4$-164 of SEQ ID NO:2, where $n^4$ is an integer in the range of 1 to 159. Polynucleotides encoded by these polypeptides are also encompassed by the invention.

More in particular, the invention provides polynucleotides encoding polypeptides comprising, or alternatively consisting of, the amino acid sequence of residues of P-1 to H-164; A-2 to H-164; L-3 to H-164; P-4 to H-164; S-5 to H-164; C-6 to H-164; K-7 to H-164; E-8 to H-164; D-9 to H-164; E-10 to H-164; Y-11 to H-164; P-12 to H-164; V-13 to H-164; G-14 to H-164; S-15 to H-164; E-16 to H-164; C-17 to H-164; C-18 to H-164; P-19 to H-164; K-20 to H-164; C-21 to H-164; S-22 to H-164; P-23 to H-164; G-24 to H-164; Y-25 to H-164; R-26 to H-164; V-27 to H-164; K-28 to H-164; E-29 to H-164; A-30 to H-164; C-31 to H-164; G-32 to H-164; E-33 to H-164; L-34 to H-164; T-35 to H-164; G-36 to H-164; T-37 to H-164; V-38 to H-164; C-39 to H-164; E-40 to H-164; P-41 to H-164; C-42 to H-164; P-43 to H-164; P-44 to H-164; G-45 to H-164; T-46 to H-164; Y-47 to H-164; I-48 to H-164; A-49 to H-164; H-50 to H-164; L-51 to H-164; N-52 to H-164; G-53 to H-164; L-54 to H-164; S-55 to H-164; K-56 to H-164; C-57 to H-164; L-58 to H-164; Q-59 to H-164; C-60 to H-164; Q-61 to H-164; M-62 to H-164; C-63 to H-164; D-64 to H-164; P-65 to H-164; A-66 to H-164; M-67 to H-164; G-68 to H-164; L-69 to H-164; R-70 to H-164; A-71 to H-164; S-72 to H-164; R-73 to H-164; N-74 to H-164; C-75 to H-164; S-76 to H-164; R-77 to H-164; T-78 to H-164; E-79 to H-164; N-80 to H-164; A-81 to H-164; V-82 to H-164; C-83 to H-164; G-84 to H-164; C-85 to H-164; S-86 to H-164; P-87 to H-164; G-88 to H-164; H-89 to H-164; F-90 to H-164; C-91 to H-164; I-92 to H-164; V-93 to H-164; Q-94 to H-164; D-95 to H-164; G-96 to H-164; D-97 to H-164; H-98 to H-164; C-99 to H-164; A-100 to H-164; A-101 to H-164; C-102 to H-164; R-103 to H-164; A-104 to H-164; Y-105 to H-164; A-106 to H-164; T-107 to H-164; S-108 to H-164; S-109 to H-164; P-110 to H-164; G-111 to H-164; Q-112 to H-164; R-113 to H-164; V-114 to H-164; Q-115 to H-164; K-116 to H-164; G-117 to H-164; G-118 to H-164; T-119 to H-164; E-120 to H-164; S-121 to H-164; Q-122 to H-164; D-123 to H-164; T-124 to H-164; L-125 to H-164; C-126 to H-164; Q-127 to H-164; N-128 to H-164; C-129 to H-164; P-130 to H-164; P-131 to H-164; G-132 to H-164; T-133 to H-164; F-134 to H-164; S-135 to H-164; P-136 to H-164; N-137 to H-164; G-138 to H-164; T-139 to H-164; L-140 to H-164; E-141 to H-164; E-142 to H-164; C-143 to H-164; Q-144 to H-164; H-145 to H-164; Q-146 to H-164; T-147 to H-164; K-148 to H-164; C-149 to H-164; S-150 to H-164; W-151 to H-164; L-152 to H-164; V-153 to H-164; T-154 to H-164; K-155 to H-164; A-156 to H-164; G-157 to H-164; A-158 to H-164; and G-159 to H-164 of the TR2 amino acid sequence shown in SEQ ID NO:2 (which is identical to that shown in FIG. 1A-1B, with the exception that the amino acid residues in FIG. 1A-1B are numbered consecutively from 1 through 283 from the N-terminus to the C-terminus, while the amino acid residues in SEQ ID NO:2 are numbered consecutively from −36 through 247 to reflect the position of the predicted signal peptide). The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

The present invention further provides polypeptides having one or more residues deleted from the carboxy terminus of the predicted extracellular domain of the amino acid sequence of the TR2 shown in SEQ ID NO:2 (FIG. 1A-1B), up to the cysteine residue at position number 6 in SEQ ID NO:2, and polynucleotides encoding such polypeptides. In particular, the present invention provides polypeptides comprising, or alternatively consisting of, the amino acid sequence of residues 1-$m^4$ of SEQ ID NO:2 (FIG. 1A-1B), where $m^4$ is an integer in the range of 6 to 164. Polynucleotides encoded by these polypeptides are also encompassed by the invention.

More in particular, the invention provides polynucleotides encoding polypeptides comprising, or alternatively consisting of, the amino acid sequence of residues P-1 to H-164; P-1 to S-163; P-1 to S-162; P-1 to S-161; P-1 to T-160; P-1 to G-159; P-1 to A-158; P-1 to G-157; P-1 to A-156; P-1 to K-155; P-1 to T-154; P-1 to V-153; P-1 to L-152; P-1 to W-151; P-1 to S-150; P-1 to C-149; P-1 to K-148; P-1 to T-147; P-1 to Q-146; P-1 to H-145; P-1 to Q-144; P-1 to C-143; P-1 to E-142; P-1 to E-141; P-1 to L-140; P-1 to T-139; P-1 to G-138; P-1 to N-137; P-1 to P-136; P-1 to S-135; P-1 to F-134; P-1 to T-133; P-1 to G-132; P-1 to P-131; P-1 to P-130; P-1 to C-129; P-1 to N-128; P-1 to Q-127; P-1 to C-126; P-1 to L-125; P-1 to T-124; P-1 to D-123; P-1 to Q-122; P-1 to S-121; P-1 to E-120; P-1 to T-119; P-1 to G-118; P-1 to G-117; P-1 to K-116; P-1 to Q-115; P-1 to V-114; P-1 to R-113; P-1 to Q-112; P-1 to G-111; P-1 to P-110; P-1 to S-109; P-1 to S-108; P-1 to T-107; P-1 to A-106; P-1 to Y-105; P-1 to A-104; P-1 to R-103; P-1 to C-102; P-1 to A-101; P-1 to A-100; P-1 to C-99; P-1 to H-98; P-1 to D-97; P-1 to G-96; P-1 to D-95; P-1 to Q-94; P-1 to V-93; P-1 to I-92; P-1 to C-91; P-1 to F-90; P-1 to H-89; P-1 to G-88; P-1 to P-87; P-1 to S-86; P-1 to C-85; P-1 to G-84; P-1 to C-83; P-1 to V-82; P-1 to A-81; P-1 to N-80; P-1 to E-79; P-1 to T-78; P-1 to R-77; P-1 to S-76; P-1 to C-75; P-1 to N-74; P-1 to R-73; P-1 to S-72; P-1 to A-71; P-1 to R-70; P-1 to L-69; P-1 to G-68; P-1 to M-67; P-1 to A-66; P-1 to P-65; P-1 to D-64; P-1 to C-63; P-1 to M-62; P-1 to Q-61; P-1 to C-60; P-1 to Q-59; P-1 to L-58; P-1 to C-57; P-1 to K-56; P-1 to S-55; P-1 to L-54; P-1 to G-53; P-1 to N-52; P-1 to L-51; P-1 to H-50; P-1 to A-49; P-1 to I-48; P-1 to Y-47; P-1 to T-46; P-1 to G-45; P-1 to P-44; P-1 to P-43; P-1 to C-42; P-1 to P-41; P-1 to E-40; P-1 to C-39; P-1 to V-38; P-1 to T-37; P-1 to G-36; P-1 to T-35; P-1 to L-34; P-1 to E-33; P-1 to G-32; P-1 to C-31; P-1 to A-30; P-1 to E-29; P-1 to K-28; P-1 to V-27; P-1 to R-26; P-1 to Y-25; P-1 to G-24; P-1 to P-23; P-1 to S-22; P-1 to C-21; P-1 to K-20; P-1 to P-19; P-1 to C-18; P-1 to C-17; P-1 to E-16; P-1 to S-15; P-1 to G-14; P-1 to V-13; P-1 to P-12; P-1 to Y-11; P-1 to E-10; P-1 to D-9; P-1 to E-8; P-1 to K-7; and P-1 to C-6 of the sequence of the TR2 sequence shown in SEQ ID NO:2 (which is identical to the sequence shown as FIG. 1A-1B, with the exception that the amino acid residues in FIG. 1A-1B are numbered consecutively from 1 through 283 from the N-terminus to the C-terminus, while the amino acid residues in SEQ ID NO:2 are numbered consecutively from −36 through 247 to reflect the position of the predicted signal peptide). The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

The invention also provides polypeptides having one or more amino acids deleted from both the amino and the carboxyl termini of a soluble TR2 polypeptide, which may be described generally as having residues $n^4$-$m^4$ of SEQ ID NO:2 (FIG. 1A-1B), where $n^4$ and $m^4$ are integers as described above. Polynucleotides encoded by these polypeptides are also encompassed by the invention.

In addition, the present invention further provides polypeptides having one or more residues deleted from the amino terminus of the predicted extracellular domain of the TR2-SV1 amino acid sequence shown in SEQ ID NO:5 (FIG. 4A-4B), up to the threonine residue at position number 144 and polynucleotides encoding such polypeptides. In particular, the present invention provides polypeptides comprising, or alternatively consisting of, the amino acid sequence of residues $n^5$-149 of SEQ ID NO:5, where $n^5$ is an integer in the range of 1 to 144. Polynucleotides encoded by these polypeptides are also encompassed by the invention.

More in particular, the invention provides polynucleotides encoding polypeptides comprising, or alternatively consisting of, the amino acid sequence of residues of P-1 to A-149; A-2 to A-149; L-3 to A-149; P-4 to A-149; S-5 to A-149; C-6 to A-149; K-7 to A-149; E-8 to A-149; D-9 to A-149; E-10 to A-149; Y-11 to A-149; P-12 to A-149; V-13 to A-149; G-14 to A-149; S-15 to A-149; E-16 to A-149; C-17 to A-149; C-18 to A-149; P-19 to A-149; K-20 to A-149; C-21 to A-149; S-22 to A-149; P-23 to A-149; G-24 to A-149; Y-25 to A-149; R-26 to A-149; V-27 to A-149; K-28 to A-149; E-29 to A-149; A-30 to A-149; C-31 to A-149; G-32 to A-149; E-33 to A-149; L-34 to A-149; T-35 to A-149; G-36 to A-149; T-37 to A-149; V-38 to A-149; C-39 to A-149; E-40 to A-149; P-41 to A-149; C-42 to A-149; P-43 to A-149; P-44 to A-149; G-45 to A-149; T-46 to A-149; Y-47 to A-149; I-48 to A-149; A-49 to A-149; H-50 to A-149; L-51 to A-149; N-52 to A-149; G-53 to A-149; L-54 to A-149; S-55 to A-149; K-56 to A-149; C-57 to A-149; L-58 to A-149; Q-59 to A-149; C-60 to A-149; Q-61 to A-149; M-62 to A-149; C-63 to A-149; D-64 to A-149; P-65 to A-149; D-66 to A-149; I-67 to A-149; G-68 to A-149; S-69 to A-149; P-70 to A-149; C-71 to A-149; D-72 to A-149; L-73 to A-149; R-74 to A-149; G-75 to A-149; R-76 to A-149; G-77 to A-149; H-78 to A-149; L-79 to A-149; E-80 to A-149; A-81 to A-149; G-82 to A-149; A-83 to A-149; H-84 to A-149; L-85 to A-149; S-86 to A-149; P-87 to A-149; G-88 to A-149; R-89 to A-149; Q-90 to A-149; K-91 to A-149; G-92 to A-149; E-93 to A-149; P-94 to A-149; D-95 to A-149; P-96 to A-149; E-97 to A-149; V-98 to A-149; A-99 to A-149; F-100 to A-149; E-101 to A-149; S-102 to A-149; L-103 to A-149; S-104 to A-149; A-105 to A-149; E-106 to A-149; P-107 to A-149; V-108 to A-149; H-109 to A-149; A-110 to A-149; A-111 to A-149; N-112 to A-149; G-113 to A-149; S-114 to A-149; V-115 to A-149; P-116 to A-149; L-117 to A-149; E-118 to A-149; P-119 to A-149; H-120 to A-149; A-121 to A-149; R-122 to A-149; L-123 to A-149; S-124 to A-149; M-125 to A-149; A-126 to A-149; S-127 to A-149; A-128 to A-149; P-129 to A-149; C-130 to A-149; G-131 to A-149; Q-132 to A-149; A-133 to A-149; G-134 to A-149; L-135 to A-149; H-136 to A-149; L-137 to A-149; R-138 to A-149; D-139 to A-149; R-140 to A-149; A-141 to A-149; D-142 to A-149; G-143 to A-149; and T-144 to A-149 of the TR2-SV1 amino acid sequence shown in SEQ ID NO:5 (which is identical to that shown in FIG. 4A-4B, with the exception that the amino acid residues in FIG. 4A-4B are numbered consecutively from 1 through 185 from the N-terminus to the C-terminus, while the amino acid residues in SEQ ID NO:5 are numbered consecutively from −36 through 149 to reflect the position of the predicted signal peptide). The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

The present invention further provides polypeptides having one or more residues deleted from the carboxy terminus of the predicted extracellular domain of the amino acid sequence of the TR2-SV1 shown in SEQ ID NO:5 (FIG. 4A-4B), up to the cysteine residue at position number 6 in SEQ ID NO:5, and polynucleotides encoding such polypeptides. In particular, the present invention provides polypeptides comprising, or alternatively consisting of, the amino acid sequence of residues 1-$m^5$ of SEQ ID NO:5 (FIG. 4A-4B), where $m^5$ is an integer in the range of 6 to 149. Polynucleotides encoded by these polypeptides are also encompassed by the invention.

More in particular, the invention provides polynucleotides encoding polypeptides comprising, or alternatively consisting of, the amino acid sequence of residues P-1 to A-149; P-1 to R-148; P-1 to G-147; P-1 to G-146; P-1 to P-145; P-1 to T-144; P-1 to G-143; P-1 to D-142; P-1 to A-141; P-1 to R-140; P-1 to D-139; P-1 to R-138; P-1 to L-137; P-1 to H-136; P-1 to L-135; P-1 to G-134; P-1 to A-133; P-1 to Q-132; P-1 to G-131; P-1 to C-130; P-1 to P-129; P-1 to A-128; P-1 to S-127; P-1 to A-126; P-1 to M-125; P-1 to S-124; P-1 to L-123; P-1 to R-122; P-1 to A-121; P-1 to H-120; P-1 to P-119; P-1 to E-118; P-1 to L-117; P-1 to P-116; P-1 to V-115; P-1 to S-114; P-1 to G-113; P-1 to N-112; P-1 to A-111; P-1 to A-110; P-1 to H-109; P-1 to V-108; P-1 to P-107; P-1 to E-106; P-1 to A-105; P-1 to S-104; P-1 to L-103; P-1 to S-102; P-1 to E-101; P-1 to F-100; P-1 to A-99; P-1 to V-98; P-1 to E-97; P-1 to P-96; P-1 to D-95; P-1 to P-94; P-1 to E-93; P-1 to G-92; P-1 to K-91; P-1 to Q-90; P-1 to R-89; P-1 to G-88; P-1 to P-87; P-1 to S-86;

P-1 to L-85; P-1 to H-84; P-1 to A-83; P-1 to G-82; P-1 to A-81; P-1 to E-80; P-1 to L-79; P-1 to H-78; P-1 to G-77; P-1 to R-76; P-1 to G-75; P-1 to R-74; P-1 to L-73; P-1 to D-72; P-1 to C-71; P-1 to P-70; P-1 to S-69; P-1 to G-68; P-1 to I-67; P-1 to D-66; P-1 to P-65; P-1 to D-64; P-1 to C-63; P-1 to M-62; P-1 to Q-61; P-1 to C-60; P-1 to Q-59; P-1 to L-58; P-1 to C-57; P-1 to K-56; P-1 to S-55; P-1 to L-54; P-1 to G-53; P-1 to N-52; P-1 to L-51; P-1 to H-50; P-1 to A-49; P-1 to I-48; P-1 to Y-47; P-1 to T-46; P-1 to G-45; P-1 to P-44; P-1 to P-43; P-1 to C-42; P-1 to P-41; P-1 to E-40; P-1 to C-39; P-1 to V-38; P-1 to T-37; P-1 to G-36; P-1 to T-35; P-1 to L-34; P-1 to E-33; P-1 to G-32; P-1 to C-31; P-1 to A-30; P-1 to E-29; P-1 to K-28; P-1 to V-27; P-1 to R-26; P-1 to Y-25; P-1 to G-24; P-1 to P-23; P-1 to S-22; P-1 to C-21; P-1 to K-20; P-1 to P-19; P-1 to C-18; P-1 to C-17; P-1 to E-16; P-1 to S-15; P-1 to G-14; P-1 to V-13; P-1 to P-12; P-1 to Y-11; P-1 to E-10; P-1 to D-9; P-1 to E-8; P-1 to K-7; and P-1 to C-6 of the sequence of the TR2-SV1 sequence shown in SEQ ID NO:5 (which is identical to the sequence shown as FIG. 4A-4B, with the exception that the amino acid residues in FIG. 4A-4B are numbered consecutively from 1 through 185 from the N-terminus to the C-terminus, while the amino acid residues in SEQ ID NO:5 are numbered consecutively from −36 through 149 to reflect the position of the predicted signal peptide). The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

The invention also provides polypeptides having one or more amino acids deleted from both the amino and the carboxyl termini of a soluble TR2-SV1 polypeptide, which may be described generally as having residues $n^5$-$m^5$ of SEQ ID NO:5 (FIG. 4A-4B), where $n^5$ and $m^5$ are integers as described above. Polynucleotides encoded by these polypeptides are also encompassed by the invention.

Additionally, one or more of the amino acid residues of the polypeptides of the invention (e.g., arginine and lysine residues) may be deleted or substituted with another residue to eliminate undesired processing by proteases such as, for example, furins or kexins.

The invention further provides for the proteins containing polypeptide sequences encoded by the polynucleotides of the invention.

Among the especially preferred fragments of the invention are fragments characterized by structural or functional attributes of TR2 receptors of the invention. Such fragments include amino acid residues that comprise, or alternatively consist of, alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) TR2 receptor (SEQ ID NO:2). Certain preferred regions are those set out in FIG. 3 and include, but are not limited to, regions of the aforementioned types identified by analysis of the amino acid sequence depicted in FIG. 1A-1B (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of TR2 receptors. Preferred embodiments of the invention in this regard include fragments that comprise, or alternatively consist of, one, two, three, four or more of one or more of the following functional domains: alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of TR2 receptors.

Figure 6:
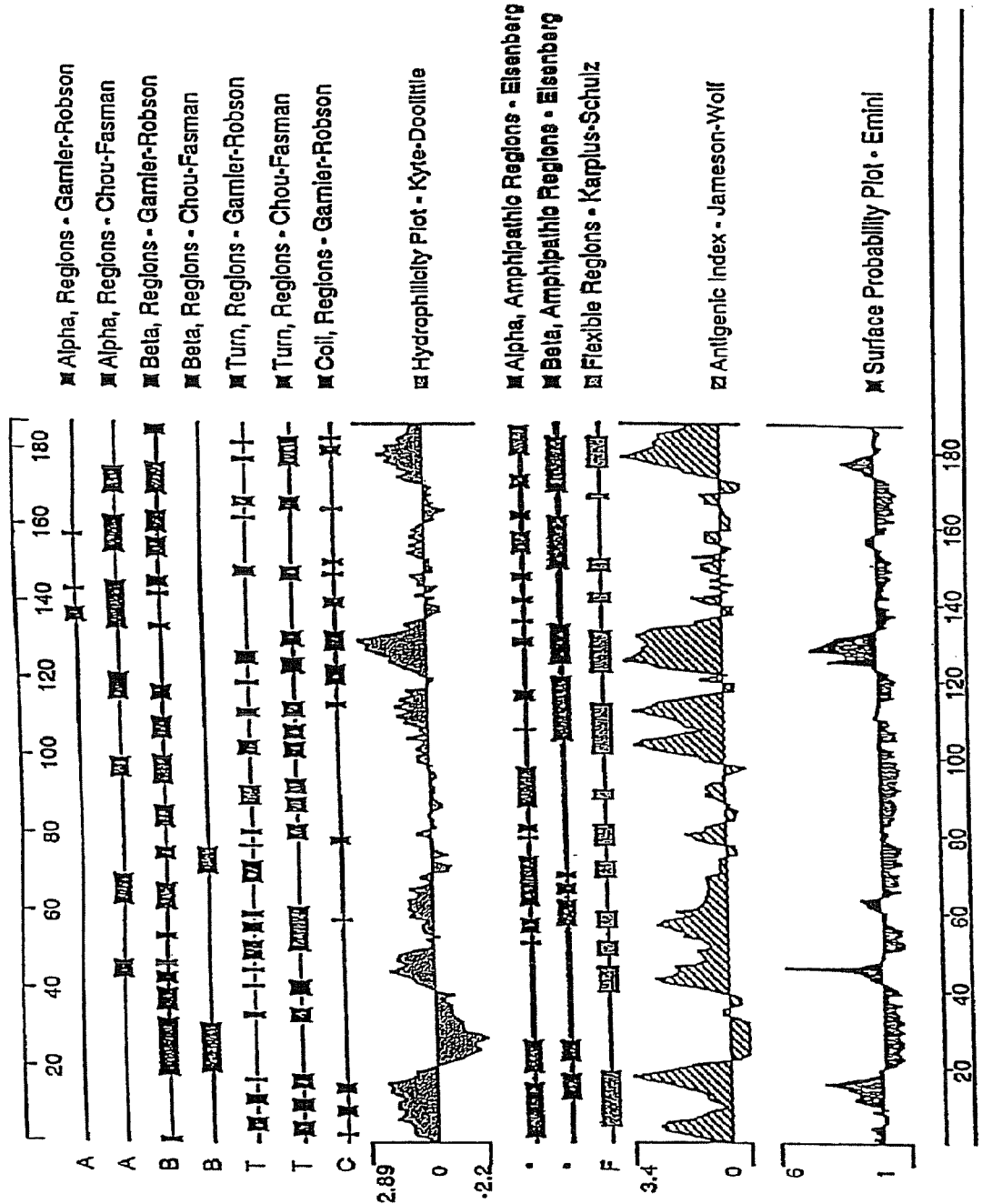
FIG. 6 shows an analysis of the TR2-SV1 receptor amino acid sequence. Alpha, beta, turn and coil regions; hydrophilicity and hydrophobicity; amphipathic regions; flexible regions; antigenic index and surface probability are shown. In the "Antigenic Index-Jameson-Wolf" graph, amino acid residues 39 to 70, 99 to 136 and 171 to 185 in FIG. 4A-4B (amino acid residues 3 to 34, 63 to 100 and 135 to 149 in SEQ ID NO:5) correspond to the shown highly antigenic regions of the TR2-SV1 receptor protein.
Figure 9:
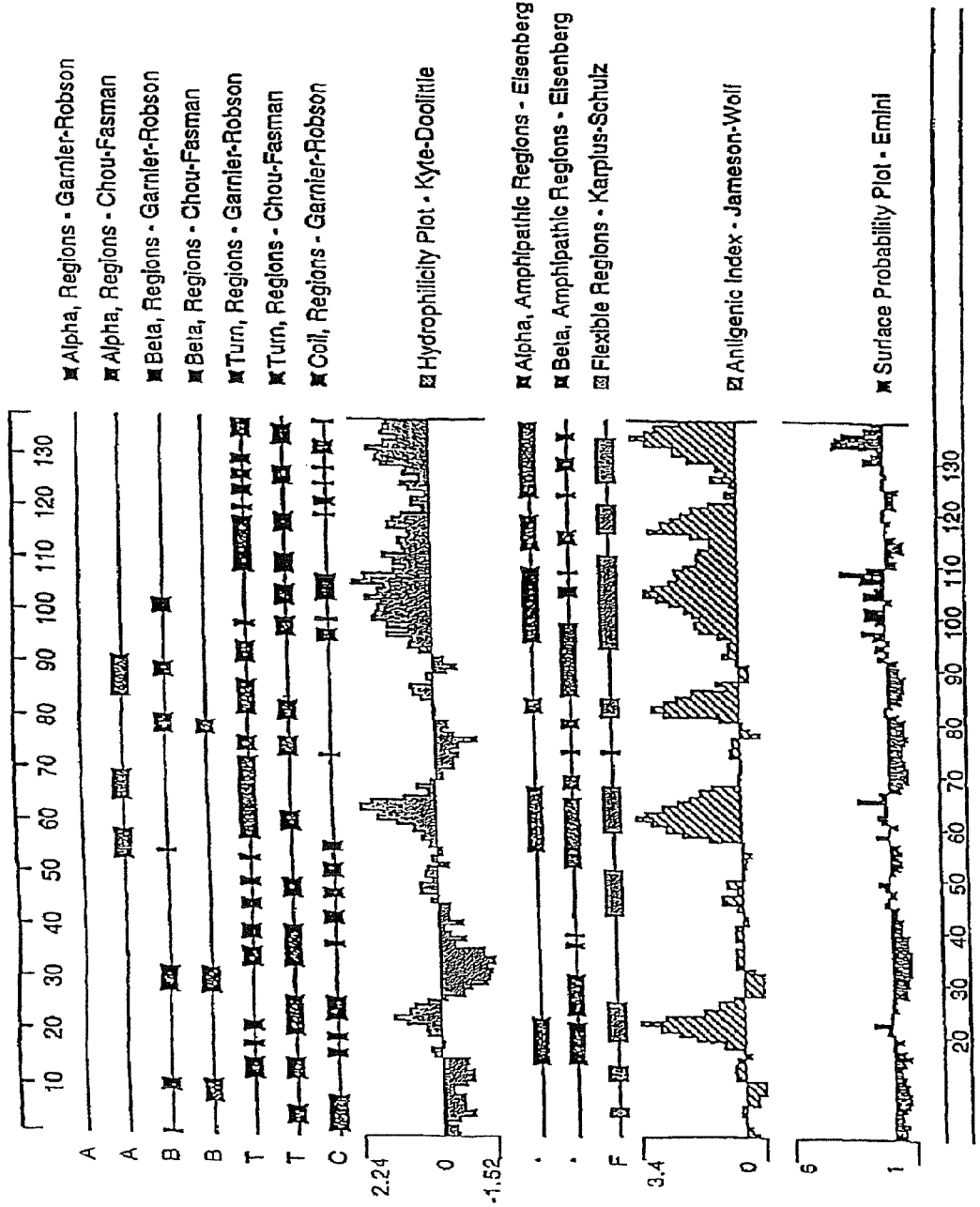
FIG. 9 shows an analysis of the TR2-SV2 receptor amino acid sequence. Alpha, beta, turn and coil regions; hydrophilicity and hydrophobicity; amphipathic regions; flexible regions; antigenic index and surface probability are shown. In the "Antigenic Index-Jameson-Wolf" graph, amino acid residues 56 to 68 and 93 to 136 in FIG. 7A-7B (SEQ ID NO:8) correspond to the shown highly antigenic regions of the TR2-SV2 receptor protein.

The data representing the structural or functional attributes of the TR2 receptors set forth in FIGS. 3, 6 and 9 and Tables II, II and IX were generated using the various identified modules and algorithms of the DNA*STAR set on default parameters. In a preferred embodiment, the data presented in columns VIII, IX, XIII, and XIV of Table II can be used to determine regions of TR2 receptors which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIGS. 3, 6 and 9, but may, as shown in Tables II, III and IV, respectively, be represented or identified by using tabular representations of the data presented in FIGS. 3, 6 and 9. The DNA*STAR computer algorithm used to generate FIGS. 3, 6 and 9 (set on the original default parameters) was used to present the data in FIGS. 3, 6 and 9 in a tabular format. (See Tables II, III and IV, respectively).

The above-mentioned preferred regions set out in FIGS. 3, 6 and 9 and in Tables II, III and IV include, but are not limited to, regions of the aforementioned types identified by analysis of the amino acid sequence set out in FIGS. 1, 4 and 7. As set out in FIGS. 3, 6 and 9, and in Tables II, III and IV, such preferred regions include Garnier-Robson alpha-regions, beta-regions, turn-regions, and coil-regions (columns I, III, V, and VII in Tables II, III and IV), Chou-Fasman alpha-regions, beta-regions, and turn-regions (columns II, IV, and VI in Tables II, III and IV), Kyte-Doolittle hydrophilic regions (column VIII in Tables II, III and IV), Hopp-Woods hydrophobic regions (column IX in Tables II, III and IV), Eisenberg alpha- and beta-amphipathic regions (columns X and XI in Tables II, III and IV), Karplus-Schulz flexible regions (column XII in Tables II, III and IV), Jameson-Wolf regions of high antigenic index (column XIII in Tables II, III and IV), and Emini surface-forming regions (column XIV in Tables II, III and IV).

TABLE II

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.58 | −0.24 | . | . | . | 1.15 | 1.53 |
| Glu | 2 | . | . | B | . | . | . | . | 0.97 | −0.24 | . | * | . | 1.40 | 1.19 |
| Pro | 3 | . | . | . | . | . | T | C | 1.07 | −0.67 | * | * | . | 2.35 | 1.55 |
| Pro | 4 | . | . | . | . | . | T | T | 1.11 | −0.19 | * | * | . | 2.50 | 1.65 |
| Gly | 5 | . | . | . | . | . | T | T | 1.29 | −0.37 | . | * | F | 2.25 | 0.94 |
| Asp | 6 | . | . | . | . | . | T | T | 1.68 | 0.06 | * | * | F | 1.40 | 0.94 |
| Trp | 7 | . | . | . | . | . | T | . | 1.47 | 0.06 | . | . | F | 0.95 | 0.94 |
| Gly | 8 | . | . | . | . | . | . | C | 1.39 | 0.06 | * | * | F | 0.65 | 1.47 |
| Pro | 9 | . | . | . | . | . | T | C | 1.71 | 0.54 | * | * | F | 0.15 | 0.93 |
| Pro | 10 | . | . | . | . | . | T | C | 1.76 | 0.54 | * | * | F | 0.30 | 1.73 |
| Pro | 11 | . | . | . | . | T | T | . | 1.44 | 0.01 | * | * | F | 0.80 | 2.34 |
| Trp | 12 | . | . | . | . | T | T | . | 1.52 | 0.07 | * | * | F | 0.80 | 2.18 |
| Arg | 13 | . | . | . | . | T | . | . | 1.91 | 0.07 | * | * | F | 0.94 | 2.18 |
| Ser | 14 | . | . | . | . | . | . | C | 1.81 | −0.36 | * | * | F | 1.68 | 2.82 |
| Thr | 15 | . | . | . | . | . | T | C | 2.02 | −0.30 | * | * | F | 2.22 | 3.88 |
| Pro | 16 | . | . | . | . | . | T | C | 1.38 | −1.21 | . | * | F | 2.86 | 3.30 |
| Lys | 17 | . | . | . | . | T | T | . | 0.86 | −0.57 | . | * | F | 3.40 | 1.83 |
| Thr | 18 | . | . | B | . | . | T | . | 0.86 | −0.27 | . | * | F | 2.36 | 1.05 |
| Asp | 19 | . | . | B | B | . | . | . | 0.34 | −0.76 | * | . | F | 1.92 | 1.32 |
| Val | 20 | . | . | B | B | . | . | . | −0.20 | −0.50 | * | * | . | 1.28 | 0.55 |
| Leu | 21 | . | . | B | B | . | . | . | −0.80 | 0.14 | * | . | . | 0.04 | 0.28 |
| Arg | 22 | . | . | B | B | . | . | . | −1.09 | 0.34 | * | * | . | −0.30 | 0.14 |
| Leu | 23 | . | . | B | B | . | . | . | −1.59 | 1.10 | * | * | . | −0.60 | 0.29 |
| Val | 24 | . | . | B | B | . | . | . | −1.90 | 1.14 | * | * | . | −0.60 | 0.29 |
| Leu | 25 | . | . | B | B | . | . | . | −1.74 | 0.94 | * | * | . | −0.60 | 0.22 |
| Tyr | 26 | . | . | B | B | . | . | . | −1.74 | 1.73 | * | * | . | −0.60 | 0.23 |
| Leu | 27 | . | . | B | B | . | . | . | −2.20 | 1.73 | * | * | . | −0.60 | 0.25 |
| Thr | 28 | . | . | B | B | . | . | . | −1.98 | 1.51 | . | . | . | −0.60 | 0.30 |
| Phe | 29 | . | . | B | B | . | . | . | −1.33 | 1.33 | . | . | . | −0.60 | 0.19 |
| Leu | 30 | . | . | B | B | . | . | . | −1.19 | 1.00 | . | . | . | −0.60 | 0.37 |
| Gly | 31 | . | . | B | B | . | . | . | −1.19 | 0.89 | . | . | . | −0.60 | 0.14 |
| Ala | 32 | . | . | B | . | . | . | T | −0.97 | 1.16 | . | . | . | −0.20 | 0.25 |
| Pro | 33 | . | . | . | . | T | T | . | −0.87 | 0.87 | . | . | . | 0.20 | 0.30 |
| Cys | 34 | . | . | . | . | T | T | . | −0.76 | 0.61 | . | . | . | 0.20 | 0.47 |
| Tyr | 35 | . | . | B | . | . | T | . | −0.76 | 0.69 | . | . | . | −0.20 | 0.47 |
| Ala | 36 | . | . | B | . | . | . | . | −0.62 | 0.87 | . | . | . | −0.40 | 0.25 |
| Pro | 37 | . | . | B | . | . | . | . | −0.33 | 0.87 | . | . | . | −0.40 | 0.72 |
| Ala | 38 | . | . | B | . | . | . | . | −0.79 | 0.69 | . | . | . | −0.14 | 0.62 |
| Leu | 39 | . | . | B | . | . | . | . | −0.08 | 0.50 | . | . | . | 0.32 | 0.33 |
| Pro | 40 | . | . | B | . | . | T | . | 0.17 | 0.00 | . | . | F | 1.03 | 0.42 |
| Ser | 41 | . | . | . | . | T | T | . | 0.76 | −0.43 | . | . | F | 2.29 | 0.73 |
| Cys | 42 | . | . | B | . | . | T | . | 0.97 | −0.93 | . | . | F | 2.60 | 1.47 |
| Lys | 43 | . | A | B | . | . | . | . | 1.31 | −1.61 | . | . | F | 1.94 | 1.65 |
| Glu | 44 | . | A | B | . | . | . | . | 1.91 | −1.29 | . | . | F | 1.68 | 1.93 |
| Asp | 45 | . | A | . | . | T | . | . | 1.27 | −1.24 | . | . | F | 1.82 | 5.56 |
| Glu | 46 | . | A | B | . | . | . | . | 1.22 | −1.17 | . | . | F | 1.16 | 2.06 |
| Tyr | 47 | . | A | B | . | . | . | . | 1.59 | −0.74 | . | . | . | 0.75 | 1.18 |
| Pro | 48 | . | . | . | . | . | T | . | 1.54 | −0.36 | . | . | . | 0.90 | 0.95 |
| Val | 49 | . | . | . | . | . | T | . | 0.88 | −0.36 | . | . | F | 1.05 | 0.95 |
| Gly | 50 | . | . | . | . | T | T | . | 0.21 | 0.21 | . | . | F | 0.65 | 0.32 |
| Ser | 51 | . | . | . | . | T | T | . | 0.00 | 0.03 | . | * | F | 0.65 | 0.11 |
| Glu | 52 | . | . | . | . | T | T | . | 0.29 | 0.03 | . | * | F | 0.90 | 0.23 |
| Cys | 53 | . | . | B | . | . | T | . | −0.17 | −0.61 | . | * | . | 1.50 | 0.47 |
| Cys | 54 | . | . | B | . | . | T | . | 0.39 | −0.47 | . | * | . | 1.45 | 0.19 |
| Pro | 55 | . | . | . | . | . | T | . | 0.52 | −0.47 | . | . | . | 2.10 | 0.15 |
| Lys | 56 | . | . | . | . | T | T | . | 0.48 | −0.04 | . | . | F | 2.50 | 0.42 |
| Cys | 57 | . | . | . | . | T | T | . | 0.23 | −0.19 | * | * | F | 2.25 | 0.78 |
| Ser | 58 | . | . | . | . | . | T | C | 1.01 | 0.00 | * | * | F | 1.20 | 0.79 |
| Pro | 59 | . | . | . | . | T | T | . | 0.82 | −0.43 | . | * | F | 1.75 | 0.77 |
| Gly | 60 | . | . | . | . | T | T | . | 1.08 | 0.21 | . | * | F | 1.05 | 1.07 |
| Tyr | 61 | . | . | B | . | . | T | . | 1.03 | −0.36 | . | * | . | 0.85 | 1.60 |
| Arg | 62 | . | A | B | . | . | . | . | 1.11 | −0.74 | * | * | . | 0.75 | 1.79 |
| Val | 63 | . | A | B | . | . | . | . | 0.74 | −0.67 | * | * | . | 0.75 | 1.83 |
| Lys | 64 | . | A | B | . | . | . | . | 0.61 | −0.53 | * | * | . | 0.60 | 0.63 |
| Glu | 65 | . | A | B | . | . | . | . | 0.96 | −0.86 | * | * | . | 0.60 | 0.32 |
| Ala | 66 | . | A | B | . | . | . | . | 0.39 | −0.86 | * | * | . | 0.60 | 0.74 |
| Cys | 67 | . | A | B | . | . | . | . | −0.03 | −0.81 | * | * | . | 0.60 | 0.30 |
| Gly | 68 | . | A | . | . | . | T | . | 0.48 | −0.33 | * | * | . | 0.70 | 0.25 |
| Glu | 69 | . | A | . | . | . | T | . | 0.12 | 0.10 | * | * | F | 0.25 | 0.25 |
| Leu | 70 | . | . | . | B | . | T | . | −0.73 | 0.09 | * | * | F | 0.25 | 0.67 |
| Thr | 71 | . | . | . | B | . | T | . | −0.81 | 0.16 | * | * | F | 0.25 | 0.50 |
| Gly | 72 | . | . | . | B | . | T | . | −0.14 | 0.30 | * | * | F | 0.25 | 0.16 |
| Thr | 73 | . | . | . | B | . | T | . | −0.01 | 0.30 | * | * | F | 0.25 | 0.33 |
| Val | 74 | . | . | B | B | . | . | . | −0.68 | 0.04 | * | * | . | −0.30 | 0.35 |
| Cys | 75 | . | . | B | B | . | . | . | −0.08 | 0.13 | . | . | . | −0.30 | 0.19 |
| Glu | 76 | . | . | B | B | . | . | . | 0.02 | 0.13 | . | . | . | −0.23 | 0.20 |
| Pro | 77 | . | . | . | . | . | T | . | 0.02 | 0.07 | . | . | F | 0.59 | 0.42 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Cys | 78 | . | . | . | . | . | . | C | 0.02 | −0.14 | . | . | F | 1.06 | 0.78 |
| Pro | 79 | . | . | . | . | . | T | C | 0.63 | −0.23 | . | . | F | 1.33 | 0.65 |
| Pro | 80 | . | . | . | . | T | T | . | 0.41 | 0.53 | . | . | F | 0.70 | 0.66 |
| Gly | 81 | . | . | . | . | T | T | . | −0.18 | 0.79 | . | . | F | 0.63 | 0.86 |
| Thr | 82 | . | . | B | . | . | T | . | 0.00 | 0.71 | . | . | F | 0.16 | 0.56 |
| Tyr | 83 | . | . | B | . | . | . | . | −0.14 | 0.79 | . | . | . | −0.26 | 0.49 |
| Ile | 84 | . | . | B | . | . | . | . | 0.07 | 1.04 | . | . | . | −0.33 | 0.41 |
| Ala | 85 | . | . | B | . | . | . | . | −0.07 | 1.01 | . | . | . | −0.40 | 0.46 |
| His | 86 | . | . | B | . | . | T | . | −0.53 | 0.96 | . | . | . | −0.20 | 0.29 |
| Leu | 87 | . | . | B | . | . | T | . | −0.52 | 0.89 | * | . | . | −0.20 | 0.34 |
| Asn | 88 | . | . | . | . | T | T | . | −0.23 | 0.59 | * | * | . | 0.20 | 0.45 |
| Gly | 89 | . | . | . | . | T | T | . | −0.01 | 0.09 | * | . | F | 0.65 | 0.66 |
| Leu | 90 | . | . | . | . | T | . | . | −0.23 | 0.16 | * | * | F | 0.45 | 0.43 |
| Ser | 91 | . | . | . | . | T | . | . | −0.20 | 0.16 | * | . | F | 0.65 | 0.22 |
| Lys | 92 | . | . | . | . | T | T | . | −0.06 | 0.16 | * | * | . | 0.50 | 0.39 |
| Cys | 93 | . | . | B | . | . | T | . | −0.06 | 0.30 | * | * | . | 0.10 | 0.25 |
| Leu | 94 | . | . | B | . | . | T | . | −0.31 | 0.01 | * | . | . | 0.10 | 0.33 |
| Gln | 95 | . | A | B | . | . | . | . | −0.17 | 0.24 | * | . | . | −0.30 | 0.16 |
| Cys | 96 | . | A | B | . | . | . | . | 0.13 | 0.81 | * | . | . | −0.60 | 0.16 |
| Gln | 97 | . | A | B | . | . | . | . | −0.12 | 0.24 | * | . | . | −0.30 | 0.33 |
| Met | 98 | . | A | B | . | . | . | . | −0.04 | −0.01 | . | . | . | 0.30 | 0.29 |
| Cys | 99 | . | A | B | . | . | . | . | 0.17 | 0.09 | . | * | . | −0.30 | 0.55 |
| Asp | 100 | . | . | B | . | . | . | . | −0.18 | 0.13 | . | . | . | −0.10 | 0.31 |
| Pro | 101 | . | . | B | . | . | . | . | −0.32 | 0.16 | . | * | . | −0.10 | 0.31 |
| Ala | 102 | . | A | B | . | . | . | . | −0.21 | 0.23 | . | . | . | −0.30 | 0.48 |
| Met | 103 | . | A | B | . | . | . | . | −0.20 | −0.34 | . | * | . | 0.30 | 0.57 |
| Gly | 104 | . | A | B | . | . | . | . | 0.17 | 0.16 | * | * | . | −0.30 | 0.37 |
| Leu | 105 | . | A | B | . | . | . | . | 0.28 | 0.11 | * | * | . | −0.30 | 0.49 |
| Arg | 106 | . | A | B | . | . | . | . | 0.49 | −0.39 | * | * | . | 0.64 | 0.97 |
| Ala | 107 | . | A | B | . | . | . | . | 0.41 | −0.60 | * | * | . | 1.43 | 1.58 |
| Ser | 108 | . | . | . | . | T | T | . | 0.71 | −0.46 | * | * | F | 2.42 | 1.03 |
| Arg | 109 | . | . | . | . | T | T | . | 1.17 | −0.76 | * | * | F | 2.91 | 0.70 |
| Asn | 110 | . | . | . | . | T | T | . | 1.67 | −0.76 | * | * | F | 3.40 | 1.36 |
| Cys | 111 | . | . | . | . | T | T | . | 1.56 | −0.77 | * | * | F | 3.06 | 1.47 |
| Ser | 112 | . | . | . | . | T | . | . | 2.14 | −1.16 | * | . | F | 2.52 | 1.30 |
| Arg | 113 | . | A | . | . | T | . | . | 1.86 | −0.76 | * | * | F | 1.98 | 1.30 |
| Thr | 114 | . | A | . | . | T | . | . | 0.89 | −0.66 | * | * | F | 1.64 | 2.44 |
| Glu | 115 | . | A | . | . | T | . | . | 0.22 | −0.59 | * | . | F | 1.30 | 1.35 |
| Asn | 116 | . | A | B | . | . | . | . | 0.54 | −0.40 | * | . | F | 0.45 | 0.37 |
| Ala | 117 | . | A | B | . | . | . | . | 0.18 | 0.03 | * | . | . | −0.30 | 0.25 |
| Val | 118 | . | A | . | . | T | . | . | −0.23 | 0.11 | * | * | . | 0.10 | 0.08 |
| Cys | 119 | . | . | . | . | T | . | . | −0.13 | 0.50 | . | . | . | 0.00 | 0.07 |
| Gly | 120 | . | . | . | . | T | . | . | −0.48 | 0.53 | . | . | . | 0.00 | 0.10 |
| Cys | 121 | . | . | . | . | T | . | . | −0.51 | 0.46 | . | . | . | 0.00 | 0.13 |
| Ser | 122 | . | . | . | . | . | T | C | −0.62 | 0.31 | . | . | . | 0.30 | 0.34 |
| Pro | 123 | . | . | . | . | . | T | T | −0.43 | 0.53 | . | * | F | 0.35 | 0.30 |
| Gly | 124 | . | . | . | . | . | T | T | −0.66 | 0.67 | . | . | . | 0.20 | 0.30 |
| His | 125 | . | . | B | . | . | . | T | −1.17 | 0.79 | . | . | . | −0.20 | 0.16 |
| Phe | 126 | . | . | B | B | . | . | . | −0.50 | 1.04 | . | . | . | −0.60 | 0.07 |
| Cys | 127 | . | . | B | B | . | . | . | −0.20 | 1.01 | . | . | . | −0.32 | 0.13 |
| Ile | 128 | . | . | B | B | . | . | . | −0.33 | 0.59 | * | . | . | −0.04 | 0.16 |
| Val | 129 | . | . | B | . | . | T | . | 0.01 | 0.51 | * | . | . | 0.64 | 0.18 |
| Gln | 130 | . | . | . | . | T | T | . | 0.01 | −0.27 | . | . | F | 2.37 | 0.57 |
| Asp | 131 | . | . | . | . | T | T | . | 0.04 | −0.34 | * | . | F | 2.80 | 1.11 |
| Gly | 132 | . | . | . | . | T | T | . | 0.12 | −0.46 | * | . | F | 2.37 | 0.80 |
| Asp | 133 | . | A | . | . | T | . | . | 0.42 | −0.60 | * | . | F | 1.99 | 0.47 |
| His | 134 | . | A | . | . | T | . | . | 0.61 | −0.50 | . | * | . | 1.56 | 0.28 |
| Cys | 135 | . | A | B | . | . | . | . | 0.72 | 0.07 | . | * | . | −0.02 | 0.15 |
| Ala | 136 | . | A | B | . | . | . | . | 0.13 | −0.36 | . | * | . | 0.30 | 0.18 |
| Ala | 137 | . | A | B | . | . | . | . | 0.23 | 0.14 | . | * | . | −0.30 | 0.13 |
| Cys | 138 | . | A | B | . | . | . | . | −0.36 | 0.40 | . | * | . | −0.30 | 0.39 |
| Arg | 139 | . | A | B | . | . | . | . | −0.63 | 0.33 | . | * | . | −0.30 | 0.39 |
| Ala | 140 | . | A | B | . | . | . | . | −0.27 | 0.31 | . | * | . | −0.30 | 0.56 |
| Tyr | 141 | . | . | B | . | . | . | . | 0.02 | 0.20 | . | * | . | 0.05 | 1.39 |
| Ala | 142 | . | . | B | . | . | . | . | 0.40 | 0.01 | * | * | . | −0.10 | 0.95 |
| Thr | 143 | . | . | . | . | T | . | . | 0.72 | 0.44 | . | * | F | 0.30 | 1.45 |
| Ser | 144 | . | . | . | . | . | . | C | 0.61 | 0.37 | * | * | F | 0.25 | 0.92 |
| Ser | 145 | . | . | . | . | . | T | C | 1.31 | 0.01 | * | * | F | 0.60 | 1.57 |
| Pro | 146 | . | . | . | . | . | T | C | 0.70 | −0.49 | * | * | F | 1.20 | 2.14 |
| Gly | 147 | . | . | . | . | T | T | . | 1.29 | −0.33 | * | . | F | 1.40 | 1.18 |
| Gln | 148 | . | . | B | . | . | T | . | 1.64 | −0.31 | * | . | F | 1.00 | 1.53 |
| Arg | 149 | . | . | B | . | . | . | . | 1.60 | −0.70 | * | . | F | 1.40 | 1.98 |
| Val | 150 | . | . | B | . | . | . | . | 1.56 | −0.70 | * | . | F | 1.70 | 1.98 |
| Gln | 151 | . | . | B | . | . | T | . | 1.46 | −0.70 | * | . | F | 2.20 | 1.13 |
| Lys | 152 | . | . | B | . | . | T | . | 1.80 | −0.61 | * | . | F | 2.35 | 0.83 |
| Gly | 153 | . | . | . | . | . | T | C | 1.50 | −0.61 | * | . | F | 3.00 | 1.94 |
| Gly | 154 | . | . | . | . | . | T | C | 1.39 | −0.87 | * | * | F | 2.70 | 1.50 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Thr | 155 | . | . | . | . | . | . | C | 2.24 | −0.87 | * | . | F | 2.45 | 1.30 |
| Glu | 156 | . | . | . | . | . | . | C | 1.93 | −0.87 | * | . | F | 2.40 | 2.20 |
| Ser | 157 | . | . | B | . | T | T | . | 1.08 | −0.81 | * | . | F | 2.75 | 3.20 |
| Gln | 158 | . | . | . | . | . | T | T | 0.76 | −0.56 | * | . | F | 2.70 | 1.83 |
| Asp | 159 | . | . | . | . | . | T | T | 1.10 | −0.47 | * | . | F | 2.50 | 0.57 |
| Thr | 160 | . | . | B | . | . | . | T | 1.41 | −0.07 | * | . | F | 1.85 | 0.73 |
| Leu | 161 | . | . | . | . | . | T | . | 0.74 | −0.06 | * | . | . | 1.65 | 0.68 |
| Cys | 162 | . | . | . | . | . | T | T | 0.83 | 0.11 | . | . | . | 1.00 | 0.22 |
| Gln | 163 | . | . | . | . | . | T | T | 0.62 | 0.54 | . | . | . | 0.45 | 0.23 |
| Asn | 164 | . | . | . | . | . | T | T | 0.28 | 0.49 | * | . | . | 0.20 | 0.44 |
| Cys | 165 | . | . | B | . | . | . | T | 0.28 | 0.23 | . | . | F | 0.25 | 0.81 |
| Pro | 166 | . | . | . | . | . | T | C | 0.39 | 0.14 | . | . | F | 0.45 | 0.67 |
| Pro | 167 | . | . | . | . | . | T | T | 0.76 | 0.53 | . | . | F | 0.35 | 0.36 |
| Gly | 168 | . | . | . | . | . | T | T | 0.54 | 0.51 | . | . | F | 0.35 | 0.91 |
| Thr | 169 | . | . | . | . | . | T | T | 0.54 | 0.37 | . | * | F | 0.65 | 0.91 |
| Phe | 170 | . | . | B | . | . | . | . | 0.87 | 0.34 | . | * | F | 0.05 | 0.94 |
| Ser | 171 | . | . | . | . | . | T | C | 0.77 | 0.34 | . | * | F | 0.45 | 0.94 |
| Pro | 172 | . | . | . | . | . | T | C | 0.17 | 0.40 | . | * | F | 0.45 | 0.94 |
| Asn | 173 | . | . | . | . | . | T | T | 0.51 | 0.60 | . | * | F | 0.35 | 0.90 |
| Gly | 174 | . | . | . | . | . | T | C | 0.82 | −0.19 | . | * | F | 1.20 | 1.16 |
| Thr | 175 | . | A | . | . | . | . | C | 0.86 | −0.57 | . | * | F | 1.10 | 1.30 |
| Leu | 176 | . | A | . | . | . | . | C | 1.16 | −0.43 | . | . | F | 0.65 | 0.43 |
| Glu | 177 | . | A | B | . | . | . | . | 1.33 | −0.43 | . | . | F | 0.45 | 0.76 |
| Glu | 178 | . | A | B | . | . | . | . | 1.33 | −0.36 | . | . | . | 0.30 | 0.72 |
| Cys | 179 | . | A | B | . | . | . | . | 1.37 | −0.44 | . | * | . | 0.45 | 1.50 |
| Gln | 180 | . | A | . | . | T | . | . | 1.72 | −0.64 | * | * | . | 1.15 | 1.25 |
| His | 181 | . | A | . | . | T | . | . | 1.87 | −0.64 | . | * | . | 1.15 | 1.45 |
| Gln | 182 | . | A | . | . | T | . | . | 1.57 | −0.07 | . | * | F | 1.00 | 1.45 |
| Thr | 183 | . | . | . | . | T | T | . | 1.28 | −0.26 | . | * | F | 1.40 | 1.12 |
| Lys | 184 | . | . | . | . | T | T | . | 1.13 | 0.26 | . | * | F | 0.65 | 0.87 |
| Cys | 185 | . | . | . | . | T | T | . | 0.28 | 0.44 | . | * | . | 0.20 | 0.41 |
| Ser | 186 | . | . | . | . | T | T | . | −0.00 | 0.69 | . | . | . | 0.20 | 0.21 |
| Trp | 187 | . | . | B | B | . | . | . | 0.04 | 0.69 | . | * | . | −0.60 | 0.15 |
| Leu | 188 | . | . | B | B | . | . | . | −0.23 | 0.69 | * | . | . | −0.60 | 0.57 |
| Val | 189 | . | . | B | B | . | . | . | −0.62 | 0.61 | * | . | . | −0.60 | 0.43 |
| Thr | 190 | . | . | B | B | . | . | . | −0.54 | 0.66 | . | . | . | −0.39 | 0.40 |
| Lys | 191 | . | . | B | B | . | . | . | −0.59 | 0.24 | . | . | F | 0.27 | 0.50 |
| Ala | 192 | . | . | B | . | . | . | . | −0.61 | −0.01 | . | . | F | 1.28 | 0.66 |
| Gly | 193 | . | . | . | . | . | T | C | −0.10 | −0.17 | . | . | F | 1.89 | 0.66 |
| Ala | 194 | . | . | . | . | . | T | C | 0.46 | −0.27 | . | . | F | 2.10 | 0.44 |
| Gly | 195 | . | . | . | . | . | T | C | 0.47 | 0.11 | . | . | F | 1.29 | 0.59 |
| Thr | 196 | . | . | . | . | . | T | C | 0.39 | −0.00 | . | . | F | 1.68 | 0.80 |
| Ser | 197 | . | . | . | . | . | . | C | 0.69 | 0.07 | . | . | F | 0.82 | 1.07 |
| Ser | 198 | . | . | . | . | . | T | C | 0.18 | 0.49 | . | . | F | 0.51 | 1.14 |
| Ser | 199 | . | . | . | . | . | T | C | 0.48 | 0.70 | . | . | F | 0.15 | 0.59 |
| His | 200 | . | . | . | . | T | T | . | 0.53 | 1.13 | . | . | . | 0.20 | 0.46 |
| Trp | 201 | . | . | B | . | . | T | . | 0.14 | 1.66 | . | . | . | −0.20 | 0.36 |
| Val | 202 | . | . | B | B | . | . | . | −0.37 | 2.06 | . | . | . | −0.60 | 0.23 |
| Trp | 203 | . | . | B | B | . | . | . | −0.37 | 2.36 | . | . | . | −0.60 | 0.14 |
| Trp | 204 | . | . | B | B | . | . | . | −0.41 | 2.24 | . | . | . | −0.60 | 0.18 |
| Phe | 205 | . | . | B | B | . | . | . | −0.68 | 1.76 | . | . | . | −0.60 | 0.24 |
| Leu | 206 | . | . | . | . | . | T | C | −1.20 | 1.50 | . | . | . | 0.00 | 0.31 |
| Ser | 207 | . | . | . | . | . | T | C | −1.20 | 1.27 | . | * | F | 0.15 | 0.24 |
| Gly | 208 | . | . | . | . | T | T | . | −1.80 | 1.00 | . | . | F | 0.35 | 0.21 |
| Ser | 209 | . | . | . | . | T | T | C | −2.37 | 0.90 | . | * | F | 0.15 | 0.17 |
| Leu | 210 | . | . | . | B | . | . | C | −2.56 | 0.86 | . | . | . | −0.40 | 0.10 |
| Val | 211 | . | . | B | B | . | . | . | −2.60 | 1.16 | . | * | . | −0.60 | 0.07 |
| Ile | 212 | . | . | B | B | . | . | . | −2.97 | 1.37 | . | . | . | −0.60 | 0.04 |
| Val | 213 | . | . | B | B | . | . | . | −2.92 | 1.56 | . | . | . | −0.60 | 0.02 |
| Ile | 214 | . | . | B | B | . | . | . | −2.93 | 1.26 | . | . | . | −0.60 | 0.04 |
| Val | 215 | . | . | B | B | . | . | . | −2.98 | 1.10 | . | . | . | −0.60 | 0.09 |
| Cys | 216 | . | . | B | B | . | . | . | −2.47 | 1.06 | . | . | . | −0.60 | 0.09 |
| Ser | 217 | . | . | B | B | . | . | . | −2.39 | 0.84 | . | . | . | −0.60 | 0.13 |
| Thr | 218 | . | . | B | B | . | . | . | −2.42 | 0.84 | . | . | . | −0.60 | 0.14 |
| Val | 219 | . | . | B | B | . | . | . | −2.42 | 0.89 | . | . | . | −0.60 | 0.19 |
| Gly | 220 | . | . | B | B | . | . | . | −2.23 | 1.00 | . | . | . | −0.60 | 0.10 |
| Leu | 221 | . | . | B | B | . | . | . | −2.42 | 1.19 | . | * | . | −0.60 | 0.04 |
| Ile | 222 | . | . | B | B | . | . | . | −2.08 | 1.34 | * | . | . | −0.60 | 0.04 |
| Ile | 223 | . | . | B | B | . | . | . | −1.66 | 0.70 | * | * | . | −0.60 | 0.07 |
| Cys | 224 | . | . | B | B | . | . | . | −0.69 | 0.27 | . | . | . | −0.30 | 0.18 |
| Val | 225 | . | . | B | B | . | . | . | −0.30 | −0.41 | . | . | . | 0.30 | 0.49 |
| Lys | 226 | . | . | B | B | . | . | . | 0.30 | −1.10 | . | * | F | 1.24 | 1.40 |
| Arg | 227 | . | . | B | B | . | . | . | 1.30 | −1.36 | * | * | F | 1.78 | 4.04 |
| Arg | 228 | . | . | . | . | . | T | . | 1.84 | −1.93 | . | * | F | 2.52 | 10.65 |
| Lys | 229 | . | . | . | . | . | T | C | 2.51 | −2.14 | . | * | F | 2.86 | 5.27 |
| Pro | 230 | . | . | . | . | . | T | T | 2.51 | −2.14 | . | * | F | 3.40 | 4.49 |
| Arg | 231 | . | . | . | . | . | T | T | 1.61 | −1.50 | . | * | F | 3.06 | 1.70 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 232 | . | . | . | . | T | T | . | 1.54 | −0.86 | * | * | F | 2.57 | 0.63 |
| Asp | 233 | . | . | B | B | . | . | . | 0.58 | −0.86 | * | . | F | 1.43 | 0.82 |
| Val | 234 | . | . | B | B | . | . | . | −0.36 | −0.64 | * | * | F | 1.09 | 0.31 |
| Val | 235 | . | . | B | B | . | . | . | −1.00 | 0.04 | . | * | . | −0.30 | 0.22 |
| Lys | 236 | . | . | B | B | . | . | . | −1.41 | 0.26 | * | * | . | −0.30 | 0.10 |
| Val | 237 | . | . | B | B | . | . | . | −1.92 | 0.64 | * | * | . | −0.60 | 0.18 |
| Ile | 238 | . | . | B | B | . | . | . | −1.92 | 0.64 | * | . | . | −0.60 | 0.18 |
| Val | 239 | . | . | B | B | . | . | . | −0.96 | 0.40 | * | * | . | −0.30 | 0.15 |
| Ser | 240 | . | . | B | B | . | . | . | −0.06 | 0.40 | * | * | . | −0.08 | 0.40 |
| Val | 241 | . | . | B | B | . | . | . | 0.01 | −0.24 | * | * | . | 0.89 | 1.15 |
| Gln | 242 | . | . | B | B | . | . | . | 0.87 | −0.93 | * | . | F | 1.56 | 3.03 |
| Arg | 243 | . | . | . | B | . | . | C | 1.76 | −1.17 | . | . | F | 1.98 | 3.91 |
| Lys | 244 | . | . | . | B | . | . | C | 2.02 | −1.56 | . | * | F | 2.20 | 9.13 |
| Arg | 245 | . | A | . | . | . | . | C | 2.32 | −1.70 | . | * | F | 1.98 | 5.33 |
| Gln | 246 | . | A | . | . | . | . | C | 2.83 | −2.10 | . | * | F | 1.76 | 4.71 |
| Glu | 247 | . | A | . | . | . | . | C | 2.83 | −1.67 | . | * | F | 1.54 | 2.33 |
| Ala | 248 | . | A | . | . | . | . | C | 2.13 | −1.67 | . | * | F | 1.32 | 2.06 |
| Glu | 249 | . | A | . | . | . | . | C | 1.78 | −1.17 | . | * | F | 1.10 | 1.20 |
| Gly | 250 | . | A | . | . | . | . | C | 0.81 | −1.09 | * | * | F | 1.10 | 1.00 |
| Glu | 251 | A | A | . | B | . | . | . | −0.08 | −0.44 | . | * | F | 0.45 | 0.74 |
| Ala | 252 | A | A | . | B | . | . | . | −0.08 | −0.26 | . | * | F | 0.45 | 0.30 |
| Thr | 253 | A | A | . | B | . | . | . | −0.08 | −0.26 | * | * | . | 0.30 | 0.52 |
| Val | 254 | A | A | . | B | . | . | . | −0.89 | −0.19 | * | . | . | 0.30 | 0.30 |
| Ile | 255 | . | A | B | B | . | . | . | −0.54 | 0.50 | . | . | . | −0.60 | 0.25 |
| Glu | 256 | . | A | B | B | . | . | . | −1.13 | 0.40 | . | . | . | −0.30 | 0.30 |
| Ala | 257 | . | A | B | . | . | . | . | −0.76 | 0.41 | * | . | . | −0.60 | 0.41 |
| Leu | 258 | . | A | B | . | . | . | . | −0.66 | 0.20 | * | . | . | −0.30 | 0.89 |
| Gln | 259 | . | A | . | . | . | . | C | 0.20 | −0.06 | * | * | . | 0.78 | 0.80 |
| Ala | 260 | . | A | . | . | . | . | C | 0.23 | −0.06 | * | * | F | 1.36 | 1.32 |
| Pro | 261 | . | . | . | . | . | T | C | −0.08 | 0.09 | * | * | F | 1.44 | 1.19 |
| Pro | 262 | . | . | . | . | T | T | . | 0.20 | −0.11 | * | * | F | 2.37 | 0.99 |
| Asp | 263 | . | . | . | . | T | T | . | 0.16 | −0.03 | * | * | F | 2.80 | 1.42 |
| Val | 264 | . | . | B | . | . | T | . | −0.43 | 0.11 | * | * | F | 1.37 | 0.68 |
| Thr | 265 | . | . | B | B | . | . | . | −0.70 | 0.19 | * | . | F | 0.69 | 0.44 |
| Thr | 266 | . | . | B | B | . | . | . | −0.49 | 0.40 | . | . | . | 0.26 | 0.20 |
| Val | 267 | . | . | B | B | . | . | . | −0.28 | 0.40 | . | . | . | −0.02 | 0.46 |
| Ala | 268 | . | . | B | B | . | . | . | −0.59 | −0.24 | . | * | . | 0.30 | 0.55 |
| Val | 269 | . | . | B | B | . | . | . | −0.62 | −0.24 | . | . | . | 0.30 | 0.55 |
| Glu | 270 | . | . | B | B | . | . | . | −0.52 | −0.04 | . | . | F | 0.45 | 0.52 |
| Glu | 271 | . | . | B | B | . | . | . | −0.51 | −0.26 | * | . | F | 0.45 | 0.80 |
| Thr | 272 | . | . | B | B | . | . | . | −0.36 | −0.37 | * | . | F | 0.60 | 1.44 |
| Ile | 273 | . | . | B | B | . | . | . | −0.08 | −0.23 | * | . | F | 0.45 | 0.72 |
| Pro | 274 | . | . | B | B | . | . | . | 0.43 | 0.26 | * | * | F | −0.15 | 0.60 |
| Ser | 275 | . | . | . | B | T | . | . | 0.54 | 0.69 | * | * | F | −0.05 | 0.41 |
| Phe | 276 | . | . | . | B | T | . | . | 0.24 | 0.20 | * | * | F | 0.40 | 1.15 |
| Thr | 277 | . | . | . | B | T | . | . | 0.34 | −0.10 | * | . | F | 0.85 | 1.00 |
| Gly | 278 | . | . | . | . | T | . | . | 1.23 | −0.10 | * | * | F | 1.45 | 1.15 |
| Arg | 279 | . | . | . | . | . | . | C | 1.41 | −0.09 | * | * | F | 1.50 | 2.14 |
| Ser | 280 | . | . | . | . | . | T | C | 1.32 | −0.37 | * | * | F | 1.95 | 2.01 |
| Pro | 281 | . | . | . | . | . | T | C | 1.63 | −0.43 | * | * | F | 2.05 | 2.60 |
| Asn | 282 | . | . | . | . | . | T | . | 1.56 | −0.43 | * | . | . | 2.50 | 1.70 |
| His | 283 | . | . | . | . | . | T | C | 1.51 | −0.00 | * | . | . | 2.05 | 1.62 |

TABLE III

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.58 | −0.24 | . | . | . | 1.15 | 1.53 |
| Glu | 2 | . | . | B | . | . | . | . | 0.97 | −0.24 | * | . | . | 1.40 | 1.19 |
| Pro | 3 | . | . | . | . | . | T | C | 1.07 | −0.67 | * | . | . | 2.35 | 1.55 |
| Pro | 4 | . | . | . | . | T | T | . | 1.11 | −0.19 | * | . | . | 2.50 | 1.65 |
| Gly | 5 | . | . | . | . | T | T | . | 1.29 | −0.37 | * | . | F | 2.25 | 0.94 |
| Asp | 6 | . | . | . | . | T | T | . | 1.68 | 0.06 | * | . | F | 1.40 | 0.94 |
| Trp | 7 | . | . | . | . | T | . | . | 1.47 | 0.06 | * | . | F | 0.95 | 0.94 |
| Gly | 8 | . | . | . | . | . | . | C | 1.39 | 0.06 | * | . | F | 0.65 | 1.47 |
| Pro | 9 | . | . | . | . | . | T | C | 1.71 | 0.54 | * | . | F | 0.15 | 0.93 |
| Pro | 10 | . | . | . | . | . | T | C | 1.76 | 0.54 | * | . | F | 0.30 | 1.73 |
| Pro | 11 | . | . | . | . | T | T | . | 1.44 | 0.01 | * | . | F | 0.80 | 2.34 |
| Trp | 12 | . | . | . | . | T | T | . | 1.52 | 0.07 | * | * | F | 0.80 | 2.18 |
| Arg | 13 | . | . | . | . | T | . | . | 1.98 | 0.07 | * | * | F | 0.94 | 2.18 |
| Ser | 14 | . | . | . | . | . | . | C | 1.88 | −0.36 | * | * | F | 1.68 | 2.77 |
| Thr | 15 | . | . | . | . | . | T | C | 2.09 | −0.30 | * | * | F | 2.22 | 3.80 |
| Pro | 16 | . | . | . | . | . | T | C | 1.44 | −1.21 | * | * | F | 2.86 | 3.24 |
| Arg | 17 | . | . | . | . | T | T | . | 0.92 | −0.57 | . | * | F | 3.40 | 1.79 |

TABLE III-continued

| Res | Position | I | II | III | IV | V | VI | VII | VIII | IX | X | XI | XII | XIII | XIV |
|---|---|---|---|---|---|---|---|---|---|---|---|---|---|---|---|
| Thr | 18 | . | . | B | . | . | T | . | 0.92 | −0.27 | . | * | F | 2.36 | 1.02 |
| Asp | 19 | . | . | B | B | . | . | . | 0.41 | −0.76 | . | . | F | 1.92 | 1.30 |
| Val | 20 | . | . | B | B | . | . | . | −0.13 | −0.50 | * | . | . | 1.28 | 0.55 |
| Leu | 21 | . | . | B | B | . | . | . | −0.73 | 0.14 | * | . | . | 0.04 | 0.28 |
| Arg | 22 | . | . | B | B | . | . | . | −1.09 | 0.34 | * | * | . | −0.30 | 0.14 |
| Leu | 23 | . | . | B | B | . | . | . | −1.59 | 1.10 | * | * | . | −0.60 | 0.29 |
| Val | 24 | . | . | B | B | . | . | . | −1.90 | 1.14 | * | * | . | −0.60 | 0.29 |
| Leu | 25 | . | . | B | B | . | . | . | −1.74 | 0.94 | * | * | . | −0.60 | 0.22 |
| Tyr | 26 | . | . | B | B | . | . | . | −1.74 | 1.73 | * | * | . | −0.60 | 0.23 |
| Leu | 27 | . | . | B | B | . | . | . | −2.20 | 1.73 | * | * | . | −0.60 | 0.25 |
| Thr | 28 | . | . | B | B | . | . | . | −1.98 | 1.51 | . | . | . | −0.60 | 0.30 |
| Phe | 29 | . | . | B | B | . | . | . | −1.33 | 1.33 | . | . | . | −0.60 | 0.19 |
| Leu | 30 | . | . | B | B | . | . | . | −1.19 | 1.00 | . | . | . | −0.60 | 0.37 |
| Gly | 31 | . | . | B | B | . | . | . | −1.19 | 0.89 | . | . | . | −0.60 | 0.14 |
| Ala | 32 | . | . | . | B | . | . | T | −0.97 | 1.16 | . | . | . | −0.20 | 0.25 |
| Pro | 33 | . | . | . | . | . | T | T | −0.87 | 0.87 | . | . | . | 0.20 | 0.30 |
| Cys | 34 | . | . | . | . | . | T | T | . | −0.76 | 0.61 | . | . | . | 0.20 | 0.47 |
| Tyr | 35 | . | . | B | . | . | . | T | . | −0.76 | 0.69 | . | . | . | −0.20 | 0.47 |
| Ala | 36 | . | . | . | B | . | . | . | −0.62 | 0.87 | . | . | . | −0.40 | 0.25 |
| Pro | 37 | . | . | . | B | . | . | . | −0.33 | 0.87 | . | . | . | −0.40 | 0.72 |
| Ala | 38 | . | . | . | B | . | . | . | −0.79 | 0.69 | . | . | . | −0.14 | 0.62 |
| Leu | 39 | . | . | . | B | . | . | T | −0.08 | 0.50 | . | . | . | 0.32 | 0.33 |
| Pro | 40 | . | . | . | B | . | . | T | 0.17 | 0.00 | . | . | F | 1.03 | 0.42 |
| Ser | 41 | . | . | . | . | . | T | T | 0.76 | −0.43 | . | . | F | 2.29 | 0.73 |
| Cys | 42 | . | . | B | . | . | T | . | 0.97 | −0.93 | . | . | F | 2.60 | 1.47 |
| Lys | 43 | . | A | B | . | . | . | . | 1.31 | −1.61 | . | . | F | 1.94 | 1.65 |
| Glu | 44 | . | A | B | . | . | . | . | 1.91 | −1.29 | . | . | F | 1.68 | 1.93 |
| Asp | 45 | . | A | . | . | T | . | . | 1.27 | −1.24 | . | . | F | 1.82 | 5.56 |
| Glu | 46 | . | A | B | . | . | . | . | 1.22 | −1.17 | . | . | F | 1.16 | 2.06 |
| Tyr | 47 | . | A | B | . | . | . | . | 1.59 | −0.74 | . | . | . | 0.75 | 1.18 |
| Pro | 48 | . | . | . | . | . | T | . | 1.54 | −0.36 | . | . | . | 0.90 | 0.95 |
| Val | 49 | . | . | . | . | T | . | . | 0.88 | −0.36 | . | . | F | 1.05 | 0.95 |
| Gly | 50 | . | . | . | . | T | T | . | 0.21 | 0.21 | . | . | F | 0.65 | 0.32 |
| Ser | 51 | . | . | . | . | T | T | . | 0.00 | 0.03 | . | . | F | 0.65 | 0.11 |
| Glu | 52 | . | . | . | . | T | T | . | 0.29 | 0.03 | * | . | F | 0.90 | 0.23 |
| Cys | 53 | . | . | B | . | . | T | . | −0.17 | −0.61 | . | . | . | 1.50 | 0.47 |
| Cys | 54 | . | . | B | . | . | T | . | 0.39 | −0.47 | . | . | . | 1.45 | 0.19 |
| Pro | 55 | . | . | . | . | T | T | . | 0.52 | −0.47 | * | . | . | 2.10 | 0.15 |
| Lys | 56 | . | . | . | . | T | T | . | 0.48 | −0.04 | * | . | F | 2.50 | 0.42 |
| Cys | 57 | . | . | . | . | T | T | . | 0.23 | −0.19 | * | * | F | 2.25 | 0.78 |
| Ser | 58 | . | . | . | . | . | T | C | 1.01 | 0.00 | * | * | F | 1.20 | 0.79 |
| Pro | 59 | . | . | . | . | T | T | . | 0.82 | −0.43 | . | * | F | 1.75 | 0.77 |
| Gly | 60 | . | . | . | . | T | T | . | 1.08 | 0.21 | . | * | F | 1.05 | 1.07 |
| Tyr | 61 | . | . | B | . | . | T | . | 1.03 | −0.36 | . | * | . | 0.85 | 1.60 |
| Arg | 62 | . | A | B | . | . | . | . | 1.11 | −0.74 | * | * | . | 0.75 | 1.79 |
| Val | 63 | . | A | B | . | . | . | . | 0.74 | −0.67 | * | * | . | 0.75 | 1.83 |
| Lys | 64 | . | A | B | . | . | . | . | 0.61 | −0.53 | * | . | . | 0.60 | 0.63 |
| Glu | 65 | . | A | B | . | . | . | . | 0.96 | −0.86 | * | * | . | 0.60 | 0.32 |
| Ala | 66 | . | A | B | . | . | . | . | 0.39 | −0.86 | * | * | . | 0.60 | 0.74 |
| Cys | 67 | . | A | B | . | . | . | . | −0.03 | −0.81 | * | * | . | 0.60 | 0.30 |
| Gly | 68 | . | A | . | . | T | . | . | 0.48 | −0.33 | * | . | . | 0.70 | 0.25 |
| Glu | 69 | . | A | . | . | T | . | . | 0.12 | 0.10 | * | * | F | 0.25 | 0.25 |
| Leu | 70 | . | . | . | B | T | . | . | −0.73 | 0.09 | * | * | F | 0.25 | 0.67 |
| Thr | 71 | . | . | . | B | T | . | . | −0.81 | 0.16 | * | . | F | 0.25 | 0.50 |
| Gly | 72 | . | . | . | B | T | . | . | −0.14 | 0.30 | * | . | F | 0.25 | 0.16 |
| Thr | 73 | . | . | . | B | T | . | . | −0.01 | 0.30 | * | . | F | 0.25 | 0.33 |
| Val | 74 | . | . | B | B | . | . | . | −0.68 | 0.04 | * | . | . | −0.30 | 0.35 |
| Cys | 75 | . | . | B | B | . | . | . | −0.08 | 0.13 | . | . | . | −0.30 | 0.19 |
| Glu | 76 | . | . | B | B | . | . | . | 0.02 | 0.13 | . | . | . | −0.23 | 0.20 |
| Pro | 77 | . | . | . | . | . | T | . | 0.02 | 0.07 | . | . | F | 0.59 | 0.42 |
| Cys | 78 | . | . | . | . | . | . | C | 0.02 | −0.14 | . | . | F | 1.06 | 0.78 |
| Pro | 79 | . | . | . | . | . | T | C | 0.63 | −0.23 | * | . | F | 1.33 | 0.65 |
| Pro | 80 | . | . | . | . | T | T | . | 0.41 | 0.53 | . | . | F | 0.70 | 0.66 |
| Gly | 81 | . | . | . | . | T | T | . | −0.18 | 0.79 | * | . | F | 0.63 | 0.86 |
| Thr | 82 | . | . | B | . | . | T | . | 0.00 | 0.71 | * | . | F | 0.16 | 0.56 |
| Tyr | 83 | . | . | B | . | . | . | . | −0.14 | 0.79 | . | . | . | −0.26 | 0.49 |
| Ile | 84 | . | . | B | . | . | . | . | 0.07 | 1.04 | . | . | . | −0.33 | 0.41 |
| Ala | 85 | . | . | B | . | . | . | . | −0.07 | 1.01 | . | . | . | −0.40 | 0.46 |
| His | 86 | . | . | B | . | . | . | T | −0.53 | 0.96 | . | . | . | −0.20 | 0.29 |
| Leu | 87 | . | . | B | . | . | . | T | −0.52 | 0.89 | * | . | . | −0.20 | 0.34 |
| Asn | 88 | . | . | . | . | T | T | . | −0.23 | 0.59 | * | . | . | 0.20 | 0.45 |
| Gly | 89 | . | . | . | . | T | T | . | −0.01 | 0.09 | * | . | F | 0.65 | 0.66 |
| Leu | 90 | . | . | . | . | T | T | . | −0.23 | 0.16 | * | . | F | 0.45 | 0.43 |
| Ser | 91 | . | . | . | . | T | T | . | −0.20 | 0.16 | * | . | F | 0.65 | 0.22 |
| Lys | 92 | . | . | . | . | T | T | . | −0.06 | 0.16 | * | . | . | 0.50 | 0.39 |
| Cys | 93 | . | . | B | . | . | T | . | −0.06 | 0.30 | * | . | . | 0.10 | 0.25 |
| Leu | 94 | . | . | B | . | . | T | . | −0.31 | 0.01 | * | . | . | 0.10 | 0.33 |

TABLE III-continued

| Res | Position | I | II | III | IV | V | VI | VII | VIII | IX | X | XI | XII | XIII | XIV |
|---|---|---|---|---|---|---|---|---|---|---|---|---|---|---|---|
| Gln | 95 | . | A | B | . | . | . | . | −0.17 | 0.24 | * | . | . | −0.30 | 0.16 |
| Cys | 96 | . | A | B | . | . | . | . | 0.13 | 0.81 | * | . | . | −0.60 | 0.16 |
| Gln | 97 | . | A | B | . | . | . | . | −0.12 | 0.24 | * | . | . | −0.30 | 0.33 |
| Met | 98 | . | A | B | . | . | . | . | 0.54 | −0.01 | . | . | . | 0.61 | 0.29 |
| Cys | 99 | . | A | B | . | . | . | . | 0.47 | −0.41 | . | . | . | 0.92 | 0.91 |
| Asp | 100 | . | . | B | . | . | . | T | 0.12 | −0.30 | . | . | . | 1.63 | 0.37 |
| Pro | 101 | . | . | . | . | . | T | T | 0.49 | −0.27 | . | . | F | 2.49 | 0.37 |
| Asp | 102 | . | . | . | . | . | T | T | 0.28 | −0.50 | . | . | F | 3.10 | 0.92 |
| Ile | 103 | . | . | . | . | . | T | T | 0.21 | −0.64 | . | . | F | 2.79 | 0.85 |
| Gly | 104 | . | . | . | . | . | T | . | 0.88 | −0.07 | . | * | F | 1.98 | 0.29 |
| Ser | 105 | . | . | . | B | . | . | T | 0.07 | −0.50 | . | * | F | 1.77 | 0.29 |
| Pro | 106 | . | . | . | B | . | . | T | 0.39 | 0.19 | . | * | F | 0.56 | 0.35 |
| Cys | 107 | . | . | . | B | . | . | T | 0.04 | −0.50 | * | * | F | 1.46 | 0.69 |
| Asp | 108 | . | . | . | B | . | . | T | 1.04 | −0.50 | . | * | F | 1.77 | 0.51 |
| Leu | 109 | . | . | . | B | . | . | . | 1.04 | −0.89 | . | * | F | 1.88 | 0.64 |
| Arg | 110 | . | . | . | B | . | . | . | 1.31 | −0.89 | . | * | F | 2.34 | 1.19 |
| Gly | 111 | . | . | . | . | . | T | T | 0.71 | −0.96 | . | * | F | 3.10 | 0.97 |
| Arg | 112 | . | . | . | . | . | T | T | 1.38 | −0.27 | . | * | F | 2.49 | 0.97 |
| Gly | 113 | . | . | . | . | . | T | C | 0.79 | −0.96 | . | * | F | 2.28 | 0.85 |
| His | 114 | . | . | . | . | . | T | C | 1.26 | −0.46 | . | * | . | 1.52 | 0.87 |
| Leu | 115 | . | A | B | . | . | . | . | 0.56 | −0.46 | * | * | . | 0.61 | 0.44 |
| Glu | 116 | . | A | B | . | . | . | . | 0.87 | 0.04 | * | * | . | −0.30 | 0.45 |
| Ala | 117 | . | A | B | . | . | . | . | −0.06 | 0.11 | * | * | . | −0.30 | 0.45 |
| Gly | 118 | . | A | B | . | . | . | . | −0.01 | 0.30 | . | * | . | −0.30 | 0.45 |
| Ala | 119 | . | A | . | . | T | . | C | −0.19 | −0.00 | . | * | . | 0.70 | 0.35 |
| His | 120 | . | A | . | . | . | . | C | 0.28 | 0.43 | . | * | . | −0.06 | 0.53 |
| Leu | 121 | . | A | . | . | . | . | C | 0.39 | 0.36 | . | . | . | 0.58 | 0.53 |
| Ser | 122 | . | . | . | . | . | T | C | 0.98 | −0.07 | . | . | F | 2.22 | 1.03 |
| Pro | 123 | . | . | . | . | . | T | C | 1.37 | −0.17 | . | . | F | 2.56 | 1.32 |
| Gly | 124 | . | . | . | . | T | T | . | 1.61 | −0.67 | . | * | F | 3.40 | 3.19 |
| Arg | 125 | . | . | . | . | T | T | . | 1.64 | −0.93 | . | * | F | 3.06 | 2.35 |
| Gln | 126 | . | . | . | . | T | . | . | 2.24 | −1.31 | . | * | F | 2.82 | 2.64 |
| Lys | 127 | . | . | . | . | T | . | . | 2.54 | −1.31 | . | * | F | 2.78 | 4.12 |
| Gly | 128 | . | . | . | . | . | . | C | 2.54 | −1.74 | . | * | F | 2.54 | 3.51 |
| Glu | 129 | . | . | . | . | . | T | C | 2.89 | −1.31 | . | * | F | 2.70 | 3.14 |
| Pro | 130 | . | . | . | . | . | T | C | 1.92 | −1.71 | * | * | F | 3.00 | 2.72 |
| Asp | 131 | . | . | . | . | . | T | C | 1.33 | −1.07 | . | * | F | 2.70 | 2.04 |
| Pro | 132 | . | . | . | . | . | T | C | 0.59 | −1.00 | . | * | F | 2.40 | 1.19 |
| Glu | 133 | . | A | B | . | . | . | . | 0.93 | −0.21 | . | * | . | 0.90 | 0.67 |
| Val | 134 | . | A | B | . | . | . | . | 0.63 | −0.64 | . | * | . | 0.90 | 0.69 |
| Ala | 135 | A | A | . | . | . | . | . | 0.03 | −0.26 | * | . | . | 0.30 | 0.60 |
| Phe | 136 | A | A | . | . | . | . | . | −0.27 | 0.00 | . | . | . | −0.30 | 0.28 |
| Glu | 137 | A | A | . | . | . | . | . | −0.64 | 0.39 | . | . | . | −0.30 | 0.51 |
| Ser | 138 | A | A | . | . | . | . | . | −0.64 | 0.24 | . | . | . | −0.30 | 0.51 |
| Leu | 139 | . | A | . | . | . | . | C | 0.00 | −0.26 | . | . | . | 0.65 | 1.03 |
| Ser | 140 | . | A | . | . | . | . | C | −0.27 | −0.61 | * | . | F | 0.95 | 0.92 |
| Ala | 141 | . | A | . | . | . | . | C | 0.40 | 0.03 | * | . | F | 0.05 | 0.51 |
| Glu | 142 | . | A | B | . | . | . | . | −0.19 | 0.14 | . | . | F | −0.15 | 0.84 |
| Pro | 143 | A | A | . | . | . | . | . | −0.48 | −0.04 | . | . | . | 0.30 | 0.63 |
| Val | 144 | . | A | B | . | . | . | . | 0.33 | 0.07 | . | . | . | −0.30 | 0.63 |
| His | 145 | . | A | B | . | . | . | . | 0.29 | −0.03 | . | . | . | 0.30 | 0.59 |
| Ala | 146 | . | . | B | . | . | . | T | 0.58 | 0.40 | . | . | . | −0.20 | 0.38 |
| Ala | 147 | . | . | . | . | T | T | C | −0.28 | 0.36 | * | . | . | 0.50 | 0.68 |
| Asn | 148 | . | . | . | . | T | T | . | −0.28 | 0.36 | . | . | F | 0.65 | 0.37 |
| Gly | 149 | . | . | . | . | T | T | . | −0.23 | 0.29 | . | * | F | 0.65 | 0.57 |
| Ser | 150 | . | . | . | . | . | . | C | −0.20 | 0.47 | . | * | F | −0.05 | 0.46 |
| Val | 151 | . | . | . | . | . | . | C | 0.18 | −0.03 | . | * | F | 0.85 | 0.50 |
| Pro | 152 | . | . | B | . | . | . | . | 0.73 | 0.00 | . | * | . | −0.10 | 0.78 |
| Leu | 153 | . | A | B | . | . | . | . | 0.14 | 0.07 | * | * | . | −0.30 | 0.79 |
| Glu | 154 | . | A | B | . | . | . | . | 0.60 | 0.19 | * | * | . | −0.15 | 1.08 |
| Pro | 155 | . | A | B | . | . | . | . | 0.09 | −0.46 | * | * | . | 0.45 | 1.36 |
| His | 156 | . | A | B | . | . | . | . | 0.64 | −0.20 | * | * | . | 0.45 | 1.36 |
| Ala | 157 | A | A | . | . | . | . | . | 0.26 | −0.50 | * | * | . | 0.45 | 1.05 |
| Arg | 158 | . | A | B | . | . | . | . | 0.48 | 0.11 | * | * | . | −0.30 | 0.68 |
| Leu | 159 | . | A | B | . | . | . | . | 0.18 | 0.19 | * | * | . | −0.30 | 0.50 |
| Ser | 160 | . | A | B | . | . | . | . | −0.20 | 0.07 | . | * | . | −0.30 | 0.66 |
| Met | 161 | . | A | B | . | . | . | . | −0.38 | 0.07 | * | * | . | −0.30 | 0.34 |
| Ala | 162 | . | A | B | . | T | . | . | −0.46 | 0.50 | * | * | . | −0.20 | 0.64 |
| Ser | 163 | . | . | B | . | . | . | . | −0.91 | 0.39 | * | . | . | −0.10 | 0.26 |
| Ala | 164 | . | . | . | . | . | T | C | −0.10 | 0.43 | . | . | . | 0.00 | 0.26 |
| Pro | 165 | . | . | . | . | T | T | . | −0.39 | 0.21 | . | . | . | 0.50 | 0.44 |
| Cys | 166 | . | . | . | . | T | T | . | −0.13 | 0.21 | . | . | . | 0.50 | 0.33 |
| Gly | 167 | . | . | . | . | T | T | . | −0.36 | 0.26 | . | . | F | 0.65 | 0.33 |
| Gln | 168 | . | A | B | . | . | . | . | −0.09 | 0.44 | . | . | F | −0.45 | 0.17 |
| Ala | 169 | . | A | B | . | . | . | . | −0.31 | 0.51 | . | * | . | −0.60 | 0.44 |
| Gly | 170 | . | A | B | . | . | . | . | 0.01 | 0.63 | * | * | . | −0.60 | 0.37 |
| Leu | 171 | . | A | B | . | . | . | . | 0.68 | 0.20 | * | * | . | −0.30 | 0.42 |

TABLE III-continued

| Res | Position | I | II | III | IV | V | VI | VII | VIII | IX | X | XI | XII | XIII | XIV |
|---|---|---|---|---|---|---|---|---|---|---|---|---|---|---|---|
| His | 172 | . | A | B | . | . | . | . | 1.13 | −0.20 | * | * | . | 0.30 | 0.69 |
| Leu | 173 | . | A | B | . | . | . | . | 0.54 | −0.70 | . | * | . | 1.09 | 1.36 |
| Arg | 174 | . | A | B | . | . | . | . | 1.13 | −0.63 | . | * | . | 1.43 | 1.66 |
| Asp | 175 | . | A | B | . | . | . | . | 1.13 | −1.31 | . | * | F | 1.92 | 2.04 |
| Arg | 176 | . | . | B | . | . | T | . | 1.63 | −1.39 | . | * | F | 2.66 | 2.45 |
| Ala | 177 | . | . | . | . | T | T | . | 1.46 | −1.59 | . | * | F | 3.40 | 1.81 |
| Asp | 178 | . | . | . | . | T | T | . | 1.92 | −1.16 | . | * | F | 3.06 | 1.67 |
| Gly | 179 | . | . | . | . | . | T | C | 1.47 | −0.73 | * | * | F | 2.55 | 0.85 |
| Thr | 180 | . | . | . | . | . | T | C | 1.58 | −0.30 | * | * | F | 2.09 | 0.83 |
| Pro | 181 | . | . | . | . | . | T | C | 0.88 | −0.80 | * | * | F | 2.23 | 0.97 |
| Gly | 182 | . | . | . | . | T | T | . | 1.08 | −0.30 | * | * | F | 1.97 | 0.99 |
| Gly | 183 | . | . | . | . | . | T | C | 0.69 | −0.30 | * | * | . | 1.80 | 0.88 |
| Arg | 184 | . | . | B | . | . | . | . | 0.64 | −0.36 | * | . | . | 1.22 | 0.73 |
| Ala | 185 | . | . | B | . | . | . | . | 0.57 | −0.36 | * | . | . | 1.04 | 0.94 |

TABLE IV

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | −0.42 | 0.50 | . | . | . | −0.40 | 0.44 |
| Leu | 2 | . | . | B | . | . | . | . | −0.38 | 0.46 | . | . | . | −0.40 | 0.46 |
| Gly | 3 | . | . | B | . | . | T | . | −0.02 | 0.46 | . | . | . | −0.20 | 0.35 |
| Thr | 4 | . | . | . | . | . | T | C | −0.44 | 0.53 | . | . | . | 0.00 | 0.49 |
| Ser | 5 | . | . | . | . | . | T | C | −0.91 | 0.60 | . | . | F | 0.15 | 0.49 |
| Gly | 6 | . | . | B | . | . | T | . | −0.60 | 0.56 | . | . | F | −0.05 | 0.37 |
| His | 7 | . | . | B | B | . | . | . | −0.60 | 1.04 | . | . | . | −0.60 | 0.27 |
| Leu | 8 | . | . | B | B | . | . | . | −0.56 | 1.24 | . | . | . | −0.60 | 0.16 |
| Val | 9 | . | . | B | B | . | . | . | −0.24 | 1.24 | . | . | . | −0.60 | 0.22 |
| Trp | 10 | . | . | B | B | . | . | . | −0.29 | 1.21 | . | . | . | −0.60 | 0.28 |
| Leu | 11 | . | . | B | B | . | . | . | −0.64 | 1.14 | . | . | . | −0.60 | 0.34 |
| Ser | 12 | . | . | B | . | . | T | . | −0.91 | 1.24 | . | . | F | −0.05 | 0.40 |
| Gln | 13 | . | . | B | . | . | T | . | −0.91 | 0.99 | . | . | F | −0.05 | 0.50 |
| Gly | 14 | . | . | . | . | T | T | . | −0.64 | 0.76 | . | . | F | 0.35 | 0.50 |
| Phe | 15 | . | . | B | . | . | T | . | −0.70 | 0.57 | * | * | . | −0.20 | 0.38 |
| Ser | 16 | . | . | B | . | . | . | . | 0.22 | 0.61 | * | * | . | −0.40 | 0.22 |
| Leu | 17 | . | . | B | . | . | . | . | 0.31 | 0.21 | * | * | . | −0.10 | 0.43 |
| Ala | 18 | . | . | B | . | . | . | . | −0.03 | 0.21 | * | * | . | 0.24 | 0.77 |
| Gly | 19 | . | . | . | . | . | . | C | 0.01 | −0.14 | * | * | F | 1.53 | 0.57 |
| Arg | 20 | . | . | . | . | . | T | C | 0.41 | −0.14 | * | * | F | 2.07 | 0.92 |
| Pro | 21 | . | . | . | . | T | T | . | 0.50 | −0.44 | * | * | F | 2.76 | 1.22 |
| Gly | 22 | . | . | . | . | T | T | . | 1.02 | −0.51 | * | * | F | 3.40 | 1.91 |
| Ser | 23 | . | . | . | . | . | T | C | 1.40 | −0.03 | * | . | F | 2.56 | 1.02 |
| Ser | 24 | . | . | . | . | . | T | C | 0.89 | 0.40 | . | * | F | 1.32 | 1.02 |
| Pro | 25 | . | . | . | . | . | T | C | 0.78 | 0.61 | . | * | F | 0.83 | 0.77 |
| Trp | 26 | . | . | B | . | . | T | . | 0.40 | 0.19 | . | * | F | 0.59 | 0.96 |
| Pro | 27 | . | . | B | . | . | T | . | −0.11 | 0.30 | . | * | . | 0.10 | 0.72 |
| Val | 28 | . | . | B | B | . | . | . | −0.62 | 0.56 | . | * | . | −0.60 | 0.35 |
| Asp | 29 | . | . | B | B | . | . | . | −0.91 | 0.81 | . | * | . | −0.60 | 0.27 |
| Ala | 30 | . | . | B | B | . | . | . | −1.37 | 0.40 | . | * | . | −0.60 | 0.18 |
| Val | 31 | . | . | B | B | . | . | . | −1.42 | 0.54 | . | * | . | −0.60 | 0.13 |
| Leu | 32 | . | . | B | B | . | . | . | −1.50 | 0.33 | . | . | . | −0.30 | 0.08 |
| Ala | 33 | . | . | B | . | . | T | . | −1.31 | 1.24 | . | . | . | −0.20 | 0.08 |
| Cys | 34 | . | . | . | . | T | T | . | −1.52 | 1.31 | . | . | . | 0.20 | 0.06 |
| Gly | 35 | . | . | . | . | T | T | . | −1.28 | 1.10 | . | . | . | 0.20 | 0.11 |
| Trp | 36 | . | . | . | . | T | T | . | −1.23 | 0.84 | . | . | . | 0.20 | 0.10 |
| Cys | 37 | . | . | B | . | . | T | . | −0.46 | 1.03 | . | * | . | −0.20 | 0.16 |
| Pro | 38 | . | . | . | . | T | T | . | −0.72 | 0.96 | . | . | . | 0.20 | 0.22 |
| Gly | 39 | . | . | . | . | T | T | . | −0.27 | 1.17 | . | * | . | 0.20 | 0.16 |
| Leu | 40 | . | . | B | . | . | T | . | −0.13 | 0.69 | . | . | . | −0.20 | 0.45 |
| His | 41 | . | . | B | . | . | . | . | −0.66 | 0.54 | . | . | . | −0.40 | 0.45 |
| Val | 42 | . | . | B | . | . | . | . | −0.29 | 0.80 | . | . | . | −0.40 | 0.38 |
| Pro | 43 | . | . | B | . | . | . | . | −0.29 | 0.76 | . | . | F | −0.25 | 0.61 |
| Pro | 44 | . | . | . | . | T | . | . | −0.24 | 0.50 | . | . | F | 0.15 | 0.70 |
| Leu | 45 | . | . | . | . | T | . | . | 0.27 | 0.39 | . | . | F | 0.60 | 1.26 |
| Ser | 46 | . | . | . | . | . | T | C | 0.01 | 0.13 | . | . | F | 0.60 | 1.09 |
| Pro | 47 | . | . | . | . | . | T | C | 0.56 | 0.61 | . | . | F | 0.15 | 0.74 |
| Ser | 48 | . | . | . | . | T | T | . | 0.56 | 0.67 | . | . | F | 0.50 | 1.29 |
| Ser | 49 | . | . | . | . | T | T | . | 0.18 | 0.41 | . | . | F | 0.50 | 1.49 |
| Trp | 50 | . | . | B | . | . | . | . | 0.39 | 0.53 | . | . | F | −0.25 | 0.98 |
| Thr | 51 | . | . | B | . | . | . | . | 0.34 | 0.71 | . | . | F | −0.25 | 0.72 |
| Pro | 52 | . | . | B | . | . | . | . | −0.26 | 0.76 | . | * | . | −0.40 | 0.53 |
| Ala | 53 | . | A | B | . | . | . | . | 0.16 | 1.06 | . | * | . | −0.60 | 0.42 |
| Met | 54 | . | A | B | . | . | . | . | −0.13 | 0.14 | . | * | . | −0.30 | 0.57 |
| Gly | 55 | . | A | B | . | . | . | . | −0.14 | 0.16 | * | * | . | −0.30 | 0.37 |

TABLE IV-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 56 | . | A | B | . | . | . | . | 0.28 | 0.11 | * | * | . | -0.30 | 0.49 |
| Arg | 57 | . | A | B | . | . | . | . | 0.49 | -0.39 | * | * | . | 0.64 | 0.97 |
| Ala | 58 | . | A | B | . | . | . | . | 0.41 | -0.60 | * | * | . | 1.43 | 1.58 |
| Ser | 59 | . | . | . | . | T | T | . | 0.71 | -0.46 | * | * | F | 2.42 | 1.03 |
| Arg | 60 | . | . | . | . | T | T | . | 1.17 | -0.76 | * | * | F | 2.91 | 0.70 |
| Asn | 61 | . | . | . | . | T | T | . | 1.67 | -0.76 | * | * | F | 3.40 | 1.36 |
| Cys | 62 | . | . | . | . | T | T | . | 1.56 | -0.77 | * | * | F | 3.06 | 1.47 |
| Ser | 63 | . | . | . | . | T | . | . | 2.14 | -1.16 | * | * | F | 2.52 | 1.30 |
| Arg | 64 | . | A | . | . | T | . | . | 1.86 | -0.76 | * | * | F | 1.98 | 1.30 |
| Thr | 65 | . | A | . | . | T | . | . | 0.89 | -0.66 | * | * | F | 1.64 | 2.44 |
| Glu | 66 | . | A | . | . | T | . | . | 0.22 | -0.59 | * | . | F | 1.30 | 1.35 |
| Asn | 67 | . | A | B | . | . | . | . | 0.54 | -0.40 | * | * | F | 0.45 | 0.37 |
| Ala | 68 | . | A | B | . | . | . | . | 0.18 | 0.03 | . | * | . | -0.30 | 0.25 |
| Val | 69 | . | A | . | . | T | . | . | -0.23 | 0.11 | . | * | . | 0.10 | 0.08 |
| Cys | 70 | . | . | . | . | T | . | . | -0.13 | 0.50 | . | . | . | 0.00 | 0.07 |
| Gly | 71 | . | . | . | . | T | . | . | -0.48 | 0.53 | . | . | . | 0.00 | 0.10 |
| Cys | 72 | . | . | . | . | T | . | . | -0.51 | 0.46 | . | . | . | 0.00 | 0.13 |
| Ser | 73 | . | . | . | . | . | T | C | -0.62 | 0.31 | . | . | . | 0.30 | 0.34 |
| Pro | 74 | . | . | . | . | T | T | . | -0.43 | 0.53 | . | * | F | 0.35 | 0.30 |
| Gly | 75 | . | . | . | . | T | T | . | -0.66 | 0.67 | . | . | . | 0.20 | 0.30 |
| His | 76 | . | . | B | . | . | T | . | -1.17 | 0.79 | . | . | . | -0.20 | 0.16 |
| Phe | 77 | . | . | B | B | . | . | . | -0.50 | 1.04 | . | . | . | -0.60 | 0.07 |
| Cys | 78 | . | . | B | B | . | . | . | -0.20 | 1.01 | . | . | . | -0.32 | 0.13 |
| Ile | 79 | . | . | B | B | . | . | . | -0.33 | 0.59 | . | * | . | -0.04 | 0.16 |
| Val | 80 | . | . | B | . | . | T | . | 0.01 | 0.51 | . | * | . | 0.64 | 0.18 |
| Gln | 81 | . | . | . | . | T | T | . | 0.01 | -0.27 | . | . | F | 2.37 | 0.57 |
| Asp | 82 | . | . | . | . | T | T | . | 0.04 | -0.34 | * | . | F | 2.80 | 1.11 |
| Gly | 83 | . | . | . | . | T | T | . | 0.12 | -0.46 | * | . | F | 2.37 | 0.80 |
| Asp | 84 | . | A | . | . | T | . | . | 0.42 | -0.60 | * | . | F | 1.99 | 0.47 |
| His | 85 | . | A | . | . | T | . | . | 0.61 | -0.50 | . | * | . | 1.56 | 0.28 |
| Cys | 86 | . | A | B | . | . | . | . | 0.72 | 0.07 | . | * | . | -0.02 | 0.15 |
| Ala | 87 | . | A | B | . | . | . | . | 0.13 | -0.36 | * | * | . | 0.30 | 0.18 |
| Ala | 88 | . | A | B | . | . | . | . | 0.23 | 0.14 | * | * | . | -0.30 | 0.13 |
| Cys | 89 | . | A | B | . | . | . | . | -0.36 | 0.40 | . | * | . | -0.30 | 0.39 |
| Arg | 90 | . | A | B | . | . | . | . | -0.63 | 0.33 | . | * | . | -0.30 | 0.39 |
| Ala | 91 | . | A | B | . | . | . | . | -0.27 | 0.31 | . | * | . | -0.30 | 0.56 |
| Tyr | 92 | . | . | B | . | . | . | . | 0.02 | 0.20 | . | * | . | 0.05 | 1.39 |
| Ala | 93 | . | . | B | . | . | . | . | 0.40 | 0.01 | . | * | . | -0.10 | 0.95 |
| Thr | 94 | . | . | . | . | T | . | . | 0.72 | 0.44 | . | * | F | 0.30 | 1.45 |
| Ser | 95 | . | . | . | . | . | . | C | 0.61 | 0.37 | * | * | F | 0.25 | 0.92 |
| Ser | 96 | . | . | . | . | . | T | C | 1.31 | 0.01 | * | * | F | 0.60 | 1.57 |
| Pro | 97 | . | . | . | . | . | T | C | 0.70 | -0.49 | * | * | F | 1.20 | 2.14 |
| Gly | 98 | . | . | . | . | T | T | . | 1.29 | -0.33 | * | * | F | 1.40 | 1.18 |
| Gln | 99 | . | . | B | . | . | T | . | 1.64 | -0.31 | * | . | F | 1.00 | 1.53 |
| Arg | 100 | . | . | B | . | . | . | . | 1.60 | -0.70 | * | . | F | 1.40 | 1.98 |
| Val | 101 | . | . | B | . | . | . | . | 1.56 | -0.70 | * | . | F | 1.70 | 1.98 |
| Gln | 102 | . | . | B | . | . | T | . | 1.46 | -0.70 | * | . | F | 2.20 | 1.13 |
| Lys | 103 | . | . | B | . | . | T | . | 1.80 | -0.61 | * | . | F | 2.35 | 0.83 |
| Gly | 104 | . | . | . | . | . | T | C | 1.50 | -0.61 | * | * | F | 3.00 | 1.94 |
| Gly | 105 | . | . | . | . | . | T | C | 1.39 | -0.87 | * | * | F | 2.70 | 1.50 |
| Thr | 106 | . | . | . | . | . | . | C | 2.24 | -0.87 | * | . | F | 2.45 | 1.30 |
| Glu | 107 | . | . | . | . | . | . | C | 1.93 | -0.87 | * | . | F | 2.40 | 2.20 |
| Ser | 108 | . | . | B | . | T | T | . | 1.08 | -0.81 | * | * | F | 2.75 | 3.20 |
| Gln | 109 | . | . | . | . | T | T | . | 0.76 | -0.56 | * | . | F | 2.70 | 1.83 |
| Asp | 110 | . | . | . | . | T | T | . | 1.10 | -0.47 | . | . | F | 2.50 | 0.57 |
| Thr | 111 | . | . | B | . | . | T | . | 1.41 | -0.07 | . | . | F | 1.85 | 0.73 |
| Leu | 112 | . | . | . | . | . | T | . | 0.74 | -0.06 | . | . | . | 1.65 | 0.68 |
| Cys | 113 | . | . | . | . | T | . | . | 0.83 | 0.11 | * | . | . | 1.05 | 0.22 |
| Gln | 114 | . | . | B | . | . | . | . | 0.94 | 0.54 | * | * | . | 0.35 | 0.23 |
| Asn | 115 | . | . | B | . | . | . | . | 0.60 | 0.06 | * | * | . | 0.65 | 0.56 |
| Cys | 116 | . | . | B | . | . | T | . | 0.70 | -0.20 | * | * | F | 2.00 | 1.03 |
| Pro | 117 | . | . | . | . | T | T | . | 1.21 | -0.34 | * | . | F | 2.50 | 0.92 |
| Arg | 118 | . | . | . | . | T | T | . | 1.07 | -0.36 | * | . | F | 2.25 | 0.76 |
| Gly | 119 | . | . | . | . | . | T | C | 0.86 | -0.07 | * | . | F | 1.95 | 1.17 |
| Pro | 120 | . | . | . | . | T | . | . | 0.26 | -0.21 | . | . | F | 1.70 | 1.17 |
| Ser | 121 | . | . | . | . | . | . | C | 0.58 | -0.03 | . | . | F | 1.10 | 0.59 |
| Leu | 122 | . | . | B | . | . | . | . | 0.58 | 0.40 | . | . | . | -0.10 | 0.59 |
| Pro | 123 | . | . | B | . | . | . | . | 0.18 | 0.40 | * | * | . | -0.10 | 0.59 |
| Met | 124 | . | . | B | . | . | . | . | 0.63 | 0.89 | * | . | . | -0.40 | 0.47 |
| Gly | 125 | . | . | . | . | T | . | . | 0.84 | 0.50 | * | . | . | -0.05 | 1.11 |
| Pro | 126 | . | . | . | . | T | T | . | 0.29 | 0.21 | * | . | F | 0.80 | 1.15 |
| Trp | 127 | . | . | . | . | T | T | . | 0.80 | 0.43 | * | . | F | 0.35 | 0.86 |
| Arg | 128 | . | . | B | . | . | . | . | 0.70 | 0.20 | * | * | . | 0.40 | 1.17 |
| Asn | 129 | . | . | B | . | . | . | . | 1.41 | 0.26 | * | * | . | 0.20 | 1.09 |
| Val | 130 | . | . | B | . | . | . | . | 1.54 | -0.17 | * | * | F | 1.11 | 2.03 |
| Ser | 131 | . | . | B | . | . | . | . | 1.46 | -0.66 | * | . | F | 1.72 | 1.60 |
| Thr | 132 | . | . | . | . | . | . | C | 1.79 | -0.27 | * | . | F | 1.93 | 1.34 |

TABLE IV-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 133 | . | . | . | . | . | T | C | 1.29 | −0.67 | * | . | F | 2.74 | 3.60 |
| Pro | 134 | . | . | . | . | T | T | . | 0.90 | −0.89 | * | * | . | 3.10 | 3.43 |
| Ser | 135 | . | . | . | . | T | T | . | 1.37 | −0.84 | * | * | . | 2.79 | 3.04 |
| Lys | 136 | . | . | . | . | T | T | . | 1.28 | −0.90 | * | . | . | 2.48 | 1.98 |

Among highly preferred fragments in this regard are those that comprise, or alternatively consist of, regions of TR2 receptors that combine several structural features, such as several of the features set out above. Polynucleotides encoding these polypeptides are also encompassed by the invention.

As one of skill in the art will appreciate, TR2 polypeptides of the present invention and epitope-bearing fragments thereof can be combined with heterologous polypeptide sequences. For example, the polypeptides of the present invention may be fused with the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life.

The present invention is further directed to isolated polypeptides comprising, or alternatively consisting of, fragments of TR2, TR2-SV1, and TR2-SV2. In particular, the invention provides isolated polypeptides comprising, or alternatively consisting of, the amino acid sequences of a member selected from the group consisting of amino acids −36 to 24, −26 to 34, −16 to 44, −6 to 54, 1 to 60, 11 to 70, 21 to 80, 31 to 90, 41 to 100, 51 to 110, 61 to 120, 71 to 130, 81 to 140, 91 to 150, 101 to 160, 111 to 170, 121 to 180, 131 to 190, 141 to 200, 151 to 210, 161 to 220, 171 to 230, 181 to 240, and 191 to 247 of SEQ ID NO:2, as well as isolated polynucleotides which encode these polypeptides. The invention further provides isolated polypeptides comprising, or alternatively consisting of, the amino acid sequences of a member selected from the group consisting of amino acids −36 to 24, −26 to 34, −16 to 44, −6 to 54, 1 to 60, 11 to 70, 21 to 80, 31 to 90, 41 to 100, 51 to 0, 61 to 120, 71 to 130, 81 to 140, and 91 to 149 of SEQ ID NO:5, as well as isolated polynucleotides which encode these polypeptides. The invention also provides isolated polypeptides comprising, or alternatively consisting of, the amino acid sequences of a member selected from the group consisting of amino acids 1 to 60, 11 to 70, 21 to 80, 31 to 90, 41 to 100, 51 to 110, 61 to 120, 71 to 130, and 81 to 136 of SEQ ID NO:8, as well as isolated polynucleotides which encode these polypeptides.

The present invention is also directed to isolated polypeptides comprising, or alternatively consisting of, domains of TR2, TR2-SV1, and TR2-SV2. In particular, the invention provides polypeptides comprising, or alternatively consisting of, beta-sheet regions of TR2, TR2-SV1, and TR2-SV2 set out in Tables II, III and IV. These polypeptides include polypeptides comprising, or alternatively consisting of, amino acid sequences of a member selected from the group consisting of amino acid residues from about −19 to about −5, amino acid residues from about −18 to about −6, amino acid residues from about −2 to about 4, amino acid residues from about 25 to about 31, amino acid residues from about 46 to about 51, amino acid residues from about 57 to about 71, amino acid residues from about 99 to about 104, amino acid residues from about 151 to about 156, amino acid residues from about 175 to about 191, amino acid residues from about 174 to about 190, amino acid residues from about 197 to about 206, amino acid residues from about 197 to about 208, amino acid residues from about 215 to about 220, amino acid residues from about 228 to about 238, and amino acid residues from about 229 to about 241 of SEQ ID NO:2; amino acid residues from about −19 to about −5, amino acid residues from about −18 to about −6, amino acid residues from about −2 to about 3, amino acid residues from about 26 to about 31, amino acid residues from about 34 to about 40, amino acid residues from about 46 to about 50, amino acid residues from about 57 to about 64, amino acid residues from about 69 to about 74, amino acid residues from about 122 to about 128, and amino acid residues from about 132 to about 140 of SEQ ID NO:5; and amino acid residues from about 6 to about 13, amino acid residues from about 26 to about 33, amino acid residues from about 50 to about 58, and amino acid residues from about 86 to about 93 of SEQ ID NO:8. The invention is further directed to isolated polynucleotides comprising, or alternatively consisting of, nucleic acid molecules which encode the beta-sheet regions set out in Tables II, III and IV, and isolated polypeptides comprising, or alternatively consisting of, amino acid sequences at least 80% identical, and more preferably at least 85%, 90%, 92%, 95%, 96%, 97%, 98% or 99% identical to nucleic acid molecules encoding beta-sheet regions of the TR2, TR2-SV1, and TR2-SV2 proteins.

The TR2 receptor proteins of the invention may be in monomers or multimers (i.e., dimers, trimers, tetramers, and higher multimers). Accordingly, the present invention relates to monomers and multimers of the TR2 receptor proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only TR2 receptor proteins of the invention (including TR2 receptor fragments, variants, and fusion proteins, as described herein). These homomers may contain TR2 receptor proteins having identical or different polypeptide sequences. In a specific embodiment, a homomer of the invention is a multimer containing only TR2 receptor proteins having an identical polypeptide sequence. In another specific embodiment, a homomer of the invention is a multimer containing TR2 receptor proteins having different polypeptide sequences. In specific embodiments, the multimer of the invention is a homodimer (e.g., containing TR2 receptor proteins having identical or different polypeptide sequences) or a homotrimer (e.g., containing TR2 receptor proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the TR2 receptor gene) in addition to the TR2 receptor proteins of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the TR2 receptor proteins of the invention. Such covalent associations may involve one or more amino acid residues contained in the polypeptide sequence of the TR2 receptor proteins (e.g., the polypeptide sequence recited in SEQ ID NO:2, SEQ ID NO:5, SEQ ID NO:8, or SEQ ID NO:26, or the polypeptides encoded by the cDNAs contained in ATCC™ Deposit Numbers 97059, 97058, or 97057). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TR2 receptor fusion protein. In one example, covalent associations are between the heterologous sequence contained in a fusion protein of the invention (see, e.g., U.S. Pat. No. 5,478,925). In a specific example, the covalent associations are between the heterologous sequence contained in a TR2 receptor-Fc fusion protein of the invention (as described herein). In another specific example, covalent associations of fusion proteins of the invention are between heterologous polypeptide sequences from another TNF family ligand/receptor member that is capable of forming covalently associated multimers, such as for example, osteoprotegerin (see, e.g., International Publication No. WO 98/49305, the contents of which are herein incorporated by reference in its entirety). In another embodiment, two or more TR2 polypeptides of the invention are joined through synthetic linkers (e.g., peptide, carbohydrate or soluble polymer linkers). Examples include, but are not limited to, those peptide linkers described in U.S. Pat. No. 5,073,627 (hereby incorporated by reference). Proteins comprising multiple TR2 polypeptides separated by peptide linkers may be produced using conventional recombinant DNA technology.

Another method for preparing multimer TR2 polypeptides of the invention involves use of TR2 polypeptides fused to a leucine zipper polypeptide sequence. Leucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric TR2 proteins are those described in PCT application WO 94/10308, hereby incorporated by reference. Recombinant fusion proteins comprising a soluble TR2 polypeptide fused to a peptide that dimerizes or trimerizes in solution are expressed in suitable host cells, and the resulting soluble multimeric TR2 is recovered from the culture supernatant using techniques known in the art.

Certain members of the TNF family of proteins are believed to exist in trimeric form (Beutler and Huffel, Science 264:667, 1994; Banner et al., Cell 73:431, 1993). Thus, trimeric TR2 may offer the advantage of enhanced biological activity. Preferred leucine zipper moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric TR2.

In another example, proteins of the invention are associated by interactions between Flag® polypeptide sequence contained in Flag®-TR2 or Flag®-TR2 fusion proteins of the invention. In a further embodiment, associations proteins of the invention are associated by interactions between heterologous polypeptide sequence contained in Flag®-TR2 or Flag®-TR2 fusion proteins of the invention and anti-Flag® antibody.

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C-terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

The present invention encompasses polypeptides comprising, or alternatively consisting of, an epitope of the polypeptide having an amino acid sequence of SEQ ID NO:2, SEQ ID NO:5, SEQ ID NO:8, or SEQ ID NO:26, or an epitope of the polypeptide sequence encoded by a polynucleotide sequence contained in the deposited cDNA identified as ATCC™ Accession No. 97059, 97058 or 97057 or encoded by a polynucleotide that hybridizes to the complement of the polynucleotide sequence of SEQ ID NO:1, SEQ ID NO:4, SEQ ID NO:7, or SEQ ID NO:25, or contained in the deposited cDNA identified as ATCC™ Accession No. 97059, 97058 or 97057 under stringent hybridization conditions or lower stringency hybridization conditions as defined herein. The present invention further encompasses polynucleotide sequences encoding an epitope of a polypeptide sequence of the invention (such as, for example, the sequence disclosed in SEQ ID NO:2, SEQ ID NO:5, SEQ ID NO:8, or SEQ ID NO:26), polynucleotide sequences of the complementary strand of a polynucleotide sequence encoding an epitope of the invention, and polynucleotide sequences which hybridize to the complementary strand under stringent hybridization conditions or lower stringency hybridization conditions defined herein.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767-778 (1984) at 777.

Antigenic epitopes of the invention preferably contain a sequence of at least 4, at least 5, at least 6, at least 7, more preferably at least 8, at least 9, at least 10, at least 15, at least 20, at least 25, and, most preferably, between about 15 to about 30 amino acids. In this context "about" includes the particularly recited value and values larger or smaller by several (5, 4, 3, 2, or 1) amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, for instance, Wilson et al., *Cell* 37:767-778 (1984); Sutcliffe et al., *Science* 219:660-666 (1983)).

Non-limiting examples of antigenic polypeptides or peptides that can be used to generate TR2 receptor-specific antibodies include: a polypeptide comprising, or alternatively consisting of, amino acid residues from about 39 to about 70 in FIG. 1 (amino acid residues 3 to 34 in SEQ ID NO:2); a polypeptide comprising, or alternatively consisting of, amino acid residues from about 106 to about 120 in FIG. 1A-1B (amino acid residues 70 to 84 in SEQ ID NO:2); a polypeptide comprising, or alternatively consisting of, amino acid residues from about 142 to about 189 in FIG. 1A-1B (amino acid residues 106 to 153 in SEQ ID NO:2); a polypeptide comprising, or alternatively consisting of, amino acid residues from about 276 to about 283 in FIG. 1 (amino acid residues 240 to 247 in SEQ ID NO:2); a polypeptide comprising, or alternatively consisting of, amino acid residues from about 39 to about 70 in FIG. 4A-4B (amino acid residues 3 to 34 in SEQ ID NO:5); a polypeptide comprising, or alternatively consisting of, amino acid residues from about 99 to about 136 in FIG. 4A-4B (amino acid residues 63 to 100 in SEQ ID NO:5); a polypeptide comprising, or alternatively consisting of, amino acid residues from about 171 to about 185 in FIG. 4A-4B (amino acid residues 135 to 149 in SEQ ID NO:5); a polypeptide comprising, or alternatively consisting of, amino acid residues from about 56 to about 68 in FIG. 7A-7B (SEQ ID NO:8); and a polypeptide comprising, or alternatively consisting of, amino acid residues from about 93 to about 136 in FIG. 7A-7B (SEQ ID NO:8). In this context "about" includes the particularly recited value and values larger or smaller by several (5, 4, 3, 2, or 1) amino acids. As indicated above, the inventors have determined that the above polypeptide fragments are antigenic regions of the TR2 receptor proteins.

The epitope-bearing peptides and polypeptides of the invention may be produced by any conventional means. Houghten, R. A. (1985). General method for the rapid solid-phase synthesis of large numbers of peptides: specificity of antigen-antibody interaction at the level of individual amino acids. *Proc. Natl. Acad. Sci. USA* 82:5131-5135. This "Simultaneous Multiple Peptide Synthesis (SMPS)" process is further described in U.S. Pat. No. 4,631,211 to Houghten et al. (1986).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). A preferred immunogenic epitope includes the secreted protein. The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724-33 (1997); Harayama, Trends Biotechnol. 16(2):76-82 (1998); Hansson et al., J. Mol. Biol. 287:265-76 (1999); and Lorenzo and Blasco, BioTechniques 24(2):308-13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules.

Proteins of the invention can be chemically synthesized using techniques known in the art (e.g., see Creighton, 1983, Proteins: Structures and Molecular Principles, W.H. Freeman & Co., N.Y., and Hunkapiller, M., et al., Nature 310:105-111 (1984)). For example, a peptide corresponding to a fragment of the TR2 receptor polypeptides of the invention can be synthesized by use of a peptide synthesizer. Furthermore, if desired, nonclassical amino acids or chemical amino acid analogs can be introduced as a substitution or addition into the TR2 receptor polypeptide sequence. Non-classical amino acids include, but are not limited to, to the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., Nucl. Acids Res. 13:4331 (1986); and Zoller et al., Nucl. Acids Res. 10:6487 (1982)), cassette mutagenesis (see, e.g., Wells et al., Gene 34:315 (1985)), restriction selection mutagenesis (see, e.g., Wells et al., Philos. Trans. R. Soc. London SerA 317:415 (1986)).

The invention additionally, encompasses TR2 receptor polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH$_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of TR2, TR2-SV1 and TR2-SV2 receptor polypeptides which may provide additional advantages such as increased solubility, stability and circulating time of the polypeptides, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J. of Hematol.* 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride (ClSO$_2$CH$_2$CF$_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoroethane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

Antibodies

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes monoclonal, polyclonal, chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al., *J. Immunol.* 147:60-69 (1991); U.S. Pat. Nos. 5,573,920, 4,474,893, 5,601,819, 4,714,681, 4,925,648; Kostelny, S. A. et al., *J. Immunol.* 148:1547-1553 (1992).

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-5}$M, and $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., *Blood* 92(6):1981-1988 (1998); Chen et al., *Cancer Res.* 58(16):3668-3678 (1998); Harrop et al., *J. Immunol.* 161(4): 1786-1794 (1998); Zhu et al., *Cancer Res.* 58(15):3209-3214 (1998); Yoon et al., *J. Immunol.* 160(7):3170-3179 (1998); Prat et al., *J. Cell. Sci.* 111(Pt2):237-247 (1998); Pitard et al., *J. Immunol. Methods* 205(2):177-190 (1997); Liautard et al., *Cytokine* 9(4):233-241 (1997); Carlson et al., *J. Biol. Chem.* 272(17):11295-11301 (1997); Taryman et al., *Neuron* 14(4): 755-762 (1995); Muller et al., *Structure* 6(9):1153-1167 (1998); Bartunek et al., *Cytokine* 8(1):14-20 (1996) (which are all incorporated by reference herein in their entireties).

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be prepared by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981) (said references incorporated by reference in their entireties). The term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant and phage display technology.

Hybridoma techniques include those known in the art and taught in Harlow et al., ANTIBODIES: A LABORATORY MANUAL, (Cold Spring Harbor Laboratory Press, 2nd ed. 1988); and Hammerling, et al., in: MONOCLONAL ANTIBODIES AND T-CELL HYBRIDOMAS 563-681 (Elsevier, N.Y., 1981) (said references incorporated by reference in their entireties).

Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al., *J. Immunol. Methods* 182:41-50 (1995); Ames, R. S. et al., *J. Immunol. Methods* 184:177-186 (1995); Kettleborough, C. A. et al., *Eur. J. Immunol.* 24:952-958 (1994); Persic, L. et al., *Gene* 187:9-18 (1997); Burton, D. R. et al., *Advances in Immunology* 57:191-280 (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al., *BioTechniques* 12:864-869 (1992); and Sawai, H. et al. *AJRI* 34:26-34 (1995); and Better, M. et al., *Science* 240: 1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu, L. et al., *PNAS* 90:7995-7999 (1993); and Skerra, A. et al., *Science* 240: 1038-1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, *Science* 229:1202 (1985); Oi et al., *BioTechniques* 4:214 (1986); Gillies, S. D. et al., *J. Immunol. Methods* 125: 191-202 (1989); and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., *Molecular Immunology* 28(4/5):489-498 (1991); Studnicka G. M. et al., *Protein Engineering* 7:805-814 (1994); Roguska M. A. et al., *PNAS* 91:969-973 (1994)), and chain shuffling (U.S. Pat. No. 5,565,332). Human antibodies can be made by a variety of methods known in the art including phage display methods described above. See also, U.S. Pat. Nos. 4,444,887, 4,716, 111, 5,545,806, and 5,814,318; and WO 98/46645, WO 98/50433, WO 98/24893, WO 98/16654, WO 96/34096, WO 96/33735 and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra and WO 93/21232; EP 0 439 095; Naramura, M. et al., *Immunol. Lett.* 39:91-99 (1994); U.S. Pat. No. 5,474,981; Gillies, S. O. et al., *PNAS* 89:1428-1432 (1992); Fell, H. P. et al., *J. Immunol.* 146:2446-2452 (1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) PNAS 88:10535-10539; Zheng, X. X. et al. (1995) J. Immunol. 154:5590-5600; and Vil, H. et al. (1992) PNAS 89:11337-11341 (said references incorporated by reference in their entireties).

The invention further relates to antibodies which act as agonists or antagonists of the polypeptides of the present invention. Antibodies which act as agonists or antagonists of the polypeptides of the present invention include, for example, antibodies which disrupt receptor/ligand interactions with the polypeptides of the invention either partially or fully. For example, the present invention includes antibodies which disrupt the ability of the proteins of the invention to multimerize. In another example, the present invention includes antibodies which allow the proteins of the invention to multimerize, but disrupts the ability of the proteins of the invention to bind one or more TR2 receptor(s) or ligand(s) (e.g., AIM II (International Publication No. WO 97/34911), Lymphotoxin-α, and the Herpes virus protein HSV1 gD). In yet another example, the present invention includes antibodies which allow the proteins of the invention to multimerize, and bind TR2 receptor(s) or ligand(s) (e.g., AIM II (International Publication No. WO 97/34911), Lymphotoxin-α, and the Herpes virus protein HSV1 gD), but blocks biological activity associated with the TR2 receptor/ligand complex.

Antibodies which act as agonists or antagonists of the polypeptides of the present invention also include, both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al., *Blood* 92:1981-1988 (1998); Chen, Z. et al., *Cancer Res.* 58:3668-3678 (1998); Harrop, J. A. et al., *J. Immunol.* 161:1786-1794 (1998); Zhu, Z. et al., *Cancer Res.* 58:3209-3214 (1998); Yoon, D. Y. et al., *J. Immunol.* 160:3170-3179 (1998); Prat, M. et al., *J. Cell. Sci.* 111(Pt2):237-247 (1998); Pitard, V. et al., *J. Immunol. Methods* 205:177-190 (1997); Liautard, J. et al., *Cytokine* 9(4):233-241 (1997); Carlson, N. G. et al., *J. Biol. Chem.* 272:11295-11301 (1997); Taryman, R. E. et al., *Neuron* 14:755-762 (1995); Muller, Y. A. et al., *Structure* 6:1153-1167 (1998); Bartunek, P. et al., *Cytokine* 8:14-20 (1996) (said references incorporated by reference in their entireties).

Methods for producing and screening for specific antibodies using hybridoma technology are routine and well-known in the art and are discussed in detail in Example 17. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC™. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and Gen-Pharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988)).

As discussed above, antibodies to the TR2 receptor proteins of the invention can, in turn, be utilized to generate anti-idiotype antibodies that "mimic" TR2 receptors using techniques well known to those skilled in the art. (See, e.g., Greenspan & Bona, *FASEB J.* 7(5):437-444; (1989) and Nissinoff, *J. Immunol.* 147(8):2429-2438 (1991)). For example, antibodies which bind to TR2 receptors and competitively inhibit TR2 receptor multimerization and/or binding to ligand can be used to generate anti-idiotypes that "mimic" TR2 receptor multimerization and/or binding domain and, as a consequence, bind to and neutralize TR2 receptors and/or their ligand(s). Such neutralizing anti-idiotypes or Fab fragments of such anti-idiotypes can be used in therapeutic regimens to neutralize TR2 receptor ligand(s). For example, such anti-idiotypic antibodies can be used to bind TR2 receptors, or to bind TR2 receptors or ligands, and thereby block TR2 receptor mediated inhibition of apoptosis.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined herein, to polynucleotides that encode an antibody, preferably, that specifically binds to a polypeptide of the invention, preferably, an antibody that binds to a polypeptide having the amino acid sequence of SEQ ID NO:2, SEQ ID NO:5, SEQ ID NO:8, or SEQ ID NO:26.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably polyA+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, Proc. Natl. Acad. Sci. 81:851-855; Neuberger et al., 1984, Nature 312: 604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334: 544-54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, Science 242:1038-1041).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; Cockett et al., 1990, Bio/Technology 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, 1984, Proc. Natl. Acad. Sci. USA 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260: 926-932; and Morgan and Anderson, 1993, Ann. Rev. Biochem. 62:191-217; May, 1993, TIB TECH 11(5):155-215); and hygro, which confers resistance to hygromycin (Santerre et al., 1984, Gene 30:147). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As discussed, supra, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270: 3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5 receptor, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).

Moreover, the antibodies or fragments thereof of the present invention can be fused to marker sequences, such as a peptide to facilitate their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, autoimmune diseases, disorders, or conditions associated with such diseases or disorders, including, but not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, ulcerative colitis, dense deposit disease, rheumatic heart disease, glomerulonephritis (e.g., IgA nephropathy), pemphigus vulgaris, discoid lupus, Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis), systemic lupus erythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, graft v. host diseases (GVHD) and other inflammatory, granulamatous, degenerative, and atrophic disorders).

In a specific embodiment, antibodies of the invention are be used to treat, inhibit, prognose, diagnose or prevent rheumatoid arthritis.

In another specific embodiment, antibodies of the invention are used to treat, inhibit, prognose, diagnose or prevent systemic lupus erythematosis.

Additionally, the antibodies of the invention can be used to treat, inhibit or prevent diseases, disorders or conditions associated with immunodeficiencies including, but not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, autoimmune neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleo side phosphorylase deficiency (PNP), MHC Class II deficiency (Bare Lymphocyte Syndrome) and severe combined immunodeficiency.

Antibodies of the invention are used to prevent graft rejection and inflammation and for the treatment of arthritis.

The treatment and/or prevention of diseases and disorders associated with aberrant expression and/or activity of a polypeptide of the invention includes, but is not limited to, alleviating symptoms associated with those diseases and disorders. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g., as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Transgenic Non-Human Animals

The proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., *Appl. Microbiol. Biotechnol.* 40:691-698 (1994); Carver et al., *Biotechnology (NY)* 11:1263-1270 (1993); Wright et al., *Biotechnology (NY)* 9:830-834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148-6152 (1985)), blastocysts or embryos; gene targeting in embryonic stem cells (Thompson et al., *Cell* 56:313-321 (1989)); electroporation of cells or embryos (Lo, *Mol. Cell. Biol.* 3:1803-1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717-723 (1989); etc. For a review of such techniques, see Gordon, "Transgenic Animals," *Intl. Rev. Cytol.* 115:171-229 (1989), which is incorporated by reference herein in its entirety. See, also, U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety. Further, the contents of each of the documents recited in this paragraph is herein incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64-66 (1996); Wilmut et al., *Nature* 385:810-813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al (Lasko et al., *Proc. Natl. Acad. Sci. USA* 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., *Science* 265:103-106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of TR2 receptor polypeptides, studying conditions and/or disorders associated with aberrant TR2 receptor expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, e.g., Anderson et al U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Detection of Disease States

The TNF-family ligands induce various cellular responses by binding to TNF-family receptors, including the TR2 receptors of the present invention. TNF-β, a potent ligand of the TNF receptor proteins, is known to be involved in a number of biological processes including lymphocyte development, tumor necrosis, induction of an antiviral state, activation of polymorphonuclear leukocytes, induction of class I major histocompatibility complex antigens on endothelial cells, induction of adhesion molecules on endothelium and growth hormone stimulation (Ruddle and Homer, *Prog. Allergy,* 40:162-182 (1988)). TNF-α, also a ligand of the TNF receptor proteins, has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al., *J. Immunol.* 136(7):2483 (1987); Porter, *Tibtech* 9:158-162 (1991)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death.

Cells which express the TR2 polypeptides and are believed to have a potent cellular response to TR2 receptor ligands include B lymphocytes ($CD19^+$), both $CD4^+$ and $CD8^+$ T lymphocytes, monocytes, endothelial cells and other cell types shown in Tables V and VI. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased cell proliferation or the inhibition of increased cell proliferation, such as by the inhibition of apoptosis. Apoptosis—programmed cell death—is a physiological mechanism involved in the deletion of peripheral T lymphocytes of the immune system, and its dysregulation can lead to a number of different pathogenic processes (Ameisen, J. C., *AIDS* 8:1197-1213 (1994); Krammer, P. H. et al., *Curr. Opin. Immunol.* 6:279-289 (1994)).

It is believed that certain tissues in mammals with specific disease states associated with aberrant cell survival express significantly altered levels of TR2 receptor protein and mRNA encoding TR2 receptor protein when compared to a corresponding "standard" mammal, i.e., a mammal of the same species not having the disease state. Further, since some forms of this protein are secreted, it is believed that enhanced levels of TR2 receptor protein can be detected in certain body fluids (e.g., sera, plasma, urine, and spinal fluid) from mammals with the disease state when compared to sera from mammals of the same species not having the disease state. Thus, the invention provides a diagnostic method useful during diagnosis of disease states, which involves assaying the expression level of the gene encoding TR2 receptor protein in mammalian cells or body fluid and comparing the gene expression level with a standard TR2 receptor gene expression level, whereby an increase or decrease in the gene expression level over the standard is indicative of certain disease states associated with aberrant cell survival.

Where diagnosis of a disease state involving the TR2 receptors of the present invention has already been made according to conventional methods, the present invention is useful as a prognostic indicator, whereby patients exhibiting significantly aberrant TR2 receptor gene expression will experience a worse clinical outcome relative to patients expressing the gene at a lower level.

By "assaying the expression level of the gene encoding TR2 receptor protein" is intended qualitatively or quantitatively measuring or estimating the level of TR2, TR2-SV1 and/or TR2-SV2 receptor protein or the level of the mRNA encoding TR2, TR2-SV1 and/or TR2-SV2 receptor protein in a first biological sample either directly (e.g., by determining or estimating absolute protein level or mRNA level) or relatively (e.g., by comparing to TR2, TR2-SV1 and/or TR2-SV2 receptor protein level or mRNA level in a second biological sample).

Preferably, TR2 receptor protein level or mRNA level in the first biological sample is measured or estimated and compared to a standard TR2 receptor protein level or mRNA level, the standard being taken from a second biological sample obtained from an individual not having the disease state. As will be appreciated in the art, once a standard TR2 receptor protein level or mRNA level is known, it can be used repeatedly as a standard for comparison.

By "biological sample" is intended any biological sample obtained from an individual, cell line, tissue culture, or other source which contains TR2 receptor protein or mRNA. Biological samples include mammalian body fluids (such as sera, plasma, urine, synovial fluid and spinal fluid) which contain secreted mature TR2 receptor protein, and thymus, prostate, heart, placenta, muscle, liver, spleen, lung, kidney and other tissues. Methods for obtaining tissue biopsies and body fluids from mammals are well known in the art. Where the biological sample is to include mRNA, a tissue biopsy is the preferred source.

Diseases associated with increased cell survival, or the inhibition of apoptosis, include cancers (such as follicular lymphomas, carcinomas with p53 mutations, and hormone-dependent tumors, including, but not limited to, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as systemic lupus erythematosus and immune-related glomerulonephritis rheumatoid arthritis) and viral infections (such as Herpes viruses, pox viruses and adenoviruses), information graft v. host disease, acute graft rejection, and chronic graft rejection. Diseases associated with decreased cell survival, or increased apoptosis, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

In preferred embodiments TR2, TR2-SV1 and/or TR2-SV2 polynucleotides or polypeptides of the invention are used to treat or prevent autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment TR2, TR2-SV1 and/or TR2-SV2 polynucleotides or polypeptides of the invention are used to activate, differentiate or proliferate cancerous cells or tissue (e.g., B cell lineage related cancers (e.g., CLL and MLL), lymphocytic leukemia, or lymphoma) and thereby render the cells more vulnerable to cancer therapy (e.g., chemotherapy or radiation therapy).

Assays available to detect levels of soluble receptors are well known to those of skill in the art, for example, radioimmunoassays, competitive-binding assays, Western blot analysis, and preferably an ELISA assay may be employed.

TR2 receptor-protein specific antibodies can be raised against intact TR2 receptor protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (mAb) is meant to include intact molecules as well as antibody fragments (such as, for example, Fab and F(ab')$_2$ fragments) which are capable of specifically binding to TR2 receptor protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies of the present invention may be prepared by any of a variety of methods. For example, cells expressing TR2, TR2-SV1 and/or TR2-SV2 receptor protein or an antigenic fragment thereof can be administered to an animal in order to induce the production of sera containing polyclonal antibodies. In a preferred method, a preparation of TR2, TR2-SV1 and/or TR2-SV2 receptor protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or TR2 receptor protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., (1981) pp. 563-681). In general, such procedures involve immunizing an animal (preferably a mouse) with a TR2 receptor protein antigen or, more preferably, with a TR2 receptor protein-expressing cell. Suitable cells can be recognized by their capacity to bind anti-TR2 receptor protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (*Gastroenterology* 80:225-232 (1981)). The hybridoma cells obtained through such a selection are then assayed to identify clones which secrete antibodies capable of binding the TR2 receptor protein antigen.

Agonists and Antagonists of TR2 Receptor Function

In one aspect, the present invention is directed to a method for inhibiting a TR2 activity induced by a TNF-family ligand (e.g., cell proliferation, hematopoietic development), which involves administering to a cell which expresses a TR2 polypeptide an effective amount of a TR2 receptor ligand, analog or an antagonist capable of decreasing TR2 receptor mediated signaling. Preferably, TR2 receptor mediated signaling is increased to treat a disease wherein increased cell proliferation is exhibited. An antagonist can include soluble forms of the TR2 receptors and antibodies directed against the TR2 polypeptides which block TR2 receptor mediated signaling. Preferably, TR2 receptor mediated signaling is decreased to treat a disease.

In a further aspect, the present invention is directed to a method for increasing cell proliferation induced by a TNF-family ligand, which involves administering to a cell which expresses a TR2 polypeptide an effective amount of an agonist capable of increasing TR2 receptor mediated signaling. Preferably, TR2 receptor mediated signaling is increased to treat a disease wherein decreased cell proliferation is exhibited. Agonists of the present invention include monoclonal antibodies directed against the TR2 polypeptides which stimulate TR2 receptor mediated signaling. Preferably, TR2 receptor mediated signaling is increased to treat a disease.

By "agonist" is intended naturally occurring and synthetic compounds capable of enhancing cell proliferation and differentiation mediated by TR2 polypeptides. Such agonists include agents which increase expression of TR2 receptors or increase the sensitivity of the expressed receptor. By "antagonist" is intended naturally occurring and synthetic compounds capable of inhibiting TR2 mediated cell proliferation and differentiation. Such antagonists include agents which decrease expression of TR2 receptors or decrease the sensitivity of the expressed receptor. Whether any candidate "agonist" or "antagonist" of the present invention can enhance or inhibit cell proliferation and differentiation can be determined using art-known TNF-family ligand/receptor cellular response assays, including those described in more detail below.

One such screening technique involves the use of cells which express the receptor (for example, transfected CHO cells) in a system which measures extracellular pH changes caused by receptor activation, for example, as described in Science 246:181-296 (October 1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Soluble forms of the polypeptides of the present invention may be utilized in the ligand binding assay described above. These forms of the TR2 receptors are contacted with ligands in the extracellular medium after they are secreted. A determination is then made as to whether the secreted protein will bind to TR2 receptor ligands.

Further screening assays for agonist and antagonist of the present invention are described in Tartaglia, L. A., and Goeddel, D. V., J. Biol. Chem. 267(7):4304-4307 (1992).

Thus, in a further aspect, a screening method is provided for determining whether a candidate agonist or antagonist is capable of enhancing or inhibiting a cellular response to a TNF-family ligand. The method involves contacting cells which express TR2 polypeptides with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing a TR2 polypeptide can be contacted with either an endogenous or exogenously administered TNF-family ligand.

In an additional aspect, a thymocyte proliferation assay may be employed to identify both ligands and potential drug candidates. For example, thymus cells are disaggregated from tissue and grown in culture medium. Incorporation of DNA precursors such as $^3$H-thymidine or 5-bromo-2'-deoxyuridine (BrdU) is monitored as a parameter for DNA synthesis and cellular proliferation. Cells which have incorporated BrdU into DNA can be detected using a monoclonal antibody against BrdU and measured by an enzyme or fluorochrome-conjugated second antibody. The reaction is quantitated by fluorimetry or by spectrophotometry. Two control wells and an experimental well are set up as above and TNF-β or cognate ligand is added to all wells while soluble receptor polypeptides of the present invention are added individually to the second control wells, with the experimental well containing a compound to be screened. The ability of the compound to be screened to stimulate or inhibit the above interaction may then be quantified.

Agonists according to the present invention include compounds such as, for example, TNF-family ligand peptide fragments, transforming growth factor β, and neurotransmitters (such as glutamate, dopamine, N-methyl-D-aspartate). Preferred agonist include polyclonal and monoclonal antibodies raised against a TR2 polypeptide, or a fragment thereof. Such agonist antibodies raised against a TNF-family receptor are disclosed in Tartaglia, L. A., et al., Proc. Natl. Acad. Sci. USA 88:9292-9296 (1991); and Tartaglia, L. A., and Goeddel, D. V., J. Biol. Chem. 267 (7):4304-4307 (1992). See, also, PCT Application WO 94/09137. Further preferred agonists include chemotherapeutic drugs such as, for example, cisplatin, doxorubicin, bleomycin, cytosine arabinoside, nitrogen mustard, methotrexate and vincristine. Others include ethanol and β-amyloid peptide. (Science 267:1457-1458 (1995)).

Antagonist according to the present invention include soluble forms of the TR2 receptors (e.g., fragments of the TR2 receptor shown in FIG. 1A-1B that include the ligand binding domain from the extracellular region of the full length receptor). Such soluble forms of the receptor, which may be naturally occurring or synthetic, antagonize TR2, TR2-SV1 or TR2-SV2 mediated signaling by competing with the cell surface bound forms of the receptor for binding to TNF-family ligands. Antagonists of the present invention also include antibodies specific for TNF-family ligands and TR2-Fc fusion proteins such as the one described below in Examples 5 and 6.

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to, TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF).

The experiments set forth in Example 6 demonstrate that the TR2 receptors of the present invention are capable of inducing the proliferation of lymphocytes. Further, such proliferation can be inhibited by a TR2 protein fragment fused to an Fc antibody fragment. Thus, specifically included within the scope of the invention are TR2 receptor/Fc fusion proteins, and nucleic acid molecules which encode such proteins. These fusion proteins include those having amino acid sequences of the extracellular domains of the TR2 proteins of the invention. Examples of portions of TR2 extracellular domains which are useful in the preparation of TR2 receptor/Fc fusion proteins include amino acids 1 to 192, 37 to 192, 50 to 192 and 100 to 192 in SEQ ID NO:2.

TNFα has been shown to protect mice from infection with Herpes simplex virus type 1 (HSV-1). Rossol-Voth, R. et al., *J. Gen. Virol.* 72:143-147 (1991). The mechanism of the protective effect of TNFα is unknown but appears to involve neither interferons not NK cell killing. One member of the TNFR family has been shown to mediate HSV-1 entry into cells. Montgomery, R. et al., *Eur. Cytokine Newt.* 7:159 (1996). Further, antibodies specific for the extracellular domain of this TNFR block HSV-1 entry into cells. Thus, TR2 receptors of the present invention include both TR2 amino acid sequences and antibodies capable of preventing TNFR mediated viral entry into cells. Such sequences and antibodies can function by either competing with cell surface localized TNFR for binding to virus or by directly blocking binding of virus to cell surface receptors.

Similarly, antibodies specific for the extracellular domain of the TR2 receptors of the invention, as well as other TR2 antagonists, can also block HSV-1 entry into cells. These antagonists are thus useful in the treatment and prevention of Herpes simplex infections.

Antibodies according to the present invention may be prepared by any of a variety of methods using TR2 receptor immunogens of the present invention. Such TR2 receptor immunogens include the TR2 receptor protein shown in SEQ ID NO:26, FIG. 1A-1B (SEQ ID NO:2) and the TR2-SV1 (FIG. 4A-4B (SEQ ID NO:5)) and TR2-SV2 (FIG. 7A-7B (SEQ ID NO:8)) polypeptides (any of which may or may not include a leader sequence) and polypeptide fragments of the receptors comprising, or alternatively consisting of, the ligand binding, extracellular, transmembrane, the intracellular domains of the TR2 receptors, or any combination thereof.

Polyclonal and monoclonal antibody agonist or antagonist according to the present invention can be raised according to the methods disclosed in Tartaglia and Goeddel, *J. Biol. Chem.* 267(7):4304-4307 (1992)); Tartaglia et al., *Cell* 73:213-216 (1993)), and PCT Application WO 94/09137. The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl Med.* 24:316-325 (1983)).

In a preferred method, antibodies according to the present invention are mAbs. Such mAbs can be prepared using hybridoma technology (Kohler and Millstein, *Nature* 256:495-497 (1975) and U.S. Pat. No. 4,376,110; Harlow et al., *Antibodies: A Laboratory Manual*, Cold Spring Harbor Laboratory Press, Cold Spring Harbor, N.Y., 1988; *Monoclonal Antibodies and Hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Proteins and other compounds which bind the TR2 receptor domains are also candidate agonist and antagonist according to the present invention. Such binding compounds can be "captured" using the yeast two-hybrid system (Fields and Song, *Nature* 340:245-246 (1989)). A modified version of the yeast two-hybrid system has been described by Roger Brent and his colleagues (Gyuris, J. et al., *Cell* 75:791-803 (1993); Zervos, A. S. et al., *Cell* 72:223-232 (1993)). Preferably, the yeast two-hybrid system is used according to the present invention to capture compounds which bind to the ligand binding, extracellular, intracellular, and transmembrane domains of the TR2 receptors. Such compounds are good candidate agonist and antagonist of the present invention.

Using the two-hybrid assay described above, the intracellular domain of the TR2 receptor, or a portion thereof, may be used to identify cellular proteins which interact with the receptor in vivo. Such an assay may also be used to identify ligands with potential agonistic or antagonistic activity of TR2 receptor function. This screening assay has previously been used to identify protein which interact with the cytoplasmic domain of the murine TNF-RII and led to the identification of two receptor associated proteins. Rothe, M. et al., *Cell* 78:681 (1994). Such proteins and amino acid sequences which bind to the cytoplasmic domain of the TR2 receptors are good candidate agonist and antagonist of the present invention.

Other screening techniques include the use of cells which express the polypeptide of the present invention (for example, transfected CHO cells) in a system which measures extracellular pH changes caused by receptor activation, for example, as described in *Science,* 246:181-296 (1989). In another example, potential agonists or antagonists may be contacted with a cell which expresses the polypeptide of the present invention and a second messenger response, e.g., signal transduction may be measured to determine whether the potential antagonist or agonist is effective.

The TR2 receptor agonists may be employed to stimulate ligand activities, such as inhibition of tumor growth and necrosis of certain transplantable tumors. The agonists may also be employed to stimulate cellular differentiation, for example, T-cell, fibroblasts and hemopoietic cell differentiation. Agonists to the TR2 receptor may also augment TR2's role in the host's defense against microorganisms and prevent related diseases (infections such as that from *Listeria monocytogenes*) and Chlamidiae. The agonists may also be employed to protect against the deleterious effects of ionizing radiation produced during a course of radiotherapy, such as denaturation of enzymes, lipid peroxidation, and DNA damage.

Agonists to the receptor polypeptides of the present invention may be used to augment TNF's role in host defenses against microorganisms and prevent related diseases. The agonists may also be employed to protect against the deleterious effects of ionizing radiation produced during a course of radiotherapy, such as denaturation of enzymes, lipid peroxidation, and DNA damage.

The agonists may also be employed to mediate an anti-viral response, to regulate growth, to mediate the immune response and to treat immunodeficiencies related to diseases such as HIV by increasing the rate of lymphocyte proliferation and differentiation.

The antagonists to the polypeptides of the present invention may be employed to inhibit ligand activities, such as stimulation of tumor growth and necrosis of certain transplantable tumors. The antagonists may also be employed to inhibit cellular differentiation, for example, T-cell, fibroblasts and hemopoietic cell differentiation. Antagonists may also be employed to treat autoimmune diseases, for example, graft versus host rejection and allograft rejection, and T-cell mediated autoimmune diseases such as AIDS. It has been shown that T-cell proliferation is stimulated via a type 2 TNF receptor. Accordingly, antagonizing the receptor may prevent the proliferation of T-cells and treat T-cell mediated autoimmune diseases.

The state of immunodeficiency that defines AIDS is secondary to a decrease in the number and function of CD4+ T-lymphocytes. Recent reports estimate the daily loss of CD4+ T cells to be between $3.5 \times 10^7$ and $2 \times 10^9$ cells (Wei X., et al., *Nature* 373:117-122 (1995)). One cause of CD4+ T cell depletion in the setting of HIV infection is believed to be HIV-induced apoptosis. Indeed, HIV-induced apoptotic cell death has been demonstrated not only in vitro but also, more importantly, in infected individuals (Ameisen, J. C., *AIDS* 8:1197-1213 (1994); Finkel, T. H., and Banda, N. K., *Curr. Opin. Immunol.* 6:605-615 (1995); Muro-Cacho, C. A. et al., *J. Immunol.* 154:5555-5566 (1995)). Furthermore, apoptosis and CD4+ T-lymphocyte depletion is tightly correlated in different animal models of AIDS (Brunner, T., et al., *Nature* 373:441-444 (1995); Gougeon, M. L., et al., *AIDS Res. Hum. Retroviruses* 9:553-563 (1993)) and, apoptosis is not observed in those animal models in which viral replication does not result in AIDS (Gougeon, M. L. et al., *AIDS Res. Hum. Retroviruses* 9:553-563 (1993)). Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A. D. et al., *J. Virol.* 70:199-206 (1996)). Further the TNF-family ligand was detectable in uninfected macrophages and its expression was upregulated following HIV infection resulting in selective killing of uninfected CD4+ T-lymphocytes (Badley, A. D et al., *J. Virol.* 70:199-206 (1996)).

As shown in Example 6, the TR2 receptor shown in FIG. 1A-1B is expressed in CD4+ T-lymphocytes and is capable of inducing lymphocyte proliferation. Thus, by the invention, a method for treating HIV+ individuals is provided which involves administering an agonist of the present invention to increase the rate of proliferation and differentiation of CD4+ T-lymphocytes. Such agonists include agents capable of inducing the expression of TR2 receptors (e.g., TNFα, PMA and DMSO) or enhancing the signal of such receptors which induces lymphocyte proliferation and differentiation. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. Antagonists of the present invention are able to suppress the immune response to both allografts and xenografts by decreasing the rate of TR2 mediated lymphocyte proliferation and differentiation. Such antagonists include the TR2-Fc fusion protein described in Examples 5 and 6. Thus, the present invention further provides a method for suppression of immune responses.

In addition, TNF-α has been shown to prevent diabetes in strains of animals which are prone to this affliction resulting from autoimmunity. See Porter, A., *Tibtech* 9:158-162 (1991). Thus, agonists and antagonists of the present invention may be useful in the treatment of autoimmune diseases such as type 1 diabetes.

In addition, the role played by the TR2 receptors in cell proliferation and differentiation indicates that agonist or antagonist of the present invention may be used to treat disease states involving aberrant cellular expression of these receptors. TR2 receptors may in some circumstances induce an inflammatory response, and antagonists may be useful reagents for blocking this response. Thus TR2 receptor antagonists (e.g., soluble forms of the TR2 receptors; neutralizing antibodies) may be useful for treating inflammatory diseases, such as rheumatoid arthritis, osteoarthritis, psoriasis, septicemia, and inflammatory bowel disease.

Antagonists to the TR2 receptor may also be employed to treat and/or prevent septic shock, which remains a critical clinical condition. Septic shock results from an exaggerated host response, mediated by protein factors such as TNF and IL-1, rather than from a pathogen directly. For example, lipopolysaccharides have been shown to elicit the release of TNF leading to a strong and transient increase of its serum concentration. TNF causes shock and tissue injury when administered in excessive amounts. Accordingly, it is believed that antagonists to the TR2 receptor will block the actions of TNF and treat/prevent septic shock. These antagonists may also be employed to treat meningococcemia in children which correlates with high serum levels of TNF.

Among other disorders which may be treated by the antagonists to TR2 receptors, there are included, inflammation which is mediated by TNF receptor ligands, and the bacterial infections cachexia and cerebral malaria. The TR2 receptor antagonists may also be employed to treat inflammation mediated by ligands to the receptor such as TNF.

In specific embodiments, antagonists according to the present invention are nucleic acids corresponding to the sequences contained in SEQ ID NO:25, FIG. 1A-1B (SEQ ID NO:1), FIG. 4A-4B (SEQ ID NO:4) or FIG. 7A-7B (SEQ ID NO:7) or the complementary strand thereof, and/or to the deposited nucleotide sequences of ATCC™ Deposit Numbers 97059, 97058 or 97057. In one embodiment, antisense sequence is generated internally by the organism, in another embodiment, the antisense sequence is separately administered (see, e.g. O'Connor, *J. Neurochem.* 56:560 (1991), and Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the TR2 receptor antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TR2 receptor antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding a TR2 receptor, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304-310 (1981), the promoter contained in the 3' long terminal repeat of Rous sarcoma virus (Yamamoto et al., Cell 22:787-797 (1980), the Herpes thymidine promoter (Wagner et al., Proc. Natl. Acad. Sci. U.S.A. 78:1441-1445 (1981), the regulatory sequences of the metallothionein gene (Brinster, et al., Nature 296:39-42 (1982)), etc.

The antisense nucleic acids of the invention comprise a sequence complementary to at least a portion of an RNA transcript of a TR2 receptor gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TR2 receptor antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a TR2 receptor RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature 372:333-335 (1994). Thus, oligonucleotides complementary to either the 5'- or 3'-non-translated, non-coding regions of the TR2 receptor shown in SEQ ID NO:25, FIG. 1A-1B (SEQ ID NO:1), FIG. 4A-4B (SEQ ID NO:4) or FIG. 7A-7B (SEQ ID NO:7) could be used in an antisense approach to inhibit translation of endogenous TR2 receptor mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of TR2 receptor mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci. 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., BioTechniques 6:958-976 (1988)) or intercalating agents. (See, e.g., Zon, Pharm. Res. 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5™-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids Res. 15:6625-6641 (1987)). The oligonucleotide is a 2'-0-methylribonucleotide (Inoue et al., Nucl. Acids Res. 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448-7451 (1988)), etc.

While antisense nucleotides complementary to TR2 receptor coding region sequences could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al., *Science* 247:1222-1225 (1990). While ribozymes that cleave mRNA at site specific recognition sequences can be used to destroy TR2 receptor mRNAs, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art and is described more fully in Haseloff and Gerlach, *Nature* 334:585-591 (1988). There are numerous potential hammerhead ribozyme cleavage sites within the nucleotide sequence of the TR2 receptors (SEQ ID NO:25, FIG. 1A-1B (SEQ ID NO:1), FIG. 4A-4B (SEQ ID NO:4) and FIG. 7A-7B (SEQ ID NO:7)). Preferably, the ribozyme is engineered so that the cleavage recognition site is located near the 5' end of the subject TR2 receptor mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express TR2 receptors in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TR2 receptor messages and inhibit translation. Since ribozymes unlike antisense molecules, are catalytic, a lower intracellular concentration is required for efficiency.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, inhibition or stimulation of proliferation. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Endogenous gene expression can also be reduced by inactivating or "knocking out" the TR2 receptor gene and/or its promoter using targeted homologous recombination. (See, e.g., Smithies et al., *Nature* 317:230-234 (1985); Thomas & Capecchi, *Cell* 51:503-512 (1987); Thompson et al., *Cell* 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (see, e.g., Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In other embodiments, antagonists according to the present invention include soluble forms of TR2 receptor (e.g., fragments of the TR2 receptors shown in SEQ ID NO:26, FIG. 1A-1B (SEQ ID NO:2), FIG. 4A-4B (SEQ ID NO:5) or FIG. 7A-7B (SEQ ID NO:8)) that include the ligand binding domain from the extracellular region of the full length receptor). Such soluble forms of the TR2 receptor, which may be naturally occurring or synthetic, antagonize TR2 receptor mediated signaling by competing with the cell surface bound forms of the receptor for binding to TNF-family ligands. Antagonists of the present invention also include antibodies specific for TNF-family ligands and TR2 receptor-Fc fusion proteins.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-α, lymphotoxin-α (LT-α, also known as TNF-β), LT-β (found in complex heterotrimer LT-α 2-β), FasL, VEGI (International Publication No. WO 96/14328), AIM I (International Publication No. WO 97/33899), AIM II (International Publication No. WO 97/34911), APRIL (*J. Exp. Med.* 188(6): 1185-1190), endokine-α (International Publication No. WO 98/07880), neutrokine-α (International Publication No. WO 98/18921), CD40L, CD27L, CD30L, 4-1BBL, OX40L and nerve growth factor (NGF).

TNF-α has been shown to protect mice from infection with Herpes simplex virus type 1 (HSV-1). Rossol-Voth et al., *J. Gen. Virol.* 72:143-147 (1991). The mechanism of the protective effect of TNF-α is unknown but appears to involve neither interferons nor NK cell killing. One member of the family has been shown to mediate HSV-1 entry into cells. Montgomery et al., *Eur. Cytokine Newt.* 7:159 (1996). Further, antibodies specific for the extracellular domain of this block HSV-1 entry into cells. Thus, TR2 receptor antagonists of the present invention include both TR2 receptor amino acid sequences and antibodies capable of preventing mediated viral entry into cells. Such sequences and antibodies can function by either competing with cell surface localized for binding to virus or by directly blocking binding of virus to cell surface receptors.

Antibodies according to the present invention may be prepared by any of a variety of standard methods using TR2 receptor immunogens of the present invention. Such TR2 receptor immunogens include the TR2 receptor proteins shown in SEQ ID NO:26, FIG. 1A-1B (SEQ ID NO:2), FIG. 4A-4B (SEQ ID NO:5) and FIG. 7A-7B (SEQ ID NO:8) (which may or may not include a leader sequence) and polypeptide fragments of the receptor comprising the ligand binding, extracellular (e.g., one or more of the cysteine repeat regions), transmembrane, the intracellular domains of TR2 receptor, or any combination thereof.

Polyclonal and monoclonal antibody agonists or antagonists according to the present invention can be raised according to the methods disclosed herein and/or known in the art, such as, for example, those methods described in Tartaglia and Goeddel, *J. Biol. Chem.* 267:4304-4307 (1992)); Tartaglia et al., *Cell* 73:213-216 (1993)), and PCT Application WO 94/09137 (the contents of each of these three applications are herein incorporated by reference in their entireties), and are preferably specific to polypeptides of the invention having the amino acid sequence of SEQ ID NO:2, SEQ ID NO:5, SEQ ID NO:8, or SEQ ID NO:26.

The techniques of gene-shuffling, motif-shuffling, exon-shuffling, and/or codon-shuffling (collectively referred to as "DNA shuffling") may be employed to modulate the activities of TR2 thereby effectively generating agonists and antagonists of TR2. See generally, U.S. Pat. Nos. 5,605,793, 5,811,238, 5,830,721, 5,834,252, and 5,837,458, and Patten, P. A., et al., *Curr. Opinion Biotechnol.* 8:724-33 (1997); Harayama, S., *Trends Biotechnol.* 16(2):76-82 (1998); Hansson, L. O. et al., *J. Mol. Biol.* 287:265-76 (1999); and Lorenzo, M. M. and Blasco, R., *BioTechniques* 24(2):308-13 (1998) (each of these patents and publications are hereby incorporated by reference). In one embodiment, alteration of TR2 polynucleotides and corresponding polypeptides may be achieved by DNA shuffling. DNA shuffling involves the assembly of two or more DNA segments into a desired TR2 molecule by homologous, or site-specific, recombination. In another embodiment, TR2 polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of TR2 may be recombined with one or more components, motifs, sections, parts, domains, fragments, etc. of one or more heterologous molecules. In preferred embodiments, the heterologous molecules are, for example, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM I (International Publication No. WO 97/33899), AIM II (International Publication No. WO 97/34911), APRIL (*J. Exp. Med.* 188(6): 1185-1190), endokine-alpha (International Publication No. WO 98/07880), Neutrokine-alpha (International Publication No. WO 98/18921), OPG, and neutrokine-alpha (International Publication No. WO 98/18921, OX40, and nerve growth factor (NGF), and soluble forms of Fas, CD30, CD27, CD40 and 4-IBB, DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), TR12, and TNF-R1, TRAMP/DR3/APO-3/WSL/LARD, TRAIL-R1/DR4/APO-2, TRAIL-R2/DR5, DcR1/TRAIL-R3/TRID/LIT, DcR2/TRAIL-R4, CAD, TRAIL, TRAMP, v-FLIP.

In further preferred embodiments, the heterologous molecules are any member of the TNF family.

Therapeutic and Other Uses

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V., et al., "Tumor Necrosis Factors: Gene Structure and Biological Activities," *Symp. Quant. Biol.* 51:597-609, Cold Spring Harbor (1986); Beutler, B., and Cerami, A., *Annu. Rev. Biochem.* 57:505-518 (1988); Old, L. J., *Sci. Am.* 258:59-75 (1988); Fiers, W., *FEBS Lett.* 285:199-224 (1991)). The TNF-family ligands induce such various cellular responses by binding to TNF-family receptors.

TR2 polynucleotides or polypeptides, or agonists of TR2, can be used in the treatment of infectious agents. For example, by increasing the immune response, particularly increasing the proliferation and differentiation of B cells, infectious diseases may be treated. The immune response may be increased by either enhancing an existing immune response, or by initiating a new immune response. Alternatively, TR2 polynucleotides or polypeptides, or agonists or antagonists of TR2, may also directly inhibit the infectious agent, without necessarily eliciting an immune response.

As noted above, TR2 polynucleotides and polypeptides, and anti-TR2 antibodies, are useful for diagnosis of conditions involving abnormally high or low expression of TR2, TR2-SV1 and/or TR2-SV2 and/or TR2, TR2-SV1 and/or TR2-SV2 activities. Given the cells and tissues where TR2, TR2-SV1 and/or TR2-SV2 is expressed as well as the activities modulated by TR2, TR2-SV1 and/or TR2-SV2, it is readily apparent that a substantially altered (increased or decreased) level of expression of TR2, TR2-SV1 and/or TR2-SV2 in an individual compared to the standard or "normal" level produces pathological conditions related to the bodily system(s) in which TR2, TR2-SV1 and/or TR2-SV2 is expressed and/or is active.

It will also be appreciated by one of ordinary skill that, since the TR2 polypeptides of the invention are members of the TNF family, the extracellular domains of the respective proteins may be released in soluble form from the cells which express TR2, TR2-SV1 and/or TR2-SV2 by proteolytic cleavage and therefore, when TR2, TR2-SV1 and/or TR2-SV2 polypeptide (particularly a soluble form of the respective extracellular domains) is added from an exogenous source to cells, tissues or the body of an individual, the polypeptide will exert its modulating activities on any of its target cells of that individual. Also, cells expressing this type II transmembrane protein may be added to cells, tissues or the body of an individual whereby the added cells will bind to cells expressing receptor for TR2, TR2-SV1 and/or TR2-SV2 whereby the cells expressing TR2, TR2-SV1 and/or TR2-SV2 can cause actions (e.g., reduced proliferation or cytotoxicity) on the receptor-bearing target cells.

In one embodiment, the invention provides a method of delivering compositions containing the polypeptides of the invention (e.g., compositions containing TR2, TR2-SV1 and/or TR2-SV2 polypeptides or anti-TR2, anti-TR2-SV1 and/or anti-TR2-SV2 antibodies associated with heterologous polypeptides, heterologous nucleic acids, toxins, or prodrugs) to targeted cells, such as, for example, B cells expressing a TR2, TR2-SV1 and/or TR2-SV2 receptor, or monocytes expressing the cell surface bound form of TR2, TR2-SV1 and/or TR2-SV2. TR2, TR2-SV1 and/or TR2-SV2 polypeptides or anti-TR2, anti-TR2-SV1 and/or anti-TR2-SV2 antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., TR2, TR2-SV1 and/or TR2-SV2 polypeptides or anti-TR2, anti- TR2-SV1 and/or anti-TR2-SV2 antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., TR2, TR2-SV1 and/or TR2-SV2 polypeptides or anti-TR2, anti-TR2-SV1 and/or anti-TR2-SV2 antibodies) in association with toxins or cytotoxic prodrugs.

In a specific embodiment, the invention provides a method for the specific destruction of cells of B cell lineage (e.g., B cell related leukemias or lymphomas) by administering TR2, TR2-SV1 and/or TR2-SV2 polypeptides and/or anti-TR2 antibodies in association with toxins or cytotoxic prodrugs.

By "toxin" is meant compounds that bind and activate endogenous cytotoxic effector systems, radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{116}$Rhenium, $^{166}$Holmium, and $^{188}$Rhenium; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, cis-dichlorodiamine platinum (II) (DDP), cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

It will be appreciated that conditions caused by a decrease in the standard or normal level of TR2, TR2-SV1 and/or TR2-SV2 activity in an individual, particularly disorders of the immune system, can be treated by administration of TR2, TR2-SV1 and/or TR2-SV2 polypeptide (in the form of soluble extracellular domain or cells expressing the complete protein) or agonist. Thus, the invention also provides a method of treatment of an individual in need of an increased level of TR2, TR2-SV1 and/or TR2-SV2 activity comprising administering to such an individual a pharmaceutical composition comprising an amount of an isolated TR2, TR2-SV1 and/or TR2-SV2 polypeptide of the invention, or agonist thereof, effective to increase the TR2, TR2-SV1 and/or TR2-SV2 activity level in such an individual.

It will also be appreciated that conditions caused by a increase in the standard or normal level of TR2, TR2-SV1 and/or TR2-SV2 activity in an individual, particularly disorders of the immune system, can be treated by administration of TR2, TR2-SV1 and/or TR2-SV2 polypeptides (in the form of soluble extracellular domain or cells expressing the complete protein) or antagonist (e.g., an anti-TR2 antibody). Thus, the invention also provides a method of treatment of an individual in need of an decreased level of TR2, TR2-SV1 and/or TR2-SV2 activity comprising administering to such an individual a pharmaceutical composition comprising an amount of an isolated TR2, TR2-SV1 and/or TR2-SV2 polypeptide of the invention, or antagonist thereof, effective to decrease the TR2, TR2-SV1 and/or TR2-SV2 activity level in such an individual.

TR2 polynucleotides or polypeptides of the invention, or agonists or antagonists of TR2 can be used in the treatment of infectious agents. For example, by increasing the immune response, particularly increasing the proliferation and differentiation of B cells, infectious diseases may be treated. The immune response may be increased by either enhancing an existing immune response, or by initiating a new immune response. Alternatively, TR2 polynucleotides or polypeptides, or agonists of TR2 may also directly inhibit the infectious agent, without necessarily eliciting an immune response.

Viruses are one example of an infectious agent that can cause disease or symptoms that can be treated by TR2, TR2-SV1 and/or TR2-SV2 polynucleotides or polypeptides, or agonists of TR2, TR2-SV1 and/or TR2-SV2. Examples of viruses, include, but are not limited to the following DNA and RNA viruses and viral families Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus).

Viruses falling within these families can cause a variety of diseases or symptoms, including, but not limited to: arthritis, bronchiolitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. TR2, TR2-SV1 and/or TR2-SV2 polynucleotides or polypeptides, or agonists or antagonists of TR2, TR2-SV1 and/or TR2-SV2, can be used to treat, prevent, diagnose, and/or detect any of these symptoms or diseases. In specific embodiments, TR2, TR2-SV1 and/or TR2-SV2 polynucleotides, polypeptides, or agonists are used to treat, prevent, and/or diagnose: meningitis, Dengue, EBV, and/or hepatitis (e.g., hepatitis B). In an additional specific embodiment TR2, TR2-SV1 and/or TR2-SV2 polynucleotides, polypeptides, or agonists are used to treat patients nonresponsive to one or more other commercially available hepatitis vaccines. In a further specific embodiment, TR2, TR2-SV1 and/or TR2-SV2 polynucleotides, polypeptides, or agonists are used to treat, prevent, and/or diagnose AIDS. In an additional specific embodiment TR2, TR2-SV1 and/or TR2-SV2 receptor polynucleotides, polypeptides, agonists, and/or antagonists are used to treat, prevent, and/or diagnose patients with cryptosporidiosis.

Similarly, bacterial or fungal agents that can cause disease or symptoms and that can be treated by TR2, TR2-SV1 and/or TR2-SV2 polynucleotides or polypeptides, or agonists or antagonists of TR2, TR2-SV1 and/or TR2-SV2, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*, Brucellosis, Candidiasis, *Campylobacter*, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi* and *Salmonella paratyphi*), *Serratia, Yersinia*), Erysipelothrix, Helicobacter, Legionellosis, Leptospirosis, *Listeria* (e.g., *Listeria monocytogenes*), Mycoplasmatales, *Mycobacterium leprae, Vibrio cholerae*, Neisseriaceae (e.g., *Acinetobacter*, Gonorrhea, Menigococca), *Meisseria meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Emphysema, sepsis, Lyme Disease, Cat-Scratch Disease, Dysentery, Paratyphoid Fever, food poisoning, Typhoid, pneumonia, Gonorrhea, meningitis (e.g., meningitis types A and B), *Chlamydia*, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. TR2, TR2-SV1 and/or TR2-SV2 polynucleotides or polypeptides, or agonists or antagonists of TR2, TR2-SV1 and/or TR2-SV2, can be used to treat, prevent, diagnose, and/or detect any of these symptoms or diseases. In specific embodiments, TR2 polynucleotides, polypeptides, or agonists thereof are used to treat, prevent, and/or diagnose: tetanus, Diphtheria, botulism, and/or meningitis type B.

Moreover, parasitic agents causing disease or symptoms that can be treated by TR2, TR2-SV1 and/or TR2-SV2 polynucleotides or polypeptides, or agonists of TR2, TR2-SV1 and/or TR2-SV2, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and *Trichomonas* and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. TR2, TR2-SV1 and/or TR2-SV2 polynucleotides or polypeptides, or agonists or antagonists of TR2, TR2-SV1 and/or TR2-SV2, can be used to treat, prevent, diagnose, and/or detect any of these symptoms or diseases. In specific embodiments, TR2, TR2-SV1 and/or TR2-SV2 polynucleotides, polypeptides, or agonists thereof are used to treat, prevent, and/or diagnose malaria.

TR2 receptor polynucleotides, polypeptides, agonists or antagonists of the invention may be used in developing treatments for any disorder mediated (directly or indirectly) by defective, or insufficient amounts of TR2. TR2, TR2-SV1 and/or TR2-SV2 receptor polypeptides, agonists or antagonists may be administered to a patient (e.g., mammal, preferably human) afflicted with such a disorder. Alternatively, a gene therapy approach may be applied to treat such disorders. Disclosure herein of TR2 receptor nucleotide sequences permits the detection of defective TR2 receptor genes, and the replacement thereof with normal TR2 receptor-encoding genes. Defective genes may be detected in in vitro diagnostic assays, and by comparison of the TR2 receptor nucleotide sequence disclosed herein with that of a TR2 receptor gene derived from a patient suspected of harboring a defect in this gene.

In another embodiment, the polypeptides of the present invention are used as a research tool for studying the biological effects that result from inhibiting AIM II/TR2 receptor and/or lymphotoxin-α/TR2 receptor interactions on different cell types. TR2 receptor polypeptides also may be employed in in vitro assays for detecting AIM II, lymphotoxin-α or TR2 receptor or the interactions thereof.

In another embodiment, a purified TR2 receptor polypeptide or antagonist is used to inhibit binding of AIM-II or lymphotoxin-α to endogenous cell surface AIM II and/or lymphotoxin-α receptors. Certain ligands of the TNF family (of which AIM II and lymphotoxin-α are members) have been reported to bind to more than one distinct cell surface receptor protein. AIM II and lymphotoxin-α likewise are believed to bind multiple cell surface proteins. By binding AIM II and/or lymphotoxin-α, soluble TR2 receptor polypeptides of the present invention may be employed to inhibit the binding of AIM II and/or lymphotoxin-α not only to cell surface TR2 receptor, but also to AIM II and/or lymphotoxin-α receptor proteins that are distinct from TR2 receptor. Thus, in another embodiment, TR2 receptor polynucleotides, polypeptides, agonists or antagonists are used to inhibit a biological activity of AIM II and/or lymphotoxin-α, in in vitro or in vivo procedures. By inhibiting binding of AIM II and/or lymphotoxin-α to cell surface receptors, TR2 receptor polynucleotides, polypeptides, agonists or antagonists also inhibit biological effects that result from the binding of AIM II and/or lymphotoxin-α to endogenous receptors. Various forms of TR2 receptor may be employed, including, for example, the above-described TR2 receptor fragments, derivatives, and variants that are capable of binding AIM II and/or lymphotoxin-α. In one preferred embodiment, a soluble TR2 receptor polypeptide is employed to inhibit a biological activity of AIM-II (e.g., to inhibit AIM II-mediated apoptosis of cells susceptible to such apoptosis). In another preferred embodiment, a soluble TR2 receptor polypeptide is employed to inhibit a biological activity of lymphotoxin-α (e.g., induction of inflammation and immune responses, maintenance of lymphoid tissues, induction of B cell proliferation).

In a further embodiment, a TR2 receptor polynucleotide, polypeptide, agonist or antagonist is administered to a mammal (e.g., a human) to treat a AIM II-mediated and/or lymphotoxin-α mediated disorder. Such AIM II-mediated and/or lymphotoxin-α mediated disorders include conditions caused (directly or indirectly) or exacerbated by AIM II and/or lymphotoxin-α.

Diseases associated with increased cell survival, or the inhibition of apoptosis, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Karposi's sarcoma and ovarian cancer); autoimmune disorders (such as, multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection. In preferred embodiments, TR2 receptor polynucleotides, polypeptides, agonists, or antagonists of the invention are used to inhibit growth, progression, and/or metastasis of cancers, in particular those listed above or in the paragraph that follows.

Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Grave's disease Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, and rheumatoid arthritis) myelodysplastic syndromes (such as aplastic anemia), graft vs. host disease (acute and/or chronic), ischemic injury (such as that caused by myocardial infarction, stroke and reperfusion injury), liver injury or disease (e.g., hepatitis related liver injury, cirrhosis, ischemia/reperfusion injury, cholestosis (bile duct injury) and liver cancer); toxin-induced liver disease (such as that caused by alcohol), septic shock, ulcerative colitis, cachexia and anorexia. In preferred embodiments, TR2 receptor polynucleotides, polypeptides, agonists, and/or antagonists are used to treat the diseases and disorders listed above.

Many of the pathologies associated with HIV are mediated by apoptosis, including HIV-induced nephropathy and HIV encephalitis. Thus, in additional preferred embodiments, TR2 receptor polynucleotides, polypeptides, agonists or antagonists of the invention are used to treat AIDS and pathologies associated with AIDS.

Another embodiment of the present invention is directed to the use of TR2 receptor polynucleotides, polypeptides, agonists or antagonists to reduce AIM II-mediated death of T cells in HIV-infected patients. The role of T cell apoptosis in the development of AIDS has been the subject of a number of studies (see, for example, Meyaard et al., *Science* 257:217-219 (1992); Groux et al., *J. Exp. Med.* 175:331 (1992); and Oyaizu et al., in "*Cell Activation and Apoptosis in HIV Infection*," Andrieu and Lu, eds., Plenum Press, New York, pp. 101-114 (1995). Fas-mediated apoptosis has been implicated in the loss of T cells in HIV individuals (Katsikis et al., *J. Exp. Med.* 181:2029-2036 (1995). It is also likely that T cell apoptosis occurs through multiple mechanisms. For example, at least some of the T cell death seen in HIV patients is likely to be mediated by AIM II.

Activated human T cells are induced to undergo programmed cell death (apoptosis) upon triggering through the CD3/T cell receptor complex, a process termed activated-induced cell death (AICD). AICD of CD4 T cells isolated from HIV-Infected asymptomatic individuals has been reported (Groux et al., supra). Thus, AICD may play a role in the depletion of CD4+ T cells and the progression to AIDS in HIV-infected individuals. Thus, the present invention provides a method of inhibiting AIM II-mediated T cell death in HIV patients, comprising administering a TR2 receptor polynucleotides, polypeptides, agonists or antagonists of the invention (preferably, a soluble TR2 receptor polypeptide) to the patients. In one embodiment, the patient is asymptomatic when treatment with TR2 receptor polynucleotides, polypeptides, agonists or antagonists commences. If desired, prior to treatment, peripheral blood T cells may be extracted from an HIV patient, and tested for susceptibility to AIM II-mediated cell death by procedures known in the art. In one embodiment, a patient's blood or plasma is contacted with TR2 receptor polypeptides of the invention ex vivo. The TR2 receptor polypeptides may be bound to a suitable chromatography matrix by procedures known in the art. The patient's blood or plasma flows through a chromatography column containing TR2 receptor polypeptide bound to the matrix, before being returned to the patient. The immobilized TR2 receptor polypeptide binds AIM II, thus removing AIM-II protein from the patient's blood.

In additional embodiments a TR2 receptor polynucleotide, polypeptide, agonist or antagonist of the invention is administered in combination with other inhibitors of T cell apoptosis. For example, as discussed above, Fas-mediated apoptosis also has been implicated in loss of T cells in HIV individuals (Katsikis et al., *J. Exp. Med.* 181:2029-2036 (1995). Thus, a patient susceptible to both Fas ligand mediated and AIM II mediated T cell death may be treated with both an agent that blocks AIM II/AIM II receptor interactions and an agent that blocks Fas-ligand/Fas interactions. Suitable agents for blocking binding of Fas-ligand to Fas include, but are not limited to, soluble Fas polypeptides; multimeric forms of soluble Fas polypeptides (e.g., dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Preferably, the antibodies employed according to this method are monoclonal antibodies. Examples of suitable agents for blocking Fas-ligand/Fas interactions, including blocking anti-Fas monoclonal antibodies, are described in WO 95/10540, hereby incorporated by reference.

In another example, agents which block binding of TRAIL to a TRAIL receptor are administered with the TR2 receptor polynucleotides, polypeptides, agonists or antagonists of the invention. Such agents include, but are not limited to, soluble TRAIL receptor polypeptides (e.g., a soluble form of OPG, DR4 (WO 98/32856); TR5 (WO 98/30693); DR5 (WO 98/41629); and TR10 (WO 98/54202)); multimeric forms of soluble TRAIL receptor polypeptides; and TRAIL receptor antibodies that bind the TRAIL receptor without transducing the biological signal that results in apoptosis, anti-TRAIL antibodies that block binding of TRAIL to one or more TRAIL receptors, and muteins of TRAIL that bind TRAIL receptors but do not transduce the biological signal that results in apoptosis. Preferably, the antibodies employed according to this method are monoclonal antibodies.

Another embodiment of the present invention is directed to the use of TR2 as a regulator of B cell proliferation and differentiation. The assays and experiments described herein clearly provide the scientific rational for the use of TR2 as a regulator of B cell proliferation and differentiation. The possible uses of the soluble or membrane bound TR2, its native ligand and various ligand antagonists are diverse and include treatment of autoimmune disorders and immunodeficiencies resulting from infection, anti-neoplastic therapy and/or inherited disorders. Moreover, many of the pre-neoplastic monoclonal gammopathies and neoplastic B cell diseases such as multiple myeloma may utilize TR2 or its ligand as either inducing or progressing factors.

Accordingly, TR2 or derived, functional agonists (including anti-TR2 antibodies, soluble forms having amino acids sequences contained in the extracellular domain of TR2 (e.g., TR2-Fc) and TR2 ligands), may find application as the following:

As an agent to direct an individuals immune system towards development of a humoral response (i.e., TH2) as opposed to a TH1 cellular response.

As an antigen for the generation of antibodies to inhibit or enhance TR2 mediated responses.

As a means of activating T cells.

As a means of regulating secreted cytokines that are elicited by TR2.

Antagonists of TR2 include binding and/or inhibitory antibodies, antisense nucleic acids, ribozymes, soluble forms of TR2 (e.g., TR2-fc) and TR2 ligand(s). These would be expected to reverse many of the activities of the receptor described above as well as find clinical or practical application as:

Antagonists of TR2 activities can also be used to treat or prevent Herpes viral infections. Such antagonists include full-length and mature TR2 polypeptides of the invention, TR2 fragments (e.g., soluble fragments), and antibodies having specificity for TR2 polypeptides. While not wishing to be limited to a specific mechanism, TR2 antagonist are believed to function in the treatment or prevention Herpes viral infections by blocking Herpes viral entry into cells.

An additional condition, disease or symptom that can be treated by TR2 polynucleotides or polypeptides, or agonists of TR2, is osteomyelitis.

Preferably, treatment using TR2 polynucleotides or polypeptides, or agonists of TR2, could either be by administering an effective amount of TR2 polypeptide to the patient, or by removing cells from the patient, supplying the cells with TR2 polynucleotide, and returning the engineered cells to the patient (ex vivo therapy). Moreover, as further discussed herein, the TR2 polypeptides or polynucleotides can be used as an adjuvant in a vaccine to raise an immune response against infectious disease.

In another embodiment, TR2, TR2-SV1 and/or TR2-SV2 polynucleotides or polypeptides of the invention and/or agonists and/or antagonists thereof, are used to treat, prevent, and/or diagnose inner ear infection (such as, for example, otitis media), as well as other infections characterized by infection with *Streptococcus pneumoniae* and other pathogenic organisms.

In a specific embodiment, TR2, TR2-SV1 and/or TR2-SV2 polynucleotides or polypeptides, or agonists or antagonists thereof (e.g., anti-TR2, anti-TR2-SV1 and/or anti-TR2-SV2 antibodies) are used to treat or prevent a disorder characterized by deficient serum immunoglobulin production, recurrent infections, and/or immune system dysfunction. Moreover, TR2, TR2-SV1 and/or TR2-SV2 polynucleotides or polypeptides, or agonists or antagonists thereof (e.g., anti-TR2, anti-TR2-SV1 and/or anti-TR2-SV2 antibodies) may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or *pneumocystis carnii*.

TR2, TR2-SV1 and/or TR2-SV2 polynucleotides or polypeptides of the invention, or agonists or antagonists thereof, may be used to diagnose, prognose, treat or prevent one or more of the following diseases or disorders, or conditions associated therewith: primary immuodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

Additionally, TR2, TR2-SV1 and/or TR2-SV2 polynucleotides or polypeptides of the invention, or agonists or antagonists thereof, may be used to diagnose, prognose, treat or prevent one or more of the following diseases, disorders, or conditions associated therewith, Guillain-Barre syndrome, anemia (e.g., anemia associated with parvovirus B19, patients with stable multiple myeloma who are at high risk for infection (e.g., recurrent infection), autoimmune hemolytic anemia (e.g., warm-type autoimmune hemolytic anemia), thrombocytopenia (e.g., neonatal thrombocytopenia), and immune-mediated neutropenia), transplantation (e.g., cytamegalovirus (CMV)-negative recipients of CMV-positive organs), hypogammaglobulinemia (e.g., hypogammaglobulinemic neonates with risk factor for infection or morbidity), epilepsy (e.g., intractable epilepsy), systemic vasculitic syndromes, myasthenia gravis (e.g., decompensation in myasthenia gravis), dermatomyositis, and polymyositis.

Additional preferred embodiments of the invention include, but are not limited to, the use of TR2, TR2-SV1 and/or TR2-SV2 polypeptides, TR2, TR2-SV1 and/or TR2-SV2 polynucleotides, and functional agonists thereof, in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response. In a specific nonexclusive embodiment, TR2, TR2-SV1 and/or TR2-SV2 polypeptides of the invention, and/or agonists thereof, are administered to boost the immune system to produce increased quantities of IgG. In another specific nonexclusive embodiment, TR2, TR2-SV1 and/or TR2-SV2 polypeptides of the invention and/or agonists thereof, are administered to boost the immune system to produce increased quantities of IgA. In another specific nonexclusive embodiment, TR2, TR2-SV1 and/or TR2-SV2 polypeptides of the invention and/or agonists thereof, are administered to boost the immune system to produce increased quantities of IgM.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741).

A vaccine adjuvant that enhances immune responsiveness to specific antigen. In a specific embodiment, the vaccine adjuvant is a TR2, TR2-SV1 and/or TR2-SV2 polypeptide described herein. In another specific embodiment, the vaccine adjuvant is a TR2, TR2-SV1 and/or TR2-SV2 polynucleotide described herein (i.e., the TR2, TR2-SV1 and/or TR2-SV2 polynucleotide is a genetic vaccine adjuvant). As discussed herein, TR2, TR2-SV1 and/or TR2-SV2 polynucleotides may be administered using techniques known in the art, including but not limited to, liposomal delivery, recombinant vector delivery, injection of naked DNA, and gene gun delivery.

An adjuvant to enhance tumor-specific immune responses.

An adjuvant to enhance anti-viral immune responses. Anti-viral immune responses that may be enhanced using the compositions of the invention as an adjuvant, include, but are not limited to, virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions of the invention are used as an adjuvant to enhance an immune response to the HIV gp120 antigen.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B *streptococcus, Shigella* spp., Enterotoxigenic *Escherichia coli*, Enterohemorrhagic *E. coli, Borrelia burgdorferi*, and *Plasmodium* (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria).

As a stimulator of B cell responsiveness to pathogens.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among B cell immunodeficient individuals, such as, for example, an individual who has undergone a partial or complete splenectomy. B cell immunodeficiencies that may be ameliorated or treated by administering the TR2, TR2-SV1 and/or TR2-SV2 polypeptides or polynucleotides of the invention, or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleo side phosphorylase deficiency (PNP), MHC Class II deficiency (Bare Lymphocyte Syndrome) and severe combined immunodeficiency.

As an agent to boost immunoresponsiveness among individuals having an acquired loss of B cell function. Conditions resulting in an acquired loss of B cell function that may be ameliorated or treated by administering the TR2, TR2-SV1 and/or TR2-SV2 polypeptides or polynucleotides of the invention, or agonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the TR2, TR2-SV1 and/or TR2-SV2 polypeptides or polynucleotides of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, and/or B-cells. In one embodiment, TR2, TR2-SV1 and/or TR2-SV2 polypeptides (in soluble, membrane-bound or transmembrane forms) or polynucleotides enhance antigen presentation or antagonize antigen presentation in vitro or in vivo. Moreover, in related embodiments, this enhancement or antagonization of antigen presentation may be useful in anti-tumor treatment or to modulate the immune system.

As a mediator of mucosal immune responses. The expression of TR2 by monocytes and the responsiveness of B cells to this factor suggests that it may be involved in exchange of signals between B cells and monocytes or their differentiated progeny. This activity is in many ways analogous to the CD40-CD154 signaling between B cells and T cells. TR2 may therefore be an important regulator of T cell independent immune responses to environmental pathogens. In particular, the unconventional B cell populations (CD5+) that are associated with mucosal sites and responsible for much of the innate immunity in humans may respond to TR2 thereby enhancing an individual's protective immune status.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a B cell specific binding protein to which specific activators or inhibitors of cell growth may be attached. The result would be to focus the activity of such activators or inhibitors onto normal, diseased, or neoplastic B cell populations.

As a means of detecting B-lineage cells by virtue of its specificity. This application may require labeling the protein with biotin or other agents (e.g., as described herein) to afford a means of detection.

As a stimulator of B cell production in pathologies such as AIDS, chronic lymphocyte disorder and/or Common Variable Immunodeficiency.

As part of a B cell selection device the function of which is to isolate B cells from a heterogenous mixture of cell types. TR2 could be coupled to a solid support to which B cells would then specifically bind. Unbound cells would be washed out and the bound cells subsequently eluted. A nonlimiting use of this selection would be to allow purging of tumor cells from, for example, bone marrow or peripheral blood prior to transplant.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance TR2, TR2-SV1 and/or TR2-SV2 mediated responses.

As a means of activating monocytes/macrophages to defend against parasitic diseases that effect monocytes such as *Leshmania*.

As pretreatment of bone marrow samples prior to transplant. Such treatment would increase B cell representation and thus accelerate recover.

As a means of regulating secreted cytokines that are elicited by TR2, TR2-SV1 and/or TR2-SV2.

TR2, TR2-SV1 and/or TR2-SV2 polypeptides or polynucleotides of the invention, or agonists may be used to modulate IgE concentrations in vitro or in vivo.

Additionally, TR2, TR2-SV1 and/or TR2-SV2 polypeptides or polynucleotides of the invention, or agonists thereof, may be used to treat, prevent, and/or diagnose IgE-mediated allergic reactions. Such allergic reactions include, but are not limited to, asthma, rhinitis, and eczema.

In a specific embodiment, TR2, TR2-SV1 and/or TR2-SV2 polypeptides or polynucleotides of the invention, or agonists thereof, is administered to treat, prevent, diagnose, and/or ameliorate selective IgA deficiency.

In another specific embodiment, TR2, TR2-SV1 and/or TR2-SV2 polypeptides or polynucleotides of the invention, or agonists thereof, is administered to treat, prevent, diagnose, and/or ameliorate ataxia-telangiectasia.

In another specific embodiment, TR2, TR2-SV1 and/or TR2-SV2 polypeptides or polynucleotides of the invention, or agonists thereof, is administered to treat, prevent, diagnose, and/or ameliorate common variable immunodeficiency.

In another specific embodiment, TR2, TR2-SV1 and/or TR2-SV2 polypeptides or polynucleotides of the invention, or agonists thereof, is administered to treat, prevent, diagnose, and/or ameliorate X-linked agammaglobulinemia.

In another specific embodiment, TR2, TR2-SV1 and/or TR2-SV2 polypeptides or polynucleotides of the invention, or agonists thereof, is administered to treat, prevent, diagnose, and/or ameliorate severe combined immunodeficiency (SCID).

In another specific embodiment, TR2, TR2-SV1 and/or TR2-SV2 polypeptides or polynucleotides of the invention, or agonists thereof, is administered to treat, prevent, diagnose, and/or ameliorate Wiskott-Aldrich syndrome.

In another specific embodiment, TR2, TR2-SV1 and/or TR2-SV2 polypeptides or polynucleotides of the invention, or agonists thereof, is administered to treat, prevent, diagnose, and/or ameliorate X-linked Ig deficiency with hyper IgM.

In another specific embodiment, TR2, TR2-SV1 and/or TR2-SV2 polypeptides or polynucleotides of the invention, or agonists or antagonists (e.g., anti-TR2 antibodies) thereof, is administered to treat, prevent, and/or diagnose chronic myelogenous leukemia, acute myelogenous leukemia, leukemia, hystiocytic leukemia, monocytic leukemia (e.g., acute monocytic leukemia), leukemic reticulosis, Shilling Type monocytic leukemia, and/or other leukemias derived from monocytes and/or monocytic cells and/or tissues.

In another specific embodiment, TR2, TR2-SV1 and/or TR2-SV2 polypeptides or polynucleotides of the invention, or agonists thereof, is administered to treat, prevent, diagnose, and/or ameliorate monocytic leukemoid reaction, as seen, for example, with tuberculosis.

In another specific embodiment, TR2, TR2-SV1 and/or TR2-SV2 polypeptides or polynucleotides of the invention, or agonists thereof, is administered to treat, prevent, diagnose, and/or ameliorate monocytic leukocytosis, monocytic leukopenia, monocytopenia, and/or monocytosis.

In a specific embodiment, TR2, TR2-SV1 and/or TR2-SV2 polynucleotides or polypeptides of the invention, and/or anti-TR2 antibodies and/or agonists or antagonists thereof, are used to treat, prevent, detect, and/or diagnose primary B lymphocyte disorders and/or diseases, and/or conditions associated therewith. In one embodiment, such primary B lymphocyte disorders, diseases, and/or conditions are characterized by a complete or partial loss of humoral immunity. Primary B lymphocyte disorders, diseases, and/or conditions associated therewith that are characterized by a complete or partial loss of humoral immunity and that may be prevented, treated, detected and/or diagnosed with compositions of the invention include, but are not limited to, X-Linked Agammaglobulinemia (XLA), severe combined immunodeficiency disease (SCID), and selective IgA deficiency.

In a preferred embodiment, TR2, TR2-SV1 and/or TR2-SV2 polynucleotides, polypeptides, and/or agonists and/or antagonists thereof are used to treat, prevent, and/or diagnose diseases or disorders affecting or conditions associated with any one or more of the various mucous membranes of the body. Such diseases or disorders include, but are not limited to, for example, mucositis, mucoclasis, mucocolitis, mucocutaneous leishmaniasis (such as, for example, American leishmaniasis, leishmaniasis americana, nasopharyngeal leishmaniasis, and New World leishmaniasis), mucocutaneous lymph node syndrome (for example, Kawasaki disease), mucoenteritis, mucoepidermoid carcinoma, mucoepidermoid tumor, mucoepithelial dysplasia, mucoid adenocarcinoma, mucoid degeneration, myxoid degeneration; myxomatous degeneration; myxomatosis, mucoid medial degeneration (for example, cystic medial necrosis), mucolipidosis (including, for example, mucolipidosis I, mucolipidosis II, mucolipidosis III, and mucolipidosis IV), mucolysis disorders, mucomembranous enteritis, mucoenteritis, mucopolysaccharidosis (such as, for example, type I mucopolysaccharidosis (i.e., Hurler's syndrome), type IS mucopolysaccharidosis (i.e., Scheie's syndrome or type V mucopolysaccharidosis), type II mucopolysaccharidosis (i.e., Hunter's syndrome), type III mucopolysaccharidosis (i.e., Sanfilippo's syndrome), type IV mucopolysaccharidosis (i.e., Morquio's syndrome), type VI mucopolysaccharidosis (i.e., Maroteaux-Lamy syndrome), type VII mucopolysaccharidosis (i.e., mucopolysaccharidosis due to beta-glucuronidase deficiency), and mucosulfatidosis), mucopolysacchariduria, mucopurulent conjunctivitis, mucopus, mucormycosis (i.e., zygomycosis), mucosal disease (i.e., bovine virus diarrhea), mucous colitis (such as, for example, mucocolitis and myxomembranous colitis), and mucoviscidosis (such as, for example, cystic fibrosis, cystic fibrosis of the pancreas, Clarke-Hadfield syndrome, fibrocystic disease of the pancreas, mucoviscidosis, and viscidosis). In a highly preferred embodiment, TR2, TR2-SV1 and/or TR2-SV2 polynucleotides, polypeptides, and/or agonists and/or antagonists thereof are used to treat, prevent, and/or diagnose mucositis, especially as associated with chemotherapy.

In a preferred embodiment, TR2, TR2-SV1 and/or TR2-SV2 polynucleotides, polypeptides, and/or agonists and/or antagonists thereof are used to treat, prevent, and/or diagnose diseases or disorders affecting or conditions associated with sinusitis.

An additional condition, disease or symptom that can be treated, prevented, and/or diagnosed by TR2, TR2-SV1 and/or TR2-SV2 polynucleotides or polypeptides, or agonists of TR2, TR2-SV1 and/or TR2-SV2, is osteomyelitis.

An additional condition, disease or symptom that can be treated, prevented, and/or diagnosed by TR2, TR2-SV1 and/or TR2-SV2 polynucleotides or polypeptides, or agonists of TR2, TR2-SV1 and/or TR2-SV2, is endocarditis.

Antagonists of TR2, TR2-SV1 and/or TR2-SV2 include binding and/or inhibitory antibodies, antisense nucleic acids, ribozymes, and TR2, TR2-SV1 and/or TR2-SV2 polypeptides of the invention. These would be expected to reverse many of the activities of the ligand described above as well as find clinical or practical application as:

A means of blocking various aspects of immune responses to foreign agents or self. Examples include autoimmune disorders such as lupus, and arthritis, as well as immunoresponsiveness to skin allergies, inflammation, bowel disease, injury and pathogens. Although our current data speaks directly to the potential role of TR2 in B cell and monocyte related pathologies, it remains possible that other cell types may gain expression or responsiveness to TR2. Thus, TR2 may, like CD40 and its ligand, be regulated by the status of the immune system and the microenvironment in which the cell is located.

A therapy for preventing the B cell proliferation and immunoglobin secretion associated with autoimmune diseases such as idiopathic thrombocytopenic purpura, systemic lupus erythematosus and MS.

An inhibitor of graft versus host disease or transplant rejection.

A therapy for B cell malignancies such as ALL, Hodgkin's disease, non-Hodgkin lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and immunoglobin associated with Chronic Myelogenous Leukemia.

An immunosuppressive agent(s).

TR2, TR2-SV1 and/or TR2-SV2 polypeptides or polynucleotides of the invention, or antagonists may be used to modulate IgE concentrations in vitro or in vivo.

In another embodiment, administration of TR2, TR2-SV1 and/or TR2-SV2 polypeptides or polynucleotides of the invention, or antagonists thereof, may be used to treat, prevent, and/or diagnose IgE-mediated allergic reactions including, but not limited to, asthma, rhinitis, and eczema.

An inhibitor of signaling pathways involving ERK1, COX2 and Cyclin D2 which have been associated with TR2 induced B cell activation.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

The agonists and antagonists may be employed in a composition with a pharmaceutically acceptable carrier, e.g., as described herein.

The antagonists may be employed for instance to inhibit TR2-mediated, TR2-SV1-mediated and/or TR2-SV2-mediated chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat, prevent, and/or diagnose infectious diseases including silicosis, sarcoidosis, idiopathic pulmonary fibrosis by preventing the recruitment and activation of mononuclear phagocytes. They may also be employed to treat, prevent, and/or diagnose idiopathic hyper-eosinophilic syndrome by preventing eosinophil production and migration. Endotoxic shock may also be treated by the antagonists by preventing the migration of macrophages and their production of the TR2, TR2-SV1 and/or TR2-SV2 polypeptides of the present invention. The antagonists may also be employed for treating atherosclerosis, by preventing monocyte infiltration in the artery wall. The antagonists may also be employed to treat, prevent, and/or diagnose histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat, prevent, and/or diagnose chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat, prevent, and/or diagnose rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by TR2, TR2-SV1 and/or TR2-SV2. The antagonists may also be employed to treat, prevent, and/or diagnose cases of bone marrow failure, for example, aplastic anemia and myelodysplastic syndrome. The antagonists may also be employed to treat, prevent, and/or diagnose asthma and allergy by preventing eosinophil accumulation in the lung. The antagonists may also be employed to treat, prevent, and/or diagnose subepithelial basement membrane fibrosis which is a prominent feature of the asthmatic lung. The antagonists may also be employed to treat, prevent, and/or diagnose lymphomas (e.g., one or more of the extensive, but not limiting, list of lymphomas provided herein).

TR2, TR2-SV1 and/or TR2-SV2 polynucleotides or polypeptides of the invention and/or agonists and/or antagonists thereof, may be used to treat, prevent, and/or diagnose various immune system-related disorders and/or conditions associated with these disorders, in mammals, preferably humans. Many autoimmune disorders result from inappropriate recognition of self as foreign material by immune cells. This inappropriate recognition results in an immune response leading to the destruction of the host tissue. Therefore, the administration of TR2, TR2-SV1 and/or TR2-SV2 polynucleotides or polypeptides of the invention and/or agonists and/or antagonists thereof that can inhibit an immune response, particularly the proliferation of B cells and/or the production of immunoglobulins, may be an effective therapy in treating and/or preventing autoimmune disorders. Thus, in preferred embodiments, TR2, TR2-SV1 and/or TR2-SV2 antagonists of the invention (e.g., polypeptide fragments of TR2, TR2-SV1 and/or TR2-SV2 and anti-TR2 antibodies) are used to treat, prevent, and/or diagnose an autoimmune disorder.

Autoimmune disorders and conditions associated with these disorders that may be treated, prevented, and/or diagnosed with the TR2, TR2-SV1 and/or TR2-SV2 polynucleotides, polypeptides, and/or antagonist of the invention (e.g., anti-TR2 antibodies), include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitus, and autoimmune inflammatory eye disease.

Additional autoimmune disorders (that are highly probable) that may be treated, prevented, and/or diagnosed with the compositions of the invention include, but are not limited to, autoimmune thyroiditis, hypothyroidism (i.e., Hashimoto's thyroiditis) (often characterized, e.g., by cell-mediated and humoral thyroid cytotoxicity), systemic lupus erhythematosus (often characterized, e.g., by circulating and locally generated immune complexes), Goodpasture's syndrome (often characterized, e.g., by anti-basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.

Additional autoimmune disorders (that are probable) that may be treated, prevented, and/or diagnosed with the compositions of the invention include, but are not limited to, rheumatoid arthritis (often characterized, e.g., by immune complexes in joints), schleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis/dermatomyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes) such as primary glomerulonephritis and IgA nephropathy, bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), inflammatory myopathies, and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using anti-TR2, anti-TR2-SV1 and/or anti-TR2-SV2 antibodies.

In a specific preferred embodiment, rheumatoid arthritis is treated, prevented, and/or diagnosed using anti-TR2, anti-TR2-SV1 and/or anti-TR2-SV2 antibodies and/or other antagonist of the invention.

In a specific preferred embodiment, lupus is treated, prevented, and/or diagnosed using anti-TR2, anti-TR2-SV1 and/or anti-TR2-SV2 antibodies and/or other antagonist of the invention.

In a specific preferred embodiment, nephritis associated with lupus is treated, prevented, and/or diagnosed using anti-TR2, anti-TR2-SV1 and/or anti-TR2-SV2 antibodies and/or other antagonist of the invention.

In a specific embodiment, TR2, TR2-SV1 and/or TR2-SV2 polynucleotides or polypeptides, or antagonists thereof (e.g., anti-TR2, anti-TR2-SV1 and/or anti-TR2-SV2 antibodies) are used to treat or prevent systemic lupus erythematosus and/or diseases, disorders or conditions associated therewith. Lupus-associated diseases, disorders, or conditions that may be treated or prevented with TR2, TR2-SV1 and/or TR2-SV2 polynucleotides or polypeptides, or antagonists of the invention, include, but are not limited to, hematologic disorders (e.g., hemolytic anemia, leukopenia, lymphopenia, and thrombocytopenia), immunologic disorders (e.g., anti-DNA antibodies, and anti-Sm antibodies), rashes, photosensitivity, oral ulcers, arthritis, fever, fatigue, weight loss, serositis (e.g., pleuritus (pleuricy)), renal disorders (e.g., nephritis), neurological disorders (e.g., seizures, peripheral neuropathy, CNS related disorders), gastroinstestinal disorders, Raynaud phenomenon, and pericarditis. In a preferred embodiment, the TR2, TR2-SV1 and/or TR2-SV2 polynucleotides or polypeptides, or antagonists thereof (e.g., anti-TR2, anti-TR2-SV1 and/or anti-TR2-SV2 antibodies) are used to treat or prevent renal disorders associated with systemic lupus erythematosus. In a most preferred embodiment, TR2, TR2-SV1 and/or TR2-SV2 polynucleotides or polypeptides, or antagonists thereof (e.g., anti-TR2, anti-TR2-SV1 and/or anti-TR2-SV2 antibodies) are used to treat or prevent nephritis associated with systemic lupus erythematosus.

Similarly, allergic reactions and conditions, such as asthma (particularly allergic asthma) or other respiratory problems, may also be treated by TR2, TR2-SV1 and/or TR2-SV2 polynucleotides or polypeptides of the invention and/or agonists and/or antagonists thereof. Moreover, these molecules can be used to treat, prevent, and/or diagnose anaphylaxis, hypersensitivity to an antigenic molecule, or blood group incompatibility.

TR2, TR2-SV1 and/or TR2-SV2 polynucleotides or polypeptides of the invention and/or agonists and/or antagonists thereof, may also be used to treat, prevent, and/or diagnose organ rejection or graft-versus-host disease (GVHD) and/or conditions associated therewith. Organ rejection occurs by host immune cell destruction of the transplanted tissue through an immune response. Similarly, an immune response is also involved in GVHD, but, in this case, the foreign transplanted immune cells destroy the host tissues. The administration of TR2, TR2-SV1 and/or TR2-SV2 polynucleotides or polypeptides of the invention and/or agonists and/or antagonists thereof, that inhibits an immune response, particularly the proliferation, differentiation, or chemotaxis of T-cells, may be an effective therapy in preventing organ rejection or GVHD.

Similarly, TR2, TR2-SV1 and/or TR2-SV2 polynucleotides or polypeptides of the invention and/or agonists and/or antagonists thereof, may also be used to modulate inflammation. For example, TR2, TR2-SV1 and/or TR2-SV2 polynucleotides or polypeptides of the invention and/or agonists and/or antagonists thereof, may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1).

In a specific embodiment, anti-TR2, anti-TR2-SV1 and/or anti-TR2-SV2 antibodies of the invention are used to treat, prevent, modulate, detect, and/or diagnose inflammation.

In a specific embodiment, anti-TR2, anti-TR2-SV1 and/or anti-TR2-SV2 antibodies of the invention are used to treat, prevent, modulate, detect, and/or diagnose inflammatory disorders.

In another specific embodiment, anti-TR2, anti-TR2-SV1 and/or anti-TR2-SV2 antibodies of the invention are used to treat, prevent, modulate, detect, and/or diagnose allergy and/or hypersensitivity.

Antibodies against TR2, TR2-SV1 and/or TR2-SV2 may be employed to bind to and inhibit TR2, TR2-SV1 and/or TR2-SV2 activity to treat, prevent, and/or diagnose ARDS, by preventing infiltration of neutrophils into the lung after injury. The agonists and antagonists of the instant may be employed in a composition with a pharmaceutically acceptable carrier, e.g., as described hereinafter.

TR2, TR2-SV1 and/or TR2-SV2 and/or TR2 receptor polynucleotides or polypeptides of the invention and/or agonists and/or antagonists thereof, are used to treat, prevent, and/or diagnose diseases and disorders of the pulmonary system (e.g., bronchi such as, for example, sinopulmonary and bronchial infections and conditions associated with such diseases and disorders and other respiratory diseases and disorders. In specific embodiments, such diseases and disorders include, but are not limited to, bronchial adenoma, bronchial asthma, pneumonia (such as, e.g., bronchial pneumonia, bronchopneumonia, and tuberculous bronchopneumonia), chronic obstructive pulmonary disease (COPD), bronchial polyps, bronchiectasia (such as, e.g., bronchiectasia sicca, cylindrical bronchiectasis, and saccular bronchiectasis), bronchiolar adenocarcinoma, bronchiolar carcinoma, bronchiolitis (such as, e.g., exudative bronchiolitis, bronchiolitis fibrosa obliterans, and proliferative bronchiolitis), bronchiolo-alveolar carcinoma, bronchitic asthma, bronchitis (such as, e.g., asthmatic bronchitis, Castellani's bronchitis, chronic bronchitis, croupous bronchitis, fibrinous bronchitis, hemorrhagic bronchitis, infectious avian bronchitis, obliterative bronchitis, plastic bronchitis, pseudomembranous bronchitis, putrid bronchitis, and verminous bronchitis), bronchocentric granulomatosis, bronchoedema, bronchoesophageal fistula, bronchogenic carcinoma, bronchogenic cyst, broncholithiasis, bronchomalacia, bronchomycosis (such as, e.g., bronchopulmonary aspergillosis), bronchopulmonary spirochetosis, hemorrhagic bronchitis, bronchorrhea, bronchospasm, bronchostaxis, bronchostenosis, Biot's respiration, bronchial respiration, Kussmaul respiration, Kussmaul-Kien respiration, respiratory acidosis, respiratory alkalosis, respiratory distress syndrome of the newborn, respiratory insufficiency, respiratory scleroma, respiratory syncytial virus, and the like.

In a specific embodiment, TR2, TR2-SV1 and/or TR2-SV2 polynucleotides or polypeptides of the invention and/or agonists and/or antagonists thereof, are used to treat, prevent, and/or diagnose chronic obstructive pulmonary disease (COPD).

In another embodiment, TR2, TR2-SV1 and/or TR2-SV2 polynucleotides or polypeptides of the invention and/or agonists and/or antagonists thereof, are used to treat, prevent, and/or diagnose fibroses and conditions associated with fibroses, such as, for example, but not limited to, cystic fibrosis (including such fibroses as cystic fibrosis of the pancreas, Clarke-Hadfield syndrome, fibrocystic disease of the pancreas, mucoviscidosis, and viscidosis), endomyocardial fibrosis, idiopathic retroperitoneal fibrosis, leptomeningeal fibrosis, mediastinal fibrosis, nodular subepidermal fibrosis, pericentral fibrosis, perimuscular fibrosis, pipestem fibrosis, replacement fibrosis, subadventitial fibrosis, and Symmers' clay pipestem fibrosis.

The TNF family ligands are known to be among the most pleiotropic cytokines, inducing a large number of cellular responses, including cytotoxicity, anti-viral activity, immunoregulatory activities, and the transcriptional regulation of several genes (D. V. Goeddel et al., "Tumor Necrosis Factors: Gene Structure and Biological Activities," *Symp. Quant. Biol.* 51:597-609 (1986), Cold Spring Harbor; B. Beutler and A. Cerami, *Annu. Rev. Biochem.* 57:505-518 (1988); L. J. Old, *Sci. Am.* 258:59-75 (1988); W. Fiers, *FEBS Lett.* 285:199-224 (1991)). The TNF-family ligands, including TR2, TR2-SV1 and/or TR2-SV2 polypeptides of the present invention, induce such various cellular responses by binding to TNF-family receptors. TR2, TR2-SV1 and/or TR2-SV2 polypeptides are believed to elicit a potent cellular response including any genotypic, phenotypic, and/or morphologic change to the cell, cell line, tissue, tissue culture or patient. As indicated, such cellular responses include not only normal physiological responses to TNF-family ligands, but also diseases associated with increased apoptosis or the inhibition of apoptosis. Apoptosis—programmed cell death—is a physiological mechanism involved in the deletion of peripheral B and/or T lymphocytes of the immune system, and its disregulation can lead to a number of different pathogenic processes (J. C. Ameisen, *AIDS* 8:1197-1213 (1994); P. H. Krammer et al., *Curr. Opin. Immunol.* 6:279-289 (1994)).

Diseases associated with increased cell survival, or the inhibition of apoptosis that may be diagnosed, treated, or prevented with the TR2, TR2-SV1 and/or TR2-SV2 polynucleotides or polypeptides of the invention, and agonists and antagonists thereof, include cancers (such as follicular lymphomas, carcinomas with p53 mutations, and hormone-dependent tumors, including, but not limited to, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. Thus, in preferred embodiments TR2, TR2-SV1 and/or TR2-SV2 polynucleotides or polypeptides of the invention and/or agonists or antagonists thereof, are used to treat, prevent, and/or diagnose autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment TR2, TR2-SV1 and/or TR2-SV2 polynucleotides or polypeptides of the invention are used to activate, differentiate or proliferate cancerous cells or tissue (e.g., B cell lineage related cancers (e.g., CLL and MLL), lymphocytic leukemia, or lymphoma) and thereby render the cells more vulnerable to cancer therapy (e.g., chemotherapy or radiation therapy).

Moreover, in other embodiments, TR2, TR2-SV1 and/or TR2-SV2 polynucleotides or polypeptides of the invention or agonists or antagonists thereof, are used to inhibit the growth, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that may be diagnosed, treated, or prevented with the TR2, TR2-SV1 and/or TR2-SV2 polynucleotides or polypeptides of the invention, and agonists and antagonists thereof, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia. Thus, in preferred embodiments TR2, TR2-SV1 and/or TR2-SV2 polynucleotides or polypeptides of the invention and/or agonists or antagonists thereof, are used to treat, prevent, and/or diagnose the diseases and disorders listed above.

In preferred embodiments, TR2, TR2-SV1 and/or TR2-SV2 polypeptides of the invention and/or agonists or antagonists thereof (e.g., anti-TR2 antibodies) inhibit the growth of human histiocytic lymphoma U-937 cells in a dose-dependent manner. In additional preferred embodiments, TR2, TR2-SV1 and/or TR2-SV2 polypeptides of the invention and/ or agonists or antagonists thereof (e.g., anti-TR2 antibodies) inhibit the growth of PC-3 cells, HT-29 cells, HeLa cells, MCF-7 cells, and A293 cells. In highly preferred embodiments, TR2, TR2-SV1 and/or TR2-SV2 polynucleotides or polypeptides of the invention and/or agonists or antagonists thereof (e.g., anti-TR2 antibodies) are used to inhibit growth, progression, and/or metastasis of prostate cancer, colon cancer, cervical carcinoma, and breast carcinoma.

Thus, in additional preferred embodiments, the present invention is directed to a method for enhancing apoptosis induced by a TNF-family ligand, which involves administering to a cell which expresses a TR2, TR2-SV1 and/or TR2-SV2 receptor an effective amount of TR2, TR2-SV1 and/or TR2-SV2, or an agonist or antagonist thereof, capable of increasing or decreasing TR2, TR2-SV1 and/or TR2-SV2 mediated signaling. Preferably, TR2, TR2-SV1 and/or TR2-SV2 mediated signaling is increased or decreased to treat, prevent, and/or diagnose a disease wherein decreased apoptosis or decreased cytokine and adhesion molecule expression is exhibited. An agonist or antagonist can include soluble forms of TR2, TR2-SV1 and/or TR2-SV2 and monoclonal antibodies directed against the TR2, TR2-SV1 and/or TR2-SV2 polypeptide.

In a further aspect, the present invention is directed to a method for inhibiting apoptosis induced by a TNF-family ligand, which involves administering to a cell which expresses the TR2, TR2-SV1 and/or TR2-SV2 receptor an effective amount of an agonist or antagonist capable of increasing or decreasing TR2, TR2-SV1 and/or TR2-SV2 mediated signaling. Preferably, TR2, TR2-SV1 and/or TR2-SV2 mediated signaling is increased or decreased to treat, prevent, and/or diagnose a disease wherein increased apoptosis or NF-kappaB expression is exhibited. An agonist or antagonist can include soluble forms of TR2, TR2-SV1 and/ or TR2-SV2 and monoclonal antibodies directed against the TR2, TR2-SV1 and/or TR2-SV2 polypeptide.

Because TR2, TR2-SV1 and TR2-SV2 belong to the TNF superfamily, the polypeptides should also modulate angiogenesis. In addition, since TR2, TR2-SV1 and TR2-SV2 inhibit immune cell functions, the polypeptides will have a wide range of anti-inflammatory activities. TR2, TR2-SV1 and/or TR2-SV2 may be employed as an anti-neovascularizing agent to treat, prevent, and/or diagnose solid tumors by stimulating the invasion and activation of host defense cells, e.g., cytotoxic T cells and macrophages and by inhibiting the angiogenesis of tumors. Those of skill in the art will recognize other non-cancer indications where blood vessel proliferation is not wanted. They may also be employed to enhance host defenses against resistant chronic and acute infections, for example, mycobacterial infections via the attraction and activation of microbicidal leukocytes. TR2, TR2-SV1 and/or TR2-SV2 may also be employed to inhibit T-cell proliferation by the inhibition of IL-2 biosynthesis for the treatment of T-cell mediated auto-immune diseases and lymphocytic leukemias (including, for example, chronic lymphocytic leukemia (CLL)). TR2, TR2-SV1 and/or TR2-SV2 may also be employed to stimulate wound healing, both via the recruitment of debris clearing and connective tissue promoting inflammatory cells. In this same manner, TR2, TR2-SV1 and/or TR2-SV2 may also be employed to treat, prevent, and/or diagnose other fibrotic disorders, including liver cirrhosis, osteoarthritis and pulmonary fibrosis. TR2, TR2-SV1 and/or TR2-SV2 also increases the presence of eosinophils that have the distinctive function of killing the larvae of parasites that invade tissues, as in schistosomiasis, trichinosis and ascariasis. It may also be employed to regulate hematopoiesis, by regulating the activation and differentiation of various hematopoietic progenitor cells, for example, to release mature leukocytes from the bone marrow following chemotherapy, i.e., in stem cell mobilization. TR2, TR2-SV1 and/or TR2-SV2 may also be employed to treat, prevent, and/or diagnose sepsis.

Polynucleotides and/or polypeptides of the invention and/or agonists and/or antagonists thereof are useful in promoting angiogenesis, wound healing (e.g., wounds, burns, and bone fractures) and regulating hematopoiesis. Polynucleotides and/or polypeptides of the invention and/or agonists and/or antagonists thereof are also useful as an adjuvant to enhance immune responsiveness to specific antigen, anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

Preferably, treatment using TR2, TR2-SV1 and/or TR2-SV2 polynucleotides or polypeptides, and/or agonists or antagonists of TR2, TR2-SV1 and/or TR2-SV2 (e.g., anti-TR2 antibody), could either be by administering an effective amount of TR2, TR2-SV1 and/or TR2-SV2 polypeptide of the invention, or agonist or antagonist thereof, to the patient, or by removing cells from the patient, supplying the cells with TR2, TR2-SV1 and/or TR2-SV2 polynucleotide, and returning the engineered cells to the patient (ex vivo therapy). Moreover, as further discussed herein, the TR2, TR2-SV1 and/or TR2-SV2 polypeptide or polynucleotide can be used as an adjuvant in a vaccine to raise an immune response against infectious disease.

The agonists and antagonists may be employed in a composition with a pharmaceutically acceptable carrier, e.g., as described herein.

All of the above described applications may be used in veterinary medicine, as well as in human treatment regimens.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Cardiovascular Disorders

TR2 polynucleotides, polypeptides, agonists or antagonists of the invention may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

In one embodiment, a TR2 receptor polynucleotide, polypeptide, agonist, or antagonist of the invention is used to treat thrombotic microangiopathies. One such disorder is thrombotic thrombocytopenic purpura (TTP) (Kwaan, H. C., Semin. Hematol. 24:71 (1987); Thompson et al., Blood 80:1890 (1992)). Increasing TTP-associated mortality rates have been reported by the U.S. Centers for Disease Control (Torok et al., Am. J. Hematol. 50:84 (1995)). Plasma from patients afflicted with TTP (including HIV+ and HIV− patients) induces apoptosis of human endothelial cells of dermal microvascular origin, but not large vessel origin (Laurence et al., Blood 87:3245 (1996)). Plasma of TTP patients thus is thought to contain one or more factors that directly or indirectly induce apoptosis. Another thrombotic microangiopathy is hemolytic-uremic syndrome (HUS) (Moake, J. L., Lancet, 343:393 (1994); Melnyk et al., Arch. Intern. Med. 155:2077 (1995); Thompson et al., supra). Thus, in one embodiment, the invention is directed to use of TR2 receptor to treat the condition that is often referred to as "adult HUS" (even though it can strike children as well). A disorder known as childhood/diarrhea-associated HUS differs in etiology from adult HUS. In another embodiment, conditions characterized by clotting of small blood vessels may be treated using TR2 receptor. Such conditions include, but are not limited to, those described herein. For example, cardiac problems seen in about 5-10% of pediatric AIDS patients are believed to involve clotting of small blood vessels. Breakdown of the microvasculature in the heart has been reported in multiple sclerosis patients. As a further example, treatment of systemic lupus erythematosus (SLE) is contemplated. In one embodiment, a patient's blood or plasma is contacted with TR2 receptor polypeptides of the invention ex vivo. The TR2 receptor polypeptides of the invention may be bound to a suitable chromatography matrix by procedures known in the art. According to this embodiment, the patient's blood or plasma flows through a chromatography column containing TR2 receptor polynucleotides and/or polypeptides of the invention bound to the matrix, before being returned to the patient. The immobilized TR2 receptor binds AIM II, thus removing AIM II protein from the patient's blood. Alternatively, TR2 receptor polynucleotides, polypeptides, agonists or antagonists of the invention may be administered in vivo to a patient afflicted with a thrombotic microangiopathy. In one embodiment, a soluble form of TR2 receptor polypeptide of the invention is administered to the patient. Thus, the present invention provides a method for treating a thrombotic microangiopathy, involving use of an effective amount of TR2 receptor polynucleotide, polypeptide, agonist or antagonist. A TR2 receptor polypeptide may be employed in in vivo or ex vivo procedures, to inhibit AIM II-mediated damage to (e.g., apoptosis of) microvascular endothelial cells.

While not intending to be bound by theory, cells which express TR2 are believed to interact with cells that express AIM II.

TR2 receptor polynucleotides, polypeptides, agonists or antagonists of the invention may be employed in combination with other agents useful in treating a particular disorder. For example, in an in vitro study reported by Laurence et al., Blood 87:3245 (1996), some reduction of TTP plasma-mediated apoptosis of microvascular endothelial cells was achieved by using an anti-Fas blocking antibody, aurintricarboxylic acid, or normal plasma depleted of cryoprecipitate. Thus, a patient may be treated with a polynucleotide and/or polypeptide of the invention in combination with an agent that inhibits Fas-ligand-mediated apoptosis of endothelial cells, such as, for example, an agent described above. In one embodiment, a TR2 receptor polynucleotide, polypeptide, agonist or antagonist, and an anti-FAS blocking antibody are both administered to a patient afflicted with a disorder characterized by thrombotic microangiopathy, such as TTP or HUS. Examples of blocking monoclonal antibodies directed against Fas antigen (CD95) are described in WO 95/10540, hereby incorporated by reference.

The naturally occurring balance between endogenous stimulators and inhibitors of angiogenesis is one in which inhibitory influences predominate. Rastinejad et al., Cell 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail.

Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., Biotech. 9:630-634 (1991); Folkman et al., N. Engl. J. Med. 333:1757-1763 (1995); Auerbach et al., J. Microvasc. Res. 29:401-411 (1985); Folkman, Advances in Cancer Research, Klein and Weinhouse, eds., Academic Press, New York, pp. 175-203 (1985); Patz, Am. J. Opthalmol. 94:715-743 (1982); and Folkman et al., Science 221:719-725 (1983). In a number of pathological conditions, the process of angiogenesis contributes to the disease state. For example, significant data have accumulated which suggest that the growth of solid tumors is dependent on angiogenesis (Folkman and Klagsbrun, Science 235:442-447 (1987)).

The present invention provides for treatment of diseases or disorders associated with neovascularization by administration of the TR2 receptor polynucleotides and/or polypeptides of the invention (including TR2 receptor agonists and/or antagonists). Malignant and metastatic conditions which can be treated with the polynucleotides and polypeptides of the invention include, but are not limited to those malignancies, solid tumors, and cancers described herein and otherwise known in the art (for a review of such disorders, see Fishman et al., *Medicine,* 2nd Ed., J. B. Lippincott Co., Philadelphia (1985)).

Additionally, ocular disorders associated with neovascularization which can be treated with the TR2 receptor polynucleotides and polypeptides of the present invention (including TR2 receptor agonists and TR2 receptor antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704-710 (1978) and Gartner et al., *Surv. Ophthal.* 22:291-312 (1978).

Additionally, disorders which can be treated with the TR2 receptor polynucleotides and polypeptides of the present invention (including TR2 receptor agonists and TR2 receptor antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Polynucleotides and/or polypeptides of the invention, and/or agonists and/or antagonists thereof, are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis) and bone formation (e.g., regulator of osteoclast differentiation), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, myasthenia gravis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are also useful as an adjuvant to enhance immune responsiveness to specific antigen and/or anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

All of the above described applications may be used in veterinary medicine, as well as in human treatment regimens.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, 1989, Proc. Natl. Acad. Sci. USA 86:8932-8935; Zijlstra et al., 1989, Nature 342:435-438). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al); WO 92/22635 dated Dec. 23, 1992 (Wilson et al); WO92/20316 dated Nov. 26, 1992 (Findeis et al); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, viral vectors that contains nucleic acid sequences encoding an antibody of the invention are used. For example, a retroviral vector can be used (see Miller et al., 1993, Meth. Enzymol. 217:581-599). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., PCT Publication WO 94/08598, dated Apr. 28, 1994; Stemple and Anderson, 1992, Cell 71:973-985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Modes of Administration

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit TR2 receptor mediated activity. Of course, where cell proliferation and/or differentiation is to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or pro-drug form. The agonist or antagonist may be administered in compositions in combination with one or more pharmaceutically acceptable excipients.

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diphtheria, hepatitis A, hepatitis B, *Haemophilus influenzae* B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In another specific embodiment, compositions of the invention are used in combination with PNEUMOVAX-23™ to treat, prevent, and/or diagnose infection and/or any disease, disorder, and/or condition associated therewith. In one embodiment, compositions of the invention are used in combination with PNEUMOVAX-23™ to treat, prevent, and/or diagnose any Gram positive bacterial infection and/or any disease, disorder, and/or condition associated therewith. In another embodiment, compositions of the invention are used in combination with PNEUMOVAX-23™ to treat, prevent, and/or diagnose infection and/or any disease, disorder, and/or condition associated with one or more members of the genus *Enterococcus* and/or the genus *Streptococcus*. In another embodiment, compositions of the invention are used in any combination with PNEUMOVAX-23™ to treat, prevent, and/or diagnose infection and/or any disease, disorder, and/or condition associated with one or more members of the Group B streptococci. In another embodiment, compositions of the invention are used in combination with PNEUMOVAX-23™ to treat, prevent, and/or diagnose infection and/or any disease, disorder, and/or condition associated with *Streptococcus pneumoniae*.

The compositions of the invention may be administered alone or in combination with other therapeutic agents, including but not limited to, TNFs, TNF blocking agents (e.g., antibodies which bind specifically to TNFs, such as TNF-α, TNF-β, or TNF-γ), chemotherapeutic agents, antibiotics, antivirals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF, lymphotoxin (LT, also known as TNF-beta), LT-beta (found in complex heterotrimer LT 2-beta), OPGL, FasL, CD27L, CD30L, CD40L, 4-1BBL, DcR3, OX40L, TNF-gamma (International Publication No. WO 96/14328), AIM I (International Publication No. WO 97/33899), AIM II (International Publication No. WO 97/34911), APRIL (J. Exp. Med. 188(6):1185-1190), endokine (International Publication No. WO 98/07880), TR6 (International Publication No. WO 98/30694), OPG (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), TR12, and soluble forms CD154, CD70 and CD153.

In another embodiment, the compositions of the invention are administered in combination with one or more TNF blocking agents. TNF blocking agents are believed to be useful in the treatment of arthritis (e.g., rheumatoid arthritis).

In a preferred embodiment, the compositions of the invention are administered in combination with CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat, prevent, and/or diagnose AIDS and/or to treat, prevent, and/or diagnose HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic *Pneumocystis carnii* pneumonia infection. In another specific embodiment, compositions of the invention are used in any combination with ISONIAZID™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, compositions of the invention are used in any combination with LEUCOVORIN™ and/or NEUPOGEN™ to prophylactically treat, prevent, and/or diagnose an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs, cyclophosphamide, cyclophosphamide IV, methylprednisolone, prednisolone, azathioprine, FK-506, 15-deoxyspergualin, and other immunosuppressive agents that act by suppressing the function of responding T cells.

In specific embodiments, compositions of the invention are administered in combination with immunosuppressants. Immunosuppressants preparations that may be administered with the compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine.

In a preferred embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (Warner-Lambert).

In a preferred embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, and prednisolone.

In a more preferred embodiment, the compositions of the invention are administered in combination with an antimalarial, methotrexate, anti-TNF antibody, ENBREL™ and/or sulfasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with sulfasalazine. In another specific embodiment, the compositions of the invention are administered in combination with methotrexate, anti-TNF antibody, and sulfasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and sulfasalazine. In another embodiment, the compositions of the invention are administered in combination with ENBREL™, methotrexate and sulfasalazine. In other embodiments, one or more antimalarial is combined with one of the above-recited combinations. In a specific embodiment, the compositions of the invention are administered in combination with an antimalarial (e.g., hydroxychloroquine), ENBREL™, methotrexate and sulfasalazine. In another specific embodiment, the compositions of the invention are administered in combination with an antimalarial (e.g., hydroxychloroquine), sulfasalazine, anti-TNF antibody, and methotrexate.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, ε-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin C, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituxmab and CHOP, or Rituxmab and any combination of the components of CHOP.

In an additional embodiment, the compositions of the invention are administered in combination with cytokines. Cytokines that may be administered with the compositions of the invention include, but are not limited to, GM-CSF, G-CSF, IL-2, IL-3, IL-4, IL-5, IL-6, IL-7, IL-10, IL-12, IL-13, IL-15, anti-CD40, CD40L, IFN, IFN-beta, IFN-gamma, TNF, and TNF-beta. In another embodiment, compositions of the invention may be administered with any interleukin, including, but not limited to, IL-1 alpha, IL-1 beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, the compositions of the invention are administered in combination with IL-4 and IL-10. Both IL-4 and IL-10 have been observed by the inventors to enhance TR2 mediated B cell proliferation.

In an additional embodiment, the compositions of the invention are administered with a chemokine. In another embodiment, the compositions of the invention are administered with chemokine beta-8, chemokine beta-1, and/or macrophage inflammatory protein-4. In a preferred embodiment, the compositions of the invention are administered with chemokine beta-8.

In an additional embodiment, the compositions of the invention are administered in combination with an IL-4 antagonist. IL-4 antagonists that may be administered with the compositions of the invention include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, the compositions of the invention are administered in combination with hematopoietic growth factors. Hematopoietic growth factors that may be administered with the compositions of the invention include, but are not limited to, LEUKINE™ (SARGRAMOSTIM™) and NEUPOGEN™ (FILGRASTIM™).

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE 19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy. Such therapy may be administered sequentially and/or concomitantly It will be understood that, when administered to a human patient, the total daily usage of the compounds and compositions of the present invention will be decided by the attending physician within the scope of sound medical judgement. The specific therapeutically effective dose level for any particular patient will depend upon factors well known in the medical arts.

As a general proposition, the total pharmaceutically effective amount of a TR2 polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TR2 polypeptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed.

The invention provides methods of treatment, inhibition and prophylaxis by administration to a subject of an effective amount of a compound or pharmaceutical composition of the invention (e.g., an antibody of the invention). In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Pharmaceutical compositions containing the TR2 receptor polypeptides of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

TR2 compositions of the invention are also suitably administered by sustained-release systems. Suitable examples of sustained-release compositions include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(-)-3-hydroxybutyric acid (EP 133,988).

Sustained-release compositions also include liposomally entrapped compositions of the invention (see generally, Langer, Science 249:1527-1533 (1990); Treat et al., in Liposomes in the Therapy of Infectious Disease and Cancer, Lopez-Berestein and Fidler (eds.), Liss, New York, pp. 317-327 and 353-365 (1989)). Liposomes containing TR2 polypeptide my be prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal TR2 polypeptide therapy.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides.

Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, M. et al., J. Cell. Biol. 101:976-985 (1985); Jalkanen, M. et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of the interest in an animal, preferably a mammal and most preferably a human. In one embodiment, diagnosis comprises: (a) administering (for example, parenterally, subcutaneously, or intraperitoneally) to a subject an effective amount of a labeled molecule which specifically binds to the polypeptide of interest; (b) waiting for a time interval following the administering for permitting the labeled molecule to preferentially concentrate at sites in the subject where the polypeptide is expressed (and for unbound labeled molecule to be cleared to background level); (c) determining background level; and (d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Having generally described the invention, the same will be more readily understood by reference to the following examples, which are provided by way of illustration and are not intended as limiting.

Example 1

Expression and Purification of TR2 in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6×His tag") covalently linked to the carboxyl terminus of that polypeptide. However, in this example, the polypeptide coding sequence is inserted such that translation of the six His codons is prevented and, therefore, the polypeptide is produced with no 6×His tag.

The DNA sequence encoding the desired portion of the TR2 protein lacking the hydrophobic leader sequence is amplified from the deposited cDNA using PCR oligonucleotide primers which anneal to the amino terminal sequences of the desired portion of the TR2 protein and to sequences in the deposited construct 3' to the cDNA coding sequence. Additional nucleotides containing restriction sites to facilitate cloning in the pQE60 vector are added to the 5' and 3' sequences, respectively.

For cloning the mature protein, the 5 primer has the sequence: 5' CGC<u>CCATGG</u>CCCCAGCTCTGCCGTCCT 3' (SEQ ID NO:14) containing the underlined NcoI restriction site followed by 18 nucleotides complementary to the amino terminal coding sequence of the mature TR2 sequence in FIG. 1A-1B. One of ordinary skill in the art would appreciate, of course, that the point in the protein coding sequence where the 5' primer begins may be varied to amplify a desired portion of the complete protein shorter or longer than the mature form. The 3' primer has the sequence: 5' CGC <u>AAGCTT</u>ATTGTGGGAGCTGCTGGTCCC 3' (SEQ ID NO:15) containing the underlined HindIII restriction site followed by 18 nucleotides complementary to the 3' end of the nucleotide sequence shown in FIG. 1A-1B (SEQ ID NO:1) encoding the extracellular domain of the TR2 receptor.

The amplified TR2 DNA fragments and the vector pQE60 are digested with NcoI and HindIII and the digested DNAs are then ligated together. Insertion of the TR2 DNA into the restricted pQE60 vector places the TR2 protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan$^r$"), is used in carrying out the illustrative example described herein. This strain, which is only one of many that are suitable for expressing TR2 protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3-4 hours at 4° C. in 6 M guanidine-HCl, pH 8. The cell debris is removed by centrifugation, and the supernatant containing the TR2 is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure TR2 protein. The purified protein is stored at 4° C. or frozen at −80° C.

Example 2

Example 2(a)

Cloning and Expression of a Soluble Fragment of TR2 Protein in a Baculovirus Expression System In this example, the plasmid shuttle vector pA2 GP was used to insert the cloned DNA encoding the mature extracellular domain of the TR2 receptor protein shown in FIG. 1A-1B, lacking its naturally associated secretory signal (leader) sequence, into a baculovirus. This protein was expressed using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39.

The cDNA sequence encoding essentially the mature extracellular domain (amino acids 37 to 200 shown in FIG. 1A-1B) of the TR2 receptor protein in the deposited plasmid (ATCC™ Deposit Number 97059) was amplified using PCR oligonucleotide primers corresponding to the relevant 5' and 3' sequences of the gene. The 5' primer for each of the above has the sequence:

5'CGCGGATCCCGGAGCCCCCTGCTAC 3' (SEQ ID NO:16) containing the underlined BamHI restriction enzyme site, an efficient signal for initiation of translation in eukaryotic cells, as described by Kozak, M., *J. Mol Biol.* 196:947-950 (1987), followed by 15 bases of the coding sequence of the TR2 protein shown in FIG. 1A-1B, beginning with the nucleotide 354. The 3' primer has the sequence:

5' CGCGGTACCATTGTGGGAGCTGCTGGTCCC 3' (SEQ ID NO:17) containing the underlined, Asp718 restriction sites followed by 17 nucleotides complementary to the coding sequences in FIG. 1A-1B.

The amplified fragment was isolated from a 1% agarose gel using a commercially available kit ("Geneclean," BIO 101 Inc., La Jolla, Calif.). The fragment was then digested with BamHI and Asp718 and purified on a 1% agarose gel. This fragment is designated herein "F1".

The plasmid was digested with the restriction enzymes BamHI and Asp718 dephosphorylated using calf intestinal phosphatase. The DNA was then isolated from a 1% agarose gel using a commercially available kit ("Geneclean" BIO 101 Inc., La Jolla, Calif.). This vector DNA was designated herein "V1".

Fragment F1 and the dephosphorylated plasmid V1 were ligated together with T4 DNA ligase. *E. coli* HB101 cells were transformed with the ligation mixture and spread on culture plates. Other suitable *E. coli* hosts such as XL-1 Blue (Stratagene Cloning Systems, La Jolla, Calif.) may also be used. Bacteria were identified that contain the plasmid with the human TR2 sequences using the PCR method, in which one of the primers that was used to amplify the gene and the second primer was from well within the vector so that only those bacterial colonies containing TR2 gene fragments show amplification of the DNA. The sequence of the cloned fragment was confirmed by DNA sequencing. The plasmid was designated herein pBacTR2-T.

Five μg of pBacTR2-T was co-transfected with 1.0 μg of a commercially available linearized baculovirus DNA ("BACULOGOLD™ baculovirus DNA", Pharmingen, San Diego, Calif.), using the lipofection method described by Felgner et al., *Proc. Natl. Acad. Sci. USA* 84:7413-7417 (1987). 1 μg of BACULOGOLD™ virus DNA and 5 μg of plasmid pBacTR2-T were mixed in a sterile well of a microtiter plate containing 50 μl of serum-free Grace's medium (Life Technologies Inc., Gaithersburg, Md.). Afterwards, 10 μl Lipofectin plus 90 μl Grace's medium were added, mixed and incubated for 15 minutes at room temperature. Then the transfection mixture was added drop-wise to Sf9 insect cells (ATCC™ CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation was continued at 27° C. for four days.

After four days the supernatant was collected and a plaque assay was performed, as described by Summers and Smith, supra. An agarose gel with "Blue Gal" (Life Technologies Inc., Gaithersburg) was used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10). After appropriate incubation, blue stained plaques were picked with the tip of a micropipettor (e.g., Eppendorf). The agar containing the recombinant viruses was then resuspended in a microcentrifuge tube containing 200 μl of Grace's medium and the suspension containing the recombinant baculovirus was used to infect Sf9 cells seeded in 35 mm dishes. Four days later the supernatants of these culture dishes were harvested and then they were stored at 4° C. The recombinant virus is called V-TR2-T.

To verify the expression of the gene used, Sf9 cells were grown in Grace's medium supplemented with 10% heat inactivated FBS. The cells were infected with the recombinant baculovirus V-TR2-T at a multiplicity of infection ("MOI") of about 2. Six hours later the medium was removed and replaced with SF900 II medium minus methionine and cysteine (available from Life Technologies Inc., Rockville, Md.). Forty-two hours later, 5 μCi of $^{35}$S-methionine and 5 μCi $^{35}$S-cysteine (available from Amersham) were added to radiolabel proteins. The cells were further incubated for 16 hours and then they were harvested by centrifugation. The proteins in the supernatant as well as the intracellular proteins were analyzed by SDS-PAGE followed by autoradiography. Microsequencing of the amino acid sequence of the amino terminus of purified protein was used to determine the amino terminal sequence of the mature protein and thus the cleavage point and length of the secretory signal peptide.

Example 2(b)

Cloning and Expression of TR2 Protein in a Baculovirus Expression System

Similarly to the cloning and expression of the truncated version of the TR2 receptor described in Example 2(a), recombinant baculoviruses were generated which express the full length TR2 receptor protein shown in FIG. 1A-1B (SEQ ID NO:2).

In this example, the plasmid shuttle vector pA2 was used to insert the cloned DNA encoding the complete protein, including its naturally associated secretary signal (leader) sequence, into a baculovirus to express the mature TR2 protein. Other attributes of the pA2 vector are as described for the pA2 GP vector used in Example 2(a).

The cDNA sequence encoding the full length TR2 protein in the deposited plasmid, including the AUG initiation codon and the naturally associated leader sequence shown in FIG. 1A-1B (SEQ ID NO:2), was amplified using PCR oligonucleotide primers corresponding to the 5' and 3' sequences of the gene. The 5' primer has the sequence:

5' GCGCGGATCCACCATGGAGCCTCCTGGAGACTGG 3' (SEQ ID NO:18) containing the underlined BamHI restriction enzyme site, an efficient signal for initiation of translation in eukaryotic cells, as described by Kozak, M., *J. Mol. Biol.* 196:947-950 (1987), followed by 21 bases of the sequence of the complete TR2 protein shown in FIG. 1A-1B, beginning with the AUG initiation codon. The 3' primer has the sequence:

5' GCGCGGTACCTCTACCCCAGCAGGGGCGCCA 3' (SEQ ID NO:19) containing the underlined, Asp718 restriction site followed by 21 nucleotides complementary to the 3' noncoding sequence in FIG. 1A-1B.

The amplified fragment was isolated and digested with restriction enzymes as described in Example 2(a) to produce plasmid pBacTR2

5 µg of pBacTR2 was co-transfected with 1 µg of BACU-LOGOLD™ (Pharmingen) viral DNA and 10 µl of LIPO-FECTIN (Life Technologies, Inc.) in a total volume of 200 µl serum free media. The primary viruses were harvested at 4-5 days post-infection (pi), and used in plaque assays. Plaque purified viruses were subsequently amplified and frozen, as described in Example 2(a).

For radiolabeling of expressed proteins, Sf9 cells were seeded in 12 well dishes with 2.0 ml of a cell suspension containing $0.5 \times 10^6$ cells/ml and allowed to attach for 4 hours. Recombinant baculoviruses were used to infect the cells at an MOI of 1-2. After 4 hours, the media was replaced with 1.0 ml of serum free media depleted for methionine and cysteine (-Met/-Cys). At 3 days pi, the culture media was replaced with 0.5 ml -Met/-Cys containing 2 µCi each [$^{35}$S]-Met and [$^{35}$S]-Cys. Cells were labeled for 16 hours after which the culture media was removed and clarified by centrifugation (Supernatant). The cells were lysed in the dish by addition of 0.2 ml lysis buffer (20 mM HEPES, pH 7.9; 130 mM NaCl; 0.2 mM EDTA; 0.5 mM DTT and 0.5% vol/vol NP-40) and then diluted up to 1.0 ml with $dH_2O$ (Cell Extract). 30 µl of each supernatant and cell extract were resolved by 15% SDS-PAGE. Protein gels were stained, destained, amplified, dried and autoradiographed. Labeled bands corresponding to the recombinant proteins were visible after 16-72 hours exposure.

Example 3

Cloning and Expression of TR2 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC™ 37152), pSV2dhfr (ATCC™ 37146) and pBC12MI (ATCC™ 67109). Mammalian host cells that could be used include, human HeLa 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277-279 (1991); Bebbington et al., *Bio/Technology* 10: 169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438-447 (March, 1985)) plus a fragment of the CMV-enhancer (Boshart et al., *Cell* 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pTR2 HA, is made by cloning a cDNA encoding TR2 into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding a TR2 is cloned into the polylinker region of the vector so that recombinant protein expression is directed by the CMV promoter. The plasmid construction strategy is as follows. The TR2 cDNA of the deposited plasmid is amplified using primers that contain convenient restriction sites, much as described above for construction of vectors for expression of TR2 in *E. coli*. Suitable primers include the following, which are used in this example. The 5' primer, containing the underlined BamHI site, a Kozak sequence, an AUG start codon and 6 additional codons of the 5' coding region of the complete TR2 has the following sequence: 5' GCGC GGATCCACCATGGAGCCTCCTGGAGACTGG 3' (SEQ ID NO:20). The 3' primer, containing the underlined XbaI site, a stop codon, HA tag, and 19 bp of 3' coding sequence has the following sequence (at the 3' end):

```
5'GCGCTCTAGATCAAGCGTAGTCTGGGACGTCGTATGGGTAGTGGTTTGGGCTCCTCCC 3'.    (SEQ ID NO:21)
```

The PCR amplified DNA fragment and the vector, pcDNAI/Amp, are digested with BamHI and XbaI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the TR2-encoding fragment.

For expression of recombinant TR2, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TR2 by the vector.

Expression of the TR2-HA fusion protein is detected by radiolabeling and immunoprecipitation, using methods described in, for example Harlow et al., *Antibodies: A Laboratory Manual*, 2d Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of TR2 protein. Plasmid pC4 is a derivative of the plasmid pSV2-dhfr (ATCC™ Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J Biol. Chem.* 253: 1357-1370, Hamlin, J. L. and Ma, C. 1990, *Biochem. et Biophys. Acta*, 1097:107-143, Page, M. J. and Sydenham, M. A. 1991, *Biotechnology* 9:64-68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., *Molecular and Cellular Biology*, March 1985:438-447) plus a fragment isolated from the enhancer of the immediate early gene of human cytomegalovirus (CMV) (Boshart et al., *Cell* 41:521-530 (1985)). Downstream of the promoter are BamHI, XhaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the TR2 protein in a regulated way in mammalian cells (Gossen, M., & Bujard, H. 1992, *Proc. Natl. Acad. Sci. USA* 89: 5547-5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calf intestinal phosphatase by procedures known in the art. The vector is then isolated from a 1% agarose gel.

The DNA sequence encoding the complete TR2 protein including its leader sequence is amplified using PCR oligonucleotide primers corresponding to the 5' and 3' sequences of the gene. The 5' primer has the sequence:

5'GCGC<u>GGATCC</u>ACCATGGAGCCTCCTGGAGACTGG 3' (SEQ ID NO:22) containing the underlined BamHI restriction enzyme site followed by an efficient signal for initiation of translation in eukaryotes, as described by Kozak, M., *J. Mol. Biol.* 196: 947-950 (1987), and 21 bases of the coding sequence of TR2 protein shown in FIG. 1A-1B (SEQ ID NO:1). The 3' primer has the sequence:

5' GCGC<u>GGTACC</u>TCTACCCCAGCAGGGGCGCCA 3' (SEQ ID NO:19) containing the underlined Asp718 restriction site followed by 21 nucleotides complementary to the non-translated region of the TR2 gene shown in FIG. 1A-1B (SEQ ID NO:1).

The amplified fragment is digested with the endonucleases BamHI and Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100-200 μM. Expression of the desired gene product is analyzed, for instance, by SDS-PAGE and Western blot or by reverse phase HPLC analysis.

Example 4

Tissue Distribution of TR2 mRNA Expression

Northern blot analysis is carried out to examine TR2 gene expression in human tissues, using methods described by, among others, Sambrook et al., cited above. A cDNA probe containing the entire nucleotide sequence of the TR2 protein (SEQ ID NO:1) is labeled with $^{32}$P using the REDIPRIME™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for TR2 mRNA.

Multiple Tissue Northern (MTN) blots containing various human tissues (H) or human immune system tissues (IM) are obtained from Clontech and are examined with the labeled probe using EXPRESSHYB™ hybridization solution (Clontech) according to manufacturer's protocol number PT1190-1. Following hybridization and washing, the blots are mounted and exposed to film at −70° C. overnight, and films developed according to standard procedures.

Example 5

Example 5(a)

Expression and Purification of TR2-Fc(TR2-Ig Fusion Protein) and Cleaved TR2

The putative transmembrane domain of translated TR2 receptor was determined by hydrophobicity using the method of Goldman et al (*Ann. Rev. of Biophys. Biophys. Chem.* 15:321-353 (1986)) for identifying nonpolar transbilayer helices. The region upstream of this transmembrane domain, encoding the putative leader peptide and extracellular domain, was chosen for the production of an Fc fusion protein. Primers were designed to PCR the corresponding coding region from HTXBS40 with the addition of a BglII site (single underlined), a Factor Xa protease site and an Asp718I site (double underlined) at the 3' end. PCR with this primer pair (forward 35-mer: 5'CAGGAATTCGCAGCCATGGAGCCTCCTG-GAGACTG 3' (SEQ ID NO:23), and reverse primer 53-mer:

5'CCATACCCAGGTACCCCTTCCCTCGAT AGATCTTGCCTTCGTCACCAGCCAGC 3' (SEQ ID NO:24)), which contains 18 nucleotides of the TR2 coding sequence, resulted in one band of the expected size. This was cloned into COS-Fclink to give the TR2-Fclink plasmid. The PCR product was digested with EcoRI and Asp718I and ligated into the COS-Fclink plasmid (Johansen, et al., *J. Biol. Chem.* 270:9459-9471 (1995)) to produce TR2-Fclink.

COS cells were transiently transfected with TR2-Fclink and the resulting supernatant was immunoprecipitated with protein A agarose. Western blot analysis of the immunoprecipitate using goat anti-human Fc antibodies revealed a strong band consistent with the expected size for glycosylated TR2-Fc (greater than 47.5 kD). A 15 L transient COS transfection was performed and the resulting supernatant was purified (see below). The purified protein was used to immunize mice following DNA injection for the production of mAbs.

CHO cells were transfected with TR2-Fclink to produce stable cell lines. Five lines were chosen by dot blot analysis for expansion and were adapted to shaker flasks. The line with the highest level of TR2-Fc protein expression was identified by Western blot analysis. TR2-Fc protein purified from the supernatant of this line was used for cell binding studies by flow cytometry, either as intact protein or after factor Xa cleavage and biotinylation (see below).

Clone HTXBS40 is an allelic variant of TR2 which differs from the sequence shown in FIG. 1A-1B (SEQ ID NO:1) in that HTXBS40 contains guanine at nucleotide 314, thymine at nucleotide 386 and cytosine at nucleotide 627.

A plasmid suitable for expression of the extracellular domain of TR2 was constructed as follows to immunize mice for the production of anti-TR2 mAbs. The Fc fragment was removed from TR2-Fclink by a BglII/XhaI digestion, Klenow was used to fill in the overhangs, and the blunt ends of the plasmid were religated. The resulting frame shift introduced a stop codon immediately following the amino acids which had originally been introduced into TR2-Fclink by the addition of the BglII site. Thus, the C terminus of the extracellular domain of TR2 is followed by only 2 amino acids (RS) in this constructed (TR2exlink).

Example 5(b)

Purification of TR2-Fc from CHO E1A Conditioned Media Followed by Cleavage and Biotinylation of TR2

Assays

Product purity through the purification was monitored on 15% Laemmli SDS-PAGE gels run under reducing and non-reducing conditions. Protein concentration was monitored by $A_{280}$ assuming an extinction coefficient of 0.7 for the receptor and 1.28 for the chimera, both calculated from the sequence. Extinction coefficients were confirmed by AAA.

Protein G Chromatography of the TR2-Fc Fusion Protein

All steps described below were carried out at 4° C. 15 L of CHO conditioned media (CM) (0.2μ filtered following harvest in cell culture) was applied to a 5×10 cm column of Protein G at a linear flow rate of 199 cm/h. The column had been washed with 100 mM glycine, pH 2.5 and equilibrated in 20 mM sodium phosphate, 150 mM sodium chloride, pH 7 prior to sample application. After the CM was loaded the column was washed with 5 column volumes of 20 mM sodium phosphate, 150 mM sodium chloride, pH 7 and eluted with 100 mM glycine, pH 2.5. 435 ml of eluate was immediately neutralized with 3 M Tris, pH 8.5 and 0.2μ filtered. Based on $A_{280}$, extinction coefficient 1.28, 65 mg of protein was recovered at 0.15 mg/ml.

Concentration/Dialysis 385 ml of Protein G eluate was concentrated in an Amicon stirred cell fitted with a 30K membrane to 34 ml at a final concentration of 1.7. The concentrate was dialyzed against buffer.

Factor Xa Cleavage and Purification to Generate Free Receptor

Six ml (10.2 mg) of TR2-Fc was added to 50 μg of Factor Xa resulting in a 1:200, e:s ratio. The mixture was incubated overnight at 4° C.

Protein G Chromatography of the Free TR2 Receptor

A 1 ml column of Protein G was equilibrated in 20 mM sodium phosphate, 150 mM sodium chloride, pH 6.5 in a disposable column using gravity flow. The cleaved receptor was passed over the column 3 times after which the column was washed with 20 mM sodium phosphate, 150 mM sodium chloride, pH 6.5 until no $A_{280}$ absorbance was seen. The column was eluted with 2.5 ml of 100 mM glycine, pH 2.5 neutralized with 83 μl of 3 M Tris, pH 8.5. TR2 eluted in the nonbound fraction.

Concentration

The nonbound fraction from the Protein G column, about 12 ml, was concentrated in a Centricon 10K cell (Amicon) to about 1 ml to a final concentration of 3.5 mg/ml estimated by $A_{280}$, extinction coefficient 0.7.

Mono S Chromatography

The concentrated sample was diluted to 5 ml with 20 mM sodium phosphate, pH 6 and applied to a 0.5×5 cm Mono S column equilibrated in 20 mM sodium phosphate, pH 6 at a linear flow rate of 300 cm/h. The column was washed with 20 mM sodium phosphate, pH 6 and eluted with a 20 column volume linear gradient of 20 mM sodium phosphate, pH 6 to 20 mM sodium phosphate, 1 M sodium chloride, pH 6. TR2 protein eluted in the nonbound fraction.

Concentration/Dialysis

The 3 ml nonbound fraction from the Mono S column was concentrated to 1 ml as above using a Centricon 10K cell and dialyze against 20 mM sodium phosphate, 150 mM sodium chloride, pH 7. The concentration following dialysis was 2.1 mg/ml.

Biotinylation 0.5 mg of TR2 at 2.1 mg/ml was dialyzed against 100 mM borate, pH 8.5. A 20-fold molar excess of NHS-LC Biotin was added and the mixture was left on a rotator overnight at 4° C. The biotinylated TR2 was dialyzed against. 20 mM sodium phosphate, 150 mM sodium chloride, pH 7, sterile filtered and stored at −70° C. Biotinylation was demonstrated on a Western blot probed with strepavidin HRP and subsequently developed with ECL reagent.

Example 6

The Membrane Bound Form of the TR2 Receptor is a TNFR which Induces Lymphocytes Proliferation and Differentiation The members of the tumor necrosis factor (TNFR)/nerve growth factor receptor (NGFR) superfamily are characterized by the presence of three to six repeats of a cysteine-rich motif that consists of approximately 30 to 40 amino acids in the extracellular part of the molecule (Mallett, S. and Barclay, A. N., *Immunol. Today* 12:220 (1991)). The crystal structure of TNFR-I showed that the cysteine-rich motif (TNFR domain) was composed of three elongated strands of residues held together by a twisted ladder of disulfide bonds (Banner, D. W. et al., *Cell* 73:431 (1993). These receptors contain a hinge-like region immediately adjacent to the transmembrane domain, characterized by a lack of cysteine residues and a high proportion of serine, threonine, and proline, which are likely to be glycosylated with O-linked sugars. A cytoplasmic part of these molecules shows limited sequence similarities—a finding which may be the basis for diverse cellular signaling. At present, the members identified from human cells include CD40 (Stamenkovic, I. et al., *EMBO J.* 8:1403 (1989)), 4-1BB (Kwon, B. S. and Weissman, S. M., *Proc. Natl. Acad. Sci. USA* 86:1963 (1989)), OX-40 (Mallett, S. et al., *EMBO J.* 9:1063 (1990)), TNFR-I (Loetscher, H. et al., *Cell* 61:351 (1990); Schall, T. J. et al., *Cell* 61:361 (1990)), TNFR-II (Smith, C. A. et al., *Science* 248:1019 (1990)), CD27 (Van Lier, R. A. et al., *J. Immunol.* 139:1589 (1987)), Fas (Itoh, N. et al., *Cell* 66:233 (1991)), NGFR (Johnson, D. et al., *Cell* 47:545 (1986)), CD30 (Durkop, H. et al., *Cell* 68:421 (1992)) and LTBR (Baens, M. et al., *Genomics* 16:214 (1993)). Viral open reading frames encoding soluble TNFRs have also been identified, such as SFV-T2 (Smith, C. A. et al., *Science* 248:1019 (1990)), Va53 (Howard, S. T. et al., *Virology* 180:633 (1991)), G4RG (Hu, F.-Q. et al., *Virology* 204: 343 (1994)) and crmB (Smith, G. L., *J. Gen. Viol.* 74:1725 (1993)).

Recent intensive studies have shown that these molecules are involved in diverse biological activities such as immunoregulation (Armitage, R. J., *Curr. Opin. Immunol.* 6:407 (1994); Smith, C. A. et al., *Cell* 75:959 (1994)), by regulating cell proliferation (Banchereau, J. et al., *Science* 251:70 (1991); Pollok, K. E. et al., *J. Immunol.* 150:771 (1993); Baum, P. R. et al., *EMBO J.* 13:3992 (1994)), cell survival (Grass, H.-J. et al., *Blood* 83:2045 (1994); Torcia, M. et al., *Cell* 85:345-356 (1996)), and cell death (Tartaglia, L. A. et al., *Cell* 74:845 (1993); Gillette-Ferguson, I. and Sidman, C. L., *Eur. J. Immunol.* 24:1181 (1994); Krammer, P. H. et al., *Curr. Opin. Immunol.* 6:279 (1994)).

Because of their biological significance and the diverse membership of this superfamily, we predicted that there would be further members of the superfamily. By searching an EST-data base, we have identified a new member of the TNFR superfamily. We report here the initial characterization of the molecule called TR2.

Material and Methods

Identification and Cloning of New Members of the TNFR Superfamily

An expressed sequence tag (EST) cDNA data base, obtained over 500 different cDNA libraries (Adams, M. D. et al., *Science* 252:1651 (1991); Adams, M. D. et al., *Nature* 355:632 (1992)), was screened for sequence similarity with cysteine-rich motif of the TNFR superfamily, using the blastn and tblastn algorithms (Altschul, S. F. et al., *J. Mol. Biol.* 215:403 (1990)). One EST (designated as HT1SB52) was identified in a human T cell line library which showed significant identity to TNFR-II at the amino acid level. This sequence was used to clone the missing 5' end by RACE (rapid amplification of cDNA ends) using a 5'-RACE-ready cDNA of human leukocytes (Clontech, PT1155-1. Cat. #7301-1). This sequence matched four further ESTs (HTOBH42, HTOAU65, HLHA49 and HTXBS40). Complete sequencing of these and other cDNAs indicated that they contained an identical open reading frame homologous to the TNFR superfamily and was named TR2. Analysis of several other ESTs and cDNAs indicated that some cDNAs had additional sequences inserted in the open reading frame identified above, and might represent various partially-spliced mRNAs.

Cells

The myeloid and B-cell lines studied represent cell types at different stages of the differentiation pathway. KG1a and PLB 985 (Koeffler, H. et al., *Blood* 56:265 (1980); Tucker, K. et al., *Blood* 70:372 (1987)) were obtained from Phillip Koeffler (UCLA School of Medicine), BJA-B was from Z. Jonak (SmithKline Beecham), and TF 274, a stromal cell line exhibiting osteoblastic features, was generated from the bone marrow of a healthy male donor (Tan & Jonak, unpublished). All of the other cell lines were obtained from the American Type Culture Collection (Rockville, Md.). Monocytes were prepared by differential centrifugation of peripheral blood mononuclear cells (PBMC) and adhesion to tissue culture dish. $CD19^+$, $CD4^+$ and $CD8^+$ were isolated from PBMC by immunomagnetic beads (Dynal, Lake Success, N.Y.). Endothelial cells from human coronary artery were purchased from clonetics (Clonetics, CA).

RNA and DNA Blot Hybridization

Total RNA of adult tissues was purchases from Clontech (Palo Alto, Calif.), or extracted from primary cells and cell lines with TriReagent (Molecular Research Center, Inc., Cincinnati, Ohio). 5 to 7.5 µg of total RNA was fractionated in a 1% agarose gel containing formaldehyde, as described (Sambrook et al., Molecular Cloning, Cold Springs Harbor (1989)) and transferred quantitatively to Zeta-probe nylon membrane (Biorad, Hercules, Calif.) by vacuum-blotting. The blots were prehybridized, hybridized with $^{32}$P-labeled XhoI/EcoRI fragment of TR2 or OX-40 probe, washed under stringent conditions and exposed to X-ray films.

High molecular weight human DNA was digested with various restriction enzymes and fractionated in 0.8% agarose gel. The DNA was denatured, neutralized and transferred to nylon membrane and hybridized to $^{32}$P-labeled TR-2 or its variant cDNA.

In Situ Hybridization and FISH Detection

The in situ hybridization and FISH detection of TR2 location in human chromosome were performed as previously described (Heng, H. H. Q. et al., *Proc. Natl. Acad. Sci. USA* 89:9509 (1992); Heng, H. H. Q. et al., *Human Molecular Genetics* 3:61 (1994)). FISH signals and the DAPI banding pattern were recorded separately by taking photographs, and the assignment of the FISH mapping data with chromosomal bands was achieved by superimposing FISH signals with DAPI banded chromosome (Heng, H. H. Q. and Tsui, L.-C., *Chromosoma*. 102:325 (1993)).

Production of Recombination TR2-Fc Fusion Proteins

The 5' portion of the TR2 containing the entire putative open reading frame of extracellular domain was amplified by polymerase chain reaction (Saiki, R. K. et al., *Science* 239: 487 (1988)). For correctly oriented cloning, a HindIII site on the 5' end of the forward primer and a BglII site on the 5' end of the reverse primer were created. The Fc portion of human IgG$_1$ was PCR-amplified from ARH-77 (ATCC™) cell RNA and cloned in SmaI site of pGem7 vector (Promega). The Fc fragment including hinge, CH$_2$, and CH$_3$ domain sequences contained a BglII site at its 5' end and an XhoI site at its 3' end. The HindIII-BglII fragment of TR2 cDNA was inserted into the upstream of human IgG$_1$Fc and an in frame fusion was confirmed by sequencing. The TR2-Fc fragment was released by digesting the plasmid with HindIII-XhoI and cloned it into pcDNA3 expression plasmid.

The TR2-Fc plasmid, linearized with PvuI, was transferred into NIH 3T3 by the calcium phosphate co-precipitation method. After selection in 400 µg/ml G418, neomycin-resistant colonies were picked and expanded. ELISA with anti-human IgG$_1$ and Northern analysis with $^{32}$P-labeled TR2 probe were used to select clones that produce high levels of TR2-Fc in the supernatant. In some experiments, a slightly different engineered TR2-Fc produced in Chinese hamster ovary (CHO) cells was used. The TR2-Fc was purified by protein G chromatography, and the amino acid sequence of N-terminus of the TR2-Fc fusion protein was determined by automatic peptide sequencer (ABI). TR2-Fc was used to produce polyclonal rabbit anti-TR2 antibodies.

Blocking MLR-Mediated PBMC Proliferation

PBMC were isolated from three healthy adult volunteers by Ficoll gradient centrifugation at 400×g for 30 minutes. PBMCs were recovered, washed in RPMI 1640 (GIBCO-BRL) supplemented with 10% FBS, 300 µg/ml L-glutamine and 50 µg/ml genetomycin, and adjusted to 1×10$^6$ cells/ml for two donors and to 2×10$^5$ cells/ml for the third donor.

Fifty µl of each cell suspension was added to 96-well (round bottom) plates (Falcon, Franklin Lakes, NS) together with 50 µl of TR2-Fc, IL-5R-Fc, anti-CD4 mAb or control mAb. Plates were incubated at 37° C. in 5% CO$_2$ for 96 hours. One µCi of [$^3$H]-methylthymidine (ICN Biomedicals, Costa Mesa, Calif.) was then added for an additional 16 hours. Cells were harvested and radioactivity was counted.

Results and Discussion

TR2 is a New Member of the TNFR Superfamily

FIG. 1A-1B (SEQ ID NO:2) shows the amino acid sequence of TR2 deduced from the longest open reading frame of one of the isolated cDNAs (HLHAB49). Comparison with other sequenced cDNAs and ESTs in the database indicated potential allelic variants which resulted in amino acid changes at positions 17 (either Arg or Lys) and 41 (either Ser or Phe) of the protein sequence shown in FIG. 1A-1B (amino acid residues −20 and 5 in SEQ ID NO:2).

The open reading frame encodes 283 amino acids with a calculated molecular weight of 30,417. The TR2 protein was expected to be a receptor. Therefore, the potential signal sequence and transmembrane domain were sought. A hydrophobic stretch of 23 amino acids towards the C terminus (amino acids 201-225) (FIG. 1A-1B) was assigned as a transmembrane domain because it made a potentially single helical span, but the signal sequence was less obvious. The potential ectodomain TR2 was expressed in NIH 3T3 and CHO cells as a Fc-fusion protein, and the N-terminal amino acid sequence of the recombinant TR2-Fc protein was determined in both cases. The N-terminal sequence of the processed mature TR2 started from amino acid 37, indicating that the first 36 amino acids constituted the signal sequence (FIG. 1A-1B).

Figure 16:
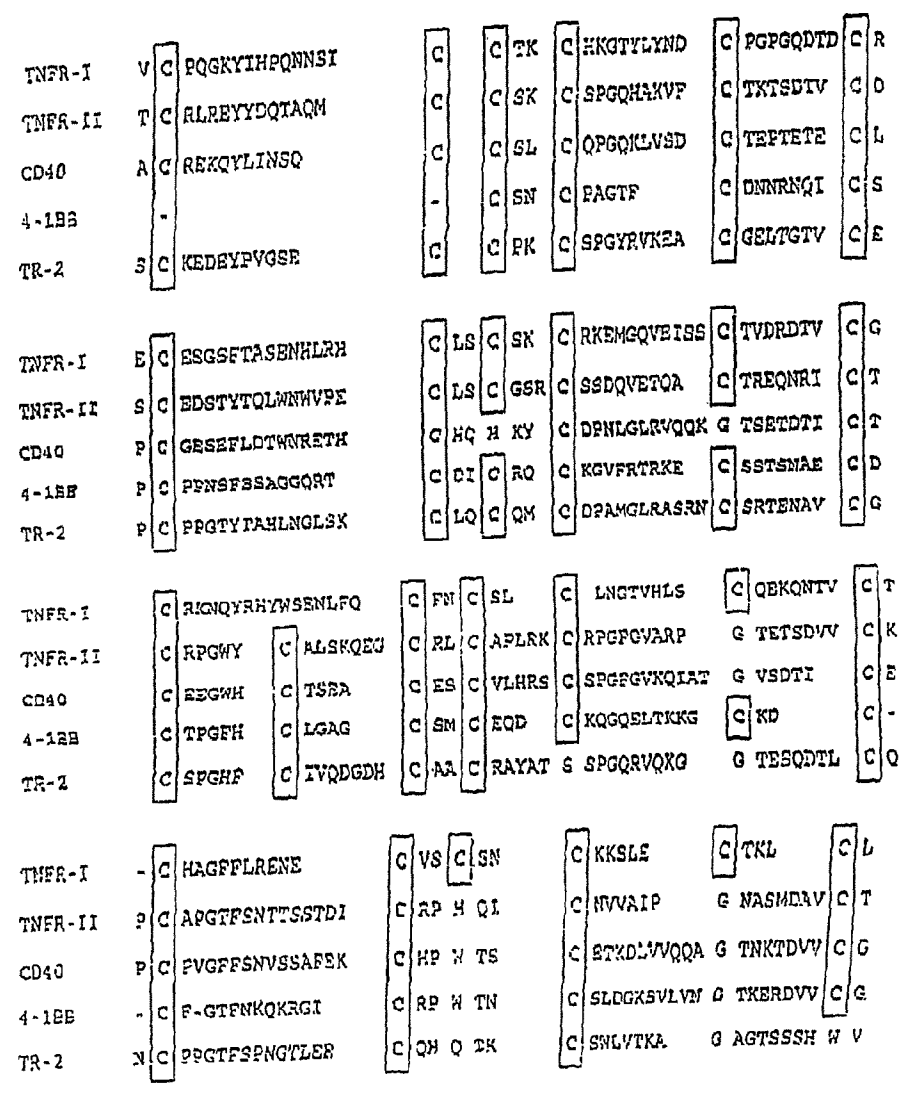

Using a polyclonal rabbit antibody raised to TR2, the molecular size of natural TR2 was determined to be 38 kD by Western analysis. Since the protein backbone of processed TR2 would be composed of 247 amino acids with an Mr of 26,000, the protein must be modified post-translationally. Two potential asparagine-linked glycosylation sites are located at amino acid positions 110 and 173 (FIG. 1A-1B). Along with the other members of the TNFR family, TR2 contains the characteristic cysteine-rich motifs which have been shown by X-ray crystallography (Banner et al., *Cell* 73:431 (1993)) to represent a repetitive structural unit (Banner, D. W. et al., *Cell* 73:431 (1993)). FIG. 16 shows the potential TNFR domain aligned among TR2 (SEQ ID NO:2), TNFR-I (SEQ ID NO:10), TNFR-II (SEQ ID NO:11), CD40 (SEQ ID NO:12) and 4-1BB (SEQ ID NO:13). TR2 contained two perfect TNFR domain and two imperfect ones.

The TR2 cytoplasmic tail (TR2 cy) appears to be more closely related to those of CD40cy and 4-1BBcy, and does not contain the death domain seen in the Fas and TNFR-I intracellular domains. Although the homology is moderate, the Thr$^{266}$ of TR2 is aligned with Thr$^{233}$ of 4-1BB and Thr$^{254}$ of CD40. This may be significant because Inui et al., (Inui, S. et al., *Eur. J. Immunol.* 20:1747 (1990)) found that Thr$^{254}$ was essential for CD40 signal transduction and when the Thr$^{254}$ of CD40 was mutated, the CD40 bd did not bind to the CD40cy (Hu, H. M. et al., *J. Biol. Chem.* 269:30069 (1994)). Signals through 4-1BB and CD40 have been shown to be costimulatory to T cells and B cells respectively (Banchereau, J. and Rousset, F., *Nature* 353:678 (1991); Hurtaldo, J. et al., *J. Immunol.* 155:3360 (1995)).

TABLE V

GENE EXPRESSION OF TR2 AND OX40 IN TISSUES AND CELLS

| SOURCE | | GENE TR2 | OX-40 |
|---|---|---|---|
| TISSUES (adult) | | | |
| Brain | | +/− | − |
| Heart | | + | − |
| Lung | | + | − |
| Thymus | | ++ | − |
| Spleen | | +++ | − |
| Liver | | + | − |
| Kidney | | + | − |
| Small Intestine | | +++ | − |
| Prostate | | ++ | − |
| Skeletal Muscle | | +/− | − |
| Ovary | | + | |
| Pancreas | | + | |
| Colon | | + | |
| Thyroid | | + | |
| Spinal Cord | | + | |
| Trachea | | + | |
| Adrenal Gland | | + | |
| Lymph Node | | +++ | |
| PRIMARY CELLS | | | |
| PBL, CD19+ | | ++ | − |
| PBL, CD8+ | | ++ | − |
| PBL, CD8+ (activated) | | ++ | ++ |
| PBL | | +++ | |
| PBL, CD4+ (activated) | | ++ | ++ |
| Bone Marrow | | + | − |
| Monocyte | | ++ | − |
| Endothelial | | + | − |
| HEMATOPOIETIC CELL LINES | | | |
| Erythroid | | | |
| K562 | | − | |
| HEL | | + | |
| Myeloid | | | |
| KG1a | (Promyeloblast) | + | + |
| KG1 | (Myeloblast) | ± | ± |
| PLB985 | (Late myeloblast) | − | |
| HL60 | (Promyelocyte) | ± | − |
| U937 | (Promonocyte) | ± | |
| THP-1 | (Monocyte) | + | − |
| B-Lymphocyte | | | |
| REH | (Pre–preB) | ± | |
| BJA-B | (Early B, IgM) | + | − |
| Raji | (Mature B, IgM) | + | |
| IM-9 | (Mature B, IgG) | − | − |
| T-Lymphocyte | | | |
| Sup-T1 | (CD4+) | − | |
| Molt-3 | (CD4+) | ± | − |
| H9 | (CD4+) | + | |
| Jurkat | (CD4+) | + | + | no entry = not tested,
− = not detected,
± to ++ = increasing amounts of RNA detected

TR2 RNA Expression

A human tissue RNA blot was used to determine tissue distribution of TR2 RNA expression. TR2 RNA was detected in several tissues with a relatively high level in the lung, spleen and thymus (Table V) but was not detected by this method in the brain, liver or skeletal muscle (Table V). TR-2 was also expressed in monocytes, CD19+ B cells, and resting or PMA plus PHA-treated CD4+ or CD8+ T cells. It was only weakly expressed in bone marrow and endothelial cells (Tables V and VI), although expression was observed in the hematopoietic cell line KG1a (Table V). For comparison, the tissue distribution of OX-40, another member of the TNFR superfamily, was examined (Table V). Unlike TR2, OX-40 was not detected in any tissues examined, and was detected only in activated T-cells and KG1a. Several cell lines were negative for TR2 expression, including TF 274 (bone marrow stromal), MG 63 and TE 85 (osteosarcoma), RL 95-2 (endometrial sarcoma), MCF-7 and T-47D (breast cancer cells), BE, HT 29 (colon cancer cells), HTB-11 and IMR-32 (neuroblastoma), although TR2 was found in the rhapdosarcoma HTB-82 (data not shown).

Several cell lines were examined for inducible TR2 expression. HL60, U937 and THP1, which belong to the myelomonocytic lineage, all increased TR2 expression in response to the differentiation agents PMA or DMSO. Increases in expression in response to these agents were observed in KG1a and Jurkat cells. In contrast, PMA did not induce TR2 expression in MG63, but unexpectedly TNF-α did.

In almost all cases, the predominant mRNA was approximately 1.7 kb in size, although several higher molecular weight species could be detected in some tissues. While many cDNAs and ESTs which were sequenced contained insertions in the coding region indicative of partial splicing, we only detected one major protein by Western blot, suggesting that if these encode alternate proteins they are not evident in the cells we examined. The abundance of higher MW mRNAs raises the possibility that TR2 may in part be regulated at the level of mRNA maturation.

TABLE VI

RELATIVE ABUNDANCE (RA) OF TR2 RNA IN VARIOUS TISSUE AND CELL TYPES

| Tissue or Cell Type | RA | Tissue or Cell Type | RA |
|---|---|---|---|
| Activated Macrophage (LPS) | 22 | Fetal Heart | 1 |
| Breast Lymph Node | 5 | Fetal Lung | 2 |
| B Cell Lymphoma | 5 | Glioblastoma | 1 |
| Activated Monocytes | 2 | Hypothalamus, Schizophrenia | 1 |
| Activated T Cells | 3 | Infant Brain | 2 |
| Activated Neutrophil | 2 | Lung | 2 |
| Tonsils | 5 | Osteosarcoma | 1 |
| Thymus | 3 | Pancreas Tumor | 1 |
| Anergic T-cell | 1 | Placenta | 2 |
| Jurkat T-Cell | 3 | Small Intestine | 1 |
| Raji Cells (Cycloheximide Treated) | 3 | Smooth Muscle | 1 |
| Atrophic Endometrium | 1 | Stomach | 2 |
| Bone Marrow | 1 | T-Cell Lymphoma | 1 |
| Brain | 1 | T-Cells | 1 |
| Breast | 1 | Testes | 3 |
| CD34 Depleted Buffy Coat (Cord Blood) | 1 | Testes Tumor | 2 |
| Cerebellum | 1 | Tongue | 1 |
| Corpus Colosum | 1 | Umbilical Vein Endothelial Cells | 2 |
| Caco-2 Cells (adenocarcinoma, colon) | 1 | White Fat | 3 |
| Fetal Dura Mater | 1 | | |

TR2 Maps at 1P36.2-P36.3

The FISH mapping procedure was applied to localize the TR2 gene to a specific human chromosomal region. The assignment of a hybridization signal to the short arm of chromosome 1 was obtained with the aid of DAPI banding. A total of 10 metatic figures. were photographed which indicated that the TR2 gene is located on the chromosome 1 region p36.2-p36.3. The TR2 position is in close proximity with CD30 (Smith, C. A. et al., Cell 73:1349-1360 (1993), 4-1BB (Kwon, B. S. et al., J. Immunol. 152:2256-2262 (1994); Goodwin, R.

G. et al., *Eur. J. Immunol.* 23:2631-2641 (1993), OX-40 (Birkeland, M. L. et al., *Eur. J. Immunol.* 25:926-930 (1995), and TNFR-II (Baker, E. et al., *Cytogenet. & Cell Genet.* 57:117-118 (1991), suggesting that it evolved through a localized gene duplication event. Interestingly, all of these receptors have stimulatory phenotypes in T cells in response to cognate ligand binding, in contrast to Fas and TNFR-I which stimulate apoptosis. This prompted us to test if TR2 might be involved in lymphocyte stimulation.

TR2-Fc Interfaces with MLR-Mediated Proliferation of PBMC

To determine the possible involvement of cell surface TR2 with its ligand in lymphocyte proliferation, we examined allogeneic MLR proliferative responses. When TR2-Fc was added to the culture, a significant reduction of maximal responses was observed (p<0.05). The addition of TR2-Fc at 100 µg/ml inhibited the proliferation up to 53%. No significant inhibition of proliferation was observed with the control IL-5R-Fc. Surprisingly, at high concentrations (10-100 µg/ml) IL-5R-Fc was shown to enhance proliferation. An anti-CD4 mAb assayed simultaneously inhibited MLR-mediated proliferation up to 60%, whereas a control anti-IL-5 mAb failed to inhibit the proliferation. It is well known that a major component of the MLR proliferative response is T cell-dependent; hence, it would appear that inhibiting the interaction of TR2 with its ligand prevents optimal T lymphocyte activation and proliferation. The inhibition of MLR proliferation by TR2-Fc at concentrations of 1-100 µg/ml compares favorably with biological effects seen with other TNFR-Fc superfamily members such as CD40-Fc (unpublished results, Jeremy Harrop).

Hence, we have identified an additional member of the TNF receptor superfamily which either plays a direct role in T cell stimulation or binds to a ligand which can stimulate T cell proliferation through one or more receptors which may include TR2. Consistent with a direct role for TR2 is the similarity of the cytoplasmic domain with CD40 and 4-1 BB. We are currently trying to identify this ligand to which TR2 binds in order to clarify its role.

Example 7

Gene Therapy Using Endogenous TR2 Receptor Gene

Another method of gene therapy according to the present invention involves operably associating the endogenous TR2 receptor sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., *Proc. Natl. Acad. Sci. USA* 86:8932-8935 (1989); and Zijlstra et al., *Nature* 342:435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous TR2 receptor, flanking the promoter. The targeting sequence will be sufficiently near the 5' end of TR2 receptor gene so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous TR2 receptor gene sequence. This results in the expression of TR2 receptors in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES, pH 7.3, 137 mM NaCl, 5 mM KCl, 0.7 mM Na2HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the TR2 receptor locus, plasmid pUC18 (MBI Fermentas, Amherst, N.Y.) is digested with HindIII. The CMV promoter is amplified by PCR with an XbaI site on the 5' end and a BamHI site on the 3' end. Two TR2 receptor gene non-coding sequences are amplified via PCR: one TR2 receptor gene non-coding sequence (TR2 gene fragment 1) is amplified with a HindIII site at the 5' end and an XbaI site at the 3' end; the other TR2 receptor gene non-coding sequence (TR2 gene fragment 2) is amplified with a BamHI site at the 5' end and a HindIII site at the 3' end. The CMV promoter and TR2 gene fragments are digested with the appropriate enzymes (CMV promoter—XbaI and BamHI; TR2 gene fragment 1—XbaI; TR2 gene fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 8

Assays to Detect Stimulation or Inhibition of B Cell Proliferation and Differentiation Background:

Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B-cell responsiveness including IL-2, IL-4, IL-5, IL-6, IL-7, IL-10, IL-13, IL-14 and IL15. Interestingly, these signals are by themselves weak effectors but can, in combination with various co-stimulatory proteins, induce activation, proliferation, differentiation, homing, tolerance and death among B cell populations. One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

Experimental Procedure:

In Vitro assay—Purified TR2 receptor protein, or truncated forms thereof, is assessed for its ability to induce (or inhibit) activation, proliferation, differentiation or inhibition and/or death in B-cell populations and their precursors. The activity of TR2 receptor protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220). Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 µg/ml streptomycin, and $10^{-5}$ dilution of SAC) in a total volume of 150 µl. Proliferation or inhibition is quantitated by a 20 h pulse (1 µCi/well) with 3H-thymidine (6.7 Ci/mM) beginning 72 h post factor addition. The positive and negative controls are IL-2 and medium respectively.

A soluble form of TR2 was prepared that consists of the extracellular domain of TR2 linked to the Fc portion of a human IgG1 immunoglobulin molecule. The ability of this protein to alter the proliferative response of human B cells was assessed in a standard co-stimulatory assay. Briefly, human tonsillar B cells were purified by magnetic bead (MACS) depletion of CD3-positive cells. The resulting cell population was routinely greater than 95% B cells as assessed by expression of CD19 and CD20 staining. Various dilutions of rHuNeutrokine-α (WO 98/18921) or the control protein rHuIL-2 were placed into individual wells of a 96-well plate to which was added $10^5$ B cells suspended in culture medium (RPMI 1640 containing 10% FBS, $5\times10^{-5}$M 2ME, 100 U/ml penicillin, 10 µg/ml streptomycin, and $10^{-5}$ dilution of formalin-fixed *Staphylococcus aureus* Cowan I (SAC) also known as Pansorbin (Pan)) in a total volume of 150 µl. TR2-Fc was then added at various concentrations. Plates were then placed in the incubator (37° C. 5% $CO_2$, 95% humidity) for three days. Proliferation was quantitated by a 20 h pulse (1 Ci/well) of $^3$H-thymidine (6.7 Ci/mM) beginning 72 h post factor addition. The positive and negative controls are IL-2 and medium respectively.

The results of three such experiments confirmed that TR2-Fc caused a dose-dependent inhibition of B cell proliferation in the co-stimulatory assays using *Staphylococcus Aureus* Cowan 1 (SAC) as priming agent and Neutrokine-α as a second signal. The inhibition observed in both experiments was greater than 50% at concentrations as low as 20 ng/mL of TR2-Fc. It is important to note that other Tumor Necrosis Factor Receptors (TNFR) fusion proteins (e.g., DR4-Fc (WO 98/32856), TR6-Fc (WO 98/31799), and TR9-Fc (WO 98/56892)) did not inhibit proliferation.

Figure 17:
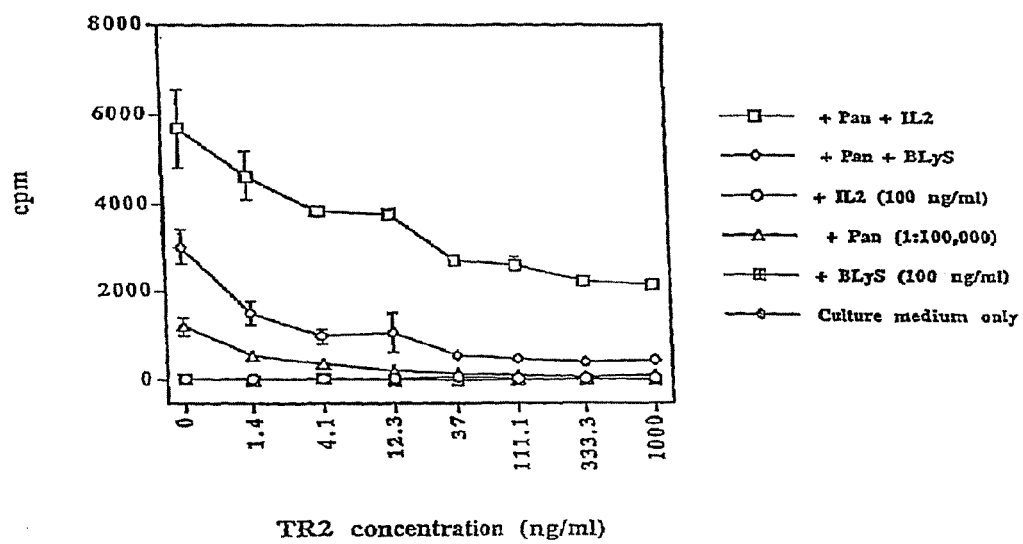
FIG. 17 shows the effect of TR2 on B cell in vitro proliferation. B lymphocytes were purified from human tonsils by immunomagnetic selection. Cells were cultured for 72 hours followed by a 24 hour $^3$H thymidine pulse in RPMI1640 medium added with 10% FBS, 4 mM 1-glutamine, $5\times10^{-5}$ M 2ME, 100 U/ml Penicillin, 100 µg/ml Streptomycin, and the indicated factors.

To determine if the inhibitory activity of TR2-Fc was specific for Neutrokine-α+SAC stimulated cells or whether it was a more general negative regulator of B cell proliferation, a similar experiment was performed in which tonsillar B cells were stimulated with IL-2+SAC. The results indicate that TR2-Fc also induced a dose-dependent inhibition of IL-2 driven B cell proliferation (See FIG. 17). Consistent with previous experiments, 50% inhibition was achieved with approximately 20 ng/mL of TR2-Fc. Accordingly, TR2-Fc appears to negatively regulate B cell proliferation independent of the stimulation of B cells with Neutrokine-α.

In Vivo assay—BALB/c mice are injected (i.p.) twice per day with buffer only, or 2 mg/Kg of TR2 receptor protein, or truncated forms thereof. Mice receive this treatment for 4 consecutive days, at which time they are sacrificed and various tissues and serum collected for analyses. Comparison of H&E sections from normal and TR2 receptor protein-treated spleens identify the results of the activity of TR2 receptor protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from TR2 receptor protein-treated mice is used to indicate whether TR2 receptor protein specifically increases the proportion of ThB+, CD45R (B220)dull B cells over that which is observed in control mice.

Likewise, a predicted consequence of increased mature B-cell representation in vivo is a relative increase in serum Ig titers. Accordingly, serum IgM and IgA levels are compared between buffer and TR2 receptor protein-treated mice.

Example 9

Isolation of Antibody Fragments Directed Against Polypeptides of the Present Invention from a Library of scFvs Naturally occurring V-genes isolated from human PBLs are constructed into a large library of antibody fragments which contain reactivities against polypeptides of the present invention to which the donor may or may not have been exposed (see, e.g., U.S. Pat. No. 5,885,793 incorporated herein in its entirety by reference).

Experimental Procedure:

Rescue of the library—A library of scFvs is constructed from the RNA of human PBLs as described in WO92/01047. To rescue phage displaying antibody fragments, approximately $10^9$ *E. coli* harbouring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, $2×10^8$ TU of delta gene 3 helper phage (M13 delta gene III, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 μg/ml ampicillin and 50 g/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harbouring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the library—Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately 1013 TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of binders—Eluted phage from the 3rd and 4th rounds of selection are used to infect *E. coli* HB 2151 and soluble scFv is produced (Marks et al., *J. Mol. Biol.* 222:581-597 (1991)) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., WO92/01047) and then by sequencing.

Example 10

Method of Determining Alterations in the TR2 Receptor Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60-120 seconds at 52-58° C.; and 60-120 seconds at 70° C., using buffer solutions described in Sidransky, D., et al., *Science* 252:706 (1991).

PCR products are then sequenced using primers labeled at their 5' end with T4 polynucleotide kinase, employing SequiTherm Polymerase. (Epicentre Technologies). The intron-exon borders of selected exons of TR2 receptor are also determined and genomic PCR products analyzed to confirm the results. PCR products harboring suspected mutations in TR2 receptor are then cloned and sequenced to validate the results of the direct sequencing.

PCR products of TR2 receptor are cloned into T-tailed vectors as described in Holton, T. A. and Graham, M. W., *Nucl. Acids Res.* 19: 1156 (1991) and sequenced with T7 polymerase (United States Biochemical). Affected individuals are identified by mutations in TR2 receptor not present in unaffected individuals.

Genomic rearrangements are also observed as a method of determining alterations in the TR2 receptor gene. Genomic clones isolated using techniques known in the art are nick-translated with digoxigenindeoxy-uridine 5'-triphosphate (Boehringer Manheim), and FISH performed as described in Johnson, C. et al., *Meth. Cell Biol.* 35:73-99 (1991). Hybridization with the labeled probe is carried out using a vast excess of human cot-1 DNA for specific hybridization to the TR2 receptor genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, C. et al., *Genet. Anal. Tech. Appl.* 8:75 (1991).) Image collection, analysis and chromosomal fractional length measurements are performed using the ISee Graphical Program System. (Inovision Corporation, Durham, N.C.) Chromosome alterations of the genomic region of TR2 receptor (hybridized by the probe) are identified as insertions, deletions, and translocations. These TR2 receptor alterations are used as a diagnostic marker for an associated disease.

Example 11

Method of Detecting Abnormal Levels of TR2 Receptor in a Biological Sample

TR2 polypeptides can be detected in a biological sample, and if an increased or decreased level of TR2 is detected, this polypeptide is a marker for a particular phenotype. Methods of detection are numerous, and thus, it is understood that one skilled in the art can modify the following assay to fit their particular needs.

For example, antibody-sandwich ELISAs are used to detect TR2 receptor in a sample, preferably a biological sample. Wells of a microtiter plate are coated with specific antibodies to TR2, at a final concentration of 0.2 to 10 µg/ml. The antibodies are either monoclonal or polyclonal and are produced using technique known in the art. The wells are blocked so that non-specific binding of TR2 receptor to the well is reduced.

The coated wells are then incubated for >2 hours at RT with a sample containing TR2 receptor. Preferably, serial dilutions of the sample should be used to validate results. The plates are then washed three times with deionized or distilled water to remove unbounded TR2 receptor.

Next, 50 µl of specific antibody-alkaline phosphatase conjugate, at a concentration of 25-400 ng, is added and incubated for 2 hours at room temperature. The plates are again washed three times with deionized or distilled water to remove unbounded conjugate.

75 µl of 4-methylumbelliferyl phosphate (MUP) or p-nitrophenyl phosphate (NPP) substrate solution is then added to each well and incubated 1 hour at room temperature to allow cleavage of the substrate and fluorescence. The fluorescence is measured by a microtiter plate reader. A standard curve is prepared using the experimental results from serial dilutions of a control sample with the sample concentration plotted on the X-axis (log scale) and fluorescence or absorbance on the Y-axis (linear scale). The TR2 receptor polypeptide concentration in a sample is then interpolated using the standard curve based on the measured fluorescence of that sample.

Example 12

Method of Treating Decreased Levels of TR2 Receptor

The present invention relates to a method for treating an individual in need of a decreased level of TR2 receptor biological activity in the body comprising, administering to such an individual a composition comprising a therapeutically effective amount of TR2 receptor antagonist. Preferred antagonists for use in the present invention are TR2 receptor-specific antibodies.

Moreover, it will be appreciated that conditions caused by a decrease in the standard or normal expression level of TR2 receptor in an individual can be treated by administering TR2 receptor, preferably in a soluble and/or secreted form. Thus, the invention also provides a method of treatment of an individual in need of an increased level of TR2 receptor polypeptide comprising administering to such an individual a pharmaceutical composition comprising an amount of TR2 receptor to increase the biological activity level of TR2 receptor in such an individual.

For example, a patient with decreased levels of TR2 receptor polypeptide receives a daily dose 0.1-100 µg/kg of the polypeptide for six consecutive days. Preferably, the polypeptide is in a soluble and/or secreted form.

Example 13

Method of Treating Increased Levels of TR2 Receptor

The present invention also relates to a method for treating an individual in need of an increased level of TR2 receptor biological activity in the body comprising administering to such an individual a composition comprising a therapeutically effective amount of TR2 receptor or an agonist thereof.

Antisense technology is used to inhibit production of TR2 receptor. This technology is one example of a method of decreasing levels of TR2 receptor polypeptide, preferably a soluble and/or secreted form, due to a variety of etiologies, such as cancer.

For example, a patient diagnosed with abnormally increased levels of TR2 receptor is administered intravenously antisense polynucleotides at 0.5, 1.0, 1.5, 2.0 and 3.0 mg/kg day for 21 days. This treatment is repeated after a 7-day rest period if the is determined to be well tolerated.

Example 14

Method of Treatment Using Gene Therapy-Ex Vivo

One method of gene therapy transplants fibroblasts, which are capable of expressing soluble and/or mature TR2 receptor polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA* 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding TR2 receptor can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanamycin for the purpose of confirming that the vector contains properly inserted TR2 receptor.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the TR2 receptor gene is then added to the media and the packaging cells transduced with the vector. The packaging cells now produce infectious viral particles containing the TR2 receptor gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether TR2 receptor protein is produced.

The engineered fibroblasts are then transplanted onto the host, either alone or after having been grown to confluence on cytodex 3 microcarrier beads.

Example 15

Method of Treatment Using Gene Therapy-In Vivo

Another aspect of the present invention is using in vivo gene therapy methods to treat disorders, diseases and conditions. The gene therapy method relates to the introduction of naked nucleic acid (DNA, RNA, and antisense DNA or RNA) TR2 receptor sequences into an animal to increase or decrease the expression of the TR2 receptor polypeptide. The TR2 receptor polynucleotide may be operatively linked to a promoter or any other genetic elements necessary for the expression of the TR2 receptor polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata, H. et al., *Cardiovasc. Res.* 35:470-479 (1997); Chao, J. et al., *Pharmacol. Res.* 35:517-522 (1997); Wolff, J. A. *Neuromuscul. Disord.* 7:314-318 (1997); Schwartz, B. et al., *Gene Ther.* 3:405-411 (1996); Tsurumi, Y. et al., *Circulation* 94:3281-3290 (1996) (incorporated herein by reference).

The TR2 receptor polynucleotide constructs may be delivered by any method that delivers injectable materials to the cells of an animal, such as, injection into the interstitial space of tissues (heart, muscle, skin, lung, liver, intestine and the like). The TR2 receptor polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the TR2 receptor polynucleotides may also be delivered in liposome formulations (such as those taught in Felgner, P. L. et al., *Ann. NY Acad. Sci.* 772:126-139 (1995) and Abdallah, B. et al., *Biol. Cell* 85:1-7 (1995)) which can be prepared by methods well known to those skilled in the art.

The TR2 receptor polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The TR2 receptor polynucleotide construct can be delivered to the interstitial space of tissues within an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked TR2 receptor polynucleotide injection, an effective dosage amount of DNA or RNA will be in the range of from about 0.05 µg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked TR2 receptor polynucleotide constructs can be delivered to arteries during angioplasty by the catheter used in the procedure.

The dose response effects of injected TR2 receptor polynucleotide in muscle in vivo are determined as follows. Suitable TR2 receptor template DNA for production of mRNA coding for TR2 receptor polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The TR2 receptor template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 µm cross-section of the individual quadriceps muscles is histochemically stained for TR2 receptor protein expression. A time course for TR2 receptor protein expression may be done in a similar fashion except that quadriceps from different mice are harvested at different times. Persistence of TR2 receptor DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using TR2 receptor naked DNA.

Example 16

Gene Therapy Using Endogenous TR2 Receptor Gene

Another method of gene therapy according to the present invention involves operably associating the endogenous TR2 receptor sequence with a promoter via homologous recombination as described, for example, in U.S. Pat. No. 5,641,670, issued Jun. 24, 1997; WO 96/29411, published Sep. 26, 1996; WO 94/12650, published Aug. 4, 1994; Koller et al., *Proc. Natl. Acad. Sci. USA* 86:8932-8935 (1989); and Zijlstra et al., *Nature* 342:435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous TR2 receptor, flanking the promoter. The targeting sequence will be sufficiently near the 5' end of TR2 receptor so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous TR2 receptor sequence. This results in the expression of TR2 receptor in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2 HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the TR2 receptor locus, plasmid pUC18 (MBI Fermentas, Amherst, N.Y.) is digested with HindIII. The CMV promoter is amplified by PCR with an XbaI site on the 5' end and a BamHI site on the 3' end. Two TR2 receptor non-coding sequences are amplified via PCR: one TR2 receptor non-coding sequence (TR2 receptor fragment 1) is amplified with a HindIII site at the 5 end and an XhaI site at the 3' end; the other TR2 receptor non-coding sequence (TR2 receptor fragment 2) is amplified with a BamHI site at the 5' end and a HindIII site at the 3' end. The CMV promoter and TR2 receptor fragments are digested with the appropriate enzymes (CMV promoter—XhaI and BamHI; TR2 receptor fragment 1—XhaI; TR2 receptor fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5.\times10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 17

Production of an Antibody Using Hybridoma Technology

The antibodies of the present invention can be prepared by a variety of methods. (See, Ausubel et al., eds., 1998, Current Protocols in Molecular Biology, John Wiley & Sons, NY, Chapter 2.) As one example of such methods, cells expressing TR2 are administered to an animal to induce the production of sera containing polyclonal antibodies. In a preferred method, a preparation of TR2 protein is prepared and purified to render it substantially free of natural contaminants. Such a preparation is then introduced into an animal in order to produce polyclonal antisera of greater specific activity.

Monoclonal antibodies specific for TR2 polypeptides are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563-681 (1981)). In general, an animal (preferably a mouse) is immunized with TR2 polypeptide or, more preferably, with a secreted TR2 polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC™. After fusion, the resulting hybridoma cells are selectively maintained in HAT medium, and then cloned by limiting dilution as described by Wands et al. (Gastroenterology 80:225-232 (1981). The hybridoma cells obtained through such a selection are then assayed to identify clones which secrete antibodies capable of binding the TR2 polypeptide.

Alternatively, additional antibodies capable of binding to TR2 polypeptides can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the TR2 protein-specific antibody can be blocked by TR2 polypeptides. Such antibodies comprise anti-idiotypic antibodies to the TR2 protein-specific antibody and are used to immunize an animal to induce formation of further TR2 protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed supra. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Bouliannne et al., Nature 312:643 (1984); Neuberger et al., Nature 314:268 (1985).)

Example 18

Expression Pattern of TNF Receptor Expression in Human Tissue

Northern blot analysis is carried out to examine the levels of expression of TNF receptor in human tissues. Total cellular RNA samples are isolated with RNAzol™ B system (Biotecx Laboratories, Inc., Houston, Tex.). About 10 µg of total RNA isolated from each human tissue specified is separated on 1% agarose gel and blotted onto a nylon filter (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column (5 Prime-3 Prime, Inc. Boulder, Colo.). The filter is then hybridized with radioactive labeled full length TNF receptor gene at 1,000,000 cpm/ml in 0.5 M NaPO$_4$, pH 7.4 and 7% SDS overnight at 65° C. After washing twice at room temperature and twice at 60° C. with 0.5×SSC, 0.1% SDS, the filter is then exposed at −70° C. overnight with an intensifying screen.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A method for inhibiting T-cell proliferation in an individual comprising administering to said individual a therapeutically effective amount of an antibody or fragment thereof which specifically binds to a polypeptide consisting of amino acids −38 to 162 of SEQ ID NO: 26, wherein said antibody or fragment thereof inhibits T-cell proliferation.

2. The method of claim 1, wherein said antibody or fragment thereof is administered in combination with a pharmaceutically acceptable carrier.

3. The method of claim 1, wherein said antibody or fragment thereof is administered in conjunction with a therapeutically effective amount of another therapeutic compound.

4. The method of claim 1, wherein said antibody or fragment thereof is a monoclonal antibody.

5. The method of claim 1, wherein said antibody or fragment thereof is selected from the group consisting of:
   (a) a polyclonal antibody;
   (b) a whole immunoglobulin;
   (c) a chimeric antibody;
   (d) a human antibody;
   (e) a humanized antibody;
   (f) a Fab fragment;
   (g) a Fab' fragment;
   (h) a F(ab')$_2$ fragment;
   (i) a Fv;

(j) a disulfide linked Fv; and
(k) a scFv fragment.

6. The method of claim 1, wherein said individual has a T-cell mediated autoimmune disease.

7. The method of claim 6, wherein said T-cell mediated autoimmune disease is selected from the group consisting of:
   (a) multiple sclerosis;
   (b) ulcerative colitis; and
   (c) rheumatoid arthritis.

8. The method of claim 1, wherein said antibody or fragment thereof is labeled.

9. The method of claim 8, wherein said label is selected from the group consisting of:
   (a) an enzyme;
   (b) a fluorescent label; and
   (c) a radioisotope.

10. A method for inhibiting T-cell proliferation in an individual comprising administering to said individual a therapeutically effective amount of an antibody or fragment thereof which specifically binds to a polypeptide consisting of amino acids 1 to 162 of SEQ ID NO: 26, wherein said antibody or fragment thereof inhibits T-cell proliferation.

11. The method of claim 10, wherein said antibody or fragment thereof is administered in combination with a pharmaceutically acceptable carrier.

12. The method of claim 10, wherein said antibody or fragment thereof is administered in conjunction with a therapeutically effective amount of another therapeutic compound.

13. The method of claim 10, wherein said antibody or fragment thereof is a monoclonal antibody.

14. The method of claim 10, wherein said antibody or fragment thereof is a polyclonal antibody.

15. The method of claim 10, wherein said antibody or fragment thereof is selected from the group consisting of:
   (a) a whole immunoglobulin;
   (b) a chimeric antibody;
   (c) a human antibody;
   (d) a humanized antibody;
   (e) a Fab fragment;
   (f) a Fab' fragment;
   (g) a F(ab')$_2$ fragment;
   (h) a Fv;
   (i) a disulfide linked Fv; and
   (j) a scFv fragment.

16. The method of claim 10, wherein said individual has a T-cell mediated autoimmune disease.

17. The method of claim 16, wherein said T-cell mediated autoimmune disease is selected from the group consisting of:
   (a) multiple sclerosis;
   (b) ulcerative colitis; and
   (c) rheumatoid arthritis.

18. The method of claim 10, wherein said antibody or fragment thereof is labeled.

19. The method of claim 18, wherein said label is selected from the group consisting of:
   (a) an enzyme;
   (b) a fluorescent label; and
   (c) a radioisotope.

\* \* \* \* \*

UNITED STATES PATENT AND TRADEMARK OFFICE
CERTIFICATE OF CORRECTION

PATENT NO. : 7,824,675 B2  Page 1 of 1
APPLICATION NO. : 12/241203
DATED : November 2, 2010
INVENTOR(S) : Ni et al.

It is certified that error appears in the above-identified patent and that said Letters Patent is hereby corrected as shown below:

On the Title Page:
At Item (60) Related U.S. Application Data, delete "provisional application No. 60/135,169, filed on May 19, 1999," and insert therefor --provisional application No. 60/135,169, filed on May 20, 1999,--.

Signed and Sealed this
First Day of February, 2011

David J. Kappos
*Director of the United States Patent and Trademark Office*

SEQUENCE LISTING

```
<160> NUMBER OF SEQ ID NOS: 26

<210> SEQ ID NO 1
<211> LENGTH: 1704
<212> TYPE: DNA
<213> ORGANISM: Homo sapiens
<220> FEATURE:
<221> NAME/KEY: CDS
<222> LOCATION: (265)..(1113)
<220> FEATURE:
<221> NAME/KEY: sig_peptide
<222> LOCATION: (265)..(372)
<220> FEATURE:
```

<221> NAME/KEY: mat_peptide
<222> LOCATION: (373)..(1113)

<400> SEQUENCE: 1

| | | |
|---|---|---|
| gcacgagctg cctcccgcag gcgccacctg tgtccccccag cgccgctcca cccagcaggc | | 60 |
| ctgagcccct ctctgctgcc agacaccccc tgctgcccac tctcctgctg ctcgggttct | | 120 |
| gaggcacagc ttgtcacacc gaggcggatt ctctttctct ttctcttct cttctggccc | | 180 |
| acagccgcag caatggcgct gagttcctct gctggagttc atcctgctag ctgggttccc | | 240 |
| gagctgccgg tctgagcctg aggc atg gag cct cct gga gac tgg ggg cct | | 291 |
|                                      Met Glu Pro Pro Gly Asp Trp Gly Pro | | |
|                                      -35                    -30 | | |
| cct ccc tgg aga tcc acc ccc aaa acc gac gtc ttg agg ctg gtg ctg | | 339 |
| Pro Pro Trp Arg Ser Thr Pro Lys Thr Asp Val Leu Arg Leu Val Leu | | |
|      -25                  -20                 -15 | | |
| tat ctc acc ttc ctg gga gcc ccc tgc tac gcc cca gct ctg ccg tcc | | 387 |
| Tyr Leu Thr Phe Leu Gly Ala Pro Cys Tyr Ala Pro Ala Leu Pro Ser | | |
|      -10                  -5                  -1   1                   5 | | |
| tgc aag gag gac gag tac cca gtg ggc tcc gag tgc tgc ccc aag tgc | | 435 |
| Cys Lys Glu Asp Glu Tyr Pro Val Gly Ser Glu Cys Cys Pro Lys Cys | | |
|                     10                    15                   20 | | |
| agt cca ggt tat cgt gtg aag gag gcc tgc ggg gag ctg acg ggc aca | | 483 |
| Ser Pro Gly Tyr Arg Val Lys Glu Ala Cys Gly Glu Leu Thr Gly Thr | | |
|                 25                    30                   35 | | |
| gtg tgt gaa ccc tgc cct cca ggc acc tac att gcc cac ctc aat ggc | | 531 |
| Val Cys Glu Pro Cys Pro Pro Gly Thr Tyr Ile Ala His Leu Asn Gly | | |
|   40                    45                   50 | | |
| cta agc aag tgt ctg cag tgc caa atg tgt gac cca gcc atg ggc ctg | | 579 |
| Leu Ser Lys Cys Leu Gln Cys Gln Met Cys Asp Pro Ala Met Gly Leu | | |
|     55                   60                   65 | | |
| cgc gcg agc cgg aac tgc tcc agg aca gag aac gcc gtg tgt ggc tgc | | 627 |
| Arg Ala Ser Arg Asn Cys Ser Arg Thr Glu Asn Ala Val Cys Gly Cys | | |
| 70                   75                   80                   85 | | |
| agc cca ggc cac ttc tgc atc gtc cag gac ggg gac cac tgc gcc gcg | | 675 |
| Ser Pro Gly His Phe Cys Ile Val Gln Asp Gly Asp His Cys Ala Ala | | |
|                     90                    95                   100 | | |
| tgc cgc gct tac gcc acc tcc agc ccg ggc cag agg gtg cag aag gga | | 723 |
| Cys Arg Ala Tyr Ala Thr Ser Ser Pro Gly Gln Arg Val Gln Lys Gly | | |
|                 105                   110                   115 | | |
| ggc acc gag agt cag gac acc ctg tgt cag aac tgc ccc ccg ggg acc | | 771 |
| Gly Thr Glu Ser Gln Asp Thr Leu Cys Gln Asn Cys Pro Pro Gly Thr | | |
|                 120                   125                   130 | | |
| ttc tct ccc aat ggg acc ctg gag gaa tgt cag cac cag acc aag tgc | | 819 |
| Phe Ser Pro Asn Gly Thr Leu Glu Glu Cys Gln His Gln Thr Lys Cys | | |
|     135                  140                   145 | | |
| agc tgg ctg gtg acg aag gcc gga gct ggg acc agc agc tcc cac tgg | | 867 |
| Ser Trp Leu Val Thr Lys Ala Gly Ala Gly Thr Ser Ser Ser His Trp | | |
| 150                  155                   160                   165 | | |
| gta tgg tgg ttt ctc tca ggg agc ctc gtc atc gtc att gtt tgc tcc | | 915 |
| Val Trp Trp Phe Leu Ser Gly Ser Leu Val Ile Val Ile Val Cys Ser | | |
|                    170                   175                   180 | | |
| aca gtt ggc cta atc ata tgt gtg aaa aga aga aag cca agg ggt gat | | 963 |
| Thr Val Gly Leu Ile Ile Cys Val Lys Arg Arg Lys Pro Arg Gly Asp | | |
|                 185                   190                   195 | | |
| gta gtc aag gtg atc gtc tcc gtc cag cgg aaa aga cag gag gca gaa | | 1011 |
| Val Val Lys Val Ile Val Ser Val Gln Arg Lys Arg Gln Glu Ala Glu | | |
|     200                  205                   210 | | |
| ggt gag gcc aca gtc att gag gcc ctg cag gcc cct ccg gac gtc acc | | 1059 |
| Gly Glu Ala Thr Val Ile Glu Ala Leu Gln Ala Pro Pro Asp Val Thr | | |

```
                     215                 220                 225
acg gtg gcc gtg gag gag aca ata ccc tca ttc acg ggg agg agc cca    1107
Thr Val Ala Val Glu Glu Thr Ile Pro Ser Phe Thr Gly Arg Ser Pro
230                 235                 240                 245 aac cac tgacccacag actctgcacc ccgacgccag agatacctgg agcgacggct     1163
Asn His gaatgaaaga ggctgtccac ctggcggaac caccggagcc cggaggcttg ggggctccac  1223
cctggactgg cttccgtctc ctccagtgga gggagaggtg gcgcccctgc tggggtagag  1283
ctggggacgc cacgtgccat tcccatgggc cagtgagggc ctggggcctc tgttctgctg  1343
tggcctgagc tccccagagt cctgaggagg agcgccagtt gcccctcgct cacagaccac  1403
acacccagcc ctcctgggcc aaccagagg gccttcagac cccagctgtg tgcgcgtctg   1463
actcttgtgg cctcagcagg acaggccccg ggcactgcct cacagccaag gctggactgg  1523
gttggctgca gtgtggtgtt tagtggatac cacatcggaa gtgattttct aaattggatt  1583
tgaattcggc tcctgttttc tatttgtcat gaaacagtgt atttggggag atgctgtggg  1643
aggatgtaaa tatcttgttt ctcctcaaaa aaaaaaaaa aaaaaaaaa aaaaaaaaa    1703 a                                                                  1704

<210> SEQ ID NO 2
<211> LENGTH: 283
<212> TYPE: PRT
<213> ORGANISM: Homo sapiens

<400> SEQUENCE: 2

Met Glu Pro Pro Gly Asp Trp Gly Pro Pro Trp Arg Ser Thr Pro
    -35                 -30                 -25

Lys Thr Asp Val Leu Arg Leu Val Leu Tyr Leu Thr Phe Leu Gly Ala
-20                 -15                 -10                 -5

Pro Cys Tyr Ala Pro Ala Leu Pro Ser Cys Lys Glu Asp Glu Tyr Pro
         -1  1                 5                      10

Val Gly Ser Glu Cys Cys Pro Lys Cys Ser Pro Gly Tyr Arg Val Lys
             15                  20                  25

Glu Ala Cys Gly Glu Leu Thr Gly Thr Val Cys Glu Pro Cys Pro Pro
         30                  35                  40

Gly Thr Tyr Ile Ala His Leu Asn Gly Leu Ser Lys Cys Leu Gln Cys
     45                  50                  55                  60

Gln Met Cys Asp Pro Ala Met Gly Leu Arg Ala Ser Arg Asn Cys Ser
                 65                  70                  75

Arg Thr Glu Asn Ala Val Cys Gly Cys Ser Pro Gly His Phe Cys Ile
             80                  85                  90

Val Gln Asp Gly Asp His Cys Ala Ala Cys Arg Ala Tyr Ala Thr Ser
         95                 100                 105

Ser Pro Gly Gln Arg Val Gln Lys Gly Gly Thr Glu Ser Gln Asp Thr
     110                 115                 120

Leu Cys Gln Asn Cys Pro Pro Gly Thr Phe Ser Pro Asn Gly Thr Leu
125                 130                 135                 140

Glu Glu Cys Gln His Gln Thr Lys Cys Ser Trp Leu Val Thr Lys Ala
                145                 150                 155

Gly Ala Gly Thr Ser Ser Ser His Trp Val Trp Phe Leu Ser Gly
            160                 165                 170

Ser Leu Val Ile Val Ile Val Cys Ser Thr Val Gly Leu Ile Ile Cys
    175                 180                 185
```

```
Val Lys Arg Arg Lys Pro Arg Gly Asp Val Val Lys Ile Val Ser
        190             195                 200

Val Gln Arg Lys Arg Gln Glu Ala Glu Gly Glu Ala Thr Val Ile Glu
205                 210                 215                 220

Ala Leu Gln Ala Pro Pro Asp Val Thr Thr Val Ala Val Glu Glu Thr
                225                 230                 235

Ile Pro Ser Phe Thr Gly Arg Ser Pro Asn His
            240                 245
```

<210> SEQ ID NO 3
<211> LENGTH: 281
<212> TYPE: PRT
<213> ORGANISM: Homo sapiens

<400> SEQUENCE: 3

```
Met Val Ser Leu Pro Arg Leu Cys Ala Leu Trp Gly Cys Leu Leu Thr
 1               5                  10                  15

Ala Val His Leu Gly Gln Cys Val Thr Cys Ser Asp Lys Gln Tyr Leu
                20                  25                  30

His Asp Gly Gln Cys Cys Asp Leu Cys Gln Pro Gly Ser Arg Leu Thr
            35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
            100                 105                 110

Ser Lys Asp Cys Glu Ala Cys Ala Gln His Thr Pro Cys Ile Pro Gly
        115                 120                 125

Phe Gly Val Met Glu Met Ala Thr Glu Thr Thr Asp Thr Val Cys His
130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
                165                 170                 175

Lys Gly Thr Ser Gln Thr Asn Val Ile Cys Gly Leu Lys Ser Arg Met
            180                 185                 190

Arg Ala Leu Leu Val Ile Pro Val Val Met Gly Ile Leu Ile Thr Ile
        195                 200                 205

Phe Gly Val Phe Leu Tyr Ile Lys Lys Val Val Lys Lys Pro Lys Asp
210                 215                 220

Asn Glu Met Leu Pro Pro Ala Ala Arg Arg Gln Asp Pro Gln Glu Met
225                 230                 235                 240

Glu Asp Tyr Pro Gly His Asn Thr Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln Val Thr Asp
        275                 280
```

<210> SEQ ID NO 4
<211> LENGTH: 2692
<212> TYPE: DNA
<213> ORGANISM: Homo sapiens

```
<220> FEATURE:
<221> NAME/KEY: CDS
<222> LOCATION: (373)..(927)
<220> FEATURE:
<221> NAME/KEY: sig_peptide
<222> LOCATION: (373)..(480)
<220> FEATURE:
<221> NAME/KEY: mat_peptide
<222> LOCATION: (481)..(927)

<400> SEQUENCE: 4
cccccttcta caggaaaccc ggagtggact ggaacggtgc aggggagaa  ctcgcccctc      60 ccatcgggcg cctccttcat accggccctt ccctcggct  ttgcctggac agctcctgcc    120
tcaggcagcg ccacctgtgt cgcccagcgc cgctccaccc agcaggcctg agcccctctc    180
tgctgccaga caccccctgc tgcccactac tcctgctgct cgggttctga ggcacagctt    240
gtcacaccga ggcggattct ctttctcttt ctctttctct tctggcccac agccgcagca    300
atggcgctga gttcctctgc tggagttcat cctgctagct gggttcccga gctgccggtc    360
tgagcctgag tc atg gag cct cct gga gac tgg ggg cct cct ccc tgg aga    411
              Met Glu Pro Pro Gly Asp Trp Gly Pro Pro Pro Trp Arg
              -35              -30              -25 tcc acc ccc aga acc gac gtc ttg agg ctg gtg ctg tat ctc acc ttc      459
Ser Thr Pro Arg Thr Asp Val Leu Arg Leu Val Leu Tyr Leu Thr Phe
        -20              -15              -10 ctg gga gcc ccc tgc tac gcc cca gct ctg ccg tcc tgc aag gag gac      507
Leu Gly Ala Pro Cys Tyr Ala Pro Ala Leu Pro Ser Cys Lys Glu Asp
    -5              -1  1                  5 gag tac cca gtg ggc tcc gag tgc tgc ccc aag tgc agt cca ggt tat      555
Glu Tyr Pro Val Gly Ser Glu Cys Cys Pro Lys Cys Ser Pro Gly Tyr
 10              15                  20                  25 cgt gtg aag gag gcc tgc ggg gag ctg acg ggc aca gtg tgt gaa ccc      603
Arg Val Lys Glu Ala Cys Gly Glu Leu Thr Gly Thr Val Cys Glu Pro
             30                  35                  40 tgc cct cca ggc acc tac att gcc cac ctc aat ggc cta agc aag tgt      651
Cys Pro Pro Gly Thr Tyr Ile Ala His Leu Asn Gly Leu Ser Lys Cys
                 45                  50                  55 ctg cag tgc caa atg tgt gac cca gat att ggt tcc ccc tgt gac ctc      699
Leu Gln Cys Gln Met Cys Asp Pro Asp Ile Gly Ser Pro Cys Asp Leu
             60                  65                  70 agg gga aga ggt cac ctg gag gct ggt gcc cac ctg agt cca ggc aga      747
Arg Gly Arg Gly His Leu Glu Ala Gly Ala His Leu Ser Pro Gly Arg
 75                  80                  85 cag aaa ggg gaa cca gac cca gag gtg gcc ttt gag tca ctg agc gca      795
Gln Lys Gly Glu Pro Asp Pro Glu Val Ala Phe Glu Ser Leu Ser Ala
 90                  95                  100                 105 gag cct gtc cat gcg gcc aac ggc tct gtc ccc ttg gag cct cat gcc      843
Glu Pro Val His Ala Ala Asn Gly Ser Val Pro Leu Glu Pro His Ala
                 110                 115                 120 agg ctc agc atg gcc agt gct ccc tgc ggc cag gca gga ctg cac ctg      891
Arg Leu Ser Met Ala Ser Ala Pro Cys Gly Gln Ala Gly Leu His Leu
             125                 130                 135 cgg gac agg gct gac ggc aca cct ggg ggc agg gcc tgagcctaca           937
Arg Asp Arg Ala Asp Gly Thr Pro Gly Gly Arg Ala
             140                 145 gggaggcaca gggcaggtgg gctagccatg aacagaagag gaagctggag tgctttgggg    997
gttcatgcat gtaggctggg atttggggct cacacctcaa cctgcatgcc cagttccatg   1057
cccctcccct cttgtgaaag cacctgtcta cttgggctga ggatgtgggg gcacaggtgg   1117
caggtgaggc tgccctcagg aggggcccag gcccagcttg taccccacct ccaccagtac   1177
```

```
ctgaagaagt ggggctctca ccctacctgc ctctgccatt ggaatggcct ggtttgcaca    1237
gatgggaaac ccgtttgagg ggtgggtgtc tgggtgggca cgtggggcga ggacctgcct    1297
gagggaccct gccctggaac tgacagtgca agctcggcgt cctgcccatc tgggcagaag    1357
gctggtttct cccatcaacg aagccctccc aggaccttcc tgcaagccct cgtcccacac    1417
gcagctctgc cgtcccttgg tgtccctccc ggcctcaggt cctccatgct gggtacctct    1477
gggcacctcg tttggctgag ccaggggttc agcctggcag ggcgccctgg cagcagtcct    1537
tggcctgtgg atgctgtcct ggcctgtgga tggtgtcccg ccctccacgt accccctctca   1597 cccccctcctc ttggactcca gccatgggcc tgcgcgcgag ccggaactgc tccaggacag    1657
agaacgccgt gtgtggctgc agcccaggcc acttctgcat cgtccaggac ggggaccact    1717
gcgccgcgtg ccgcgcttac gccacctcca gcccgggcca gagggtgcag aagggaggca    1777
ccgagagtca ggacaccctg tgtcagaact gcccccgggg gaccttctct cccaatggga    1837
ccctggagga atgtcagcac cagaccaatt ggcctaatca tatgtgtgaa agaagaaag     1897 ccaaggggtg agcacacggt ggccccatca gggttcatgt cccagccgt cacctcttgg     1957 agctctgtca ccccaagcct gggaggtggc cccagagctt ttccaggatc cgcggctcct    2017
cccagggcag ccactgcagg ctggggcagg tgtatgtagt caaggtgatc gtctccgtcc    2077
agcggtaaaa gacaggaggc agaaggtgag gccacagtca ttgagccctg caggcccctc    2137
cggacgtcac cacggtggcc gtggaggaga caatacccctc attcacgggg aggagcccaa    2197
accactgacc cacagactct gcaccccgac gccagagata cctggagaga cggctgctga    2257
tagaggctgt ccacctggcg aaaccaccgg agcccggagg cttgggggct ccgccctggg    2317
ctggtttccg tctcctccag tggagggaga ggtggtgccc ctgctggtgg tagagctggg    2377
gacgccacgt gccattccca tggttcagtg aggggctggt ggcctctgtt ctgctgtggc    2437
ctgagctccc cagagtcctg aggaggagcc ccagttgccc ctcgctcaca gaccacacac    2497
ccagccctcc tgggccaacc cagaggcccc ttcagacccc agctgtctgc gcgtctgact    2557
cttgtggcct cagcaggaca gggccccggg actgcctcac agccaaggct ggaatgggtt    2617
ggctgcagtg tggtgtttag tggataccac atcggaagtg attttctaaa aattggattt    2677
gaattcggaa aaaaa                                                     2692
```

<210> SEQ ID NO 5  
<211> LENGTH: 185  
<212> TYPE: PRT  
<213> ORGANISM: Homo sapiens

<400> SEQUENCE: 5

```
Met Glu Pro Pro Gly Asp Trp Gly Pro Pro Trp Arg Ser Thr Pro
    -35             -30              -25

Arg Thr Asp Val Leu Arg Leu Val Leu Tyr Leu Thr Phe Leu Gly Ala
-20              -15              -10                  -5

Pro Cys Tyr Ala Pro Ala Leu Pro Ser Cys Lys Glu Asp Glu Tyr Pro
        -1  1              5                   10

Val Gly Ser Glu Cys Cys Pro Lys Cys Ser Pro Gly Tyr Arg Val Lys
            15              20              25

Glu Ala Cys Gly Glu Leu Thr Gly Thr Val Cys Glu Pro Cys Pro Pro
        30              35              40

Gly Thr Tyr Ile Ala His Leu Asn Gly Leu Ser Lys Cys Leu Gln Cys
    45              50              55              60
```

```
Gln Met Cys Asp Pro Asp Ile Gly Ser Pro Cys Asp Leu Arg Gly Arg
             65                  70                  75

Gly His Leu Glu Ala Gly Ala His Leu Ser Pro Gly Arg Gln Lys Gly
             80                  85                  90

Glu Pro Asp Pro Glu Val Ala Phe Glu Ser Leu Ser Ala Glu Pro Val
             95                 100                 105

His Ala Ala Asn Gly Ser Val Pro Leu Glu Pro His Ala Arg Leu Ser
            110                 115                 120

Met Ala Ser Ala Pro Cys Gly Gln Ala Gly Leu His Leu Arg Asp Arg
125                 130                 135                 140

Ala Asp Gly Thr Pro Gly Gly Arg Ala
                145

<210> SEQ ID NO 6
<211> LENGTH: 248
<212> TYPE: PRT
<213> ORGANISM: Homo sapiens

<400> SEQUENCE: 6

Met Ala Pro Val Ala Val Trp Ala Ala Leu Ala Val Gly Leu Glu Leu
  1               5                  10                  15

Trp Ala Ala Ala His Ala Leu Pro Ala Gln Val Ala Phe Thr Pro Tyr
             20                  25                  30

Ala Pro Glu Pro Gly Ser Thr Cys Arg Leu Arg Glu Tyr Tyr Asp Gln
             35                  40                  45

Thr Ala Gln Met Cys Cys Ser Lys Cys Ser Pro Gly Gln His Ala Lys
         50                  55                  60

Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro Glu Cys Leu Ser Cys
             85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
        130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser
                245

<210> SEQ ID NO 7
<211> LENGTH: 2637
<212> TYPE: DNA
<213> ORGANISM: Homo sapiens
```

```
<220> FEATURE:
<221> NAME/KEY: CDS
<222> LOCATION: (247)..(654)

<400> SEQUENCE: 7
aaagctcggg ctccaccggg gacgaccgct cctagaaact gagtggtatc ccccgggcct      60
gcaggaattc caacctgcct gaagggaccc tgccctggaa ctgacagtgc aagctcggcg     120
tcctgcccat ctgggaagaa ggctggtttc tccatcaac gaagccctcc caggaccttc      180
ctgcaagccc tcgtcccaca cgcagctctg ccgtcccttg gtgtccctcc cggcctcagg     240 tcctcc atg ctg ggt acc tct ggg cac ctc gtt tgg ctg agc cag ggg        288
       Met Leu Gly Thr Ser Gly His Leu Val Trp Leu Ser Gln Gly
        1               5                  10 ttc agc ctg gca ggg cgc cct ggc agc agt cct tgg cct gtg gat gct       336
Phe Ser Leu Ala Gly Arg Pro Gly Ser Ser Pro Trp Pro Val Asp Ala
 15                  20                  25                  30 gtc ctg gcc tgt gga tgg tgt ccc ggc ctc cac gta ccc cct ctc agc       384
Val Leu Ala Cys Gly Trp Cys Pro Gly Leu His Val Pro Pro Leu Ser
                 35                  40                  45 ccc tcc tct tgg act cca gcc atg ggc ctg cgc gcg agc cgg aac tgc       432
Pro Ser Ser Trp Thr Pro Ala Met Gly Leu Arg Ala Ser Arg Asn Cys
             50                  55                  60 tcc agg aca gag aac gcc gtg tgt ggc tgc agc cca ggc cac ttc tgc       480
Ser Arg Thr Glu Asn Ala Val Cys Gly Cys Ser Pro Gly His Phe Cys
 65                  70                  75 atc gtc cag gac ggg gac cac tgc gcc gcg tgc cgc gct tac gcc acc       528
Ile Val Gln Asp Gly Asp His Cys Ala Ala Cys Arg Ala Tyr Ala Thr
             80                  85                  90 tcc agc ccg ggc cag agg gtg cag aag gga ggc acc gag agt cag gac       576
Ser Ser Pro Gly Gln Arg Val Gln Lys Gly Gly Thr Glu Ser Gln Asp
             95                 100                 105             110 acc ctg tgt cag aac tgc ccc cgg gga cct tct ctc cca atg gga ccc       624
Thr Leu Cys Gln Asn Cys Pro Arg Gly Pro Ser Leu Pro Met Gly Pro
                115                 120                 125 tgg agg aat gtc agc acc aga cca agt aag tgaacccggg ggaggccagc         674
Trp Arg Asn Val Ser Thr Arg Pro Ser Lys
                130                 135 tctgtgccct ggggagggggg ctccacgttg cttccctggg agatgaccgt cttctccagc    734
agaaaggttg aaggtcccac cctgagcggc accctggtca catgcctgcg tccaggagag    794
ctgcagggtg aagcctgtgt gccccagata ccccttcca tgggcccaga caaagcctca     854
tcagatctga gcttcctgga ggctcaggat gggccttccc agaagcaggc ccagagggag    914
gctgcctcca gatcccctgt ccctgggggc tgtgggtgtc cctgaatgtc agggccatgg    974 gagggccccct gggcttcagg ggttgggaa agtgaacact ctgctctttg tccaccttcg    1034
ggaggacaac cttcaaatgc tgaccctggg ccctaactg acctgagact tcagagcttc    1094
ttgggaggag ctggggtccc ccagcggagc ctggatgga gcaggatgg ctgccccagg     1154 gagggggcgg tggggccttc catcctgctc tgccctcctc gtcctctggc cccagctcag   1214
tcctgtccat ctccagctct aaccatttgt ggccgacac tggctctccc tctaccttct    1274
gtccttgtct gacactggtc tcccgtgctc tggggtctct gcactgatgg ctgcctcccg    1334
cttctctccc ctctccctct gccgtcctgt tcctgtggc cagtctctcc ttgtttctct    1394
tctcctcctt ccttctctcc acctccccat agccgagctt ggaaaagtca gacagacctc    1454
tgaggtctca tcctggagct gccaccagcc cagcctccct gggacctgtc ttcactgcct    1514
ggggccctgg gagccaggga ggctccctga ggctgagtga acactgggcg ctgcacctgc    1574
```

-continued

```
ctctcccacg tcctcggccc cactcccgca ggtgcagctg gctggtgacg aagcccggag      1634
ctgggaccag cagctcccac tgggtatggt ggtttctctc agggagcctc gtcatcgtca      1694
ttgtttgctc cacagttggc ctaatcatat gtgtgaaaag aagaaagcca aggggtgatg      1754
tagtcaaggt gatcgtctcc gtccaggtat tgatcctcct ccccctctcc ctcccccctc      1814
caccttccca cctcccctct ccccgctggg gctggtgttt ctggtgtaca tggtgggggc      1874
tcccagttct ctgagggtcc tgagtctttc aagtacagcc acggtagctc aggaaagaac      1934
ccaccccctc aaactgaaag cagtaaaatg aacccgagaa cctggagtcc cagggggggcc     1994 tgagcaggca gggtctccac gattcgtgtg ctcacagcgg gaaaagacag gaggcagaag      2054
gtgaggccac agtcattgag gccctgcagg ccctccgga cgtcaccacg gtggccgtgg       2114
aggagacaat accctcattc acgggggagg agcccaaacc actgacccac agactctgca     2174
ccccgacgcc agagatacct ggagcgacgg ctgctgaaag aggctgtcca cctggcgaaa     2234
ccaccggagc ccggaggttt gggggctccg ccctgggctg gtttccgtct cctccagtgg     2294
agggagaggt ggggcccctg ctggggtaga gctgggacg ccacgtgcca ttcccatggg      2354
ccagtgaggg cctggggcct ctgttctgct gtggcctgag ctccccagag tcctgaggag     2414
gagcgccagt tgcccctcgc tcacagacca cacaccagc cctcctgggt ccagcccaga     2474 gggccccttca gaccccagct gtctgcgcgt ctgactcttg tggcctcagc aggacaggcc   2534
ccgggcactg ccttcaagcc aaggctggac tgggttggct gcagtgtggt gtttagtgga     2594
taccacatcg gaagtgattt tctaaattgg atttgaaaaa aaa                      2637
```

<210> SEQ ID NO 8
<211> LENGTH: 136
<212> TYPE: PRT
<213> ORGANISM: Homo sapiens

<400> SEQUENCE: 8

```
Met Leu Gly Thr Ser Gly His Leu Val Trp Leu Ser Gln Gly Phe Ser
  1               5                  10                  15

Leu Ala Gly Arg Pro Gly Ser Ser Pro Trp Pro Val Asp Ala Val Leu
             20                  25                  30

Ala Cys Gly Trp Cys Pro Gly Leu His Val Pro Pro Leu Ser Pro Ser
         35                  40                  45

Ser Trp Thr Pro Ala Met Gly Leu Arg Ala Ser Arg Asn Cys Ser Arg
     50                  55                  60

Thr Glu Asn Ala Val Cys Gly Cys Ser Pro Gly His Phe Cys Ile Val
 65                  70                  75                  80

Gln Asp Gly Asp His Cys Ala Ala Cys Arg Ala Tyr Ala Thr Ser Ser
                 85                  90                  95

Pro Gly Gln Arg Val Gln Lys Gly Gly Thr Glu Ser Gln Asp Thr Leu
            100                 105                 110

Cys Gln Asn Cys Pro Arg Gly Pro Ser Leu Pro Met Gly Pro Trp Arg
        115                 120                 125

Asn Val Ser Thr Arg Pro Ser Lys
    130                 135
```

<210> SEQ ID NO 9
<211> LENGTH: 198
<212> TYPE: PRT
<213> ORGANISM: Homo sapiens

<400> SEQUENCE: 9

```
Met Ala Pro Val Ala Val Trp Ala Ala Leu Ala Val Gly Leu Glu Leu
 1               5                   10                  15

Trp Ala Ala Ala His Ala Leu Pro Ala Gln Val Ala Phe Thr Pro Tyr
             20                  25                  30

Ala Pro Glu Pro Gly Ser Thr Cys Arg Leu Arg Glu Tyr Tyr Asp Gln
         35                  40                  45

Thr Ala Gln Met Cys Cys Ser Lys Cys Ser Pro Gly Gln His Ala Lys
     50                  55                  60

Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro Glu Cys Leu Ser Cys
             85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala
            195

<210> SEQ ID NO 10
<211> LENGTH: 154
<212> TYPE: PRT
<213> ORGANISM: Homo sapiens

<400> SEQUENCE: 10

Val Cys Pro Gln Gly Lys Tyr Ile His Pro Gln Asn Asn Ser Ile Cys
 1               5                   10                  15

Cys Thr Lys Cys His Lys Gly Thr Tyr Leu Tyr Asn Asp Cys Pro Gly
             20                  25                  30

Pro Gly Gln Asp Thr Asp Cys Arg Glu Cys Glu Ser Gly Ser Phe Thr
         35                  40                  45

Ala Ser Glu Asn His Leu Arg His Cys Leu Ser Cys Ser Lys Cys Arg
     50                  55                  60

Lys Glu Met Gly Gln Val Glu Ile Ser Ser Cys Thr Val Asp Arg Asp
 65                  70                  75                  80

Thr Val Cys Gly Cys Arg Lys Asn Gln Tyr Arg His Tyr Trp Ser Glu
             85                  90                  95

Asn Leu Phe Gln Cys Phe Asn Cys Ser Leu Cys Leu Asn Gly Thr Val
            100                 105                 110

His Leu Ser Cys Gln Glu Lys Gln Asn Thr Val Cys Thr Cys His Ala
            115                 120                 125

Gly Phe Phe Leu Arg Glu Asn Glu Cys Val Ser Cys Ser Asn Cys Lys
    130                 135                 140

Lys Ser Leu Glu Cys Thr Lys Leu Cys Leu
145                 150
```

```
<210> SEQ ID NO 11
<211> LENGTH: 163
<212> TYPE: PRT
<213> ORGANISM: Homo sapiens

<400> SEQUENCE: 11

Thr Cys Arg Leu Arg Glu Tyr Tyr Asp Gln Thr Ala Gln Met Cys Cys
1               5                   10                  15

Ser Lys Cys Ser Pro Gly Gln His Ala Lys Val Phe Cys Thr Lys Thr
            20                  25                  30

Ser Asp Thr Val Cys Asp Ser Cys Glu Asp Ser Thr Tyr Thr Gln Leu
        35                  40                  45

Trp Asn Trp Val Pro Glu Cys Leu Ser Cys Gly Ser Arg Cys Ser Ser
    50                  55                  60

Asp Gln Val Glu Thr Gln Ala Cys Thr Arg Glu Gln Asn Arg Ile Cys
65                  70                  75                  80

Thr Cys Arg Pro Gly Trp Tyr Cys Ala Leu Ser Lys Gln Glu Gly Cys
                85                  90                  95

Arg Leu Cys Ala Pro Leu Arg Lys Cys Arg Pro Gly Phe Gly Val Ala
            100                 105                 110

Arg Pro Gly Thr Glu Thr Ser Asp Val Val Cys Lys Pro Cys Ala Pro
        115                 120                 125

Gly Thr Phe Ser Asn Thr Thr Ser Ser Thr Asp Ile Cys Arg Pro His
    130                 135                 140

Gln Ile Cys Asn Val Val Ala Ile Pro Gly Asn Ala Ser Met Asp Ala
145                 150                 155                 160

Val Cys Thr

<210> SEQ ID NO 12
<211> LENGTH: 163
<212> TYPE: PRT
<213> ORGANISM: Homo sapiens

<400> SEQUENCE: 12

Ala Cys Arg Glu Lys Gln Tyr Leu Ile Asn Ser Gln Cys Cys Ser Leu
1               5                   10                  15

Cys Gln Pro Gly Gln Lys Leu Val Ser Asp Cys Thr Glu Pro Thr Glu
            20                  25                  30

Thr Glu Cys Leu Pro Cys Gly Glu Ser Glu Phe Leu Asp Thr Trp Asn
        35                  40                  45

Arg Glu Thr His Cys His Gln His Lys Tyr Cys Asp Pro Asn Leu Gly
    50                  55                  60

Leu Arg Val Gln Gln Lys Gly Thr Ser Glu Thr Asp Thr Ile Cys Thr
65                  70                  75                  80

Cys Glu Glu Gly Trp His Cys Thr Ser Glu Ala Cys Glu Ser Cys Val
                85                  90                  95

Leu His Arg Ser Cys Ser Pro Gly Phe Gly Val Lys Gln Ile Ala Thr
            100                 105                 110

Gly Val Ser Asp Thr Ile Cys Glu Pro Cys Pro Val Gly Phe Phe Ser
        115                 120                 125

Asn Val Ser Ser Ala Phe Glu Lys Cys His Pro Trp Thr Ser Cys Glu
    130                 135                 140

Thr Lys Asp Leu Val Val Gln Gln Ala Gly Thr Asn Lys Thr Asp Val
145                 150                 155                 160

Val Cys Gly
```

```
<210> SEQ ID NO 13
<211> LENGTH: 132
<212> TYPE: PRT
<213> ORGANISM: Homo sapiens

<400> SEQUENCE: 13

Cys Ser Asn Cys Pro Ala Gly Thr Phe Cys Asp Asn Asn Arg Asn Gln
 1               5                  10                  15

Ile Cys Ser Pro Cys Pro Pro Asn Ser Phe Ser Ser Ala Gly Gly Gln
            20                  25                  30

Arg Thr Cys Asp Ile Cys Arg Gln Cys Lys Gly Val Phe Arg Thr Arg
        35                  40                  45

Lys Glu Cys Ser Ser Thr Ser Asn Ala Glu Cys Asp Cys Thr Pro Gly
    50                  55                  60

Phe His Cys Leu Gly Ala Gly Cys Ser Met Cys Glu Gln Asp Cys Lys
65                  70                  75                  80

Gln Gly Gln Glu Leu Thr Lys Lys Gly Cys Lys Asp Cys Cys Phe Gly
                85                  90                  95

Thr Phe Asn Lys Gln Lys Arg Gly Ile Cys Arg Pro Trp Thr Asn Cys
            100                 105                 110

Ser Leu Asp Gly Lys Ser Val Leu Val Asn Gly Thr Lys Glu Arg Asp
        115                 120                 125

Val Val Cys Gly
    130

<210> SEQ ID NO 14
<211> LENGTH: 27
<212> TYPE: DNA
<213> ORGANISM: Homo sapiens

<400> SEQUENCE: 14
cgcccatggc cccagctctg ccgtcct                                          27

<210> SEQ ID NO 15
<211> LENGTH: 30
<212> TYPE: DNA
<213> ORGANISM: Homo sapiens

<400> SEQUENCE: 15
cgcaagctta ttgtgggagc tgctggtccc                                       30

<210> SEQ ID NO 16
<211> LENGTH: 25
<212> TYPE: DNA
<213> ORGANISM: Homo sapiens

<400> SEQUENCE: 16
cgcggatccc ggagccccct gctac                                            25

<210> SEQ ID NO 17
<211> LENGTH: 30
<212> TYPE: DNA
<213> ORGANISM: Homo sapiens

<400> SEQUENCE: 17
cgcggtacca ttgtgggagc tgctggtccc                                       30

<210> SEQ ID NO 18
<211> LENGTH: 34
<212> TYPE: DNA
```

-continued

<213> ORGANISM: Homo sapiens

<400> SEQUENCE: 18
gcgcggatcc accatggagc ctcctggaga ctgg    34

<210> SEQ ID NO 19
<211> LENGTH: 31
<212> TYPE: DNA
<213> ORGANISM: Homo sapiens

<400> SEQUENCE: 19
gcgcggtacc tctaccccag caggggcgcc a    31

<210> SEQ ID NO 20
<211> LENGTH: 34
<212> TYPE: DNA
<213> ORGANISM: Homo sapiens

<400> SEQUENCE: 20
gcgcggatcc accatggagc ctcctggaga ctgg    34

<210> SEQ ID NO 21
<211> LENGTH: 58
<212> TYPE: DNA
<213> ORGANISM: Homo sapiens

<400> SEQUENCE: 21
gcgctctaga tcaagcgtag tctgggacgt cgtatgggta gtggtttggg ctcctccc    58

<210> SEQ ID NO 22
<211> LENGTH: 34
<212> TYPE: DNA
<213> ORGANISM: Homo sapiens

<400> SEQUENCE: 22
gcgcggatcc accatggagc ctcctggaga ctgg    34

<210> SEQ ID NO 23
<211> LENGTH: 35
<212> TYPE: DNA
<213> ORGANISM: Homo sapiens

<400> SEQUENCE: 23
caggaattcg cagccatgga gcctcctgga gactg    35

<210> SEQ ID NO 24
<211> LENGTH: 53
<212> TYPE: DNA
<213> ORGANISM: Homo sapiens

<400> SEQUENCE: 24
ccatacccag gtaccccttc cctcgataga tcttgccttc gtcaccagcc agc    53

<210> SEQ ID NO 25
<211> LENGTH: 881
<212> TYPE: DNA
<213> ORGANISM: Homo sapiens
<220> FEATURE:
<221> NAME/KEY: CDS
<222> LOCATION: (9)..(857)
<220> FEATURE:
<221> NAME/KEY: sig_peptide
<222> LOCATION: (9)..(122)
<220> FEATURE:
<221> NAME/KEY: mat_peptide -continued

<222> LOCATION: (123)..(857)

<400> SEQUENCE: 25

```
cctgaggc atg gag cct cct gga gac tgg ggg cct cct ccc tgg aga tcc            50
         Met Glu Pro Pro Gly Asp Trp Gly Pro Pro Pro Trp Arg Ser
             -35             -30                 -25 acc ccc aga acc gac gtc ttg agg ctg gtg ctg tat ctc acc ttc ctg             98
Thr Pro Arg Thr Asp Val Leu Arg Leu Val Leu Tyr Leu Thr Phe Leu
            -20             -15                 -10 gga gcc ccc tgc tac gcc cca gct ctg ccg tcc tgc aag gag gac gag            146
Gly Ala Pro Cys Tyr Ala Pro Ala Leu Pro Ser Cys Lys Glu Asp Glu
        -5               -1   1                  5 tac cca gtg ggc tcc gag tgc tgc ccc aag tgc agt cca ggt tat cgt            194
Tyr Pro Val Gly Ser Glu Cys Cys Pro Lys Cys Ser Pro Gly Tyr Arg
     10              15                  20 gtg aag gag gcc tgc ggg gag ctg acg ggc aca gtg tgt gaa ccc tgc            242
Val Lys Glu Ala Cys Gly Glu Leu Thr Gly Thr Val Cys Glu Pro Cys
25              30                  35                  40 cct cca ggc acc tac att gcc cac ctc aat ggc cta agc aag tgt ctg            290
Pro Pro Gly Thr Tyr Ile Ala His Leu Asn Gly Leu Ser Lys Cys Leu
                45                  50                  55 cag tgc caa atg tgt gac cca gcc atg ggc ctg cgc gcg agc cgg aac            338
Gln Cys Gln Met Cys Asp Pro Ala Met Gly Leu Arg Ala Ser Arg Asn
            60                  65                  70 tgc tcc agg aca gag aac gcc gtg tgt ggt tgc agc cca ggc cac ttc            386
Cys Ser Arg Thr Glu Asn Ala Val Cys Gly Cys Ser Pro Gly His Phe
        75                  80                  85 tgc atc gtc cag gac ggg gac cac tgc gcc gcg tgc cgc gct tac gcc            434
Cys Ile Val Gln Asp Gly Asp His Cys Ala Ala Cys Arg Ala Tyr Ala
    90                  95                  100 acc tcc agc ccg ggc cag agg gtg cag aag gga ggc acc gag agt cag            482
Thr Ser Ser Pro Gly Gln Arg Val Gln Lys Gly Gly Thr Glu Ser Gln
105                 110                 115                 120 gac acc ctg tgt cag aac tgc ccc ccg ggg acc ttc tct ccc aat ggg            530
Asp Thr Leu Cys Gln Asn Cys Pro Pro Gly Thr Phe Ser Pro Asn Gly
                125                 130                 135 acc ctg gag gaa tgt cag cac cag acc aag tgc agc tgg ctg gtg acg            578
Thr Leu Glu Glu Cys Gln His Gln Thr Lys Cys Ser Trp Leu Val Thr
            140                 145                 150 aag gcc gga gct ggg acc agc agc tcc cac tgg gta tgg tgg ttt ctc            626
Lys Ala Gly Ala Gly Thr Ser Ser Ser His Trp Val Trp Trp Phe Leu
        155                 160                 165 tca ggg agc ctc gtc atc gtc att gtt tgc tcc aca gtt ggc cta atc            674
Ser Gly Ser Leu Val Ile Val Ile Val Cys Ser Thr Val Gly Leu Ile
    170                 175                 180 ata tgt gtg aaa aga aga aag cca agg ggt gat gta gtc aag gtg atc            722
Ile Cys Val Lys Arg Arg Lys Pro Arg Gly Asp Val Val Lys Val Ile
185                 190                 195                 200 gtc tcc gtc cag cgg aaa aga cag gag gca gaa ggt gag gcc aca gtc            770
Val Ser Val Gln Arg Lys Arg Gln Glu Ala Glu Gly Glu Ala Thr Val
                205                 210                 215 att gag gcc ctg cag gcc cct ccg gac gtc acc acg gtg gcc gtg gag            818
Ile Glu Ala Leu Gln Ala Pro Pro Asp Val Thr Thr Val Ala Val Glu
            220                 225                 230 gag aca ata ccc tca ttc acg ggg agg agc cca aac cac tgacccacag             867
Glu Thr Ile Pro Ser Phe Thr Gly Arg Ser Pro Asn His
        235                 240                 245 actctgcacc ccga                                                            881
```

-continued

```
<210> SEQ ID NO 26
<211> LENGTH: 283
<212> TYPE: PRT
<213> ORGANISM: Homo sapiens

<400> SEQUENCE: 26

Met Glu Pro Pro Gly Asp Trp Gly Pro Pro Trp Arg Ser Thr Pro
            -35                 -30                 -25

Arg Thr Asp Val Leu Arg Leu Val Leu Tyr Leu Thr Phe Leu Gly Ala
            -20                 -15                 -10

Pro Cys Tyr Ala Pro Ala Leu Pro Ser Cys Lys Glu Asp Glu Tyr Pro
        -5                  -1   1                   5                      10

Val Gly Ser Glu Cys Cys Pro Lys Cys Ser Pro Gly Tyr Arg Val Lys
                    15                  20                  25

Glu Ala Cys Gly Glu Leu Thr Gly Thr Val Cys Glu Pro Cys Pro Pro
                30                  35                  40

Gly Thr Tyr Ile Ala His Leu Asn Gly Leu Ser Lys Cys Leu Gln Cys
            45                  50                  55

Gln Met Cys Asp Pro Ala Met Gly Leu Arg Ala Ser Arg Asn Cys Ser
        60                  65                  70

Arg Thr Glu Asn Ala Val Cys Gly Cys Ser Pro Gly His Phe Cys Ile
 75                  80                  85                  90

Val Gln Asp Gly Asp His Cys Ala Ala Cys Arg Ala Tyr Ala Thr Ser
                    95                 100                 105

Ser Pro Gly Gln Arg Val Gln Lys Gly Gly Thr Glu Ser Gln Asp Thr
                110                 115                 120

Leu Cys Gln Asn Cys Pro Pro Gly Thr Phe Ser Pro Asn Gly Thr Leu
            125                 130                 135

Glu Glu Cys Gln His Gln Thr Lys Cys Ser Trp Leu Val Thr Lys Ala
    140                 145                 150

Gly Ala Gly Thr Ser Ser Ser His Trp Val Trp Trp Phe Leu Ser Gly
155                 160                 165                 170

Ser Leu Val Ile Val Ile Val Cys Ser Thr Val Gly Leu Ile Ile Cys
                175                 180                 185

Val Lys Arg Arg Lys Pro Arg Gly Asp Val Val Lys Val Ile Val Ser
                190                 195                 200

Val Gln Arg Lys Arg Gln Glu Ala Glu Gly Glu Ala Thr Val Ile Glu
            205                 210                 215

Ala Leu Gln Ala Pro Pro Asp Val Thr Thr Val Ala Val Glu Glu Thr
        220                 225                 230

Ile Pro Ser Phe Thr Gly Arg Ser Pro Asn His
235                 240                 245
```